United States Patent
Guo et al.

(10) Patent No.: US 10,214,567 B2
(45) Date of Patent: Feb. 26, 2019

(54) TAGGED HEPADNAVIRUS E ANTIGEN AND ITS USE IN SCREENING ANTIVIRAL SUBSTANCES

(71) Applicants: Drexel University, Philadelphia, PA (US); Baruch S. Blumberg Institute, Doylestown, PA (US); Hoffmann-La Roche Inc., Little Falls, NJ (US)

(72) Inventors: Haitao Guo, Carmel, IN (US); Dawei Cai, Indianapolis, IN (US); Andrea Cuconati, Oreland, PA (US); Changhua Ji, Shanghai (CN)

(73) Assignees: Drexel University, Philadelphia, PA (US); Baruch S. Blumberg Institute, Doylestown, PA (US); Hoffmann-La Roche Inc., Little Falls, NJ (US)

( * ) Notice: Subject to any disclaimer, the term of this patent is extended or adjusted under 35 U.S.C. 154(b) by 0 days.

(21) Appl. No.: 15/981,316

(22) Filed: May 16, 2018

(65) Prior Publication Data
US 2018/0312546 A1    Nov. 1, 2018

Related U.S. Application Data

(62) Division of application No. 15/309,680, filed as application No. PCT/EP2015/063838 on Jun. 19, 2015, now Pat. No. 10,072,047.

(60) Provisional application No. 62/014,996, filed on Jun. 20, 2014.

(51) Int. Cl.
| | |
|---|---|
| C07K 14/02 | (2006.01) |
| C07K 14/005 | (2006.01) |
| C12Q 1/68 | (2018.01) |
| A61K 39/29 | (2006.01) |
| C12Q 1/70 | (2006.01) |
| G01N 33/50 | (2006.01) |

(52) U.S. Cl.
CPC ......... *C07K 14/005* (2013.01); *G01N 33/502* (2013.01); *C07K 2319/40* (2013.01); *C07K 2319/42* (2013.01); *C12N 2730/10122* (2013.01); *C12N 2730/10151* (2013.01); *C12N 2830/006* (2013.01); *G01N 2333/02* (2013.01)

(58) Field of Classification Search
CPC ........ C07K 14/005; C12N 2730/10122; C12N 7/00; C12N 2730/10134; A61K 39/12
See application file for complete search history.

(56) References Cited

FOREIGN PATENT DOCUMENTS

WO    WO-2013/181584 A2    12/2013

OTHER PUBLICATIONS

Cai et al., "Identification of Disubstituted Sulfonamide Compounds as Specific Inhibitors of Hepatitis B Virus Covalently CLosed Circular DNA Formation", Antimicrobial Agents and Chemotherapy, 2012, 56(8):4277-4288.*
Cai et al., "Identification of disubstituted sulfonamide compounds as specific inhibitors of hepatitis B virus covalently closed circular DNA formation," Antimicrob Agents Chemother. 56(8):4277-88 (2012).
Guo et al., "Metabolism and function of hepatitis B virus cccDNA: Implications for the development of cccDNA-targeting antiviral therapeutics," available in PMC Oct. 1, 2016, published in final edited form as: Antiviral Res. 122:91-100 (2015) (25 pages).
International Preliminary Report on Patentability for International Patent Application No. PCT/EP2015/063838, dated Aug. 31, 2016 (13 pages).
International Search Report and Written Opinion for International Patent Application No. PCT/EP2015/063838, dated Sep. 28, 2015 (10 pages).
Response to Second Written Opinion of the International Preliminary Examining Authority dated May 18, 2016, and Amended Claims for International Patent Application No. PCT/EP2015/063838, dated Jul. 6, 2016 (8 pages).
Response to Written Opinion of the International Searching Authority dated Sep. 28, 2015, and Amended Claims for International Patent Application No. PCT/EP2015/063838, dated Jan. 18, 2016 (9 pages).
Written Opinion of the International Preliminary Examining Authority for International Patent Application No. PCT/EP2015/063838, dated May 18, 2016 (6 pages).
Yang et al., "Human hepatitis B viral e antigen interacts with cellular interleukin-1 receptor accessory protein and triggers interleukin-1 response," J Biol Chem. 281(45):34525-36 (2006) (13 pages).

* cited by examiner

*Primary Examiner* — Barry A Chestnut
(74) *Attorney, Agent, or Firm* — Clark & Elbing LLP; Karen L. Elbing

(57) ABSTRACT

The present invention relates to methods and uses for screening anti-hepadnaviral substances, wherein the substances are screened for the capacity to inhibit covalently closed circular (ccc) DNA of a hepadnavirus, like hepatitis B virus. The methods and uses take advantage of cells comprising a nucleic sequence encoding a tagged hepadnavirus e antigen, like Hepatitis B virus e antigen (HBeAg). Furthermore, the present invention provides nucleic acid sequences encoding a tagged hepadnavirus e antigen and proteins encoded thereby. Also kits for use in the screening methods are provided.

Figure 1:
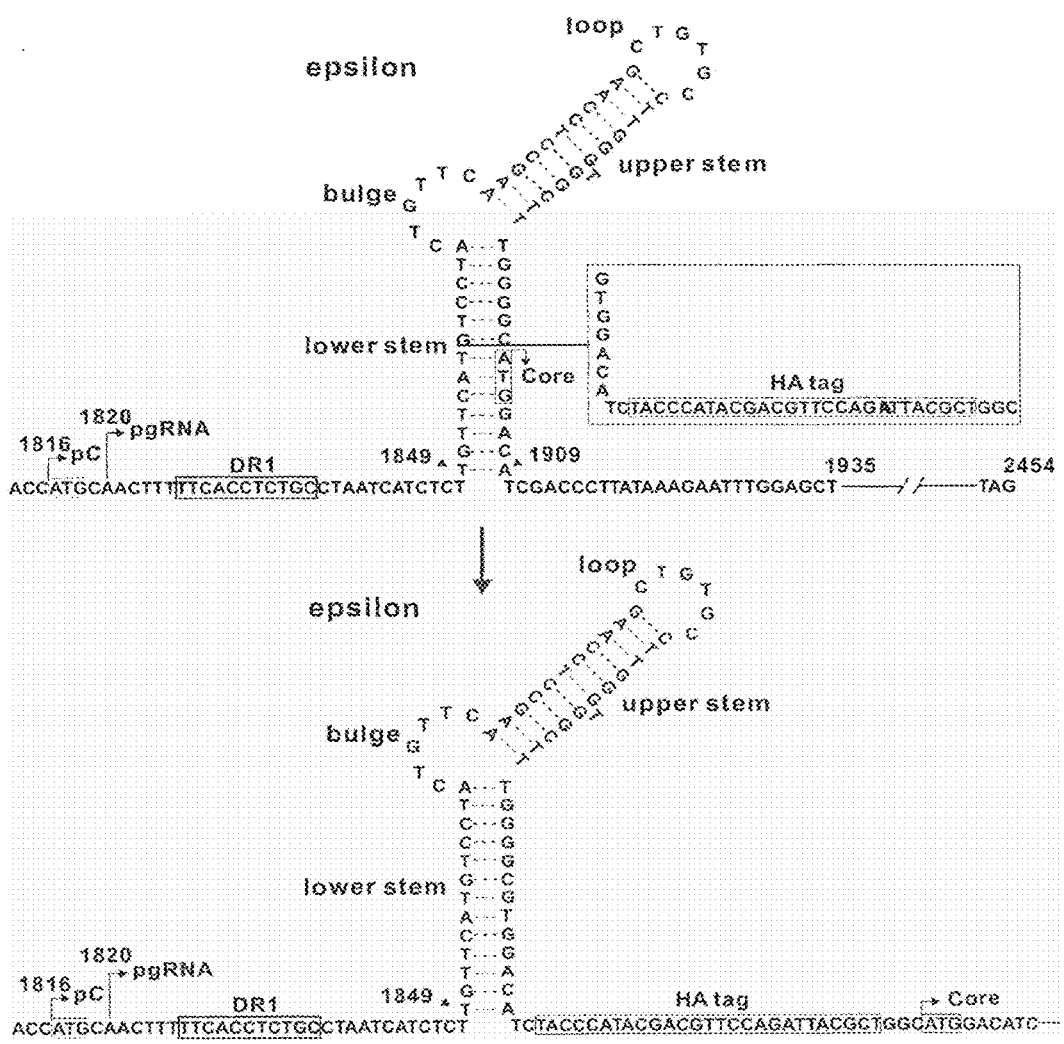

20 Claims, 11 Drawing Sheets
Specification includes a Sequence Listing.

SEQUENCE LISTING

```
<160> NUMBER OF SEQ ID NOS: 46

<210> SEQ ID NO 1
<211> LENGTH: 27
<212> TYPE: DNA
<213> ORGANISM: Hepatitis B virus

<400> SEQUENCE: 1
```

```
tacccatacg acgttccaga ttacgct                                          27

<210> SEQ ID NO 2
<211> LENGTH: 18
<212> TYPE: DNA
<213> ORGANISM: Hepatitis B virus

<400> SEQUENCE: 2
catcatcatc atcatcac                                                    18

<210> SEQ ID NO 3
<211> LENGTH: 24
<212> TYPE: DNA
<213> ORGANISM: Hepatitis B virus

<400> SEQUENCE: 3
gactacaagg acgacgacga caag                                             24

<210> SEQ ID NO 4
<211> LENGTH: 39
<212> TYPE: DNA
<213> ORGANISM: Hepatitis B virus

<400> SEQUENCE: 4
atggcatcaa tgcagaagct gatctcagag gaggacctg                             39

<210> SEQ ID NO 5
<211> LENGTH: 42
<212> TYPE: DNA
<213> ORGANISM: Hepatitis B virus

<400> SEQUENCE: 5
ggtaagccta tccctaaccc tctcctcggt ctcgattcta cg                         42

<210> SEQ ID NO 6
<211> LENGTH: 27
<212> TYPE: DNA
<213> ORGANISM: Hepatitis B virus

<400> SEQUENCE: 6
actgaaacat ctcaagtagc tccagct                                          27

<210> SEQ ID NO 7
<211> LENGTH: 66
<212> TYPE: DNA
<213> ORGANISM: Hepatitis B virus

<400> SEQUENCE: 7
gactacaaag accacgacgg tgactacaaa gaccacgaca tcgactacaa ggacgacgac      60
gacaag                                                                 66

<210> SEQ ID NO 8
<211> LENGTH: 9
<212> TYPE: PRT
<213> ORGANISM: Hepatitis B virus

<400> SEQUENCE: 8

Tyr Pro Tyr Asp Val Pro Asp Tyr Ala
1               5

<210> SEQ ID NO 9
<211> LENGTH: 6
```

```
<212> TYPE: PRT
<213> ORGANISM: Hepatitis B virus

<400> SEQUENCE: 9

His His His His His His
1               5

<210> SEQ ID NO 10
<211> LENGTH: 8
<212> TYPE: PRT
<213> ORGANISM: Hepatitis B virus

<400> SEQUENCE: 10

Asp Tyr Lys Asp Asp Asp Asp Lys
1               5

<210> SEQ ID NO 11
<211> LENGTH: 10
<212> TYPE: PRT
<213> ORGANISM: Hepatitis B virus

<400> SEQUENCE: 11

Glu Gln Lys Leu Ile Ser Glu Glu Asp Leu
1               5                   10

<210> SEQ ID NO 12
<211> LENGTH: 14
<212> TYPE: PRT
<213> ORGANISM: Hepatitis B virus

<400> SEQUENCE: 12

Gly Lys Pro Ile Pro Asn Pro Leu Leu Gly Leu Asp Ser Thr
1               5                   10

<210> SEQ ID NO 13
<211> LENGTH: 9
<212> TYPE: PRT
<213> ORGANISM: Hepatitis B virus

<400> SEQUENCE: 13

Thr Glu Thr Ser Gln Val Ala Pro Ala
1               5

<210> SEQ ID NO 14
<211> LENGTH: 22
<212> TYPE: PRT
<213> ORGANISM: Hepatitis B virus

<400> SEQUENCE: 14

Asp Tyr Lys Asp His Asp Gly Asp Tyr Lys Asp His Asp Ile Asp Tyr
1               5                   10                  15

Lys Asp Asp Asp Asp Lys
            20

<210> SEQ ID NO 15
<211> LENGTH: 639
<212> TYPE: DNA
<213> ORGANISM: Hepatitis B virus

<400> SEQUENCE: 15
atgcaacttt ttcacctctg cctaatcatc tcttgttcat gtcctactgt tcaagcctcc      60
aagctgtgcc ttgggtggct ttggggcatg gacatcgacc cttataaaga atttggagct     120
actgtggagt tactctcgtt tttgccttct gacttctttc cttcagtacg agatcttcta     180
```

```
gataccgcct cagctctgta tcgggaagcc ttagagtctc ctgagcattg ttcacctcac    240
catactgcac tcaggcaagc aattctttgc tgggggggaac taatgactct agctacctgg   300
gtgggtgtta atttggaaga tccagcatct agagacctag tagtcagtta tgtcaacact   360
aatatgggcc taaagttcag gcaactcttg tggtttcaca tttcttgtct cacttttgga   420
agagaaaccg ttatagagta tttggtgtct ttcggagtgt ggattcgcac tcctccagct   480
tatagaccac caaatgcccc tatcctatca acacttccgg aaactactgt tgttagacga   540
cgaggcaggt ccctagaag aagaactccc tcgcctcgca gacgaaggtc tcaatcgccg   600
cgtcgcagaa gatctcaatc tcgggaacct caatgttag                          639

<210> SEQ ID NO 16
<211> LENGTH: 477
<212> TYPE: DNA
<213> ORGANISM: Hepatitis B virus

<400> SEQUENCE: 16
tccaagctgt gccttgggtg gctttggggc atggacatcg acccttataa agaatttgga    60
gctactgtgg agttactctc gttttttgcct tctgacttct ttccttcagt acgagatctt   120
ctagataccg cctcagctct gtatcgggaa gccttagagt ctcctgagca ttgttcacct   180
caccatactg cactcaggca agcaattctt tgctgggggg aactaatgac tctagctacc   240
tgggtgggtg ttaatttgga agatccagca tctagagacc tagtagtcag ttatgtcaac   300
actaatatgg gcctaaagtt caggcaactc ttgtggtttc acatttcttg tctcactttt   360
ggaagagaaa ccgttataga gtatttggtg tctttcggag tgtggattcg cactcctcca   420
gcttatagac caccaaatgc ccctatccta tcaacacttc cggaaactac tgttgtt     477

<210> SEQ ID NO 17
<211> LENGTH: 212
<212> TYPE: PRT
<213> ORGANISM: Hepatitis B virus

<400> SEQUENCE: 17

Met Gln Leu Phe His Leu Cys Leu Ile Ile Ser Cys Ser Cys Pro Thr
1               5                   10                  15

Val Gln Ala Ser Lys Leu Cys Leu Gly Trp Leu Trp Gly Met Asp Ile
            20                  25                  30

Asp Pro Tyr Lys Glu Phe Gly Ala Thr Val Glu Leu Leu Ser Phe Leu
        35                  40                  45

Pro Ser Asp Phe Phe Pro Ser Val Arg Asp Leu Leu Asp Thr Ala Ser
    50                  55                  60

Ala Leu Tyr Arg Glu Ala Leu Glu Ser Pro Glu His Cys Ser Pro His
65                  70                  75                  80

His Thr Ala Leu Arg Gln Ala Ile Leu Cys Trp Gly Glu Leu Met Thr
                85                  90                  95

Leu Ala Thr Trp Val Gly Val Asn Leu Glu Asp Pro Ala Ser Arg Asp
            100                 105                 110

Leu Val Val Ser Tyr Val Asn Thr Asn Met Gly Leu Lys Phe Arg Gln
        115                 120                 125

Leu Leu Trp Phe His Ile Ser Cys Leu Thr Phe Gly Arg Glu Thr Val
    130                 135                 140

Ile Glu Tyr Leu Val Ser Phe Gly Val Trp Ile Arg Thr Pro Pro Ala
145                 150                 155                 160
```

Tyr Arg Pro Pro Asn Ala Pro Ile Leu Ser Thr Leu Pro Glu Thr Thr
                 165                 170                 175

Val Val Arg Arg Arg Gly Arg Ser Pro Arg Arg Thr Pro Ser Pro
     180                     185                 190

Arg Arg Arg Arg Ser Gln Ser Pro Arg Arg Arg Ser Gln Ser Arg
        195                 200                 205

Glu Pro Gln Cys
     210

<210> SEQ ID NO 18
<211> LENGTH: 159
<212> TYPE: PRT
<213> ORGANISM: Hepatitis B virus

<400> SEQUENCE: 18

Ser Lys Leu Cys Leu Gly Trp Leu Trp Gly Met Asp Ile Asp Pro Tyr
1               5                 10                15

Lys Glu Phe Gly Ala Thr Val Glu Leu Leu Ser Phe Leu Pro Ser Asp
          20                 25                30

Phe Phe Pro Ser Val Arg Asp Leu Leu Asp Thr Ala Ser Ala Leu Tyr
        35                 40                45

Arg Glu Ala Leu Glu Ser Pro Glu His Cys Ser Pro His His Thr Ala
   50                   55                60

Leu Arg Gln Ala Ile Leu Cys Trp Gly Glu Leu Met Thr Leu Ala Thr
65                70                75                80

Trp Val Gly Val Asn Leu Glu Asp Pro Ala Ser Arg Asp Leu Val Val
          85                 90                95

Ser Tyr Val Asn Thr Asn Met Gly Leu Lys Phe Arg Gln Leu Leu Trp
        100                105              110

Phe His Ile Ser Cys Leu Thr Phe Gly Arg Glu Thr Val Ile Glu Tyr
       115                120              125

Leu Val Ser Phe Gly Val Trp Ile Arg Thr Pro Pro Ala Tyr Arg Pro
    130                 135                140

Pro Asn Ala Pro Ile Leu Ser Thr Leu Pro Glu Thr Thr Val Val
145                150                155

<210> SEQ ID NO 19
<211> LENGTH: 678
<212> TYPE: DNA
<213> ORGANISM: Hepatitis B virus

<400> SEQUENCE: 19

```
atgcaacttt tcacctctg cctaatcatc tcttgttcat gtcctactgt tcaagcctcc      60
aagctgtgcc ttgggtggct ttggggcgtg gacatctacc catacgacgt tccagattac     120
gctggcatgg acatcgaccc ttataaagaa tttggagcta ctgtggagtt actctcgttt     180
ttgccttctg acttctttcc ttcagtacga gatcttctag ataccgcctc agctctgtat     240
cgggaagcct tagagtctcc tgagcattgt tcacctcacc atactgcact caggcaagca     300
attctttgct ggggggaact aatgactcta gctacctggg tgggtgttaa tttggaagat     360
ccagcatcta gagacctagt agtcagttat gtcaacacta tatgggcct aaagttcagg     420 caactcttgt ggtttcacat tcttgtctc acttttggaa gagaaaccgt tatagagtat     480
ttggtgtctt tcggagtgtg gattcgcact cctccagctt atagaccacc aaatgcccct     540
atcctatcaa cacttccgga aactactgtt gttagacgac gaggcaggtc ccctagaaga     600
agaactccct cgcctcgcag acgaaggtct caatcgccgc gtcgcagaag atctcaatct     660
```

```
                                             -continued cgggaacctc aatgttag                                              678

<210> SEQ ID NO 20
<211> LENGTH: 516
<212> TYPE: DNA
<213> ORGANISM: Hepatitis B virus

<400> SEQUENCE: 20
tccaagctgt gccttgggtg gctttggggc gtggacatct acccatacga cgttccagat    60
tacgctggca tggacatcga cccttataaa gaatttggag ctactgtgga gttactctcg   120
tttttgcctt ctgacttctt tccttcagta cgagatcttc tagataccgc ctcagctctg   180
tatcgggaag ccttagagtc tcctgagcat tgttcacctc accatactgc actcaggcaa   240
gcaattcttt gctgggggga actaatgact ctagctacct gggtgggtgt taatttggaa   300
gatccagcat ctagagacct agtagtcagt tatgtcaaca ctaatatggg cctaaagttc   360
aggcaactct gtggttttca catttcttgt ctcactttg gaagagaaac cgttatagag   420
tatttggtgt ctttcggagt gtggattcgc actcctccag cttatagacc accaaatgcc   480
cctatcctat caacacttcc ggaaactact gttgtt                             516

<210> SEQ ID NO 21
<211> LENGTH: 225
<212> TYPE: PRT
<213> ORGANISM: Hepatitis B virus

<400> SEQUENCE: 21

Met Gln Leu Phe His Leu Cys Leu Ile Ile Ser Cys Ser Cys Pro Thr
1               5                   10                  15

Val Gln Ala Ser Lys Leu Cys Leu Gly Trp Leu Trp Gly Val Asp Ile
            20                  25                  30

Tyr Pro Tyr Asp Val Pro Asp Tyr Ala Gly Met Asp Ile Asp Pro Tyr
        35                  40                  45

Lys Glu Phe Gly Ala Thr Val Glu Leu Leu Ser Phe Leu Pro Ser Asp
    50                  55                  60

Phe Phe Pro Ser Val Arg Asp Leu Leu Asp Thr Ala Ser Ala Leu Tyr
65                  70                  75                  80

Arg Glu Ala Leu Glu Ser Pro Glu His Cys Ser Pro His His Thr Ala
                85                  90                  95

Leu Arg Gln Ala Ile Leu Cys Trp Gly Glu Leu Met Thr Leu Ala Thr
            100                 105                 110

Trp Val Gly Val Asn Leu Glu Asp Pro Ala Ser Arg Asp Leu Val Val
        115                 120                 125

Ser Tyr Val Asn Thr Asn Met Gly Leu Lys Phe Arg Gln Leu Leu Trp
    130                 135                 140

Phe His Ile Ser Cys Leu Thr Phe Gly Arg Glu Thr Val Ile Glu Tyr
145                 150                 155                 160

Leu Val Ser Phe Gly Val Trp Ile Arg Thr Pro Pro Ala Tyr Arg Pro
                165                 170                 175

Pro Asn Ala Pro Ile Leu Ser Thr Leu Pro Glu Thr Thr Val Val Arg
            180                 185                 190

Arg Arg Gly Arg Ser Pro Arg Arg Arg Thr Pro Ser Pro Arg Arg Arg
        195                 200                 205

Arg Ser Gln Ser Pro Arg Arg Arg Ser Gln Ser Arg Glu Pro Gln
    210                 215                 220
```

Cys
225

<210> SEQ ID NO 22
<211> LENGTH: 172
<212> TYPE: PRT
<213> ORGANISM: Hepatitis B virus

<400> SEQUENCE: 22

Ser Lys Leu Cys Leu Gly Trp Leu Trp Gly Val Asp Ile Tyr Pro Tyr
1               5                   10                  15

Asp Val Pro Asp Tyr Ala Gly Met Asp Ile Asp Pro Tyr Lys Glu Phe
            20                  25                  30

Gly Ala Thr Val Glu Leu Leu Ser Phe Leu Pro Ser Asp Phe Phe Pro
        35                  40                  45

Ser Val Arg Asp Leu Leu Asp Thr Ala Ser Ala Leu Tyr Arg Glu Ala
    50                  55                  60

Leu Glu Ser Pro Glu His Cys Ser Pro His His Thr Ala Leu Arg Gln
65                  70                  75                  80

Ala Ile Leu Cys Trp Gly Glu Leu Met Thr Leu Ala Thr Trp Val Gly
                85                  90                  95

Val Asn Leu Glu Asp Pro Ala Ser Arg Asp Leu Val Val Ser Tyr Val
            100                 105                 110

Asn Thr Asn Met Gly Leu Lys Phe Arg Gln Leu Leu Trp Phe His Ile
        115                 120                 125

Ser Cys Leu Thr Phe Gly Arg Glu Thr Val Ile Glu Tyr Leu Val Ser
    130                 135                 140

Phe Gly Val Trp Ile Arg Thr Pro Pro Ala Tyr Arg Pro Pro Asn Ala
145                 150                 155                 160

Pro Ile Leu Ser Thr Leu Pro Glu Thr Thr Val Val
                165                 170

<210> SEQ ID NO 23
<211> LENGTH: 552
<212> TYPE: DNA
<213> ORGANISM: Hepatitis B virus

<400> SEQUENCE: 23
atggacatcg acccttataa agaatttgga gctactgtgg agttactctc gtttttgcct     60
tctgacttct ttccttcagt acgagatctt ctagataccg cctcagctct gtatcgggaa    120
gccttagagt ctcctgagca ttgttcacct caccatactg cactcaggca agcaattctt    180
tgctgggggg aactaatgac tctagctacc tgggtgggtg ttaatttgga agatccagca    240
tctagagacc tagtagtcag ttatgtcaac actaatatgg gcctaaagtt caggcaactc    300
ttgtggtttc acatttcttg tctcactttt ggaagagaaa ccgttataga gtatttggtg    360
tctttcggag tgtggattcg cactcctcca gcttatagac accaaatgc ccctatccta    420 tcaacacttc cggaaactac tgttgttaga cgacgaggca ggtcccctag aagaagaact    480
ccctcgcctc gcagacgaag gtctcaatcg ccgcgtcgca gaagatctca atctcgggaa    540
cctcaatgtt ag                                                        552

<210> SEQ ID NO 24
<211> LENGTH: 183
<212> TYPE: PRT
<213> ORGANISM: Hepatitis B virus

<400> SEQUENCE: 24

```
Met Asp Ile Asp Pro Tyr Lys Glu Phe Gly Ala Thr Val Glu Leu Leu
1               5                   10                  15

Ser Phe Leu Pro Ser Asp Phe Pro Ser Val Arg Asp Leu Leu Asp
            20                  25                  30

Thr Ala Ser Ala Leu Tyr Arg Glu Ala Leu Glu Ser Pro Glu His Cys
            35                  40                  45

Ser Pro His His Thr Ala Leu Arg Gln Ala Ile Leu Cys Trp Gly Glu
        50                  55                  60

Leu Met Thr Leu Ala Thr Trp Val Gly Val Asn Leu Glu Asp Pro Ala
65                  70                  75                  80

Ser Arg Asp Leu Val Val Ser Tyr Val Asn Thr Asn Met Gly Leu Lys
                85                  90                  95

Phe Arg Gln Leu Leu Trp Phe His Ile Ser Cys Leu Thr Phe Gly Arg
                100                 105                 110

Glu Thr Val Ile Glu Tyr Leu Val Ser Phe Gly Val Trp Ile Arg Thr
                115                 120                 125

Pro Pro Ala Tyr Arg Pro Pro Asn Ala Pro Ile Leu Ser Thr Leu Pro
            130                 135                 140

Glu Thr Thr Val Val Arg Arg Arg Gly Arg Ser Pro Arg Arg Arg Thr
145                 150                 155                 160

Pro Ser Pro Arg Arg Arg Arg Ser Gln Ser Pro Arg Arg Arg Arg Ser
                165                 170                 175

Gln Ser Arg Glu Pro Gln Cys
            180

<210> SEQ ID NO 25
<211> LENGTH: 61
<212> TYPE: DNA
<213> ORGANISM: Hepatitis B virus

<400> SEQUENCE: 25
tgttcatgtc ctactgttca agcctccaag ctgtgccttg ggtggctttg ggcatggac     60
a                                                                   61

<210> SEQ ID NO 26

<400> SEQUENCE: 26

000

<210> SEQ ID NO 27
<211> LENGTH: 3182
<212> TYPE: DNA
<213> ORGANISM: Hepatitis B virus

<400> SEQUENCE: 27
aattccacaa cctttcacca aactctgcaa gatcccagag tgagaggcct gtatttccct    60
gctggtggct ccagttcagg agcagtaaac cctgttccga ctactgcctc tcccttatcg   120
tcaatcttct cgaggattgg ggaccctgcg ctgaacatgg agaacatcac atcaggattc   180
ctaggacccc ttctcgtgtt acaggcgggg ttttcttgt tgacaagaat cctcacaata   240
ccgcaaagtc tagactcgtg gtggacttct ctcaatttc taggggggaac taccgtgtgt   300 cttggccaaa attcgcagtc cccaacctcc aatcactcac caacctcctg tcctccaact   360
tgtcctggtt atcgctggat gtgtctgcgg cgttttatca tcttcctctt catcctgctg   420
ctatgcctca tcttcttgtt ggttcttctg gactatcaag gtatgttgcc cgtttgtcct   480
```

```
ctaattccag gatcctcaac caccagcacg ggaccatgcc gaacctgcat gactactgct    540
caaggaacct ctatgtatcc ctcctgttgc tgtaccaaac cttcggacgg aaattgcacc    600
tgtattccca tcccatcatc ctgggctttc ggaaaattcc tatgggagtg ggcctcagcc    660
cgtttctcct ggctcagttt actagtgcca tttgttcagt ggttcgtagg gctttccccc    720
actgtttggc tttcagttat atggatgatg tggtattggg ggccaagtct gtacagcatc    780
ttgagtccct ttttaccgct gttaccaatt ttcttttgtc tttgggtata catttaaacc    840
ctaacaaaac aaagagatgg ggttactctc tgaattttat gggttatgtc attggaagtt    900
atgggtcctt gccacaagaa cacatcatac aaaaaatcaa agaatgtttt agaaaacttc    960
ctattaacag gcctattgat tggaaagtat gtcaacgaat tgtgggtctt ttgggttttg    1020
ctgccccatt tacacaatgt ggttatcctg cgttaatgcc cttgtatgca tgtattcaat    1080
ctaagcaggc tttcactttc tcgccaactt acaaggcctt tctgtgtaaa caatacctga    1140
acctttaccc cgttgcccgg caacggccag gtctgtgcca agtgtttgct gacgcaaccc    1200
ccactggctg ggcttggtc atgggccatc agcgcgtgcg tggaaccttt tcggctcctc    1260
tgccgatcca tactgcggaa ctcctagccg cttgttttgc tcgcagcagg tctggagcaa    1320
acattatcgg gactgataac tctgttgtcc tctcccgcaa atatacatcg tatccatggc    1380
tgctaggctg tgctgccaac tggatcctgc gcgggacgtc ctttgtttac gtcccgtcgg    1440
cgctgaatcc tgcggacgac ccttctcggg gtcgcttggg actctctcgt cccctctcc    1500 gtctgccgtt ccgaccgacc acggggcgca cctctctta cgcggactcc ccgtctgtgc    1560
cttctcatct gccggaccgt gtgcacttcg cttcacctct gcacgtcgca tggagaccac    1620
cgtgaacgcc caccgaatgt tgcccaaggt cttacataag aggactcttg gactctctgc    1680
aatgtcaacg accgaccttg aggcatactt caaagactgt ttgtttaaag actgggagga    1740
gttgggggag gagattagat taaaggtctt tgtactagga ggctgtaggc ataaattggt    1800
ctgcgcacca gcaccatgca actttttcac ctctgcctaa tcatctcttg ttcatgtcct    1860
actgttcaag cctccaagct gtgccttggg tggctttggg gcatggacat cgacccttat    1920
aaagaatttg gagctactgt ggagttactc tcgttttgc cttctgactt ctttccttca    1980
gtacgagatc ttctagatac cgcctcagct ctgtatcggg aagccttaga gtctcctgag    2040
cattgttcac ctcaccatac tgcactcagg caagcaattc tttgctgggg ggaactaatg    2100
actctagcta cctgggtggg tgttaatttg gaagatccag catctagaga cctagtagtc    2160
agttatgtca acactaatat gggcctaaag ttcaggcaac tcttgtggtt tcacatttct    2220
tgtctcactt ttggaagaga aaccgttata gagtatttgg tgtctttcgg agtgtggatt    2280
cgcactcctc cagcttatag accaccaaat gccctatcc tatcaacact tccgaaaact    2340
actgttgtta gacgacgagg caggtcccct agaagaagaa ctccctcgcc tcgcagacga    2400
aggtctcaat cgccgcgtcg cagaagatct caatctcggg aacctcaatg ttagtattcc    2460
ttggactcat aaggtgggga actttactgg tctttattct tctactgtac ctgtctttaa    2520
tcctcattgg aaaacaccat cttttcctaa tatacattta caccaagaca ttatcaaaaa    2580
atgtgaacag tttgtaggcc cacttacagt taatgagaaa agaagattgc aattgattat    2640
gcctgctagg ttttatccaa aggttaccaa atatttacca ttggataagg gtattaaacc    2700
ttattatcca gaacatctag ttaatcatta cttccaaact agacactatt tacacactct    2760
atggaaggcg ggtatattat ataagagaga acaacacat agcgcctcat tttgtgggtc    2820
```

| | |
|---|---:|
| accatattct tgggaacaag atctacagca tggggcagaa tctttccacc agcaatcctc | 2880 |
| tgggattctt tcccgaccac cagttggatc cagccttcag agcaaacaca gcaaatccag | 2940 |
| attgggactt caatcccaac aaggacacct ggccagacgc caacaaggta ggagctggag | 3000 |
| cattcgggct gggtttcacc ccaccgcacg gaggcctttt ggggtggagc cctcaggctc | 3060 |
| agggcatact acaaactttg ccagcaaatc cgcctcctgc ctccaccaat cgccagacag | 3120 |
| gaaggcagcc taccccgctg tctccacctt tgagaaacac tcatcctcag gccatgcagt | 3180 |
| gg | 3182 |

<210> SEQ ID NO 28
<211> LENGTH: 3221
<212> TYPE: DNA
<213> ORGANISM: Hepatitis B virus

<400> SEQUENCE: 28

| | |
|---|---:|
| aattccactg ccttccacca agctctgcag gatcccagag tcaggggtct gtattttcct | 60 |
| gctggtggct ccagttcagg aacagtaaac cctgctccga atattgcctc tcacatctcg | 120 |
| tcaatctccg cgaggactgg ggaccctgtg gcgaacatgg agaacatcac atcaggattc | 180 |
| ctaggacccc tgctcgtgtt acaggcgggg ttttcttgt tgacaagaat cctcacaata | 240 |
| ccgcagagtc tagactcgtg gtggacttct ctcaattttc taggggatc acccgtgtgt | 300 |
| cttggccaaa attcgcagtc cccaacctcc aatcactcac caacctcctg tcctccaatt | 360 |
| tgtcctggtt atcgctggat gtgtctgcgg cgttttatca tattcctctt catcctgctg | 420 |
| ctatgcctca tcttcttatt ggttcttctg gattatcaag gtatgttgcc cgtttgtcct | 480 |
| ctaattccag gatcaacaac aaccagtacg ggaccatgca aaacctgcac gactcctgct | 540 |
| caaggcaact ctatgtttcc ctcatgttgc tgtacaaaac ctacggatgg aaattgcacc | 600 |
| tgtattccca tcccatcgtc ctgggctttc gcaaaatacc tatgggagtg gcctcagtc | 660 |
| cgtttctctt ggctcagttt actagtgcca tttgttcagt ggttcgtagg gctttccccc | 720 |
| actgtttggc tttcagctat atggatgatg tggtattggg ggccaagtct gtacagcatc | 780 |
| gtgagtccct ttataccgct gttaccaatt ttcttttgtc tctgggtata catttaaacc | 840 |
| ctaacaaaac aaaaagatgg ggttattccc taaacttcat gggttacata attggaagtt | 900 |
| ggggaacttt gccacaggat catattgtac aaaagatcaa acactgtttt agaaaacttc | 960 |
| ctgttaacag gcctattgat tggaaagtat gtcaaagaat tgtgggtctt ttgggctttg | 1020 |
| ctgctccatt tacacaatgt ggatatcctg ccttaatgcc tttgtatgca tgtatacaag | 1080 |
| ctaaacaggc tttcactttc tcgccaactt acaaggcctt tctaagtaaa cagtacatga | 1140 |
| acctttaccc cgttgctcgg caacggctg gtctgtgcca agtgtttgct gacgcaaccc | 1200 |
| ccactggctg gggcttggcc ataggccatc agcgcatgcg tggaaccttt gtggctcctc | 1260 |
| tgccgatcca tactgcggaa ctcctagccg cttgttttgc tcgcagccgg tctggagcaa | 1320 |
| agctcatcgg aactgacaat tctgtcgtcc tctcgcggaa atatacatcg tttccatggc | 1380 |
| tgctaggctg tgctgccaac tggatccttc gcggaacgtc ctttgtctac gtcccgtcgg | 1440 |
| cgctgaatcc cgcggacgac ccctctcggg gccgcttggg actctctcgt ccccttctcc | 1500 |
| gtctgccgtt ccagccgacc acggggcgca cctctcttta cgcggtctcc ccgtctgtgc | 1560 |
| cttctcatct gccggtccgt gtgcacttcg cttcacctct gcacgttgca tggagaccac | 1620 |
| cgtgaacgcc catcagatcc tgcccaaggt cttacataag aggactcttg gactcccagc | 1680 |
| aatgtcaacg accgaccttg aggcctactt caaagactgt gtgtttaagg actggaggga | 1740 |

```
gctgggggag gagattaggt taaaggtctt tgtattagga ggctgtaggc ataaattggt    1800
ctgcgcacca gcaccatgca acttttcac ctctgcctaa tcatctcttg tacatgtccc    1860
actgttcaag cctccaagct gtgccttggg tggctttggg gcatggacat tgacccttat    1920
aaagaatttg gagctactgt ggagttactc tcgtttttgc cttctgactt ctttccttcc    1980
gtcagagatc tcctagacac cgcctcagct ctgtatcgag aagccttaga gtctcctgag    2040
cattgctcac ctcaccatac tgcactcagg caagccattc tctgctgggg gaattgatg    2100 actctagcta cctgggtggg taataatttg gaagatccag catccaggga tctagtagtc    2160
aattatgtta atactaacat gggtttaaag atcaggcaac tattgtggtt tcatatatct    2220
tgccttactt ttggaagaga gactgtactt gaatatttgg tctctttcgg agtgtggatt    2280
cgcactcctc cagcctatag accaccaaat gcccctatct tatcaacaat tccggaaact    2340
actgttgtta gacgacggga ccgaggcagg tccctagaa gaagaactcc ctcgcctcgc    2400
agacgcagat ctcaatcgcc gcgtcgcaga agatctcaat ctcgggaatc tcaatgttag    2460
tattccttgg actcataagg tgggaaactt tacggggctt tattcctcta cagtacctat    2520
ctttaatcct gaatggcaaa ctccttcctt tcctaagatt catttacaag aggacattat    2580
taataggtgt caacaatttg tgggccctct cactgtaaat gaaaagagaa gattgaaatt    2640
aattatgcct gctagattct atcctaccca cactaaatat ttgcccttag acaaaggaat    2700
taaaccttat tatccagatc aggtagttaa tcattacttc caaaccagac attatttaca    2760
tactctttgg aaggctggta ttctatataa gagggaaacc acacgtagcg catcattttg    2820
cgggtcacca tattcttggg aacaagagct acagcatggg aggttggtca tcaaaacctc    2880
gcaaaggcat ggggacgaat ctttctgttc ccaaccctct gggattcttt ccgatcatc    2940 agttggaccc tgcattcgga gccaactcaa acaatccaga ttgggacttc aaccccatca    3000
aggaccactg gccaacagcc aaccaggtag gagtgggagc attcgggcca gggctcaccc    3060
ctccacacgg cggtattttg ggggggagcc ctcaggctca gggcatattg accacagtgt    3120
caacaattcc tcctcctgcc tccaccaatc ggcagtcagg aaggcagcct actcccatct    3180
ctccacctct aagagacagt catcctcagg ccatgcagtg g                       3221
```

<210> SEQ ID NO 29
<211> LENGTH: 3215
<212> TYPE: DNA
<213> ORGANISM: Hepatitis B virus

<400> SEQUENCE: 29

```
aactccacca cttttcacca aactcttcaa gatcccagag tccgggctct gtactttcct     60
gctggtggct ccagttcagg aacagtaagc cctgctcaga atactgtctc tgccatatcg    120
tcaatcttat cgaagactgg ggaccctgtg ccgaacatgg agaacatcgc atcaggactc    180
ctaggacccc tgctcgtgtt acaggcgggg ttttctcttgt tgacaaaaat cctcacaata    240
ccacagagtc tagactcgtg gtggacttct ctcaatttc tagggggaac accctgtgt    300 cttggccaaa attcgcagtc ccaaatctcc agtcactcac caacctgttg tcctccaatt    360
tgtcctggtt atcgctggat gtgtctgcgg cgttttatca tcttcctctg catcctgctg    420
ctatgcctca tcttcttgtt ggttcttctg gactatcaag gtatgttgcc cgtttgtcct    480
ctaattccag gatcatcaac caccagcacg ggaccatgca agacctgcac aactcctgct    540
caaggaacct ctatgtttcc ctcatgttgc tgtacaaaac ctacggatgg aaactgcacc    600
```

```
tgtattccca tcccatcatc ttgggctttc gcaaaatacc tatgggagtg ggcctcagtc    660
cgtttctctt ggctcagttt actagtgcca tttgttcagt ggttcgtagg gctttccccc    720
actgtctggc tttcagttat atggatgatg tggtattggg ggccaagtct gtacaacatc    780
ttgagtccct ttatgccgct gttaccaatt ttcttttgtc tttgggtata catttaaacc    840
ctcacaaaac aaaaagatgg ggatattccc ttaacttcat gggatatgta attgggagtt    900
ggggcacatt gccacaggaa catattgtac aaaaaatcaa actatgtttt aggaaacttc    960
ctgtaaacag gcctattgat tggaaagtat gtcaacgaat gtgggtcttt tggggtttg    1020 ctgcccctt tacgcaatgt ggatatcctg ctttaatgcc tttatatgca tgtatacaag     1080
caaaacaggc ttttactttc tcgccaactt acaaggcctt tctaagtaaa cagtatctag    1140
ccctttaccc cgttgctcgg caacggcctg gtctgtgcca agtgtttgct gacgcaaccc    1200
ccactggttg gggcttggcc ataggccatc agcgcatgcg tggaaccttt gtgtctcctc    1260
tgccgatcca tactgcggaa ctcctagccg cttgttttgc tcgcagcagg tctggagcga    1320
aactcatcgg gactgacaat tctgtcgtgc tctcccgcaa gtatacatcg tttccatggc    1380
tgctaggctg tgctgccaac tggatcctgc gcgggacgtc ctttgtttac gtcccgtcgg    1440
cgctgaatcc cgcggacgac ccctcccggg gccgcttggg gctctaccgc ccgcttctcc    1500
gtctgccgta ccgaccgacc acggggcgca cctctcttta cgcggactcc ccgtctgtgc    1560
cttctcgtct gccggaccgt gtgcacttcg cttcacctct gcacgtcgca tggaaaccac    1620
cgtgaacgcc caccggaacc tgcccaaggt cttgcacaag aggactcttg gactttcagc    1680
aatgtcaacg accgaccttg aggcatactt caaagactgt gtgtttcatg agtgggagga    1740
gctgggggag gagattaggt taaggtcttt tgtactagga ggctgtaggc ataaattggt    1800
ctgttcacca gcaccatgca acttttttcac ctctgcctag tcatctcttg ttcatgtcct    1860
actgttcaag cctccaagct gtgccttggg tggctttggg acatggacat tgacccttat    1920
aaagaatttg gagctactgt ggagttactc tcttttttgc cttctgactt ctttccgtcg    1980
gtacgagacc tcctagatac cgctgctgct ctgtatcggg aagccttaga atctcctgaa    2040
cattgctcac ctcaccacac agcactcagg caagctattc tgtgctgggg ggaattaatg    2100
actctagcta cctgggtggg taataattta gaagatccag cgtccaggga tctagtagtc    2160
aattatgtta acactaacat gggcctaaag atcaggcaat tattgtggtt tcacatttcc    2220
tgtcttactt ttggaagaga aactgttctt gaatatttgg tgtcttttgg agtgtggatt    2280
cgcactcctc cggcctacag accaccaaat gccccctatct tatcaacact tccggaaact    2340
actgttgtta gacgacgagg caggtcccct agaagaagaa ctccctcgcc tcgcagacga    2400
aggtctcaat caccgcgtcg cagaagatct caatctcggg aatcccaatg ttagtattcc    2460
ttggactcat aaggtgggaa actttacggg gctctattct tctacagtac ctgtctttaa    2520
tcctgaatgg caaactcctt cttttccaga cattcatttg caggaggata ttgttgatag    2580
atgtaagcaa tttgtgggac cccttacagt aaatgaaaac aggagactaa aattaataat    2640
gcctgctaga ttttatccta atgttaccaa atatttgccc ttagataaag ggatcaaacc    2700
ttattatcca gagcatgtag ttaatcatta cttccagaca agacattatt tgcatactct    2760
ttggaaggcg ggtatcttat ataagagaga gtcaacacat agcgcctcat tttgcgggtc    2820
accatattct tggaacaag atctacagca tgggaggttg gtcttccaaa cctcgaaaag     2880
gcatggggac aaatctttct gtccccaatc ccctgggatt cttccccgat catcagttgg    2940
accctgcatt caaagccaac tcagaaaatc cagattggga cctcaaccca cacaaggaca    3000
```

```
actggccgga cgcccacaag gtgggagtgg gagcattcgg gccagggttc acccctcccc    3060 acggggact gttggggtgg agccctcagg ctcaggcat acttacatct gtgccagcag      3120
ctcctcctcc tgcctccacc aatcggcagt caggaaggca gcctactccc ttatctccac    3180
ctctaaggga cactcatcct caggccatgc agtgg                               3215
```

```
<210> SEQ ID NO 30
<211> LENGTH: 3215
<212> TYPE: DNA
<213> ORGANISM: Hepatitis B virus

<400> SEQUENCE: 30
```

```
aactccacaa ctttccacca agctctgcta gatcccagag tgaggggcct atactttcct     60
gctggtggct ccagttccgg aacagtaaac cctgttccga ctactgcctc tcccatatcg    120
tcaatcttca cgaggactgg ggaccctgta ccgaacatgg agaacacaac atcaggattc    180
ctaggacccc tgctcgtgtt acaggcgggg ttttcttgt tgacaagaat cctcacaata    240
ccgcagagtc tagactcgtg gtggacttct ctcaattttc taggggagc acccacgtgt    300 cctggccaaa attcgcagtc cccaacctcc aatcactcac caacctcttg tcctccaatt   360
tgtcctggct atcgctggat gtgtctgcgg cgttttatca tattcctctt catcctgctg   420
ctatgcctca tcttcttgtt ggttcttctg gactatcaag gtatgttgcc cgtttgtcct   480
ctacttccag gaacatcaac tacaagcacg ggaccatgca agacctgcac gattcctgct   540
caaggaamct ctatgtttcc ctcttgttgc tgtacaaaac cttcggacgg aaactgcact   600
tgtattccca tcccatcatc ctgggctttc gcaagattcc tatgggagtg ggcctcagtc   660 cgttctcct ggctcagttt actagtgcca tttgttcagt ggttcgtagg ctttccccc     720 actgtttggc tttcagctat atggatgatg tggtattggg ggccaagtct gtacaacatc   780
ttgagtccct ttttacctct attaccaatt ttcttttgtc tttgggtata catttgaacc   840
ctaataaaac caagcgttgg ggctactccc ttaactttat gggatatgta attggaagtt   900
ggggtacttt accacaggaa catattgttc taaaaatcaa acaatgtttt cggaaactgc   960
ctgtaaatag acctattgat tggaaagtat gtcaacgaat tgtgggtctt ctgggctttg  1020 ctgcccctt tacacaatgt gggtatcctg ccttgatgcc tttgtatgca tgtatacaag  1080
ctaagcaggc tttcactttc tcgccaactt ataaggcctt tctgtgtaaa caatatctga  1140
acctttaccc cgttgctcgg caacggtcag gtctctgcca agtatttgct gacgcaaccc  1200
ccactggatg gggcttggca ataggccatc agcgcatgcg tggaaccttt gtggctcctc  1260
tgccgatcca tactgcggaa ctcttagcag cctgctttgc tcgcagccgg tctggagcra  1320
atcttattgg aaccgacaac tccgttgtcc tctctcggaa atacacctcc tttccatggc  1380
tgctagggtg tgctgcaaac tggatcctgc gcgggacgtc ctttgtctac gtcccgtcgg  1440
cgctgaatcc agcggacgac ccgtctcggg gccgtttggg actctaccgt ccccttcttc  1500
gtctgccgtt ccggccgacc acggggcgca cctctcttta cgcggtctcc ccgtctgtgc  1560
cttctcatct gccggaccgt gtgcacttcg cttcacctct gcacgtcgca tggagaccac  1620
cgtgaacgcc caccaggtct tgcccaaggt cttacataag aggactcttg gactctcggc  1680
aatgtcaacg accgaccttg aggcatactt caaagactgt gtgtttaaag actgggagga  1740 gttggggag agattaggt taaaggtctt tgtactagga ggctgtaggc ataaattggt   1800
ctgttcacca gcaccatgca acttttcac ctctgcctaa tcatctcatg ttcatgtcct   1860
```

```
actgttcaag cctccaagct gtgccttggg tggctttggg gcatggacat tgacccgtat   1920
aaagaatttg gagcttctgt ggagttactc tcttttttgc cttctgactt ctttccttcc   1980
attcgagatc tcctcgacac cgcctctgct ctgtatcggg aggccttaga gtctccggaa   2040
cattgttcac ctcaccatac agcactcagg caagctattc tgtgttgggg tgagttgatg   2100
aatctggcca cctgggtggg aagtaatttg gaagacccag catctaggga attagtagtc   2160
agttatgtta atgttaatat gggcctaaag atcagacaac tattgtggtt tcacatttcc   2220
tgtcttactt ttggaagaga aactgttctt gagtatttgg tgtcctttgg agtgtggata   2280
cgcactcctc ccgcttacag accaccaaat gcccctatct tatcaacact tccggaaact   2340
actgttgtta gacgacgagg caggtcccct agaagaagaa ctccctcgcc tcgcagacga   2400
aggtctcaat cgccgcgtcg cagaagatct caatctcggg aatctcaatg ttagtatccc   2460
ttggactcat aaggtgggaa attttactgg gctttattct tctactgtac ctgtcttcaa   2520
tcctgagtgg caaactccct cctttcctca cattcatttg caggaggaca ttattaatag   2580
atgtcaacaa tatgtgggcc ctcttacagt taatgaaaaa aggagattaa aattaattat   2640
gcctgccagg ttttatccta accgtaccaa atatttgccc ctagataaag gcattaaacc   2700
ttattatcct gaatatacag ttaatcatta cttccaaacc aggcattatt acatactct    2760 gtggaaggct ggcattctat ataagagaga aactacacgc agcgcctcat tttgtgggtc   2820
accatattct tgggaacaag agctacagca tgggaggttg gtcctccaaa cctcgaaagg   2880
gcatggggac gaatctttct gttcccaatc ctctgggctt cttccccgat caccagttgg   2940
accctgcatt cggagccaac tcaaacaatc cggattggga cttcaatccc aacaaggatc   3000
actggccagc agcaaaccag gtaggagcgg gagccttcgg gccagggttc accccaccgc   3060
acggcggtct tttggggtgg agccctcagg ctcagggcgt attgacaaca gtgccagcag   3120
cgcctcctcc tgcctccacc aatcggcagt caggcagaca gcctactccc atctctccac   3180
ctctaagaga cagtcatcct caggccatgc agtgg                              3215

<210> SEQ ID NO 31
<211> LENGTH: 3212
<212> TYPE: DNA
<213> ORGANISM: Hepatitis B virus

<400> SEQUENCE: 31
aattccacaa cattccacca agctctgcag gatcccagag taagaggcct gtatcttcct     60
gctggtggct ccagttccgg aacagtgaac cctgttccga ctactgcctc actcatctcg    120
tcaatcttct cgaggattgg ggaccctgca ccgaacatgg aaggcatcac atcaggattc    180
ctaggacccc tgctcgtgtt acaggcgggg ttttcttgt tgacaaaaat cctcacaata    240
ccgcagagtc tagactcgtg gtggacttct ctcaattttc taggggagc tcccgtgtgt    300 cttggccaaa attcgcagtc cccaatctcc aatcactcac caacctcttg tcctccaatt    360
tgtcctggct atcgctggat gtgtctgcgg cgttttatca tcttcctctt catcctgctg    420
ctatgcctca tcttcttgtt ggttcttctg gactatcaag gtatgttgcc cgtttgtcct    480
ctaattccag gatcatcaac caccagtacg ggacctgcc gaacctgcac gactcttgct    540
caaggaacct ctatgtttcc ctcatgttgt tgtttaaaac cttcggacgg aaattgcact    600
tgtattccca tcccatcatc atgggctttc ggaaaattcc tatggagtg gcctcagcc    660 cgtttctcct ggctcagttt actagtgcca tttgttcagt ggttcgccgg ctttccccc    720 actgtctggc tttcagttat atggatgatg tggtattggg ggccaagtct gtacaacatc    780
```

```
ttgagtccct ttatacctct gttaccaatt ttcttttgtc tttgggtata catttaaatc      840
ccaacaaaac aaaagatgg ggatattccc taaatttcat gggttatgta attggtagtt       900
gggggtcatt accacaagaa cacatcagac tgaaaatcaa agactgtttt agaaagctcc      960
ctgttaacag gccattgat tggaaagtat gtcaaagaat tgtgggtctt ttgggctttg      1020
ctgccccttt tacacaatgt ggatatcctg ctttaatgcc tctatatgcg tgtattcaat     1080
ctaagcaggc tttcactttc tcgccaactt acaaggcctt tctgtgtaaa caatatatga    1140
acctttaccc cgttgcccgg caacggccag gtctgtgcca agtgtttgct gatgcaaccc     1200
ccactggctg gggcttggcc ataggccatc agcgcatgcg tggaaccttt gtggctcctc     1260
tgccgatcca tactgcggaa ctcctagccg cttgttttgc tcgcagcagg tctggagcga     1320
aactcatagg gacagataat tctgtcgttc tctcccggaa atatacatca tttccatggc    1380
tgctaggctg tgctgccaac tggatcctgc gagggacgtc ctttgtctac gtcccgtcag    1440
cgctgaatcc tgcggacgac ccctctcggg gccgcttggg ggtctatcgt ccccttctcc    1500
gtctgccgtt ccggccgacc acggggcgca cctctcttta cgcggtctcc ccgtctgtgc    1560
cttctcatct gccggaccgt gtgcacttcg cttcacctct gcacgtcgca tggagaccac    1620
cgtgaacgcc caccagatct tgcccaaggt cttacataag aggactcttg gactctctgc    1680
aatgtcaacg accgacctttg aggcatactt caaagactgt ttgtttaaag actgggagga   1740
gttgggggag gagactagat taatgatctt tgtactagga ggctgtaggc ataaattggt    1800
ctgcgcacca gcaccatgca acttttttcac ctctgcctaa tcatctcttg ttcatgtcct  1860
actgttcaag cctccaagct gtgccttggg tggctttggg acatggacat tgacccttat   1920
aaagaatttg gagctactgt ggagttactc tcgttttttgc cttctgactt ctttccttca    1980
gtaagagatc ttctagatac cgcctctgct ctgtatcggg atgccttaga atctcctgag    2040
cattgttcac ctcaccatac tgcactcagg caagccattc tttgctgggg agaattaatg   2100
actctagcta cctgggtggg tgtaaatttg gaagatccag catccaggga cctagtagtc    2160
agttatgtca atactaatat gggcctaaag ttcaggcaat tatttgtggtt tcacatttct   2220 tgtctcactt ttggaagaga aaccgtcata gagtatttgg tgtcttttgg agtgtggatt    2280
cgcactcctc cagcttatag accaccaaat gccctatct tatcaacact tccggagaat    2340
actgttgtta gacgaagagg caggtcccct agaagaagaa ctccctcgcc tcgcagacga   2400
agatctcaat cgccgcgtcg cagaagatct caatctccag cttcccaatg ttagtattcc    2460
ttggactcac aaggtgggaa attttacggg gcttttattct tctactatac ctgtctttaa   2520
tcctaactgg aaaactccat cttttcctga tattcatttg caccaggaca ttattaacaa   2580
atgtgaacaa tttgtaggtc ctytaacagt aaatgaaaaa cgaagattaa acttagtcat    2640
gcctgctaga ttttttccca tctccacgaa atatttgccc ctagagaaag gtataaaacc    2700
ttattatcca gataatgtag ttaatcatta cttccaaacc agacactatt tacatacccct   2760 atggaaggcg ggcatcttat ataaaagaga aactacccgt agcgcctcat tttgtgggtc    2820
accttattct tgggaacacg agctacatca tggggctttc ttggacggtc cctctcgaat   2880
gggggaagaa tcattccacc accaatcctc tgggattttt tcccgaccac cagttggatc    2940
cagcattcag agcaaacacc agaaatccag attgggacca caatcccaac aaagaccact   3000
ggacagaagc caacaaggta ggagtgggag catttgggcc ggggttcact cccccacacg   3060
gaggcctttt ggggtggagc cctcaggctc aaggcatgct aaaaacattg ccagcaaatc    3120
```

```
cgcctcctgc ctccaccaat cggcagtcag gaaggcagcc tacccccaatc actccacctt    3180 tgagagacac tcatcctcag gccatgcagt gg                                   3212

<210> SEQ ID NO 32
<211> LENGTH: 3215
<212> TYPE: DNA
<213> ORGANISM: Hepatitis B virus

<400> SEQUENCE: 32
aactcaaccc agttccatca ggctctgttg gatcccaggg taagggctct gtatcttcct      60
gctggtggct ccagttcagg aacacaaaac cctgctccga ctattgcctc tctcacatcc     120
tcaatcttct cgacgactgg gggccctgct atgaacatgg acaacattac atcaggactc     180
ctaggacccc tgctcgtgtt acaggcggtg tgtttcttgt tgacaaaaat cctcacaata     240
ccacagagtc tagactcgtg gtggacttct ctcaattttc taggggggact acccgggtgt     300 cctggccaaa attcgcagtc cccaacctcc aatcacttac caacctcctg tcctccaact     360
tgtcctggct atcgttggat gtgtctgcgg cgttttatca tcttcctctt catcctgctg     420
ctatgcctca tcttcttgtt ggttcttctg gactaccagg gtatgttgcc cgtttgtcct     480
ctacttccag gatccacgac caccagcacg ggaccctgca aaacctgcac aactcttgca     540
caaggaacct ctatgtttcc ctcctgttgc tgttcaaaac cctcggacgg aaactgcact     600
tgtattccca tcccatcatc ctgggcttta ggaaaatacc tatgggagtg ggcctcagcc     660
cgtttctcat ggctcagttt actagtgcaa tttgttcagt ggtgcgtagg gctttccccc     720
actgtctggc ttttagttat attgatgatc tggtattggg ggccaaatct gtgcagcacc     780
ttgagtccct ttataccgct gttaccaatt ttctgttatc tgtgggtatc catttaaata     840
cttctaaaac taagagatgg ggttacaccc tacattttat gggttatgtc attggtagtt     900
ggggatcatt acctcaagat catattgtac acaaaatcaa agaatgtttt cggaaactgc     960
ctgtaaatcg tccaattgat tggaaagtct gtcaacgcat tgtgggtctt ttgggctttg    1020
ctgccccttt cacacaatgt ggttatcctg ctctcatgcc tctgtatgct tgtattactg    1080
ctaaacaggc ttttgttttt tcgccaactt acaaggcctt tctctgtaaa caatacatga    1140
acctttaccc cgttgccagg caacggccgg gcctgtgcca agtgtttgct gacgcaaccc    1200
ccactggttg gggcttggcc attggccatc agcgcatgcg tggaaccttt gtggctcctc    1260
tgccgatcca tactgcggaa ctccttgcag cttgtttcgc tcgcagcagg tctggagcga    1320
ctctcatcgg cacggacaac tctgttgtcc tctctaggaa gtacacctcc ttcccatggc    1380
tgctcgggtg tgctgcaaac tggatcctgc gcgggacgtc ctttgtttac gtcccgtcgg    1440
cgctgaatcc cgcggacgac cctcccgggg ccgcttggg gctgtaccgc ctcttctcc     1500 gtctgccgtt ccagccgaca acgggtcgca cctctctta cgcggactcc ccgtctgttc    1560
cttctcatct gccggaccgt gtgcacttcg cttcacctct gcacgtcgca tggagaccac    1620
cgtgaacgcc ccttggagtt tgccaacagt cttacataag aggactcttg actttcagg    1680 agggtcaatg acccggattg cagaatacat caaagactgt gtatttaagg actgggagga    1740
gttgggggag gagactaggt taatgatctt tgtactagga ggctgtaggc ataaattggt    1800
ctgttcacca gcaccatgca acttttcac ctctgcctaa tcatcttttg ttcatgtcct    1860
actgttcaag cctccaagct gtgccttggg tggctttggg acatggacat tgaccctat    1920 aaagaatttg gcgcttctgt ggagttactc tcttttttgc cttctgattt ctttccatcg    1980
gttcgggacc tactcgacac cgcttcagcc ctttaccggg atgctttaga gtcacctgaa    2040
```

```
cattgcactc cccatcacac tgccctcagg caagttattt tgtgctgggg tgagttaatg    2100
actttggctt cctgggtggg caataacttg aagaccctg ctgccaggga tttagtagtt     2160
aactatgtta acactaacat gggcctaaaa attagacaac tactgtggtt tcacatttcc    2220
tgccttactt ttggaagaga tatagttctt gagtatttgg tgtcctttgg agtgtggatt    2280
cgcactcctc ctgcttacag accacaaaat gcccctatcc tatccacact tccggaaact    2340
actgttgtta gacgacgagg caggtcccct agaagaagaa ctccctcgcc tcgcagacga    2400
agatctcaat cgccgcgtcg ccgaagatct caatctccag cttcccaatg ttagtattcc    2460
ttggactcat aaggtgggaa attttacggg gctttactct tctactgtgc ctgcttttaa    2520
tcctgactgg ttaactcctt cttttcctaa tattcattta catcaagacc taatttctaa    2580
atgtgaacaa tttgtaggcc cactcactaa aaatgaatta aggaggttaa aattggttat    2640
gccagctaga ttttatccta aggttaccaa atattttcct atggagaaag gaatcaagcc    2700
ttattatcct gagcatgcag ttaatcatta ctttaaaaca agacattatt tgcatacttt    2760
atggaaggcg ggaattttat ataagagaga tccacacgt agcgcatcat tttgtgggtc     2820
accatattcc tgggaacaag agctacagca tgggagcacc tctctcaacg acaagaagag    2880
gcatgggaca gaatctttct gtgcccaatc ctctgggatt ctttccagac catcagctgg    2940
atccgctatt caaagcaaat tccagcagtc ccgactggga cttcaacaca acaaggaca    3000 gttggccaat ggcaaacaag gtaggagtgg gagcatacgg tccagggttc acacccccac    3060
acggtggcct gctggggtgg agccctcagg cacaaggtat gttaacaacc ttgccagcag    3120
atccgcctcc tgcttccacc aatcggcggt ccgggagaaa gccaacccca gtctctccac    3180
ctctaagaga cactcatcca caggcaatgc agtgg                                3215
```

<210> SEQ ID NO 33
<211> LENGTH: 3248
<212> TYPE: DNA
<213> ORGANISM: Hepatitis B virus

<400> SEQUENCE: 33

```
aactctacag cattccacca agctctacaa aatcccaaag tcagggggcct gtattttcct     60 gctggtggct ccagttcagg gatagtgaac cctgttccga ctattgcctc tcacatctcg    120
tcaatcttct ccaggattgg ggaccctgca ccgaacatgg agaacatcac atcaggattc    180
ctaggacccc tgctcgtgtt acaggcgggg ttttttcttgt tgacaagaat cctcacaata    240
ccgcagagtc tagactcgtg gtggacttct ctcaattttc taggggggagt gcccgtgtgt    300 cctggcctaa attcgcagtc cccaacctcc aatcactcac caatctcctg tcctccaact    360
tgtcctggct atcgctggat gtgtctgcgg cgttttatca tattcctctt catcctgctg    420
ctatgcctca tcttcttgtt ggttcttctg gactatcaag gtatgttgcc cgtttgtcct    480
ctgattccag gatcctcgac caccagtacg ggaccctgca aaacctgcac gactcctgct    540
caaggcaact ctatgtatcc ctcatgttgc tgtacaaaac cttcggacgg aaattgcacc    600
tgtattccca tcccatcatc ttgggctttc gcaaaatacc tatgggagtg ggcctcagtc    660
cgtttctctt ggctcagttt actagtgcca tttgttcagt ggttcgtagg ctttccccc    720 actgtctggc tttcagctat atggatgatg tggtattggg ggccaaatct gtacaacatc    780
ttgagtccct ttataccgct gttaccaatt ttcttttgtc tttgggtata catctaaacc    840
ctaacaaaac aaaaagatgg ggttattcct taaatttat gggatatgta attggaagtt    900
```

```
ggggtacttt gccacaagaa cacatcacac agaaaattaa gcaatgtttt cggaaactcc    960
ctgttaacag gccaattgat tggaaagtct gtcaacgaat aactggtctg ttgggtttcg   1020
ctgctccttt tacccaatgt ggttaccctg ccttaatgcc tttatatgca tgtatacaag   1080
ctaagcaggc ttttactttc tcgccaactt ataaggcctt tctctgtaaa caatacatga   1140
acctttaccc cgttgctagg caacggcccg gtctgtgcca agtgtttgct gacgcaaccc   1200
ccactggttg gggcttggcc atcggccatc agcgcatgcg tggaaccttt gtggctcctc   1260
tgccgatcca tactgcggaa ctcctagctg cttgttttgc tcgcagccgg tctggagcaa   1320
aactcattgg gactgacaat tctgtcgtcc tttctcggaa atatacatcc tttccatggc   1380
tgctaggctg tgctgccaac tggatccttc gcgggacgtc ctttgtttac gtcccgtcag   1440
cgctgaatcc agcggacgac ccctcccggg gccgtttggg gctctgtcgc ccccttctcc   1500
gtctgccgtt cctgccgacc acggggcgca cctctcttta cgcggtctcc ccgtctgtgc   1560
cttctcatct gccggaccgt gtgcacttcg cttcacctct gcacgttaca tggaaaccgc   1620
catgaacacc tctcatcatc tgccaaggca gttatataag aggactcttg gactgtttgt   1680
tatgtcaaca accggggtgg agaaatactt caaggactgt gttttgctg agtgggaaga   1740
attaggcaat gagtccaggt taatgacctt tgtattagga ggctgtaggc ataaattggt   1800
ctgcgcacca gcaccatgta acttttcac ctctgcctaa tcatctcttg ttcatgtcct   1860
actgttcaag cctccaagct gtgccttggg tggcttagg gcatggatag aacaactttg   1920
ccatatggcc ttttggctt agacattgac ccttataaag aatttggagc tactgtggag   1980
ttgctctcgt ttttgccttc tgactttttc ccgtctgttc gtgatcttct cgacaccgct   2040
tcagctttgt accgggaatc cttagagtcc tctgatcatt gttcgcctca ccatacagca   2100
ctcaggcaag caatcctgtg ctggggtgag ttgatgactc tagctacctg ggtgggtaat   2160
aatttggaag atccagcatc cagagatttg gtggtcaatt atgttaatac taatatgggt   2220
ttaaaaatca gcaactatt gtggtttcac atttcctgtc ttacttttgg gagagaaacc   2280
gttcttgagt atttggtgtc ttttggagtg tggattcgca ctcctcctgc ttatagacca   2340
ccaaatgccc ctatcctatc aacacttccg gagactactg ttgttagacg aagaggcagg   2400
tccctcgaa gaagaactcc ctcgcctcgc agacgaagat ctcaatcgcc gcgtcgcaga   2460
agatctgcat ctccagcttc ccaatgttag tattccttgg actcacaagg tgggaaactt   2520
tacggggctg tattcttcta ctatacctgt ctttaatcct gattggcaaa ctccttcttt   2580
tccaaatatc catttgcatc aagacattat aactaaatgt gaacaatttg tgggccctct   2640
cacagtaaat gagaaacgaa gattaaaact agttatgcct gccagatttt tcccaaactc   2700
tactaaatat ttaccattag acaaaggtat caaaccgtat tatccagaaa atgtagttaa   2760
tcattacttc cagaccagac attatttaca tacccttgg aaggcgggta ttctatataa   2820
gagagaaacg tcccgtagcg cttcattttg tgggtcacca tatacttggg aacaagatct   2880
acagcatggg gctttcttgg acggtccctc tcgagtgggg aaagaacctt tccaccagca   2940
atcctctagg attccttccc gatcaccagt tggacccagc attcagagca ataccaaca   3000
atccagattg gacttcaat cccaaaaagg acccttggcc agaggccaac aaagtaggag   3060
ttggagccta tggacccggg ttcacccctc cacacggagg ccttttgggg tggagccctc   3120
agtctcaggg cacactaaca actttgccag cagatccgcc tcctgcctcc accaatcgtc   3180
agtcagggag gcagcctact cccatctctc caccactaag agacagtcat cctcaggcca   3240
tgcagtgg                                                            3248
```

<210> SEQ ID NO 34
<211> LENGTH: 3215
<212> TYPE: DNA
<213> ORGANISM: Hepatitis B virus

<400> SEQUENCE: 34

| | | | | | |
|---|---|---|---|---|---|
| aactcaacac | agttccacca | agcactgttg | gattcgagag | taagggtct | gtattttcct | 60 |
| gctggtggct | ccagttcaga | aacacagaac | cctgctccga | ctattgcctc | tctcacatca | 120 |
| tcaatcttct | cgaagactgg | ggaccctgct | atgaacatgg | agaacatcac | atcaggactc | 180 |
| ctaggacccc | ttctcgtgtt | acaggcggtg | tgtttcttgt | tgacaaaaat | cctcacaata | 240 |
| ccacagagtc | tagactcgtg | gtggacttct | ctcaattttc | taggggtacc | acccgggtgt | 300 |
| cctggccaaa | attcgcagtc | cccaatctcc | aatcacttac | caacctcctg | tcctccaact | 360 |
| tgtcctggct | atcgttggat | gtgtctgcgg | cgttttatca | tcttcctctt | catcctgctg | 420 |
| ctatgcctca | tcttcttgtt | ggttcttctg | gactatcaag | gtatgttgcc | cgtgtgtcct | 480 |
| ctacttccag | gatctacaac | caccagcacg | ggaccctgca | aaacctgcac | cactcttgct | 540 |
| caaggaacct | ctatgtttcc | ctcctgctgc | tgtaccaaac | cttcggacgg | aaattgcacc | 600 |
| tgtattccca | tcccatcatc | ttgggctttc | ggaaaatacc | tatgggagtg | ggcctcagcc | 660 |
| cgtttctctt | ggctcagttt | actagtgcaa | tttgctcagt | ggtgcgtagg | gcttcccccc | 720 |
| actgtctggc | ttttagttat | atggatgatt | tggtattggg | ggccaaatct | gtgcagcatc | 780 |
| ttgagtccct | ttataccgct | gttaccaatt | ttttgttatc | tgtgggcatc | catttgaaca | 840 |
| cagctaaaac | aaaatggtgg | ggttattcct | tacactttat | gggttatata | attgggagtt | 900 |
| gggggacctt | gcctcaggaa | catattgtgc | ataaaatcaa | agattgcttt | cgcaaacttc | 960 |
| ccgtgaatag | acccattgat | tggaaggttt | gtcaacgcat | tgtgggtctt | ttgggctttg | 1020 |
| cagcccttt | tactcaatgt | ggttatcctg | ctctcatgcc | cttgtatgcc | tgtattaccg | 1080 |
| ctaagcaggc | ttttgttttc | tcgccaactt | acaaggcctt | tctctgtcaa | caatacatga | 1140 |
| acctttaccc | cgttgctcgg | caacggccag | gcctttgcca | agtgtttgct | gacgcaaccc | 1200 |
| ccactggctg | gggcttggcg | attggccatc | agcgcatgcg | cggaaccttt | gtggctcctc | 1260 |
| tgccgatcca | tactgcggaa | ctcctagcag | cctgtttcgc | tcgcagcagg | tctggagcgg | 1320 |
| acgttatcgg | cactgacaac | tccgttgtcc | tttctcggaa | gtacacctcc | ttcccatggc | 1380 |
| tgctaggctg | tgctgccaac | tggatcctgc | gcgggacgtc | ctttgtctac | gtcccgtcgg | 1440 |
| cgctgaatcc | tgcggacgac | ccctctcgtg | gtcgcttggg | gctctgccgc | cctcttctcc | 1500 |
| gcctaccgtt | ccggccgacg | acgggtcgca | cctctcttta | cgcggactcc | ccgcctgtgc | 1560 |
| cttctcatct | gccggcccgt | gtgcacttcg | cttcacctct | gcacgtcgca | tggagaccac | 1620 |
| cgtgaacgcc | ccttggaact | tgccaacaac | cttacataag | aggactcttg | actttcgcc | 1680 |
| ccggtcaacg | acctggattg | aggaatacat | caaagactgt | gtatttaagg | actgggagga | 1740 |
| gtcgggggag | gagttgaggt | taaaggtctt | tgtattagga | ggctgtaggc | ataaattggt | 1800 |
| ctgttcacca | gcaccatgca | acttttcac | ctctgcctaa | tcatcttttg | ttcatgtccc | 1860 |
| actgttcaag | cctccaagct | gtgccttggg | tggctttggg | gcatggacat | tgacccttat | 1920 |
| aaagaatttg | gagcttctgt | ggagttactc | tcattttgc | cttctgactt | cttcccgtct | 1980 |
| gtccgggacc | tactcgacac | cgcttcagcc | ctctaccgag | atgccttaga | atcacccgaa | 2040 |
| cattgcaccc | ccaaccacac | tgctctcagg | caagctattt | gtgctggggg | tgagttgatg | 2100 |

| | |
|---|---:|
| accttggctt cctgggtggg caataattta gaggatcctg cagcaagaga tctagtagtt | 2160 |
| aattatgtca atactaacat gggtctaaaa attagacaat tattatggtt tcacatttcc | 2220 |
| tgccttacat ttggaagaga aactgtgctt gagtatttgg tgtcttttgg agtgtggatc | 2280 |
| cgcactccac ctgcttacag accaccaaat gcccctatcc tatcaacact tccggagact | 2340 |
| actgttgtta gacaacgagg cagggcccct agaagaagaa ctccctcgcc tcgcagacga | 2400 |
| agatctcaat caccgcgtcg cagaagatct caatctccag cttcccaatg ttagtattcc | 2460 |
| ttggactcat aaggtgggaa actttaccgg tctttactcc tctactgtac ctgttttcaa | 2520 |
| tcctgactgg ttaactcctt cttttcctga cattcacttg catcaagatc tgatacaaaa | 2580 |
| atgtgaacaa tttgtaggcc cactcactac aaatgaaagg agacgattga aactaattat | 2640 |
| gccagctagg ttttatccca agttactaa atacttccct ttggataaag gtattaagcc | 2700 |
| ttactatcca gagaatgtgg ttaatcatta ctttaaaact agacattatt tacatacttt | 2760 |
| gtggaaggca ggaattctat ataagagaga atccacacat agcgcctcat tttgtgggtc | 2820 |
| accatattcc tgggaacaag agctacagca tgggagcacc tctctcaacg gcgagaaggg | 2880 |
| gcatgggaca gaatctttct gtgcccaatc ctctgggatt cttccagac accagttgg | 2940 |
| atvcactatt cagagcaaat tccagcagtc ccgattggga cttcaacaca aacaaggaca | 3000 |
| attggccaat ggcaaacaag gtaggagtgg gaggcttcgg tccagggttc acaccccac | 3060 |
| acggtggcct tctggggtgg agccctcagg cacagggcat tctgacaacc tcgccaccag | 3120 |
| atccacctcc tgcttccacc aatcggaggt caggaagaaa gccaacccca gtctctccac | 3180 |
| ctctaaggga cacacatcca caggccatgc agtgg | 3215 |

<210> SEQ ID NO 35
<211> LENGTH: 5980
<212> TYPE: DNA
<213> ORGANISM: Hepatitis B virus

<400> SEQUENCE: 35

| | |
|---|---:|
| ctcgagttta ccactcccta tcagtgatag agaaaagtga aagtcgagtt taccactccc | 60 |
| tatcagtgat agagaaaagt gaaagtcgag tttaccactc cctatcagtg atagagaaaa | 120 |
| gtgaaagtcg agtttaccac tccctatcag tgatagagaa aagtgaaagt cgagtttacc | 180 |
| actccctatc agtgatagag aaaagtgaaa gtcgagttta ccactcccta tcagtgatag | 240 |
| agaaaagtga aagtcgagtt taccactccc tatcagtgat agagaaaagt gaaagtcgag | 300 |
| ctcggtaccc gggtcgaggt aggcgtgtac ggtgggaggc ctatataagc gtcgagcacc | 360 |
| agcacctgca actttttcac ctctgcctaa tcatctcttg ttcatgtcct actgttcaag | 420 |
| cctccaagct gtgccttggg tggctttggg gcgtggacat ctaccatac gacgttccag | 480 |
| attacgctgg catggacatc gacccttata agaatttgg agctactgtg gagttactct | 540 |
| cgttttgcc ttctgacttc tttccttcag tacgagatct tctagatacc gcctcagctc | 600 |
| tgtatcggga agccttagag tctcctgagc attgttcacc tcaccatact gcactcaggc | 660 |
| aagcaattct tgctgggggg gaactaatga ctctagctac ctgggtgggt gttaatttgg | 720 |
| aagatccagc atctagagac ctagtagtca gttatgtcaa cactaatatg gcctaaagt | 780 |
| tcaggcaact cttgtggttt cacatttctt gtctcacttt tggaagagaa accgttatag | 840 |
| agtatttggt gtctttcgga gtgtggattc gcactcctcc agcttataga ccaccaaatg | 900 |
| cccctatcct atcaacactt ccggaaacta ctgttgttag acgacgaggc aggtccccta | 960 |
| gaagaagaac tccctcgcct cgcagacgaa ggtctcaatc gccgcgtcgc agaagatctc | 1020 |

```
aatctcggga acctcaatgt tagtattcct tggactcata aggtggggaa ctttactggt    1080
ctttattctt ctactgtacc tgtctttaat cctcattgga aaacaccatc ttttcctaat    1140
atacatttac accaagacat tatcaaaaaa tgtgaacagt ttgtaggccc acttacagtt    1200
aatgagaaaa aagagattgca attgattatg cctgctaggt tttatccaaa ggttaccaaa    1260
tatttaccat tggataaggg tattaaacct tattatccag aacatctagt taatcattac    1320
ttccaaacta gacactattt acacactcta tggaaggcgg gtatattata aagagagaa    1380
acaacacata gcgcctcatt ttgtgggtca ccatattctt gggaacaaga tctacagcat    1440
ggggcagaat ctttccacca gcaatcctct gggattcttt cccgaccacc agttggatcc    1500
agccttcaga gcaaacacag caaatccaga ttgggacttc aatcccaaca aggacacctg    1560
gccagacgcc aacaaggtag gagctggagc attcgggctg ggtttcaccc caccgcacgg    1620
aggccttttg gggtggagcc ctcaggctca gggcatacta caaactttgc cagcaaatcc    1680
gcctcctgcc tccaccaatc gccagacagg aaggcagcct accccgctgt ctccacccttt   1740
gagaaacact catcctcagg ccatgcagtg gaattccaca acctttcacc aaactctgca    1800
agatcccaga gtgagaggcc tgtatttccc tgctggtggc tccagttcag gagcagtaaa    1860
ccctgttccg actactgcct ctcccttatc gtcaatcttc tcgaggattg ggaccctgc     1920
gctgaacatg gagaacatca catcaggatt cctaggaccc cttctcgtgt acaggcggg     1980
gttttctag tagacaagaa tcctcacaat accgcaaagt ctagactcgt ggtggacttc    2040
tctcaatttt ctagggggaa ctaccgtgtg tcttggccaa aattcgcagt ccccaacctc    2100
caatcactca ccaacctcct gtcctccaac ttgtcctggt tatcgctgga tgtgtctgcg    2160
gcgttttatc atcttcctct tcatcctgct gctatgcctc atcttcttgt tggttcttct    2220
ggactatcaa ggtatgttgc ccgtttgtcc tctaattcca ggatcctcaa ccaccagcac    2280
gggaccatgc cgaacctgca tgactactgc tcaaggaacc tctatgtatc cctcctgttg    2340
ctgtaccaaa ccttcggacg gaaattgcac ctgtattccc atcccatcat cctgggcttt    2400
cggaaaattc ctatgggagt gggcctcagc ccgtttctcc tggctcagtt tactagtgcc    2460
atttgttcag tggttcgtag ggcttccccc cactgtttgg ctttcagtta tatggatgat    2520
gtggtattgg gggccaagtc tgtacagcat cttgagtccc ttttaccgc tgttaccaat     2580
tttcttttgt ctttgggtat acatttaaac cctaacaaaa caagagatg gggttactct    2640
ctgaatttta tgggttatgt cattggaagt tatgggtcct tgccacaaga acacatcata    2700
caaaaatca aagaatgttt tagaaaactt cctattaaca ggcctattga ttggaaagta    2760
tgtcaacgaa ttgtgggtct tttgggtttt gctgccccat ttacacaatg tggttatcct    2820
gcgttaatgc ccttgtatgc atgtattcaa tctaagcagg ctttcacttt ctcgccaact    2880
tacaaggcct ttctgtgtaa acaatacctg aacctttacc ccgttgcccg gcaacggcca    2940
ggtctgtgcc aagtgtttgc tgacgcaacc cccactggct ggggcttggt catgggccat    3000
cagcgcgtgc gtggaacctt ttcggctcct ctgccgatcc atactgcgga actcctagcc    3060
gcttgttttg ctcgcagcag gtctggagca acattatcg ggactgataa ctctgttgtc     3120
ctctcccgca aatatacatc gtatccatgg ctgctaggct gtgctgccaa ctggatcctg    3180
cgcgggacgt cctttgttta cgtcccgtcg gcgctgaatc ctgcggacga cccttctcgg    3240
ggtcgcttgg gactctctcg tccccttctc cgtctgccgt tccgaccgac cacggggcgc    3300
acctctcttt acgcggactc cccgtctgtg ccttctcatc tgccggaccg tgtgcacttc    3360
```

```
gcttcacctc tgcacgtcgc atggagacca ccgtgaacgc ccaccgaatg ttgcccaagg    3420
tcttacataa gaggactctt ggactctctg caatgtcaac gaccgacctt gaggcatact    3480
tcaaagactg tttgtttaaa gactgggagg agttgggggga ggagattaga ttaaaggtct    3540
ttgtactagg aggctgtagg cataaattgg tctgcgcacc agcaccatgc aacttttttca   3600 cctctgccta atcatctctt gttcatgtcc tactgttcaa gcctccaagc tgtgccttgg    3660
gtggctttgg ggcatggaca tcgaccctta taaagaattt ggagctactg tggagttact    3720 ctcgttttttg ccttctgact tctttccttc agtacgagat ccactagttc tagagcggcc   3780
ccaaacaatt gctcaaaccg atacaattgt actttgtccc gagcaaatat aatcctgctg    3840
acggcccatc caggcacaaa cctcctgatt ggacggcttt tccatacacc cctctctcga    3900
aagcaatata tattccacat aggctatgtg gaacttaagc ttcctcgctc actgactcgc    3960
tgcgctcggt cgttcggctg cggcgagcgg tatcagctca ctcaaaggcg gtaatacggt    4020
tatccacaga atcaggggat aacgcaggaa agaacatgtg agcaaaaggc cagcaaaagg    4080
ccaggaaccg taaaaaggcc gcgttgctgg cgtttttcca taggctccgc cccccctgacg   4140 agcatcacaa aaatcgacgc tcaagtcaga ggtggcgaaa cccgacagga ctataaagat    4200
accaggcgtt tccccctgga agctccctcg tgcgctctcc tgttccgacc ctgccgctta    4260
ccggatacct gtccgccttt ctcccttcgg gaagcgtggc gctttctcat agctcacgct    4320
gtaggtatct cagttcggtg taggtcgttc gctccaagct gggctgtgtg cacgaaccc     4380 ccgttcagcc cgaccgctgc gccttatccg gtaactatcg tcttgagtcc aacccggtaa    4440
gacacgactt atcgccactg gcagcagcca ctggtaacag gattagcaga gcgaggtatg    4500
taggcggtgc tacagagttc ttgaagtggt ggcctaacta cggctacact ataagaacag    4560
tatttggtat ctgcgctctg ctgaagccag ttaccttcgg aaaaagagtt ggtagctctt    4620
gatccggcaa acaaaccacc gctggtagcg gtggtttttt tgtttgcaag cagcagatta    4680
cgcgcagaaa aaaaggatct caagaagatc ctttgatctt ttctacgggg tctgacgctc    4740
agtggaacga aaactcacgt taagggattt tggtcatgag attatcaaaa aggatcttca    4800
cctagatcct tttaaattaa aaatgaagtt ttaaatcaat ctaaagtata tatgagtaaa    4860
cttggtctga cagttaccaa tgcttaatca gtgaggcacc tatctcagcg atctgtctat    4920
ttcgttcatc catagttgcc tgactccccg tcgtgtagat aactacgata cgggagggct    4980
taccatctgg ccccagtgct gcaatgatac cgcgagaccc acgctcaccg gctccagatt    5040
tatcagcaat aaaccagcca gccggaaggg ccgagcgcag aagtggtcct gcaactttat    5100
ccgcctccat ccagtctatt aattgttgcc gggaagctag agtaagtagt tcgccagtta    5160
atagtttgcg caacgttgtt gccattgcta caggcatcgt ggtgtcacgc tcgtcgtttg    5220
gtatggcttc attcagctcc ggttcccaac gatcaaggcg agttacatga tcccccatgt    5280
tgtgcaaaaa agcggttagc tccttcggtc ctccgatcgt tgtcagaagt aagttggccg    5340
cagtgttatc actcatggtt atggcagcac tgcataattc tcttactgtc atgccatccg    5400
taagatgctt ttctgtgact ggtgagtact caaccaagtc attctgagaa tagtgtatgc    5460
ggcgaccgag ttgctcttgc ccggcgtcaa tacgggataa taccgcgcca catagcagaa    5520
ctttaaaagt gctcatcatt ggaaaacgtt cttcggggcg aaaactctca aggatcttac    5580
cgctgttgag atccagttcg atgtaaccca ctcgtgcacc caactgatct tcagcatctt    5640
ttactttcac cagcgtttct gggtgagcaa aaacaggaag gcaaaatgcc gcaaaaaagg    5700
gaataagggc gacacggaaa tgttgaatac tcatactctt ccttttttcaa tattattgaa   5760
```

| | | |
|---|---|---|
| gcatttatca gggttattgt ctcatgagcg gatacatatt tgaatgtatt tagaaaaata | 5820 |
| aacaaatagg ggttccgcgc acatttcccc gaaaagtgcc acctgacgtc taagaaacca | 5880 |
| ttattatcat gacattaacc tataaaaata ggcgtatcac gaggcccttt cgtcttcact | 5940 |
| cgaatatctg caggcgtatc acgaggccct tcgtcttca | 5980 |

<210> SEQ ID NO 36
<211> LENGTH: 1170
<212> TYPE: DNA
<213> ORGANISM: Hepatitis B virus

<400> SEQUENCE: 36

| | |
|---|---|
| atggggcaga atctttccac cagcaatcct ctgggattct ttcccgacca ccagttggat | 60 |
| ccagccttca gagcaaacac agcaaatcca gattgggact tcaatcccaa caaggacacc | 120 |
| tggccagacg ccaacaaggt aggagctgga gcattcgggc tgggtttcac cccaccgcac | 180 |
| ggaggccttt tggggtggag ccctcaggct cagggcatac tacaaacttt gccagcaaat | 240 |
| ccgcctcctg cctccaccaa tcgccagaca ggaaggcagc ctaccccgct gtctccacct | 300 |
| ttgagaaaca ctcatcctca ggccatgcag tggaattcca caaccttcca ccaaactctg | 360 |
| caagatccca gagtgagagg cctgtatttc cctgctggtg gctccagttc aggagcagta | 420 |
| aaccctgttc cgactactgc ctctccctta tcgtcaatct tctcgaggat tgggggaccct | 480 |
| gcgctgaaca tggagaacat cacatcagga ttcctaggac cccttctcgt gttacaggcg | 540 |
| gggtttttct tgttgacaag aatcctcaca ataccgcaaa gtctagactc gtggtggact | 600 |
| tctctcaatt ttctaggggg aactaccgtg tgtcttggcc aaaattcgca gtccccaacc | 660 |
| tccaatcact caccaacctc ctgtcctcca acttgtcctg gttatcgctg gatgtgtctg | 720 |
| cggcgtttta tcatcttcct cttcatcctg ctgctatgcc tcatcttctt gttggttctt | 780 |
| ctggactatc aaggtatgtt gcccgtttgt cctctaattc caggatcctc aaccaccagc | 840 |
| acgggaccat gccgaacctg catgactact gctcaaggaa cctctatgta tccctcctgt | 900 |
| tgctgtacca aaccttcgga cggaaattgc acctgtattc ccatcccatc atcctgggct | 960 |
| ttcggaaaat tcctatggga gtgggcctca gcccgtttct cctggctcag tttactagtg | 1020 |
| ccatttgttc agtggttcgt agggctttcc cccactgttt ggctttcagt tatatggatg | 1080 |
| atgtggtatt gggggccaag tctgtacagc atcttgagtc cctttttacc gctgttacca | 1140 |
| attttctttt gtctttgggt atacatttaa | 1170 |

<210> SEQ ID NO 37
<211> LENGTH: 846
<212> TYPE: DNA
<213> ORGANISM: Hepatitis B virus

<400> SEQUENCE: 37

| | |
|---|---|
| atgcagtgga attccacaac ctttcaccaa actctgcaag atcccagagt gagaggcctg | 60 |
| tatttccctg ctggtggctc cagttcagga gcagtaaacc ctgttccgac tactgcctct | 120 |
| cccttatcgt caatcttctc gaggattggg gaccctgcgc tgaacatgga gaacatcaca | 180 |
| tcaggattcc taggaccccct ctcgtgtta caggcggggt ttttcttgtt gacaagaatc | 240 |
| ctcacaatac cgcaaagtct agactcgtgg tggacttctc tcaatttttct agggggaact | 300 |
| accgtgtgtc ttggccaaaa ttcgcagtcc ccaacctcca tcactcacc aacctcctgt | 360 |
| cctccaactt gtcctggtta tcgctggatg tgtctgcggc gttttatcat cttcctcttc | 420 |

```
atcctgctgc tatgcctcat cttcttgttg gttcttctgg actatcaagg tatgttgccc    480
gtttgtcctc taattccagg atcctcaacc accagcacgg gaccatgccg aacctgcatg    540
actactgctc aaggaacctc tatgtatccc tcctgttgct gtaccaaacc ttcggacgga    600
aattgcacct gtattcccat cccatcatcc tgggctttcg gaaaattcct atgggagtgg    660
gcctcagccc gtttctcctg gctcagttta ctagtgccat tgttcagtg gttcgtaggg     720
ctttcccccca ctgtttggct ttcagttata tggatgatgt ggtattgggg gccaagtctg   780
tacagcatct tgagtccctt tttaccgctg ttaccaattt tcttttgtct ttgggtatac    840
atttaa                                                               846
```

<210> SEQ ID NO 38
<211> LENGTH: 681
<212> TYPE: DNA
<213> ORGANISM: Hepatitis B virus

<400> SEQUENCE: 38

```
atggagaaca tcacatcagg attcctagga ccccttctcg tgttacaggc ggggttttc     60
ttgttgacaa gaatcctcac ataccgcaa agtctagact cgtggtggac ttctctcaat    120
tttctagggg gaactaccgt gtgtcttggc caaaattcgc agtccccaac ctccaatcac    180
tcaccaacct cctgtcctcc aacttgtcct ggttatcgct ggatgtgtct gcggcgtttt   240
atcatcttcc tcttcatcct gctgctatgc ctcatcttct tgttggttct tctgactat    300
caaggtatgt tgcccgtttg tcctctaatt ccaggatcct caaccaccag cacgggacca   360
tgccgaacct gcatgactac tgctcaagga acctctatgt atccctcctg ttgctgtacc   420
aaaccttcgg acggaaattg cacctgtatt cccatcccat catcctgggc tttcggaaaa   480
ttcctatggg agtgggcctc agcccgtttc tcctggctca gtttactagt gccatttgtt   540
cagtggttcg tagggctttc ccccactgtt tggctttcag ttatatggat gatgtggtat   600
tgggggccaa gtctgtacag catcttgagt ccctttttac cgctgttacc aattttcttt   660
tgtctttggg tatacattta a                                             681
```

<210> SEQ ID NO 39
<211> LENGTH: 6682
<212> TYPE: DNA
<213> ORGANISM: Hepatitis B virus

<400> SEQUENCE: 39

```
gacggatcgg gagatctccc gatccctat ggtcgactct cagtacaatc tgctctgatg    60
ccgcatagtt aagccagtat ctgctccctg cttgtgtgtt ggaggtcgct gagtagtgcg    120
cgagcaaaat ttaagctaca acaaggcaag gcttgaccga caattgcatg aagaatctgc    180
ttagggttag gcgttttgcg ctgcttcgcg atgtacgggc cagatatacg cgttgacatt    240
gattattgac tagttattaa tagtaatcaa ttacggggtc attagttcat agcccatata    300
tggagttccg cgttacataa cttacggtaa atggcccgcc tggctgaccg cccaacgacc    360
cccgcccatt gacgtcaata atgacgtatg ttcccatagt aacgccaata gggactttcc    420
attgacgtca atgggtggac tatttacggt aaactgccca cttggcagta catcaagtgt    480
atcatatgcc aagtacgccc cctattgacg tcaatgacgg taaatggccc gcctggcatt    540
atgcccagta catgacctta tgggactttc ctacttggca gtacatctac gtattagtca    600
tcgctattac catggtgatg cggttttggc agtacatcaa tgggcgtgga tagcggtttg    660
actcacgggg atttccaagt ctccacccca ttgacgtcaa tgggagtttg ttttggcacc    720
```

```
aaaatcaacg ggactttcca aaatgtcgta acaactccgc cccattgacg caaatgggcg    780
gtaggcgtgt acggtgggag gtctatataa gcagagctct ctggctaact agagaaccca    840
ctgcttactg gcttatcgaa attaatacga ctcactatag ggagacccaa gctggctagt    900
taagcttggt accgagctcg gatccaccat gcaactttt cacctctgcc taatcatctc    960
ttgttcatgt cctactgttc aagcctccaa gctgtgcctt gggtggcttt ggggcgtgga   1020
catctaccca tacgacgttc cagattacgc tggcatggac atcgacccttt ataagaatt   1080 tggagctact gtggagttac tctcgttttt gccttctgac ttctttcctt cagtacgaga   1140
tcttctagat accgcctcag ctctgtatcg ggaagcctta gagtctcctg agcattgttc   1200
acctcaccat actgcactca ggcaagcaat tctttgctgg ggggaactaa tgactctagc   1260
tacctgggtg ggtgttaatt tggaagatcc agcatctaga gacctagtag tcagttatgt   1320
caacactaat atgggcctaa agttcaggca actcttgtgg tttcacattt cttgtctcac   1380
ttttggaaga gaaaccgtta tagagtattt ggtgtctttc ggagtgtgga ttcgcactcc   1440
tccagcttat agaccaccaa atgcccctat cctatcaaca cttccggaaa ctactgttgt   1500
tagacgacga ggcaggtccc ctagaagaag aactccctcg cctcgcagac gaaggtctca   1560
atcgccgcgt cgcagaagat ctcaatctcg gaacctcaa tgttagtatt ccttggactc    1620
ataaggtggg gaactttact ggtctttatt cttctactgt acctgtcttt aatcctcatt   1680
ggaaaacacc atctttcct aatatacatt tacaccaaga cattatcaaa aatgtgaac    1740 agtttgtagg cccacttacg gaccgtgtgc acttcgcttc acctctgcac gtcgcatgga   1800
gaccaccgtg aacgcccacc gaatgttgcc caaggtctta cataagagga ctcttggact   1860
ctctgcaatg tcaacgaccg accttgaggc atacttcaaa gactgtttgt ttaaagactg   1920
ggaggagttg ggggaggaga ttagattaaa ggtctttgta ctaggaggct gtaggcataa   1980
attggtctgc gcaccagcac catgcaactt tttcacctct gcctaatcat ctcttgttca   2040
tgtcctactg ttcaagcctc caagctgtgc cttgggtggc tttggggcat ggacatcgac   2100
ccttataaag aaaagggcaa ttctgcagat atccagcaca gtggcggccg ctcgagtcta   2160
gagggcccgc ggttcgaagg taagcctatc cctaaccctc tcctcggtct cgattctacg   2220
cgtaccggtc atcatcacca tcaccattga gtttaaaccc gctgatcagc ctcgactgtg   2280
ccttctagtt gccagccatc tgttgtttgc ccctcccccg tgccttcctt gaccctggaa   2340
ggtgccactc ccactgtcct ttcctaataa aatgaggaaa ttgcatcgca ttgtctgagt   2400
aggtgtcatt ctattctggg gggtggggtg gggcaggaca gcaaggggga ggattgggaa   2460
gacaatagca ggcatgctgg ggatgcggtg ggctctatgg cttctgaggc ggaaagaacc   2520
agctggggct ctagggggta tccccacgcg ccctgtagcg gcgcattaag cgcggcgggt   2580
gtggtggtta cgcgcagcgt gaccgctaca cttgccagcg ccctagcgcc cgctcctttc   2640
gctttcttcc cttcctttct cgccacgttc gccggctttc cccgtcaagc tctaaatcgg   2700
ggcatccctt tagggttccg atttagtgct ttacggcacc tcgaccccaa aaaacttgat   2760
tagggtgatg gttcacgtag tgggccatcg ccctgataga cggttttcg ccctttgacg    2820 ttggagtcca cgttctttaa tagtggactc ttgttccaaa ctggaacaac actcaaccct   2880
atctcggtct attcttttga tttataaggg attttgggga tttcggccta ttggttaaaa   2940
aatgagctga tttaacaaaa atttaacgcg aattaattct gtggaatgtg tgtcagttag   3000
ggtgtggaaa gtccccaggc tccccaggca ggcagaagta tgcaaagcat gcatctcaat   3060
```

```
tagtcagcaa ccaggtgtgg aaagtcccca ggctccccag caggcagaag tatgcaaagc    3120
atgcatctca attagtcagc aaccatagtc ccgcccctaa ctccgcccat cccgccccta    3180
actccgccca gttccgccca ttctccgccc catggctgac taattttttt tatttatgca    3240
gaggccgagg ccgcctctgc ctctgagcta ttccagaagt agtgaggagg cttttttgga    3300
ggcctaggct tttgcaaaaa gctcccggga gcttgtatat ccattttcgg atctgatcaa    3360
gagacaggat gaggatcgtt tcgcatgatt gaacaagatg gattgcacgc aggttctccg    3420
gccgcttggg tggagaggct attcggctat gactgggcac aacagacaat cggctgctct    3480
gatgccgccg tgttccggct gtcagcgcag gggcgcccgg ttcttttttgt caagaccgac    3540
ctgtccggtg ccctgaatga actgcaggac gaggcagcgc ggctatcgtg gctggccacg    3600
acgggcgttc cttgcgcagc tgtgctcgac gttgtcactg aagcgggaag ggactggctg    3660
ctattgggcg aagtgccggg gcaggatctc ctgtcatctc accttgctcc tgccgagaaa    3720
gtatccatca tggctgatgc aatgcggcgg ctgcatacgc ttgatccggc tacctgccca    3780
ttcgaccacc aagcgaaaca tcgcatcgag cgagcacgta ctcggatgga agccggtctt    3840
gtcgatcagg atgatctgga cgaagagcat caggggctcg cgccagccga actgttcgcc    3900
aggctcaagg cgcgcatgcc cgacggcgag gatctcgtcg tgacccatgg cgatgcctgc    3960
ttgccgaata tcatggtgga aaatggccgc ttttctggat tcatcgactg tggccggctg    4020
ggtgtggcgg accgctatca ggacatagcg ttggctaccc gtgatattgc tgaagagctt    4080
ggcggcgaat gggctgaccg cttcctcgtg ctttacggta tcgccgctcc cgattcgcag    4140
cgcatcgcct tctatcgcct tcttgacgag ttcttctgag cgggactctg ggttcgcga    4200
aatgaccgac caagcgacgc ccaacctgcc atcacgagat tcgattcca ccgccgcctt    4260
ctatgaaagg ttgggcttcg gaatcgtttt ccgggacgcc ggctggatga tcctccagcg    4320
cggggatctc atgctggagt tcttcgccca ccccaacttg tttattgcag cttataatgg    4380
ttacaaataa agcaatagca tcacaaattt cacaaataaa gcattttttt cactgcattc    4440
tagttgtggt ttgtccaaac tcatcaatgt atcttatcat gtctgtatac cgtcgacctc    4500
tagctagagc ttggcgtaat catggtcata gctgtttcct gtgtgaaatt gttatccgct    4560
cacaattcca cacaacatac gagccggaag cataaagtgt aaagcctggg gtgcctaatg    4620
agtgagctaa ctcacattaa ttgcgttgcg ctcactgccc gctttccagt cgggaaacct    4680
gtcgtgccag ctgcattaat gaatcggcca acgcgcgggg agaggcggtt tgcgtattgg    4740
gcgctcttcc gcttcctcgc tcactgactc gctgcgctcg gtcgttcggc tgcggcgagc    4800
ggtatcagct cactcaaagg cggtaatacg gttatccaca gaatcagggg ataacgcagg    4860
aaagaacatg tgagcaaaag gccagcaaaa ggccaggaac cgtaaaaagg ccgcgttgct    4920
ggcgtttttc cataggctcc gcccccctga cgagcatcac aaaaatcgac gctcaagtca    4980
gaggtggcga aacccgacag gactataaag ataccaggcg tttccccctg gaagctccct    5040
cgtgcgctct cctgttccga ccctgccgct taccggatac ctgtccgcct ttctcccttc    5100
gggaagcgtg gcgctttctc aatgctcacg ctgtaggtat ctcagttcgg tgtaggtcgt    5160
tcgctccaag ctgggctgtg tgcacgaacc ccccgttcag cccgaccgct gcgccttatc    5220
cggtaactat cgtcttgagt ccaacccggt aagacacgac ttatcgccac tggcagcagc    5280
cactggtaac aggattagca gagcgaggta tgtaggcggt gctacagagt tcttgaagtg    5340
gtggcctaac tacggctaca ctagaaggac agtatttggt atctgcgctc tgctgaagcc    5400
agttaccttc ggaaaaagag ttggtagctc ttgatccggc aaacaaacca ccgctggtag    5460
```

-continued

```
cggtggtttt tttgtttgca agcagcagat tacgcgcaga aaaaaaggat ctcaagaaga    5520
tcctttgatc ttttctacgg ggtctgacgc tcagtggaac gaaaactcac gttaagggat    5580
tttggtcatg agattatcaa aaaggatctt cacctagatc cttttaaatt aaaaatgaag    5640
ttttaaatca atctaaagta tatatgagta aacttggtct gacagttacc aatgcttaat    5700
cagtgaggca cctatctcag cgatctgtct atttcgttca tccatagttg cctgactccc    5760
cgtcgtgtag ataactacga tacggggggg cttaccatct ggccccagtg ctgcaatgat    5820
accgcgagac ccacgctcac cggctccaga tttatcagca ataaaccagc cagccggaag    5880
ggccgagcgc agaagtggtc ctgcaacttt atccgcctcc atccagtcta ttaattgttg    5940
ccgggaagct agagtaagta gttcgccagt taatagtttg cgcaacgttg ttgccattgc    6000
tacaggcatc gtggtgtcac gctcgtcgtt tggtatggct tcattcagct ccggttccca    6060
acgatcaagg cgagttacat gatccccat gttgtgcaaa aaagcggtta gctccttcgg    6120
tcctccgatc gttgtcagaa gtaagttggc cgcagtgtta tcactcatgg ttatggcagc    6180
actgcataat tctcttactg tcatgccatc cgtaagatgc ttttctgtga ctggtgagta    6240
ctcaaccaag tcattctgag aatagtgtat gcggcgaccg agttgctctt gcccggcgtc    6300
aatacgggat aataccgcgc cacatagcag aactttaaaa gtgctcatca ttggaaaacg    6360
ttcttcgggg cgaaaactct caaggatctt accgctgttg agatccagtt cgatgtaacc    6420
cactcgtgca cccaactgat cttcagcatc ttttactttc accagcgttt ctgggtgagc    6480
aaaaacagga aggcaaaatg ccgcaaaaaa gggaataagg gcgacacgga aatgttgaat    6540
actcatactc ttcctttttc aatattattg aagcatttat cagggttatt gtctcatgag    6600
cggatacata tttgaatgta tttagaaaaa taaacaaata ggggttccgc gcacatttcc    6660
ccgaaaagtg ccacctgacg tc                                             6682
```

<210> SEQ ID NO 40

<400> SEQUENCE: 40

000

<210> SEQ ID NO 41
<211> LENGTH: 39
<212> TYPE: DNA
<213> ORGANISM: Hepatitis B virus

<400> SEQUENCE: 41
gtggacatct acccatacga cgttccagat tacgctggc                                39

<210> SEQ ID NO 42
<211> LENGTH: 13
<212> TYPE: PRT
<213> ORGANISM: Hepatitis B virus

<400> SEQUENCE: 42

Val Asp Ile Tyr Pro Tyr Asp Val Pro Asp Tyr Ala Gly
1               5                   10

<210> SEQ ID NO 43
<211> LENGTH: 33
<212> TYPE: DNA
<213> ORGANISM: Artificial Sequence
<220> FEATURE:
<223> OTHER INFORMATION: primer

```
<400> SEQUENCE: 43
attggatcca ccatgcaact ttttcacctc tgc                                33

<210> SEQ ID NO 44
<211> LENGTH: 34
<212> TYPE: DNA
<213> ORGANISM: Artificial Sequence
<220> FEATURE:
<223> OTHER INFORMATION: primer

<400> SEQUENCE: 44
acagtagttt ccggaagtgt tgataggata gggg                               34

<210> SEQ ID NO 45
<211> LENGTH: 123
<212> TYPE: DNA
<213> ORGANISM: Hepatitis B virus

<400> SEQUENCE: 45
accatgcaac tttttcacct ctgcctaatc atctcttgtt catgtcctac tgttcaagcc   60
tccaagctgt gccttgggtg gctttggggc atggacatcg acccttataa agaatttgga  120
gct                                                                123

<210> SEQ ID NO 46
<211> LENGTH: 138
<212> TYPE: DNA
<213> ORGANISM: Hepatitis B virus

<400> SEQUENCE: 46
accatgcaac tttttcacct ctgcctaatc atctcttgtt catgtcctac tgttcaagcc   60
tccaagctgt gccttgggtg gctttggggc gtggacatct acccatacga cgttccagat  120
tacgctggca tggacatc                                                138
```

TAGGED HEPADNAVIRUS E ANTIGEN AND ITS USE IN SCREENING ANTIVIRAL SUBSTANCES

This invention was made with government support under Contract No. R01AI094474 awarded by the National Institutes of Health. The government has certain rights in the invention.

The present invention relates to methods and uses for screening anti-hepadnaviral substances, wherein the substances are inhibitors of hepatitis B e antigen (HBeAg) which is predominantly covalently closed circular (ccc) DNA-dependent in cell lines described in this invention and might serve as a surrogate marker for cccDNA screened for the capacity to inhibit ccc DNA of a hepadnavirus, like Hepatitis B virus (HBV). The methods and uses take advantage of cells comprising a nucleic sequence encoding a tagged hepadnavirus e antigen, like Hepatitis B virus e antigen (HBeAg). Furthermore, the present invention provides nucleic acid sequences encoding a tagged hepadnavirus e antigen and proteins encoded thereby. Also kits for use in the screening methods are provided.

Chronic hepatitis B is currently a substantial public health burden affecting approximately 350 million individuals worldwide and at least 1.2 million in the United States. These patients have an elevated risk of liver cirrhosis, hepatocellular carcinoma (HCC), and other severe clinical sequelae (1, 2, 12, 14). Annually, there are about 1 million deaths due to HBV-related liver disease all over the world. It is therefore a global health priority to cure chronic HBV infection and prevent its dire consequences.

Hepatitis B virus (HBV) is a noncytopathic, liver tropic DNA virus belonging to Hepadnaviridae family. Hepadnaviruses are a family of enveloped, double-stranded viruses which can cause liver infections in humans and animals. Hepadnaviruses share the similar genome organisation. They have small genomes of partially double-stranded circular DNA. The genome consists of two strands of DNA, one having negative-sense orientation, the other strand having a positive-sense orientation. Replication involves reverse transcription of an RNA intermediate called pregenomic RNA (15, 19). Three main open reading frames (ORFs) are encoded and the virus has five known mRNAs (18, 19).

Upon infection, the viral genomic relaxed circular (rc) DNA is transported into the cell nucleus and converted to episomal covalently closed circular (ccc) DNA, which serves as the transcription template for all the viral mRNAs, specifically 3.5-3.6 kb precore mRNA encoding precore protein which is the precursor for HBeAg; 3.5 kb pregenomic (pg) RNA encoding core protein and viral polymerase; 2.4 kb/2.1 kb surface mRNAs encoding viral envelope proteins (large (L), middle (M), and small (S) antigens); and 0.7 kb X mRNA for X protein (18, 19). HBeAg is generated by two proteolytic events removing the N-terminal signal peptide and the C-terminal arginine-rich sequence of the precore protein (Wang (1991) J Virol 65(9), 5080 (10, 21). After transcription and nuclear exportation, cytoplasmic viral pgRNA is assembled with HBV polymerase and capsid proteins to form the nucleocapsid, inside of which polymerase-catalyzed reverse transcription yields minus-strand DNA, which is subsequently copied into plus-strand DNA to form the progeny rcDNA genome. The newly synthesized mature nucleocapsids will either be packaged with viral envelope proteins and egress as virion particles, or shuttled back to the nucleus to amplify the cccDNA reservoir through intracellular cccDNA amplification pathway (19). Therefore, the molecular basis for chronic hepatitis B is the persistence of viral cccDNA in the nuclei of infected hepatocytes.

There is no definitive cure for chronic hepatitis B. Currently approved drugs for HBV treatment are interferon-α (IFN-α) and 5 nucleos(t)ide analogues (lamivudine, adefovir, entecavir, telbivudine, and tenofovir). Xu (2010) J Virol (84) 9332-9340 discloses the treatment of mouse hepatocytes with mouse interferon. IFN-α only achieves sustained virological response in a minor group of patients after 48 weeks of standard treatment, and with significant adverse effects (9). The five nucleos(t)ide analogues (NAs) all act as viral polymerase inhibitors, but rarely cure HBV infection (6), and emergence of resistance dramatically limits their long-term efficacy (16, 24). It is now well acknowledged that the major limitation of current treatment is the failure to eliminate the preexisting cccDNA pool, and/or prevent cccDNA formation from trace-level wild-type or drug-resistant virus. Thus there is an urgent unmet need for the development of novel therapeutic agents that directly target cccDNA formation and maintenance.

Cai (2013) Methods in Mol Biol 1030 (151-161) disclose a southern blot assay for detection of HBV ccc (covalently closed circular) DNA from cell cultures. Yet, to date, screens for anti-cccDNA agents have been limited due to the lack of efficient in vitro HBV infection models, and a practical approach for measuring cccDNA in high to mid-throughput format was unavailable. Alternatively, cccDNA formation can be achieved through the intracellular amplification pathway in stably-transfected HBV cell cultures that constitutively or conditionally replicate HBV genome, as represented by HepG2.2.15 and HepAD38 cells (7, 11, 20).

However, the direct cccDNA detection from HBV cell lines by either Southern blot hybridization or real-time PCR assay would not be amenable to screening due to the sensitivity and specificity issues, respectively. On the other hand, there is no suitable surrogate marker for cccDNA in HepG2.2.15 cells since the most majority of viral products are derived from integrated viral transgene, which are indistinguishable from cccDNA contributions. It has been previously reported that the production of secreted HBeAg was predominantly cccDNA-dependent in HepAD38 cells and might serve as a surrogate marker for cccDNA (1, 23). Recently, Cai, et al. applied an upgraded version of a solely cccDNA-dependent HBeAg producing cell line, named HepDE19 cells (7), into 96-well format assay for screening of cccDNA inhibitors and identified two small molecule compounds that inhibit cccDNA formation (3). Such work thus provided a solid "proof-of-concept" demonstration that cccDNA biosynthesis can be directly targeted by chemical molecules, and cccDNA inhibitors could be identified from high throughput screening campaign. However, certain disadvantages of the existing HepDE19 assay system render a screen of larger libraries impractical. For instance, the traditional ELISA assay currently used for HBeAg requires multiple manipulations, exhibits a certain extent of cross reaction with viral core protein due to amino acid sequence homology, and are not suitable for larger format cell-based assay.

Thus, the technical problem underlying the present invention is the provision of means and methods to reliably screen inhibitors of hepadnaviral cccDNA.

The technical problem is solved by provision of the embodiments characterized in the claims.

Accordingly, the present invention relates to a method for assessing the capacity of a candidate molecule to inhibit ccc (covalently closed circular) DNA of a hepadnavirus comprising the steps of (a) contacting a cell comprising a nucleic acid molecule comprising a nucleic acid sequence encoding a tagged hepadnavirus e antigen with said candidate molecule;
(b) assessing the level of the tagged hepadnavirus e antigen; and
(c) selecting a candidate molecule when the level of tagged hepadnavirus e antigen is decreased compared to a control.

The methods are generally applicable to other mammalian and avian hepadnaviruses, such as the representative woodchuck hepatitis virus (WHV) and duck hepatitis B virus (DHBV) which share a similar gene organization and replication strategy with Hepatitis B virus (HBV). The herein provided explanations and experiments with regard to Hepatitis B virus apply therefore likewise to other hepadnaviruses. However, the teachings provided herein relate in preferred embodiment to "Hepatitis B virus"/HBV. The terms "hepadnavirus", "Hepatitis B virus", "duck hepatitis B virus", "woodchuck hepatitis virus (WHV)" are well known in the art and used accordingly herein. The abbreviations "HBV", "DHBV" or "WHV" are used interchangeably herein with the full terms "Hepatitis B virus", "duck hepatitis B virus" and "woodchuck hepatitis virus", respectively.

The herein preferred hepadnavirus is preferably Hepatitis B virus (HBV). Hepatitis B virus (HBV) is a noncytopathic, liver tropic DNA virus belonging to Hepadnaviridae family, i.e. HBV is a hepadnavirus. Exemplary nucleic acid sequences of HBV genomes are shown in SEQ ID NO: 27, 28, 29, 30, 31, 32, 33 or 34.

The herein preferred hepadnavirus e antigen is Hepatitis B virus e antigen (HBeAg). The terms "Hepatitis B virus e antigen" and "HBeAg" are used interchangeably herein. An exemplary nucleic acid sequence and amino acid sequence of HBeAg is shown in SEQ ID NO: 16 and 18, respectively. As used herein "hepadnavirus e antigen" (and likewise "Hepatitis B virus e antigen") refers primarily to a protein/polypeptide e.g. a protein/polypeptide having an amino acid sequences as shown in SEQ ID NO: 18.

HBeAg can be produced upon infection as follows: upon infection, the HBV virus genomic relaxed circular (rc) DNA is transported into the cell nucleus and converted to episomal cccDNA, which serves as the transcription template for all the viral mRNAs, including a 3.5-3.6 kb precore mRNA encoding precore protein which is the precursor for HBeAg. The terms "ccc DNA" and "covalently closed circular DNA" are used interchangeably herein.

Exemplary nucleic acid sequences and amino acid sequences of a HBV precore protein are shown in SEQ ID NO: 15 and 17, respectively. The HBV precore protein has an N-terminal 19-amino acid signal peptide, a 10-amino acid linker, a central amino acid stretch and a C-terminal 34-amino acid arginine-rich domain.

Exemplary nucleic acid sequences and amino acid sequences of a HBV core protein are shown in SEQ ID NO: 23 and 24, respectively. The core protein corresponds to the precore protein (see SEQ ID NO: 17) in that it comprises the C-terminal arginine-rich sequence of the precore protein; however, the core protein does not comprise the N-terminal signal peptide and the 10-amino acid linker sequence of the precore protein.

HBeAg is generated by two proteolytic events removing the N-terminal signal peptide and the C-terminal arginine-rich sequence of the precore protein (Wang (1991) J Virol 65(9), 5080 (21). Thus, Hepatitis B virus e antigen (HBeAg) corresponds to the precore protein (see SEQ ID NO: 17) in that it comprises the N-terminal 10-aa linker peptide of the precore protein; however, HBeAg does not comprise the C-terminal arginine-rich sequence of the precore protein.

The molecular basis for chronic hepatitis B is the persistence of viral cccDNA in the nuclei of infected hepatocytes.

The terms "covalently closed circular DNA" and "cccDNA" are used interchangeably herein. The term "covalently closed circular DNA"/"cccDNA" is well known in the art and used accordingly herein. Generally, "covalently closed circular DNA"/"cccDNA" as used herein refers to a DNA that serves as the authentic episomal transcription template for the hepadnaviral mRNAs.

Hepatitis B virus e antigen (HBeAg) is an accepted surrogate marker for cccDNA of HBV hepadnaviruses that in turn reflects chronic hepadnavirus infection. Yet, the known cell based assays employing HBeAg suffer from disadvantages, like cross reaction with viral core protein.

In order to improve the specificity and sensitivity of cccDNA reporter detection, herein cell lines were established that support the cccDNA-dependent production of recombinant HBeAg with a tag (like an N-terminal embedded hemagglutinin (HA) epitope tag). Moreover, chemiluminescence ELISA (CLIA) and AlphaLISA assays for the detection of (HA-)tagged HBeAg were developed. The assay system is adaptable to high throughput screening formats and full automation.

The herein provided methods take advantage of the use of established tags (like HA-tag, or His-tag, Flag-tag, c-myc-tag, V5-tag or C9-tag that can be used in the place of an HA-tag or in addition thereto). These tags can be used in the purification and detection of tagged hepadnavirus e antigen. By using antibodies specifically binding to the tag (e.g. via ELISA assays, like chemiluminescence ELISA (CLIA) and AlphaLISA), the level of tagged hepadnavirus e antigen can be reliably and rapidly assessed and cross-reactions with core protein can be avoided.

The methods provided herein employ cells comprising a nucleic acid molecule comprising a nucleic acid sequence encoding a tagged hepadnavirus e antigen. The nucleic acid molecule can comprise a sequence encoding a hepadnavirus precore protein or even a hepadnavirus genome to reflect and enable cccDNA formation of hepadnaviruses. In the art it is known that HBV genome has a highly compact gene organization which exhibits overlapped ORFs and multiple cis elements. Therefore, it was believed that gene insertion/deletion or sequence replacement would very likely affect viral DNA replication (13, 22). (Liu, et al, J Virol. 2004; 78(2):642-9.)(Wang, et al. PLoS One. 2013 2; 8(4):e60306) Previous works have replaced HBV sequence, such as pol/envelope coding region in most cases, by GFP to make recombinant HBV genome, but trans-complement of viral proteins was needed to support viral replication and virion assembly (17) (Protzer, et al, PNAS (1999). 96: 10818-23.). Moreover, this reported recombinant HBV genome can only make first round cccDNA synthesis if used to infect permissive cells, intracellular amplification of cccDNA is blocked due to the defective viral DNA replication.

The 5' stem-loop structure (epsilon) in hepadnavirus pgRNA, preferably HBV pgRNA, is an essential cis element for viral replication. It serves as the pgRNA packaging signal and DNA priming site. The epsilon overlaps with the 5' portion of precore ORF and contains the start codon of capsid (core) protein ORF. To insert a nucleic acid sequence encoding a tag downstream of the N-terminal signal peptide sequence in precore ORF without altering the integrity of epsilon structure encoded by the HBV genome, a threeamino-acid linker sequence was introduced herein (GTG GAC ATC) at the 5' end of the (HA-)tag to replace the original viral sequence (ATG GAC ATC) of the right arm at the bottom of the epsilon as encoded by the HBV genome. Thereby the base pairing of the epsilon as encoded by the HBV genome was maintained and the start codon of core ORF was moved to a position downstream of epsilon as encoded by the HBV genome. In addition, the original GGC sequence was placed between the HA-tag sequence and core AUG in order to keep the authentic Kozak motif of core start codon (FIG. 1). FIG. 1 shows part of the HBV genome encoding an epsilon structure, wherein a nucleic acid sequence encoding a tag is inserted in accordance with the present invention.

It was envisioned herein that the above modifications cause minimal effects on HBV pgRNA-dependent core expression and pgRNA encapsidation, since the epsilon and the core expression cassette were preserved, although the translation initiation site of core protein was moved 39-nt further downstream in the pgRNA template. Indeed, the recombinant HBV genome supported near wildtype level of viral DNA replication, and the HA-tagged HBeAg was successfully produced upon the reconstitution of precore ORF in cccDNA molecule.

The insertion of an oligo encoding a tag did not affect viral DNA application, so that the herein provided method allows for production of cccDNA and consequently the assessment of the capacity of substances/candidate molecules to inhibit cccDNA formation by determining the amount of the surrogate marker "tagged hepadnavirus e antigen". The herein provided means and methods are primarily useful to screen and identify candidate molecules that can be used in the therapy of chronic diseases associated with hepadnaviruses, like (chronic) hepatitis and in particular chronic hepatitis B infection.

The insertion of a nucleic acid sequence encoding a tag (like an HA-tag) into the hepadnavirus (like HBV) precore ORF leads to hepadnavirus (like HBV) cccDNA-dependent production of tagged hepadnavirus e antigen (like HBeAg) which is useful for improved antigen detection specificity. In support of the present invention, it was confirmed herein that the (HA-)tag insertion does not affect the expression of precore protein and its subsequent posttranslational processing (N-terminal signal peptide cleavage and C-terminal domain cleavage) and mature HBeAg secretion (FIG. 2). More importantly, it was shown herein that such a modification in the hepadnavirus (like HBV) genome does not hamper viral pgRNA encapsidation and reverse transcription, which are the prerequisites for cccDNA formation through intracellular amplification pathway (FIGS. 4, 6-8, 12).

The present invention relates to screen and assessment of pharmacological agents for their activities against hepadnaviruses. In particular, this invention describes the design and construction of recombinant hepatitis B virus (HBV) genome and novel cell lines for inducible expression of HBV cccDNA-dependent epitope (e.g. Human influenza hemagglutinin (HA) tag)-tagged HBV e antigen (HBeAg). The tagged HBeAg secreted into the culture fluid can be quantitatively measured for example by chemiluminescence enzyme immunoassay (CLIA) and/or AlphaLISA. This invention provides an effective cell-based HBV reporter system to screen compounds for anti-hepadnaviral activity, especially those inhibiting cccDNA formation, maintenance, and/or its transcriptional activity.

Figure 10:
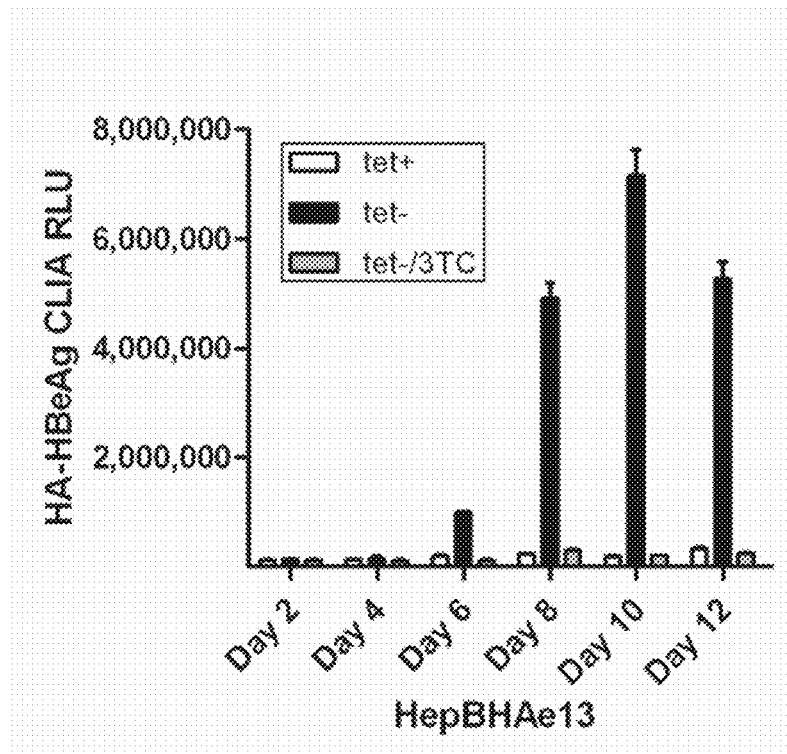

The present invention is further illustrated by FIG. 10. Here, it was shown that 3TC treatment abolished the HA-HBeAg signal in HepBHAe13 cells, although this was an extreme condition wherein 3TC blocked the viral DNA replication and thus there was no cccDNA synthesized. Further, as a proof of principle, two cccDNA formation inhibitors (CCC-0975 and CCC-0346) were tested in HepBHAe13 cells. Both compounds dose dependently reduced the HA-HBeAg level; see FIG. 11.

For example, the following non-limiting anti-hepadnaviral assays can be performed in accordance with the present invention:

1. Screen of Compounds/Candidate Molecules Regulating cccDNA Stability and/or Transcriptional Activity Using HepBHAe Cell Lines.

According to the present invention, the in vitro assay method can be used to screen/evaluate the efficacy of compounds/candidate molecules to regulate cccDNA stability or transcriptional activity in the nucleus. The compounds/candidate molecules thereby alter the level of tagged hepadnavirus e antigen (like HA-HBeAg) in culture supernatant. To perform the assay, cells can be first seeded in culture plates in the presence of tetracycline, and after cells reach confluent, the medium will be replaced with tetracycline-free medium to induce hapadnavirus (like HBV) DNA replication and cccDNA formation, which normally takes 6-8 days. After that, tetracycline can be added back to shut down the de novo viral DNA replication from integrated HBV genome, together with the addition of 3TC (or other HBV polymerase inhibitors) to block the intracellular amplification pathway of cccDNA. At the same time, test compounds can be added into culture medium for a certain period of time. Culture medium can then be used for ELISA measurement of tagged hepadnavirus e antigen (like HA-HBeAg). Media from wells that do not contain test compound can be used as control. Effective compounds that reduce tagged hepadnavirus e antigen (like HA-HBeAg) level in culture medium may have the activity to promote cccDNA turnover or silence cccDNA transcription. The phrase "effective or effectively" can be used herein to indicate that a compound, at certain testing concentration, is sufficient to prevent, and preferably reduce by at least 50%, most preferably by at least 90%, the production of tagged hepadnavirus e antigen (like HA-HBeAg) in a cell based assay system of the present invention. Direct measurement of the steady state levels of cccDNA and precore mRNA by qPCR or hybridization can be used to distinguish whether the test compound/candidate compound/candidate molecule reduces cccDNA stability or transcription, respectively.

2. Screen of Compounds/Candidate Molecules that Inhibit Hepadnavirus (Like HBV) cccDNA Formation Using HepBHAe Cell Lines.

According to another aspect of the present invention, the in vitro assay method can be used to evaluate compounds/candidate molecules that suppress cccDNA formation. Briefly, cells can be seeded into culture wells and tetracycline can be omitted at the day when cell monolayer becomes confluent. Simultaneously, test compound can be added and tagged hepadnavirus e antigen (like HA-HBeAg) in the medium can be measured by ELISA at the end of treatment (approximately 6 days). Any compound resulting in the reduction of tagged hepadnavirus e antigen (like HA-HBeAg) indicates that it may effectively block the formation of cccDNA. As an expanding aspect of this in vitro assay method, it is worth to note that the reduction of tagged hepadnavirus e antigen (like HA-HBeAg) in this assay may also indicate that the compound has the potential to inhibit hepadnavirus (like HBV) DNA replication. Such possibility can be investigated through direct measurement of viral core DNA by Southern blot and/or qPCR. The "hits" emerging from the assay described above may also include compounds that affect cccDNA stability and/or transcription. During the induction time period, the stability and/or transcription activity of the early made cccDNA may be targeted by testing compounds.

3. HepHA-HBe Cell Lines Serve as Counter-Screen System.

Theoretically, compound "hits" from the aforementioned assays may directly inhibit HA-tagged precore protein translation, or posttranslational processing, or tagged hepadnavirus e antigen (like HA-HBeAg) secretion. To rule out such non-cccDNA inhibitors, "hits" can be counter-screened in HepHA-HBe cells, which produce tagged hepadnavirus e antigen (like HA-tagged HBeAg) using transgene as template. On the other hand, HepHA-HBe cells could also be used to screen HBeAg inhibitors.

The term "inhibit covalently closed circular DNA" and grammatical versions thereof can refer to an inhibition of the stability of covalently closed circular DNA (i.e. to a reduced stability of covalently closed circular DNA), to an inhibition of transcriptional activity of covalently closed circular DNA (i.e. to a reduced transcription of hepadnaviral mRNAs using covalently closed circular DNA as a transcription template) or to an inhibition of the formation of covalently closed circular DNA (i.e. no or less cccDNA is formed).

These exemplary explanations and definitions of the term "inhibit covalently closed circular DNA" are not mutually exclusive. For example, an inhibited formation of covalently closed circular DNA can lead to/be associated with a reduced transcription of hepadnaviral mRNAs using covalently closed circular DNA as a transcription template (i.e. an inhibition of transcriptional activity of covalently closed circular DNA). An inhibited stability of covalently closed circular DNA can lead to/be associated with a reduced transcription of hepadnaviral mRNAs using covalently closed circular DNA as a transcription template.

A tagged hepadnavirus e antigen can be used herein as surrogate marker for any such inhibition of cccDNA of a hepadnavirus.

In accordance with the above, the herein provided method can be (used) for assessing the capacity of a candidate molecule to inhibit the formation of cccDNA of a hepadnavirus. In this context, the cell can be contacted with the candidate molecule before cccDNA has formed.

The herein provided method can be (used) for assessing the capacity of a candidate molecule to decrease stability of cccDNA (e.g. the amount or number of cccDNA) of a hepadnavirus. Here, the cell can be contacted with the candidate molecule after cccDNA has formed.

The herein provided method can be (used) for assessing the capacity of a candidate molecule to decrease the transcription (activity) of cccDNA of a hepadnavirus. Here, the cell can be contacted with the candidate molecule after cccDNA has formed.

The tagged hepadnavirus e antigen, the level of which is to be assessed in accordance with the present invention, can contain one or more tags. As shown herein, a reliable assessment of the tagged hepadnavirus e antigen can be achieved by using only one tag, e.g. by using an antibody specifically binding to the tag. Accordingly, it is envisaged and preferred herein that the tagged hepadnavirus e antigen contains only one tag.

The following relates to the one or more tag to be used herein.

The term "tag" as used herein refers to any chemical structure useful as a marker. Primarily, the term "tag" refers to a "protein tag". The terms "tag" and "protein tag" are known in the art; see, inter alia, Fritze C E, Anderson T R. "Epitope tagging: general method for tracking recombinant proteins". Methods Enzymol. 2000; 327: 3-16; Brizzard B, Chubet R. Epitope tagging of recombinant proteins. Curr Protoc Neurosci. 2001 May; Chapter 5: Unit 5.8; and/or Terpe K. Overview of tag protein fusions: from molecular and biochemical fundamentals to commercial systems. Appl Microbiol Biotechnol. 2003 January; 60(5):523-33.

Typically, the tag to be used herein is a protein tag that is fused to the hepadnavirus e antigen. For example, a nucleic acid encoding the tag can be fused to a nucleic acid encoding a hepadnavirus e antigen, so that a fusion protein comprising both the tag and the hepadnavirus e antigen is expressed. The tag(s) can be fused to the 5'-end of the nucleic acid encoding a hepadnavirus e antigen, inserted within the nucleic acid encoding a hepadnavirus e antigen and/or fused to the 3'-end of the nucleic acid encoding a hepadnavirus e antigen. Thus, the resulting fusion protein can comprise (a) tag(s) at the N-terminus, internally (i.e. within the hepadnavirus e antigen/as internal epitope), and/or at the C-terminus. As shown herein, an internal epitope tag can be used for reliable assessment of the level of a tagged hepadnavirus e antigen and is therefore preferred.

Various tags are known in the art and can be used in accordance with the present invention. Usually, a tag to be used herein has a low molecular weight of about 1-3 kDa, preferably of about 1 kDa. Exemplary, non-limiting low molecular weight tags are HA-tag, His-tag, Flag-tag, c-myc-tag, V5-tag or C9-tag. The use of HA-tag is preferred herein. The Flag-tag to be used herein can be 1×Flag-tag or 3×Flag-tag.

The low molecular weight is reflected in the length of the tag, i.e. the number of amino acid residues of which the tag consists. For example, His-tag (6 amino acids), HA-tag (9 amino acids), FLAG-tag (8 amino acids), or 3×FLAG-tag (22 amino acids) can be used herein. These exemplary tags support near wt-level HBV DNA replication and are therefore useful for performing the present invention.

Accordingly, a tag to be used herein can consist of 6 to 22 amino acids, e.g. 6 amino acids, 7 amino acids, 8 amino acids, 9 amino acids, 10 amino acids, 11 amino acids, 12 amino acids, 13 amino acids, 14 amino acids, 15 amino acids, 16 amino acids, 17 amino acids, 18 amino acids, 19 amino acids, 20 amino acids, 21 amino acids, or 22 amino acids.

Exemplary nucleic acid sequences encoding a tag to be used herein is a nucleic acid sequence encoding the HA tag as shown in SEQ ID NO: 1, a nucleic acid sequence encoding the His-tag as shown in SEQ ID NO: 2; nucleic acid sequence encoding the c-myc-tag as shown in SEQ ID NO: 4, a nucleic acid sequence encoding the V5-tag as shown in SEQ ID NO: 5, or a nucleic acid sequence encoding the C9-tag as shown in SEQ ID NO: 6. Herein the use of an HA tag encoded by SEQ ID NO: 1 or consisting of an amino acid sequence as shown in SEQ ID NO: 8 is preferred.

An exemplary nucleic acid sequence encoding a Flag-tag to be used herein is a nucleic acid sequence encoding a 1×Flag-tag as shown in SEQ ID NO: 3, or a nucleic acid sequence encoding a 3×Flag-tag as shown in SEQ ID NO: 7.

Exemplary amino acid sequences of a tag to be used herein is an amino acid sequence of an HA tag as shown in SEQ ID NO: 8, an amino acid sequence of the His-tag as shown in SEQ ID NO: 9, an amino acid sequence of the c-myc-tag as shown in SEQ ID NO: 11, an amino acid sequence of the V5-tag as shown in SEQ ID NO: 12, or an amino acid sequence of the C9-tag as shown in SEQ ID NO: 13.

An exemplary amino acid sequence of a Flag-tag to be used herein is an amino acid sequence of the 1×Flag-tag as shown in SEQ ID NO: 10 or an amino acid sequence of the 3×Flag-tag as shown in SEQ ID NO: 14.

The use of epitope tags is primarily envisaged herein, such as a hemagglutinin (HA) tag, His-tag, Flag-tag, c-myc-tag, V5-tag and/or C9-tag. Epitope tags are short peptide sequences which are chosen because high-affinity antibodies can be reliably produced in many different species. These tags are often derived from viral genes, which explain their high immunoreactivity. These tags are particularly useful for western blotting, immunofluorescence, immunohistochemistry, immunoaffinity chromatography and immunoprecipitation experiments. They are also used in antibody purification. Such epitope tags are particularly useful, because known and commercially available antibodies specifically binding to these tags can be used in accordance with the present invention.

Affinity tags are appended to proteins so that they can be purified from their crude biological source using an affinity technique. These include chitin binding protein (CBP), maltose binding protein (MBP), and glutathione-S-transferase (GST). The poly (His) tag is a widely used protein tag; it binds to metal matrices.

Chromatography tags are used to alter chromatographic properties of the protein to afford different resolution across a particular separation technique. Often, these consist of polyanionic amino acids, such as FLAG-tag.

Essentially any tag can be used herein. The nucleic acid encoding the tag as comprised in the nucleic acid molecule to be used herein should be able to support hepadnavirus DNA replication, cccDNA formation, and cccDNA-dependent tagged hepadnavirus antigen e production and secretion. This capacity can easily be validated using the assays provided herein e.g. the assays provided in the experiments. For example, it has been demonstrated herein that HA-tag insertion led to the wild-type level HBV DNA replication and the production of HA-tagged HBeAg from cccDNA in stable cell lines. These capacities can readily be confirmed and tested for other tags. His-tag and Flag-tag insertion do, for example, not affect viral DNA replication in transient transfection assays.

Further tags can be used without deferring from the gist of the present invention.

For example, reporter proteins can be used as tags herein, like luciferase (e.g. Firefly Luciferase, *Renilla* Luciferase, *Gaussia* Luciferase, etc), green fluorescent protein (GFP) and the like. These reporter proteins allow for an easy assessment of the level of the tagged hepadnavirus, e.g. by visual inspection, fluorescence measurements etc. Fluorescence tags are used to give visual readout on a protein. GFP and its variants are the most commonly used fluorescence tags.

Exemplary reporter proteins that can be used in the screening methods of the invention are, inter alia, luciferase, (green/red) fluorescent protein and variants thereof, EGFP (enhanced green fluorescent protein), RFP (red fluorescent protein, like DsRed or DsRed2), CFP (cyan fluorescent protein), BFP (blue green fluorescent protein), YFP (yellow fluorescent protein), β-galactosidase or chloramphenicol acetyltransferase.

Luciferase is a well known reporter; see, for example, Jeffrey (1987) Mol. Cell. Biol. 7(2), 725-737. A person skilled in the art can easily deduce further luciferase nucleic and amino acid sequences to be used in context of the present invention from corresponding databases and standard text books/review.

The reporter protein may allow the detection/assessment of a candidate molecule to inhibit cccDNA by inducing a change in the signal strength of a detectable signal. Said detectable signal can be a fluorescence resonance energy transfer (FRET) signal, a fluorescence polarization (FP) signal or a scintillation proximity (SP) signal. The detectable signal may be associated with a reporter protein as defined herein above. For example, GFP can be derived from *Aequorea victoria* (U.S. Pat. No. 5,491,084). A plasmid encoding the GFP of *Aequorea victoria* is available from the ATCC Accession No. 87451. Other mutated forms of this GFP including, but not limited to, pRSGFP, EGFP, RFP/DsRed, DSRed2, and EYFP, BFP, YFP, among others, are commercially available from, inter alia, Clontech Laboratories, Inc. (Palo Alto, Calif.).

The cultured cells/tissues comprising nucleic acid molecules comprising a nucleic acid sequence encoding a hepadnavirus e antigen fused to a reporter gene (like luciferase, GFP etc.) can be monitored for evidence of transcription of the reporter gene as a function of the concentration of test compound/candidate molecule in the culture medium. The variation in transcription levels of the reporter gene as a function of the concentration of test compound indicates the capacity of test compound/candidate molecule to inhibit cccDNA.

Reporter proteins are usually larger than the herein above described tags of low molecular weight, like epitope tags. Due to the longer insertion of, for example, a nucleic acid molecule comprising a nucleic acid sequence encoding luciferase compared to a nucleic acid sequence encoding smaller (epitope) tags (like an HA-tag), the expression of downstream viral core and pol from the recombinant pregenomic RNA can be reduced, so that transcomplement of core/pol may be required to restore the viral replication. For example, cell(s)/cell line(s) that constitutively express hepadnaviral core protein and hepadnaviral polymerase (core/pol) can be used in accordance with the present invention in particular in this context.

The use of a tagged hepadnavirus e antigen containing two or more tags is envisaged herein. The use of two or more tags can allow an even more reliable, and hence advantageous, assessment of the tagged hepadnavirus e antigen. For example, if the two or more tags are different tags (e.g. one tag is an HA-tag, the second tag is a His-tag), antibodies specifically binding to both tags can be employed. Such an assay can accordingly use e.g two epitope antibodies for example for ELISA detection to further increase the assay specificity.

It was found herein that the insertion of a 22 amino acid 3×FLAG tag insertion supports efficient HBV replication. Accordingly, it is believed that the use of e.g. tandem chimeric epitope tags, such as HA-linker-FLAG, can also be employed herein.

In accordance with the above, one tag may consist of 6 to 22 amino acids, when two or more tags are used (e.g. two or more different tags). It is particularly envisaged herein that the overall length of the tags (i.e. the sum of the amino acid residues of the two or more stages) to be used herein does not exceed a maximum of about 22 amino acids, because the expression of downstream viral core and pot from the recombinant pregenomic RNA might be reduced, as described in context of reporter proteins (like luciferase) above. If such a reduced expression of downstream viral core and pol occurs, e.g. when the overall length of the two or more tags exceeds about 22 amino acids, transcomplement of core/pol may be required to restore the viral replication. For example, cell(s)/cell line(s) that constitutively express hepadnaviral core protein and hepadnaviral polymerase (core/pol) can be used in accordance with the present invention in particular in this context.

Like a nucleic acid encoding only one tag, a nucleic acid encoding two or more tags can be fused to the 5'-end of the nucleic acid encoding a hepadnavirus e antigen, inserted within the nucleic acid encoding a hepadnavirus e antigen and/or fused to the 3'-end of the nucleic acid encoding a hepadnavirus e antigen. The tags can be separated by a linker: tag-linker-tag if two tags are used, tag-linker-tag-linker-tag, if three tags are used and so on.

Thus, the resulting fusion protein can comprise two or more tags at the N-terminus, internally (i.e. within the hepadnavirus e antigen/as internal epitope), and/or at the C-terminus. As shown herein, an internal epitope tag can be used for reliable assessment of the level of a tagged hepadnavirus e antigen and is therefore preferred. The use of resulting fusion protein with one tag e.g. at the N-terminus and e.g. a second internal tag and/or e.g a third at the C-terminus is envisaged herein. Further combinations are readily apparent and encompassed without deferring from the gist of this invention.

The two or more tags can be two or more of a hemagglutinin (HA)-tag, His-tag, Flag-tag, c-myc-tag, V5-tag and/or C9-tag. The Flag-tag can be 1×Flag-tag or 3×Flag-tag.

In the following, the nucleic acid molecule to be used in accordance with the present invention is described in more detail.

The nucleic acid molecule can comprise a nucleic acid sequence encoding a hepadnavirus precore protein, like a HBV precore protein. An exemplary nucleic acid sequence encoding a hepadnavirus precore protein is shown in SEQ ID NO: 15 and an exemplary amino acid sequence of a hepadnavirus precore protein is shown in SEQ ID NO: 17.

The nucleic acid molecule can comprise a nucleic acid sequence encoding the one or more tag as defined and explained herein above. The sequence encoding the one or more tag can be (inserted) 3' downstream of the nucleic acid sequence encoding the N-terminal signal peptide and the linker of the hepadnavirus precore protein.

In relation to Hepatitis B virus the N-terminal signal peptide and the linker constitute the N-terminal 29 amino acids of the precore protein as shown, for example, in SEQ ID NO. 17. Accordingly, the nucleic acid sequence encoding the one or more tag can be (inserted) 3' downstream of the nucleic acid sequence encoding the N-terminal 29 amino acids of a hepatitis B virus precore protein. In other words, the nucleic acid sequence encoding the one or more tag can be (inserted) 3' downstream of the nucleic acid sequence constituting the 87 nucleic acid residues from the 5' end of the nucleic acid encoding the HBV precore protein (the nucleic acid encoding the HBV precore protein being shown, for example, in SEQ ID NO. 15). On the protein level, the one or more tag can be inserted C-terminal of the amino acid residue corresponding to position 29 of a hepatitis B virus precore protein (the amino acid of a precore protein being shown, for example, in SEQ ID NO. 17).

In relation to HBeAg the linker constitutes the N-terminal 10 amino acids of the HBeAg as shown, for example, in SEQ ID NO. 18. With regard to HBeAg, the nucleic acid sequence encoding the one or more tag can be (inserted) 3' downstream of the nucleic acid sequence encoding the N-terminal 10 amino acids of HBeAg. In other words, the nucleic acid sequence encoding the one or more tag can be (inserted) 3' downstream of the nucleic acid sequence constituting the 30 nucleic acid residues from the 5' end of the nucleic acid encoding the HBV HBeAg (the nucleic acid encoding the HBeAg being shown, for example, in SEQ ID NO. 16). On the protein level, the one or more tag can be inserted C-terminal of the amino acid residue corresponding to position 10 of HBeAg (the amino acid of an HBeAg being shown, for example, in SEQ ID NO. 18).

More precisely, the nucleic acid sequence encoding the one or more tag can be (inserted) between nucleotides corresponding to positions 87 and 88 of a nucleic acid sequence encoding a HBV precore protein (the nucleic acid sequence encoding a HBV precore protein being shown e.g. in SEQ ID NO. 15). These positions delimit in the epsilon structure of pgRNA of a hepadnavirus or in the epsilon as encoded by a hepadnavirus genome the coding sequence of a linker and the ORF start codon of a nucleic acid sequence encoding the hepadnavirus core protein. In relation to HBV, position 87 is the last 3' nucleotide of a sequence encoding a linker and position 88 is the first nucleotide of a sequence encoding the core protein.

On the protein level, the one or more tag can be inserted between amino acid residues corresponding to positions 29 and 30 of a hepatitis B virus precore protein (the amino acid of a precore protein being shown, for example, in SEQ ID NO. 17).

Likewise, the nucleic acid sequence encoding the one or more tag can be (inserted) between nucleotides corresponding to positions 30 and 31 of a nucleic acid sequence encoding HBeAg (the nucleic acid sequence encoding HBeAg being shown e.g. in SEQ ID NO. 16). On the protein level, the one or more tag can be inserted between amino acid residues corresponding to positions 10 and 11 of an HBeAg (the amino acid of HBeAg being shown, for example, in SEQ ID NO. 18).

The nucleic acid encoding the one or more tag can be (inserted) 5' upstream of a nucleic acid encoding a hepadnavirus core protein, such as a HBV core protein. An exemplary nucleic acid encoding a HBV core protein is shown in SEQ ID NO: 23. An exemplary amino acid sequence of a HBV core protein is shown in SEQ ID NO: 24.

The above defined insertion site of the nucleic acid sequence encoding one or more tags can also be defined by positions of nucleotides in a hepadnavirus genome. In relation to a HBV genome the nucleic acid molecule comprising a sequence encoding the one or more tag can, in accordance with the above, be inserted between nucleotides corresponding to position C1902 and position A1903 of the HBV genome. These positions can be determined according to nomenclature, as described, for example, in Galibert, F., et al (1979), Nature 281:646-650.

It is evident that the nucleotide (positions) "C1902" and "A1903" as employed herein refer to the last nucleotide of precore region coding sequence and the first nucleotide of the core AUG, respectively. They are conserved among the different HBV genotype (A-H) sequences (as also provided herein and shown in SEQ ID NOs: 27-34). Accordingly, exemplary, non-limiting nucleic acid sequences of HBV genomes to be used herein are shown in SEQ ID NO: 27, 28, 29, 30, 31, 32, 33 or 34. Yet, nucleotide "C", but not the "A" in the core AUG, or their positions may be different in sequences from some rare (clinical) isolates. Such sequences are also comprised in this invention.

In accordance with the present invention, the nucleic acid sequence encoding one or more tags can be inserted between nucleotides corresponding to position C1902 and position A1903 of a hepadnavirus genome other than the HBV genome. These corresponding positions in hepadnavirus genomes (i.e. the positions in a hepadnavirus genome that correspond to position C1902 and position A1903 of the HBV genome) can be determined readily. In other words, the nucleic acid sequence encoding the one or more tag can be inserted between an epsilon structure of a hepadnavirus pgRNA, preferably of HBV pgRNA, or an epsilon encoded by a hepadnavirus genome (preferably, an HBV genome) and an ORF start codon of a nucleic acid sequence encoding the hepadnavirus core protein.

For example, if the nucleic acid molecule comprises a nucleic acid sequence encoding a hepadnavirus precore protein, the sequence encoding the one or more tag can be (inserted) 3' downstream of the nucleic acid sequence encoding the N-terminal signal peptide and the linker of the hepadnavirus precore protein. The nucleic acid sequence encoding the N-terminal signal peptide and the linker of the hepadnavirus precore protein can readily be determined. The sequence starts at (and hence includes) an ORF start codon of the nucleic acid sequence encoding the hepadnavirus precore protein and ends prior to an ORF start codon of the nucleic acid sequence encoding the hepadnavirus core protein (i.e. the coding sequence of the core protein is excluded). On the protein level, the one or more tag can be inserted C-terminal of the amino acid residue corresponding to the C-terminal final amino acid of the linker (the linker following the N-terminal signal peptide).

Accordingly, the nucleic acid sequence encoding the one or more tag can be (inserted) 3' downstream of the nucleic acid sequence encoding the N-terminal amino acids of a hepadnavirus e antigen. These N-terminal amino acids constitute the "linker" in a hepadnavirus precore protein. On the protein level, the one or more tag can be inserted C-terminal of the final C-terminal amino acid residue of the linker.

More precisely, the nucleic acid sequence encoding the one or more tag can be (inserted) between nucleotides corresponding to positions 87 and 88 of a nucleic acid sequence encoding a HBV precore protein (the nucleic acid sequence encoding a HBV precore protein being shown e.g. in SEQ ID NO. 15). On the protein level, the one or more tag can be inserted between amino acid residues corresponding to positions 29 and 30 of a hepatitis B virus precore protein (the amino acid of a precore protein being shown, for example, in SEQ ID NO. 17). These positions delimit in the epsilon structure of a hepadnavirus pgRNA, preferably HBV pgRNA, or in the epsilon structure as encoded by a hepadnavirus genome, preferably HBV genome, the coding sequence of a linker and the ORF start codon of a nucleic acid sequence encoding the hepadnavirus core protein. In relation to HBV, position 87 is the last 3' nucleotide of a sequence encoding a linker and position 88 is the first nucleotide of a sequence encoding the core protein. The corresponding positions in hepadnavirus HBV precore protein (i.e. the positions in a hepadnavirus genome that correspond to positions 87 and 88 of a nucleic acid sequence encoding a HBV precore protein) can be readily determined.

Likewise, the nucleic acid sequence encoding the one or more tag can be (inserted) between a nucleic acid sequence encoding the N-terminal signal peptide and linker of a hepadnavirus precore protein and a nucleic acid sequence encoding a hapadnavirus core protein.

For example, the nucleic acid sequence can be (inserted) between nucleotides corresponding to positions 30 and 31 of a nucleic acid sequence encoding HBeAg (the nucleic acid sequence encoding HBeAg being shown e.g. in SEQ ID NO. 16). On the protein level, the one or more tag can be inserted between amino acid residues corresponding to positions 10 and 11 of an HBeAg (the amino acid of HBeAg being shown, for example, in SEQ ID NO. 18). These positions delimit the coding sequence of the N-terminal hepadnavirus linker in the precore protein (or the coding sequence of the N-terminal hepadnavirus linker in a hepadnavirus e antigen) and the ORF start codon of a nucleic acid sequence encoding the hepadnavirus core protein. In relation to HBV, position 30 is the last 3' nucleotide of a sequence encoding a linker in a nucleic acid sequence encoding HBeAg. Position 31 is the first nucleotide of a sequence encoding the core protein. The corresponding positions in a nucleic acid sequence encoding hepadnavirus e antigen (i.e. the positions in a hepadnavirus e antigen that correspond to position 30 and 31 of a nucleic acid sequence encoding HBeAg) can be readily determined.

The nucleic acid encoding the one or more tag can be (inserted) 5' upstream of a nucleic acid encoding a hepadnavirus core protein, preferably a HBV core protein. An exemplary nucleic acid encoding a HBV core protein is shown in SEQ ID NO: 23. An exemplary amino acid sequence of a HBV core protein is shown in SEQ ID NO: 24. In other words, the nucleic acid encoding the one or more tag can be inserted between an epsilon structure of a hepadnavirus pgRNA, preferably HBV pgRNA, or between an epsilon structure as encoded by a hepadnavirus genome, (preferably a HBV genome) and an ORF start codon of nucleic acid sequence encoding the hepadnavirus core protein, preferably a HBV core protein.

As mentioned above, the nucleic acid molecule to be used/provided herein can comprise a sequence encoding the one or more tag wherein said sequence is inserted into the epsilon structure of a hepadnavirus pgRNA, preferably HBV pgRNA, or into an epsilon structure as encoded by a hepadnavirus genome, preferably an HBV genome. An exemplary epsilon structure encoded by the HBV genome is shown in FIG. 1. In relation to HBV, the epsilon structure as encoded by the HBV genome starts at (and includes) position T1849 and ends at (and includes) position A1909 of a HBV genome. An exemplary nucleic acid sequence of an epsilon structure encoded by a HBV genome is shown in SEQ ID NO: 25.

As described herein above, the nucleic acid molecule comprising a sequence encoding the one or more tag can be inserted into the lower stem of the epsilon structure of a hepadnavirus pgRNA, preferably HBV pgRNA, or as encoded by a hepadnavirus genome, preferably a HBV genome. An exemplary lower stem of an epsilon structure as encoded by a HBV genome is shown in FIG. 1. For example the nucleic acid sequence encoding the one or more tag can be inserted between nucleotides corresponding to positions 87 and 88 of a nucleic acid sequence encoding a HBV precore protein (the nucleic acid sequence encoding a HBV precore protein being shown e.g. in SEQ ID NO. 15), or between nucleotides corresponding to positions 30 and 31 of a nucleic acid sequence encoding HBeAg (the nucleic acid sequence encoding HBeAg being shown e.g. in SEQ ID NO. 16), or between nucleotides corresponding to position C1902 and position A1903 of a HBV genome. All these positions are in the lower stem of an epsilon structure of a hepadnavirus pgRNA, preferably HBV pgRNA, or in the lower stem of an epsilon structure as encoded by a hepadnavirus genome, preferably a HBV genome.

It is envisaged and preferred herein that the nucleic acid molecule comprises 5' of the sequence encoding the one or more tag a sequence that is capable of forming base pairs with the lower stem of the epsilon structure of a hepadnavirus pgRNA, preferably HBV pgRNA, or the lower stem of an epsilon structure as encoded by a hepadnavirus genome, preferably a HBV genome. It is believed that the experiments and teaching described and provided herein in relation to hepatitis B virus/tagged hepatitis B virus e antigen is generally applicable to hepadnaviruses/tagged hepadnavirus e antigen. The only modification to the insertion sequence used for HBV can relate to the modification of the 5' flanking sequence of the nucleic acid sequence encoding the (epitope) tag to maintain the base pairing of epsilon of a hepadnavirus pgRNA, preferably HBV pgRNA, or epsilon as encoded by a hepadnavirus genome, preferably a HBV genome, for each specific hepadnavirus, preferably HBV. Based on the teaching of the present invention, a person skilled in the art is readily capable of designing and preparing a nucleic acid sequence 5' of the nucleic acid sequence encoding the tag to maintain the base pairing with epsilon structure of a hepadnavirus pgRNA, preferably HBV pgRNA, or an epsilon structure as encoded by a hepadnavirus genome, preferably a HBV genome. In particular in terms of duck hepatitis B virus (DHBV), since the start codon of its core ORF is located downstream of epsilon it thus not even be necessary to introduce a 5' flanking sequence of the nucleic acid sequence encoding the (epitope) tag to maintain the base pairing of epsilon for DHBV.

As shown in FIG. 1 a nucleic acid sequence was inserted between nucleotides corresponding to position C1902 and A1903 of the HBV genome, wherein said nucleic acid sequence contained a 5'-flanking region of 9 nucleotides (i.e. 5' of the nucleic acid sequence encoding the one or more tag) that formed base pairs with the lower stem of the epsilon structure of a hepadnavirus pgRNA, preferably HBV pgRNA, or of an epsilon structure as encoded by a hepadnavirus genome, preferably a HBV genome, for example with nucleotides corresponding to positions T1849 to T1855 of the HBV genome.

It is an important and preferred aspect of the present invention that the nucleic acid sequence encoding the one or more tag as defined herein and/or to be inserted as described herein above further comprises a nucleic acid sequence that is capable of forming base pairs with the epsilon structure of a hepadnavirus pgRNA, preferably HBV pgRNA, or of an epsilon structure as encoded by a hepadnavirus genome, preferably a HBV genome, particularly the lower stem of the epsilon structure of a hepadnavirus pgRNA, preferably HBV pgRNA, or of an epsilon structure as encoded by a hepadnavirus genome, preferably a HBV genome. By using a nucleic acid sequence that are capable of forming base pairs with the epsilon structure, it is aimed to preserve the epsilon structure of a hepadnavirus pgRNA, preferably HBV pgRNA, or of an epsilon structure as encoded by a hepadnavirus genome, preferably a HBV genome. The epsilon structure is, in turn thought to be important for replication, production of cccDNA and expression/production of (tagged) hepadnavirus e antigen, preferably HBV e antigen.

Preferably, the sequence that is capable of forming base pairs with the lower stem of the epsilon structure of a hepadnavirus pgRNA, preferably HBV pgRNA, or of an epsilon structure as encoded by a hepadnavirus genome, preferably a HBV genome, is capable of forming base pairs with nucleotides corresponding preferably to positions T1849 to A1854 or, optionally, corresponding to positions T1849 to T1855 of the HBV genome. Typically, the formation of base pairs in pgRNA occurs between matching ribonucleotides, like A-U, G-C, and wobble base pair G-U. If the epsilon structure is maintained, replication, production of cccDNA and/or expression/production of (tagged) hepadnavirus e antigen is/are not hampered in the nucleic acid molecules to be used/provided herein.

It should be noted that the left arm of the epsilon structure is part of the nucleic acid sequence encoding the signal peptide of hepadnavirus e antigen (like HBeAg) and, thus, should be kept unchanged. The designed insertion at the right arm of the epsilon as described should not alter the base pairing of the lower stem. In the exemplified insertion shown in FIG. 1, the only nucleotide change related to A1903G (i.e. A was replaced by G at position 1903 of the HBV genome). The point mutation at position 1903 moves the core ORF out of the epsilon of hepadnavirus pgRNA, preferably HBV pgRNA, or of an epsilon as encoded by a hepadnavirus genome, preferably a HBV genome, allowing the maintenance of epsilon structure and the insertion of a tag in front of core AUG. The core protein is translated from pregenomic RNA which is transcribed after the start codon of precore ORF, so that the tag will not be incorporated into core protein.

The 5' flanking sequence of the epitope tag that is capable of forming base pairs with the (lower stem of the) epsilon structure of a hepadnavirus pgRNA, preferably HBV pgRNA, or of an epsilon structure as encoded by a hepadnavirus genome, preferably a HBV genome, of a hepadnavirus genome consists of up to 3, 6 or 9 nucleotides, typically of 9 nucleotides.

An exemplary sequence that is capable of forming base pairs with the lower stem of the epsilon structure of a hepadnavirus pgRNA, preferably HBV pgRNA, or of an epsilon structure as encoded by a hepadnavirus genome, preferably a HBV genome consists of the sequence shown in SEQ ID No. 26. An exemplary sequence that is capable of forming base pairs with the lower stem of the epsilon structure of a hepadnavirus pgRNA, preferably HBV pgRNA, or of an epsilon structure as encoded by a hepadnavirus genome, preferably a HBV genome encodes a polypeptide as shown in SEQ ID NO. 40.

The nucleic acid molecule to be used/provided herein can further comprise 3' of the sequence encoding the one or more tag a nucleic acid sequence encoding a linker. The linker can consist of one or more amino acid residues. Preferably, the linker consists of only one amino acid residue, such as a glycine residue.

For example, the nucleic acid sequence encoding the linker consists of the sequence GGC; or the nucleic acid sequence encodes a glycine residue. The GGC is copied from the original 3 nucleotides in front of the AUG of core ORF, which, together with the AUG, assemble a typical Kozak motif for optimal translation initiation. Thus, the linker that can be used/inserted is preferably and suitably selected so as to keep the authentic Kozak motif of the core start codon.

For example, the nucleic acid molecule comprising a nucleic acid sequence encoding a tagged hepadnavirus e antigen can comprise a nucleic acid sequence as shown in SEQ ID NO. 41. For example, the nucleic acid molecule comprising a nucleic acid sequence encoding a tagged hepadnavirus e antigen can comprise a nucleic acid sequence encoding an amino acid sequence as shown in SEQ ID NO. 42. The exemplary nucleic acid sequence as shown in SEQ ID NO. 41 consists of a nucleic acid sequence capable of forming base pairs with the (lower stem) of the epsilon structure (GTGGACATC; particularly the nucleotides GTGGACAT form base pairs with nucleotides corresponding to positions T1849 to T1855 of the HBV genome), a nucleic acid sequence encoding a HA-tag and a nucleic acid sequence encoding a glycine residue as linker (the latter nucleic acid sequence is primarily useful to keep the authentic Kozak motif of core start codon).

It is envisaged herein that the one or more tag is fused in frame into the hepadnavirus c antigen, preferably the Hepatitis B virus e antigen (HBeAg). Likewise it is envisaged herein that the nucleic acid sequence encoding the one or more tag (with a potential 5' flanking nucleic acid sequence capable of forming base pairs with the (lower stem of the) epsilon structure and/or with a potential 3' nucleic acid sequence keeping the authentic Kozak motif of core start condon or encoding a linker) is fused in frame to the nucleic acid sequence encoding the hepadnavirus e antigen, preferably the Hepatitis B virus e antigen (HBeAg).

The nucleic acid molecule to be used and provided in the present invention can comprise a hepadnavirus genome, preferably a Hepatitis B virus (HBV) genome. For example, the HBV genome is the genome of HBV genotype A, B, C, D, E, F, G or H. Exemplary, non-limiting nucleic acid sequences of HBV genomes to be used herein are shown in SEQ ID NO: 27, 28, 29, 30, 31, 32, 33 or 34. The HBV genome can be the genome of HBV genotype D, particularly a genome of HBV subgenotype ayw (like the HBV genome shown in SEQ ID NO: 27).

In accordance with the present invention only those nucleic acid molecules, such as hepadnavirus genomes, are to be used that allow (substantial) expression/production of (tagged) hepadnavirus e antigen. For example, some clinical HBV variants are known that to do not allow substantial expression/production of hepadnavirus e antigen. In some clinical HBV variants, the HBeAg negativity is due to either basal core promoter (BCP) double mutation (A1764T/G1766A in genotype D) or a precore (pC) mutation (G1898A in genotype D). While the BCP mutations reduce HBeAg through downregulation of precore mRNA transcription, the pC mutation introduces a premature stop codon to stall precore translation. Such hepadnavirus variants are less suitable for the herein provided methods.

In a preferred embodiment of the present invention, tagged HBeAg comprises or consists of an amino acid sequence as shown in SEQ ID NO: 22. The corresponding nucleic acid sequence encoding the tagged HBeAg is shown in SEQ ID NO: 20. These sequences are particularly useful in context of this invention but are merely examples of preferred embodiments.

A nucleic acid sequence encoding a HA-tagged precore protein, i.e. a precursor of the tagged HBeAg, is shown in SEQ ID NO: 19. Because this nucleic acid sequence encodes a precursor of the tagged HBeAg, it may be considered as a nucleic acid sequence encoding tagged HBeAg. The corresponding amino acid sequence is shown in SEQ ID NO: 21.

The following relates in more detail to the production of tagged hepadnavirus e antigen and the use thereof in the assessment of the capacity of a candidate molecule to inhibit cccDNA of a hepadnavirus.

The nucleic acid to be used/provided herein can be transcriptable into pregenomic (pg) hepadnavirus RNA, in particular pregenomic (pg) HBV RNA.

It is envisaged herein that the said nucleic acid can be designed to prevent the translation of the tagged hepadnavirus e antigen. For example, the nucleic acid does not contain a start codon ATG 5' upstream of the nucleic acid encoding a tagged hepadnavirus e antigen. In relation to HBV, the start codon of the nucleic acid encoding the precore protein can be deleted or mutated. For example, such a start codon (that is to be deleted/mutated) can correspond to nucleotides at (and including) position 1816 to (and including) position 1818 of a HBV genome; see for example FIG. 1.

Avoiding the translation of the tagged hepadnavirus e antigen can be advantageous, to avoid production/expression thereof at the start of the assay. It is the aim of the present invention that tagged hepadnavirus e antigen is used as a surrogate marker for cccDNA. If tagged hepadnavirus e antigen is produced all the time, its expression/production does not necessarily correlate with the production of cccDNA. As shown in FIG. 5, the start codon can be restored at a later stage of the assay, when/after cccDNA is formed, so that the expression/production (i.e. the level) of tagged hepadnavirus e antigen truly reflects the production/level of cccDNA of a hepadnavirus. Thus, for an even more reliable assessment of the capacity of a candidate molecule to inhibit cccDNA, it is advantageous that production/expression of the tagged hepadnavirus e antigen is inhibited at the start of the assay e.g. by removing/mutating the start codon of the corresponding nucleic acid encoding same and that the production/expression of the tagged hepadnavirus e antigen is allowed later in order to reflect the production/level of cccDNA of a hepadnavirus.

For example, a start codon ATG 5' upstream of the nucleic acid encoding a tagged hepadnavirus e antigen as defined and described herein above can be replaced by the nucleic acids TG. Accordingly, the nucleic molecule to be used and provided herein can be modified e.g. by point mutation in order to prevent the translation of a tagged hepadnavirus e antigen.

Step (a) of the method to be used in accordance with the present invention, can further comprises a step (aa) that comprises culturing a cell comprising a nucleic acid molecule comprising a nucleic acid sequence encoding a tagged hepadnavirus e antigen in conditions allowing (i) the synthesis of hepadnavirus pregenomic (pg) RNA;
(ii) the reverse transcription of said synthesized pgRNA into a minus strand DNA;
(iii) the synthesis of a second plus strand DNA so that said minus strand DNA and said plus strand DNA form a double stranded relaxed circular DNA;
(iv) formation of cccDNA from said relaxed circular double stranded DNA;
(v) restoration of conditions allowing the translation of the tagged hepadnavirus e antigen;
(vi) transcription of an mRNA encoding a tagged hepadnavirus e antigen;
(vii) translation of a tagged hepadnavirus e antigen;

The restoration of conditions allowing the translation of the tagged hepadnavirus e antigen can relate to or be the restoration of the start codon as defined and explained above.

The nucleic acid molecule comprising a nucleic acid sequence encoding the tagged hepadnavirus e antigen can be comprised in a vector, in particular an expression vector.

The vector can, for example, comprise a sequence as shown in SEQ ID NO: 35.

The nucleic acid molecule comprising a nucleic acid sequence encoding the tagged hepadnavirus e antigen, preferably Hepatitis B virus e antigen (HBeAg), can be under control of an inducible promoter. (An) exemplary, non-limiting inducible promoter(s) to be used herein (is) are (a) tetracycline-inducible promoter(s), (a) doxycline-inducible promoter(s), (an) antibiotic-inducible promoter(s), (a) copper-inducible promoter(s), (an) alcohol-inducible promoter(s), (a) steroid-inducible promoter(s), or (a) herbicide-inducible promoter(s). The tetracycline inducible promoter (commercially available from e.g. Clontech) used in the herein provided experiments works in a tet-off manner. It is believed that a tetracycline inducible promoter working in a tet-on manner can likewise be used herein. tet-on/off system are, for example, available from Clontech and Invitrogen, either in plasmid or viral (retro-, adeno) backbones. Besides tetracycline/doxycline inducible promoter, as described above other inducible promoters that respond e.g. to antibiotics, copper, alcohol, steroids, or herbicides, among other compounds, are also suitable. For example, the inducible promoter is a CMV promoter. The inducible promoter can be a tet-EF-1 alpha promoter.

Further, one or more stop codons can be introduced into the coding region of one or more hepadnavirus envelope proteins, like one or more hepadnavirus envelope proteins is/are one or more HBV envelope proteins. The one or more hepadnavirus (HBV) envelope protein can be one or more of large surface protein (L), middle surface protein (M) and small surface protein (S). In one embodiment, the HBV envelope protein is small surface protein (S). (An) exemplary coding region(s) of the one or more HBV envelope proteins (is) are shown in SEQ ID NO: 36 (L), SEQ ID NO: 37 (M) and/or SEQ ID NO: 38 (S). In HBV nucleotides 217 to 222 (TTGTTG) of SEQ ID NO: 38 (S) can be mutated to e.g. TAGTAG to prevent the expression of envelope proteins.

A candidate molecule is determined to be capable of inhibiting cccDNA of a hepadnavirus, if the (expression) level of the surrogate marker of cccDNA, tagged hepadnavirus e antigen, is decreased compared to a control.

It is to be understood that the assessed (expression) level of a tagged hepadnavirus e antigen is compared to a control, like a standard or reference value, of the (expression) level of a tagged hepadnavirus e antigen. The control (standard/reference value) may be assessed in a cell, tissue, or non-human animal as defined herein, which has not been contacted with a candidate molecule. Alternatively, the control (standard/reference value) may be assessed in a cell, tissue, or non-human animal as defined herein prior to the above contacting step. The decrease in the (expression) level of a tagged hepadnavirus e antigen upon contacting with (a) candidate molecule(s) may also be compared to the decrease of the (expression) level of a tagged hepadnavirus e antigen induced by (a) routinely used reference compound(s), like a compound known to be unable to inhibit cccDNA. A skilled person is easily in the position to determine/assess whether the (expression) level of a tagged hepadnavirus e antigen is decreased.

Vice versa, and without deferring from the gist of the present invention, a positive control can be used, for example a reference compound(s), like a compound known to be capable of inhibiting cccDNA. If the (expression) level of the surrogate marker of cccDNA, tagged hepadnavirus e antigen, is equivalent to or even increased compared to such a (positive) control, a candidate molecule is determined to be capable of inhibiting cccDNA of a hepadnavirus.

In accordance with this invention, in particular the screening or identifying methods described herein, a cell, tissue or non-human animal to be contacted with a candidate molecule comprises a nucleic acid molecule comprising a nucleic acid sequence encoding a tagged hepadnavirus e antigen as defined herein.

For example said cell, tissue or non-human animal can be capable of expressing a tagged hepadnavirus e antigen as defined herein. As explained herein, the capability of a candidate molecule to inhibit/antagonize cccDNA can, accordingly, be detected by measuring the expression level of such gene products, particular the protein expression level, of a nucleic acid sequence encoding a tagged hepadnavirus e antigen. A low(er) (protein) expression level (compared to a control (standard or reference value)) is indicative for the capacity of the candidate molecule to act as inhibitor/antagonist.

Due to the reduced transcript/expression level also the level of the translated gene product (i.e. the protein level) will be decreased. The (protein) level of the above described tagged hepadnavirus e antigen proteins typically correlates with the signal strength of a detectable signal associated with the tagged hepadnavirus e antigen proteins. Exemplary tagged hepadnavirus e antigen proteins comprise can comprise a reporter as described above (e.g. luciferase, (green/red) fluorescent protein and variants thereof, EGFP (enhanced green fluorescent protein), and the like).

Accordingly, a decrease in reporter signal upon contacting the cell/tissue/non-human animal with a candidate molecule will indicate that the candidate molecule is indeed a cccDNA inhibitor/antagonist and, thus, capable of inhibiting cccDNA. The candidate molecules which decrease the level of tagged hepadnavirus e antigen as defined herein above are selected out of the candidate molecules tested, wherein those molecules are preferably selected which strongly decrease the level of tagged hepadnavirus e antigen (reflected, for example, in a decrease in the reporter signal).

It is envisaged in the context of the present invention (in particular the screening/identifying methods disclosed herein) that also cellular extracts can be contacted (e.g. cellular extracts comprising a nucleic acid molecule comprising a nucleic acid sequence encoding a tagged hepadnavirus e antigen as described and defined herein). For example, these cellular extracts may be obtained from the (transgenic/genetically engineered) cell(s), tissue(s) and/or non-human animal(s) to be used herein, in particular to be contacted with the candidate molecule.

The use of such cellular extracts is particular advantageous since it allows the assessment of the activity of a candidate molecule in vitro. The assessing/screening methods taking advantage of such (cellular) extracts can, for example, be used in prescreening candidate molecules, wherein the molecules selected in such a prescreen are then subject to subsequent screens, for example in the cell-based methods disclosed herein, in particular in methods wherein a (transgenic) cell(s), tissue(s) and/or non-human animal(s) are contacted with a candidate molecule. In this context, it is accordingly preferred that the candidate molecule has been selected in the in vitro pre-screening method, described herein above and below.

Thus, the term "cell" as used herein encompasses (transgenic/genetically engineered) cell(s), (transgenic/genetically engineered) tissue(s) and/or non-human (transgenic/genetically engineered) animal(s) and also cellular extracts derived therefrom.

It is to be understood that in a high throughput screening routinely, many (often thousands of candidate molecules) are screened simultaneously. Accordingly, in a (first) screen candidate molecules are selected, which decrease the level of tagged hepadnavirus e antigen.

Step (a) of the screening methods of the present invention, i.e. the "contacting step" may also be accomplished by adding a (biological) sample or composition containing said candidate molecule or a plurality of candidate molecules (i.e. various different candidate molecules) to the cell to be analyzed ((a) cell(s)/tissue(s)/non-human animal comprising a nucleic acid molecule comprising a nucleic acid sequence encoding tagged hepadnavirus e antigen).

Generally, the candidate molecule(s) or a composition comprising/containing the candidate molecule(s) may for example be added to a (transfected) cell, tissue or non-human animal comprising a nucleic acid molecule comprising a nucleic acid sequence encoding tagged hepadnavirus e antigen. As defined and disclosed herein, the term "comprising a nucleic acid molecule comprising a nucleic acid sequence encoding tagged hepadnavirus e antigen" implies the use of reporters. Also reporter constructs comprising a promoter and/or enhancer region of can be used herein.

The cell(s), tissue(s) and/or non-human animals to be used or provided in the present invention, in particular in context of the screening/identifying methods, can be stably or transiently transfected with nucleic acid molecule comprising a nucleic acid sequence encoding a tagged hepadnavirus e antigen disclosed herein.

The compounds/molecules capable of inhibiting cccDNA (as reflected in a decreased level of tagged hepadnavirus e antigen), are expected to be beneficial as agents in pharmaceutical settings disclosed herein and to be used for medical purposes, in particular, in the treatment of the diseases related to hepadnaviruses, in particular chronic diseases related to hepadnaviruses, such as chronic hepatitis and in particular chronic hepatitis B.

Candidate molecules/compounds which may function as specific an "antagonist" or "inhibitor" of cccDNA of a hepadnavirus may be small binding molecules such as small (organic) compounds.

The term "small molecule" in the context of drug discovery is known in the art and relates to medical compounds having a molecular weight of less than 2,500 Daltons, preferably less than 1,000 Daltons, more preferably between 50 and 350 Daltons. (Small) binding molecules comprise natural as well as synthetic compounds. The term "compound" (or likewise "molecule") in context of this invention comprises single substances or a plurality of substances. Said compounds/molecules may be comprised in, for example, samples, e.g., cell extracts from, e.g., plants, animals or microorganisms. Furthermore, said compound(s) may be known in the art but hitherto not known to be capable of (negatively) influencing cccDNA of a hepadnavirus. The plurality of compounds may be, e.g., added to a sample in vitro, to the culture medium or injected into the cell.

Candidate agents may also comprise functional groups necessary for structural interaction with proteins, particularly hydrogen bonding, and typically include at least an amine, carbonyl, hydroxyl or carboxyl group, preferably at least two of the functional chemical groups. The candidate agents often comprise carbocyclic or heterocyclic structures and/or aromatic or polyaromatic structures substituted with one or more of the above functional groups.

Exemplary classes of candidate agents may include heterocycles, peptides, saccharides, steroids, and the like. The compounds may be modified to enhance efficacy, stability, pharmaceutical compatibility, and the like. Structural identification of an agent may be used to identify, generate, or screen additional agents. For example, where peptide agents are identified, they may be modified in a variety of ways to enhance their stability, such as using an unnatural amino acid, such as a D-amino acid, particularly D-alanine, by functionalizing the amino or carboxylic terminus, e.g. for the amino group, acylation or alkylation, and for the carboxyl group, esterification or amidification, or the like. Other methods of stabilization may include encapsulation, for example, in liposomes, etc.

As mentioned above, candidate agents are also found among other biomolecules including amino acids, fatty acids, purines, pyrimidines, nucleic acids and derivatives, structural analogs or combinations thereof. Candidate agents are obtained from a wide variety of sources including libraries of synthetic or natural compounds. For example, numerous means are available for random and directed synthesis of a wide variety of organic compounds and biomolecules, including expression of randomized oligonucleotides and oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification, etc. to produce structural analogs.

It is also envisaged in the present invention that compounds/molecules including, inter alia, peptides, proteins, nucleic acids (including cDNA expression libraries), small organic compounds, ligands, PNAs and the like can be assessed for the capacity to inhibit cccDNA. Said compounds can also be functional derivatives or analogues.

Methods for the preparation of chemical derivatives and analogues are well known to those skilled in the art and are described in, for example, Beilstein, "Handbook of Organic Chemistry", Springer Edition New York, or in "Organic Synthesis", Wiley, N.Y. Furthermore, said derivatives and analogues can be tested for their effects, i.e. their antagonistic effects on cccDNA in according with the present invention.

Furthermore, peptidomimetics and/or computer aided design of appropriate antagonists or inhibitors of cccDNA can be used. Appropriate computer systems for the computer aided design of, e.g., proteins and peptides are described in the art, for example, in Berry (1994) Biochem. Soc. Trans. 22:1033-1036; Wodak (1987), Ann. N. Y. Acad. Sci. 501:1-13; Pabo (1986), Biochemistry 25:5987-5991. The results obtained from the above-described computer analysis can be used in combination with the method of the invention for, e.g., optimizing known compounds, substances or molecules. Appropriate compounds can also be identified by the synthesis of peptidomimetic combinatorial libraries through successive chemical modification and testing the resulting compounds, e.g., according to the methods described herein. Methods for the generation and use of peptidomimetic combinatorial libraries are described in the prior art, for example in Ostresh (1996) Methods in Enzymology 267: 220-234 and Dorner (1996) Bioorg. Med. Chem. 4:709-715. Furthermore, the three-dimensional and/or crystallographic structure of antagonists of cccDNA can be used for the design of (peptidomimetic) antagonists of cccDNA (Rose (1996) Biochemistry 35:12933-12944; Rutenber (1996) Bioorg. Med. Chem. 4:1545-1558).

The identification/assessment of candidate molecules which are capable of inhibiting cccDNA may be, inter alia, performed by transfecting an appropriate host with a nucleic acid molecule comprising a nucleic acid sequence encoding a tagged hepadnavirus e antigen and contacting said host with (a) candidate molecule(s).

The cell(s)/host(s) to be used herein is(are) preferably (a) eukaryotic cell(s), in particular (a) eukaryotic cell(s) of hepatocyte origin. The eukaryotic cell(s) is(are) preferably (a) hepatoma cell(s) or (a) hepatic cell(s). The eukaryotic cell(s) may also be derived from (a) hepatoma cell(s) or (a) hepatic cell(s). A preferred cell to be used herein is eukaryotic cell HepG2 (ATCC #HB-8065). HepG2 cells are known to support functional HBV cccDNA formation and transcription. The use of other cells is envisaged herein, like hepatocyte-derived cells (e.g. Huh7). Also (a) non-hepatic cell(s)/host(s) may be used in accordance with the invention, provided that they support hepadnavirus cccDNA formation (or, in a wider sense, hapadnavirus DNA replication). For example, such (a) non-hepatic cell(s)/hosts(s) can be modified to support hepadnavirus cccDNA formation (or hepadnavirus DNA replication) if viral pregenomic RNA is introduced into the cells, or transcribed from the DNA template by an exogenous promoter. cccDNA transcription may work if liver specific transcription factors are transcomplemented in such nonhepatic cells. The nucleic acid molecule of the invention or the vector comprising same can be stably integrated in the genome of the cell(s).

The nucleic acid molecule to be used in accordance with the present invention (i.e. the nucleic acid molecule comprising a nucleic acid sequence encoding a tagged hepadnavirus e antigen) or the vector comprising same preferably consists (essentially) of DNA.

The explanations given herein above in respect of "cells" also apply to and encompass tissues/non-human animals comprising or derived from these cells. A cell to be used herein may be comprised in a sample, for example, a biological, medical or pathological sample. For example, the use of fluids that comprise cells, tissues or cell cultures is envisaged. Such a fluid may be a body fluid or also excrements and may also be a culture sample. The body fluids may comprise but are not limited to blood, serum, plasma, urine, saliva, synovial fluid, spinal fluid, cerebrospinal fluid, tears, stool and the like.

Likewise, the candidate molecule(s) may be comprised in a (biological) sample or composition. The (plurality of) candidate molecule(s) are often subject to a first screen. The samples/compositions tested positive in the first screen can be subject to subsequent screens in order to verify the previous findings and to select the most potent inhibitors/antagonists. Upon multiple screening and selection rounds those candidate molecules can be selected which show a pronounced capacity to inhibit/antagonize cccDNA as defined and disclosed herein. For example, batches (i.e. compositions/samples) containing many candidate molecules will be rescreened and batches with no or insufficient inhibitory activity of candidate molecules be discarded without re-testing.

For example, if a (biological) sample or composition with many different candidate molecules is tested and one (biological) sample or composition is tested positive, then it is either possible in a second screening to screen, preferably after purification, the individual molecule(s) of the (biological) sample or composition. It may also be possible to screen subgroups of the (biological) sample or composition of the first screen in (a) subsequent screen(s). The screening of compositions with subgroups of those candidate molecules tested in previous screening rounds will thus narrow in on (an) potential potent cccDNA inhibitor(s). This may facilitate and accelerate the screening process in particular when a large number of molecules is screened. Accordingly, the cycle number of screening rounds is reduced compared to testing each and every individual candidate molecule in (a) first (and subsequent) screen(s) (which is, of course, also possible). Thus, depending on the complexity or the number of the candidate molecules, the steps of the screening method described herein can be performed several times until the (biological) sample or composition to be screened comprises a limited number, preferably only one substance which is indicative for the capacity of screened molecule to decrease the level of tagged hepadnavirus e antigen.

Herein envisaged is the use of optical measurement techniques that allow a resolution of e.g fluorescence on the level of single cells or single cells of a tissue, for example at the subcellular level. These techniques can involve fluorescence, for example confocal microscopy, digital image recording, like a CCD camera and suitable picture analysis software. For example, step (b) is carried out after the measurement of a standard response by performing a control experiment. For example, the level of tagged hepadnavirus e antigen is determined in a cell, tissue or a non-human animal comprising tagged hepadnavirus e antigen without contacting a candidate molecule in a first screen. In a second screen, after contacting the candidate molecule, the level of tagged hepadnavirus e antigen is measured/assessed. A difference in the level indicates whether the tested candidate molecule is indeed an antagonist/inhibitor of a cccDNA.

The level of tagged hepadnavirus e antigen can be quantified by measuring, for example, the level of gene products (particularly the protein level of tagged hepadnavirus e antigen) by any of the herein described methods, in particular protein measuring/detecting/assessing techniques.

For example, the expression can be determined on the protein level by taking advantage of immunoagglutination, immunoprecipitation (e.g. immunodiffusion, immunoelectrophoresis, immune fixation), western blotting techniques (e.g. (in situ) immunohistochemistry, (in situ) immunocytochemistry, affinity chromatography, enzyme immunoassays), and the like. Amounts of purified polypeptide in solution can be determined by physical methods, e.g. photometry. Methods of quantifying a particular polypeptide in a mixture rely on specific binding, e.g. of antibodies. Specific detection and quantitation methods exploiting the specificity of antibodies comprise for example immunohistochemistry (in situ). For example, concentration/amount of the level of tagged hepadnavirus e antigen proteins in a cell, tissue or a non-human animal can be determined by enzyme linked-immunosorbent assay (ELISA).

It is envisaged herein that assessing the level of the tagged hepadnavirus e antigen according to step (b) can be performed by ELISA, CLIA or AlphaLISA.

The herein provided methods take advantage of the use of established tags (like HA-tags, or His-tag, Flag-tag, c-myc-tag, V5-tag or C9-tag that can be used in the place of an HA-tag or in addition thereto). These tags can be used in the purification and detection of tagged hepadnavirus e antigen. By using antibodies specifically binding to the tag (e.g. via ELISA assays, like chemiluminescence ELISA (CLIA) and AlphaLISA), the level of tagged hepadnavirus e antigen can be reliably and rapidly assessed and cross-reactions with core protein be avoided.

Assessing the level of the tagged hepadnavirus e antigen according to step (b) of the herein provided method can comprise the use of an antibody specifically recognizing said hepadnavirus e antigen, preferably hepatitis B virus e antigen, (like, but not limited to Anti-HBe: clone 29, Lot 20110305, Autobio Diagnostics) and one or more antibodies specifically recognizing the one or more tags (like, but not limited to, Anti-HA: cat# A01244-100, Genscript).

The following antibodies specifically recognize hepatitis B virus e antigen and may be used in accordance with the present invention:

Imai, et al. Demonstration of two distinct antigenic determinants on hepatitis B e antigen by monoclonal antibodies. J Immunol. 1982 January; 128(1):69-72.

Ferns and Tedder. Monoclonal antibodies to hepatitis B antigen (HBeAg) derived from hepatitis B core antigen (HBcAg): their use in characterization and detection of HBeAg. J Gen Virol. 1984 May; 65 (Pt 5):899-908.

Mondelli et al. Differential distribution of hepatitis B core and E antigens in hepatocytes: analysis by monoclonal antibodies. Hepatology. 1986 6(2): 199-204.

Stuckmann and Mushahwar. Re-examination and further characterization of a monoclonal antibody to hepatitis B e antigen (anti-HBe). J Virol Methods. 1986 July; 13(4): 351-62.

Korec et al. Monoclonal antibodies against hepatitis B e antigen: production, characterization, and use for diagnosis. J Virol Methods. 1990 May; 28(2):165-9.

Usuda et al. A monoclonal antibody against a hepatitis B e antigen epitope borne by six amino acids encoded by the precore region. J Virol Methods. 1997 November; 68(2): 207-15.

Sogut et al. Monoclonal antibodies specific for hepatitis B e antigen and hepatitis B core antigen. Hybridoma (Larchmt). 2011 October; 30(5):475-9.

Alternatively, Western Blot analysis or immunohistochemical staining can be performed. Western blotting combines separation of a mixture of proteins by electrophoresis and specific detection with antibodies. Electrophoresis may be multi-dimensional such as 2D electrophoresis. Usually, polypeptides are separated in 2D electrophoresis by their apparent molecular weight along one dimension and by their isoelectric point along the other direction.

A skilled person is capable of determining the amount of polypeptides/proteins, in particular the gene products described herein above, by taking advantage of a correlation, preferably a linear correlation, between the intensity of a detection signal and the amount of, for example, polypeptides/proteins to be determined. Accordingly, the level of tagged hepadnavirus e antigen can be quantified based on the protein level of the tagged hepadnavirus e antigen. A skilled person is aware of standard methods to be used in determining the amount/concentration of the level of tagged hepadnavirus e antigen protein expression product in a sample or may deduce corresponding methods from standard textbooks (e.g. Sambrook, 2001).

A candidate molecule(s) is (are) selected, if the level of tagged hepadnavirus e antigen (or of a corresponding reporter signal) is strongly decreased, preferably is very low or non-dectable. For example, the level of tagged hepadnavirus e antigen (or of a corresponding reporter signal) may be decreased by at least 50%, 60%, 70%, 80%, more preferably by at least 90% compared to the (control) standard value.

Methods for transfecting cells or tissues are known in the art. Accordingly, calcium phosphate treatment or electroporation may be used for transfecting cells or tissues to express said reporter constructs (see Sambrook (2001), loc. cit.). Furthermore, nucleic acid molecules expressing said reporter constructs can be reconstituted into liposomes for delivery to target cells. As a further alternative, cells may be transduced to express specific reporter construct using genetically engineered viral vectors.

In another embodiment, the non-human animal comprising said reporter construct for detecting cccDNA inhibition is a transgenic non-human animal. The non-human organism to be used in the described screening assays can be selected from the group consisting of *C. elegans*, yeast, *drosophila*, zebrafish, guinea pig, rat and mouse. The generation of such a transgenic animal is within the skill of a skilled artisan. Corresponding techniques are, inter alia, described in "Current Protocols in Neuroscience" (2001), John Wiley&Sons, Chapter 3.16.

Accordingly, the invention also relates to a method for the generation of a non-human transgenic animal comprising the step of introducing a nucleic acid molecule comprising a nucleic acid sequence encoding a tagged hepadnavirus e antigen as disclosed herein into an ES-cell or a germ cell. The non-human transgenic animal provided and described herein is particular useful in screening methods and pharmacological tests described herein above. The non-human transgenic animal described herein may be employed in drug screening assays as well as in scientific and medical studies wherein antagonists/inhibitors of cccDNA for the treatment of a disease associated with hepadnaviruses are tracked, selected and/or isolated.

The transgenic/genetically engineered cell(s), tissue(s), and/or non-human animals to be used in context of the present invention, in particular, the screening/identifying methods, comprise the herein described and defined nucleic acid molecule comprising a nucleic acid sequence encoding a tagged hepadnavirus e antigen.

The present invention relates to the use of a cell, tissue or a non-human animal for screening and/or validation of a compound suspected of being an inhibitor of cccDNA of a hepadnavirus.

The term "transgenic non-human-animal", "transgenic cell" or "transgenic tissue" as used herein refers to an non-human animal, tissue or cell, not being a human that comprises different genetic material of a corresponding wild-type animal, tissue or cell. The term "genetic material" in this context may be any kind of a nucleic acid molecule, or analogues thereof, for example a nucleic acid molecule, or analogues thereof as defined herein. The term "different" means that additional or fewer genetic material in comparison to the genome of the wild type animal or animal cell. An overview of different expression systems to be used for generating transgenic cell/animal refers for example to Methods in Enzymology 153 (1987), 385-516, in Bitter et al (Methods in Enzymology 153 (1987), 516-544) and in Sawers et al. (Applied Microbiology and Biotechnology 46 (1996), 1-9), Billman-Jacobe (Current Opinion in Biotechnology 7 (1996), 500-4), Hockney (Trends in Biotechnology 12 (1994), 456-463), Griffiths et al., (Methods in Molecular Biology 75 (1997), 427-440).

The present invention relates to a nucleic acid molecule as defined herein above, i.e. a nucleic acid molecule comprising a nucleic acid sequence encoding a tagged hepadnavirus e antigen. The explanations and definitions given herein above apply mutatis mutandis here. The hepadnavirus e antigen is preferably Hepatitis B virus e antigen (HBeAg).

The tagged hepadnavirus e antigen can contain only one tag. The tag can consist of 6 to 22 amino acids A typical and herein preferred (epitope) tag consists of 8, 9, 10 or 11 amino acids. 6×His is a minimal epitope tag that can be used herein. It is possible that an insertion of less than 6 amino acids may assemble into a new epitope together with the adjacent HBeAg amino acids, so that also such an insertion results in a tagged hepadnavirus. The tag can be a hemagglutinin (HA) tag, His-tag, Flag-tag, c-myc-tag, V5-tag or C9-tag. The Flag-tag can be a 1×Flag-tag or a 3×Flag-tag.

The tagged hepadnavirus e antigen can contain two or more tags. The two or more tags are preferably different tags. The entire length of said two or more tags can be from about 12 to about 31 amino acids. For example, the entire length of the two or more tags can be 12, 13, 14, 15, 16, 17, 18, 19, 20, 21, 22, 23, 24, 25, 26, 27, 28, 29, 30 or 31 amino acids. The two or more tag can be two or more of a hemagglutinin (HA) tag, His-tag, Flag-tag, c-myc-tag, V5-tag and/or C9-tag. The Flag-tag can be a 1×Flag-tag or a 3×Flag-tag.

Exemplary nucleic acid sequences encoding the tag(s) are a nucleic acid sequence encoding the HA tag as shown in SEQ ID NO: 1, a nucleic acid sequence encoding the His-tag as shown in SEQ ID NO: 2, a nucleic acid sequence encoding the c-myc-tag as shown in SEQ ID NO: 4, a nucleic acid sequence encoding the V5-tag as shown in SEQ ID NO: 5, and/or a nucleic acid sequence encoding the C9-tag as shown in SEQ ID NO: 6.

Exemplary nucleic acid sequences encoding a Flag-tag are a nucleic acid sequence encoding the 1×Flag-tag as shown in SEQ ID NO: 3, or a nucleic acid sequence encoding the 3×Flag-tag as shown in SEQ ID NO: 7.

Exemplary amino acid sequences of the tag(s) are an amino acid sequence of the HA tag as shown in SEQ ID NO: 8, an amino acid sequence of the His-tag as shown in SEQ ID NO: 9, an amino acid sequence of the c-myc-tag as shown in SEQ ID NO: 11, an amino acid sequence of the V5-tag as shown in SEQ ID NO: 12, and/or an amino acid sequence of the C9-tag as shown in SEQ ID NO: 13.

Exemplary amino acid sequences of the Flag-tag are an amino acid sequence of the 1×Flag-tag as shown in SEQ ID NO: 10 or an amino acid sequence of the 3×Flag-tag as shown in SEQ ID NO: 14.

An exemplary nucleic acid sequence encoding the HBeAg is shown in SEQ ID NO: 16. An exemplary amino acid sequence of the HBeAg is shown in SEQ ID NO: 18.

The nucleic acid molecule can comprise a nucleic acid sequence encoding a hepadnavirus precore protein. An exemplary nucleic acid sequence encoding a hepadnavirus precore protein is shown in SEQ ID NO: 15. An exemplary amino acid sequence of the hepadnavirus precore protein is shown in SEQ ID NO: 17.

The nucleic acid molecule can comprise a nucleic acid sequence encoding the one or more tag, wherein said sequence is (inserted) 3' downstream of the nucleic acid sequence encoding the N-terminal signal peptide and linker of the hepadnavirus precore protein.

The nucleic acid sequence encoding the one or more tag can be (inserted) 3' downstream of the nucleic acid sequence encoding the N-terminal 29 amino acids of a hepatitis B virus precore protein.

The nucleic acid molecule can comprise a hepadnavirus genome. Preferably, the hepadnavirus genome is a Hepatitis B virus (HBV) genome. The HBV genome can be the genome of HBV genotype A, B, C, D, E, F, G or H. The HBV genome can be the genome of HBV genotype D. Preferably, the HBV genome is a genome of HBV genotype D, subgenotype ayw.

The nucleic acid encoding the one or more tag can be (inserted) 5' upstream of the nucleic acid encoding a hepadnavirus core protein, preferably a HBV core protein. An exemplary nucleic acid sequence encoding a HBV core protein is shown in SEQ ID NO: 23. The core protein can be a HBV core protein. An exemplary amino acid sequence of a HBV core protein is shown in SEQ ID NO: 24.

The nucleic acid molecule comprising a sequence encoding the one or more tag can be inserted into the epsilon structure of a hepadnavirus pgRNA, preferably HBV pgRNA, or of an epsilon structure as encoded by a hepadnavirus genome, preferably a HBV genome as defined herein. An exemplary nucleic acid sequence of the epsilon structure as encoded by a HBV genome is shown in SEQ ID NO: 25. The nucleic acid molecule comprising a sequence encoding the one or more tag can be inserted into the lower stem of the epsilon structure of a hepadnavirus pgRNA, preferably HBV pgRNA, or of an epsilon structure as encoded by a hepadnavirus genome, preferably a HBV genome.

The nucleic acid molecule comprising a sequence encoding the one or more tag can be inserted between nucleotides corresponding to position C1902 and A1903 of the HBV genome.

The nucleic acid molecule can comprise 5' of the sequence encoding the one or more tag a sequence that is capable of forming base pairs with the lower stem of the epsilon structure of a hepadnavirus pgRNA, preferably HBV pgRNA, or of an epsilon structure as encoded by a hepadnavirus genome, preferably a HBV genome. The sequence that is capable of forming base pairs with the lower stem of the epsilon structure of (or encoded by) a hepadnavirus genome, preferably HBV, is primarily capable of forming base pairs with nucleotides preferably corresponding to positions T1849 to A1854, or optionally, corresponding to positions Ti 849 to T1855 of the HBV genome. The sequence that is capable of forming base pairs with the lower stem of the epsilon structure of a hepadnavirus genome can consist of (up to) 9 nucleotides.

An exemplary sequence that is capable of forming base pairs with the lower stem of the epsilon structure of a hepadnavirus pgRNA, preferably HBV pgRNA, or of an epsilon structure as encoded by a hepadnavirus genome, preferably a HBV genome consists of the sequence shown in SEQ ID No. 26. An exemplary sequence that is capable of forming base pairs with the lower stem of the epsilon structure of a hepadnavirus pgRNA, preferably HBV pgRNA, or of an epsilon structure as encoded by a hepadnavirus genome, preferably a HBV genome, encodes a polypeptide as shown in SEQ ID NO. 40.

The nucleic acid molecule can comprise 3' of the sequence encoding the one or more tag a sequence encoding a linker. The linker can consist of one or more amino acid residues. Preferably, the linker consists of only one amino acid residue, such as a glycine residue. The sequence encoding a linker can consist of the sequence GGC. The sequence encoding a linker can encode a glycine residue. The sequence encoding can be useful and appropriately selected to keep the authentic Kozak motif of core start codon.

The nucleic acid molecule can comprise a nucleic acid sequence encoding a tagged hepadnavirus e antigen that comprises a nucleic acid sequence as shown in SEQ ID NO. 41. The nucleic acid molecule can comprise a nucleic acid sequence encoding a tagged hepadnavirus e antigen comprises a nucleic acid sequence encoding an amino acid sequence as shown in SEQ ID NO. 42.

The one or more tag is preferably fused in frame in the hepadnavirus e antigen (or into the hepadnavirus e precore protein), preferably a Hepatitis B virus e antigen (HBeAg) (or into the Hepatitis B virus precore protein).

An exemplary nucleic acid sequence encoding the tagged HBeAg is shown in SEQ ID NO: 20. A preferred amino acid sequence of the tagged HBeAg is shown in SEQ ID NO: 22.

An exemplary nucleic acid sequence nucleic acid sequence encoding a tagged Hepatitis B virus precore protein is shown in SEQ ID NO: 19. An exemplary nucleic acid sequence amino acid sequence of the tagged Hepatitis B virus precore protein is shown in SEQ ID NO: 21.

Exemplary nucleic acid sequences of the HBV genome are shown in SEQ ID NO: 27, 28, 29, 30, 31, 32, 33 or 34.

The nucleic acid can be transcriptable into pregenomic (pg) hepadnavirus RNA. The hepadnavirus RNA is preferably HBV RNA.

The nucleic acid molecule comprising a nucleic acid sequence encoding the tagged hepadnavirus e antigen can be comprised in a vector, such as an expression vector. Preferably, the hepadnavirus e antigen is Hepatitis B virus e antigen (HBeAg).

The nucleic acid generally allows the translation of the tagged hepadnavirus e antigen, preferably Hepatitis B virus e antigen (HBeAg). The nucleic acid can be comprised in a vector that comprises a sequence as shown in SEQ ID NO: 39.

In certain embodiments the nucleic acid is designed to prevent the translation of the tagged hepadnavirus e antigen. For example, the nucleic acid does not contain a start codon ATG 5' upstream of the nucleic acid encoding a tagged hepadnavirus e antigen. For example, a start codon ATG 5' upstream of the nucleic acid encoding a tagged hepadnavirus e antigen can be replaced by the nucleic acids TG. The nucleic can be modified by point mutation in order to prevent the translation of a tagged hepadnavirus e antigen. The vector can comprise a sequence as shown in SEQ ID NO: 35.

The nucleic acid molecule comprising a nucleic acid sequence encoding the tagged hepadnavirus e antigen, preferably Hepatitis B virus e antigen (HBeAg), can be under control of an inducible promoter.

The inducible promoter can be a tetracycline-inducible promoter, a doxycline-inducible promoter, an antibiotic-inducible promoter, a copper-inducible promoter, an alcohol-inducible promoter, a steroid-inducible promoter, or a herbicide-inducible promoter.

The inducible promoter can preferably be a CMV promoter. The inducible promoter can be a tet-EF-1 alpha promoter.

One or more stop codons can be introduced into the coding region of one or more hepadnavirus envelope proteins, preferably one or more HBV envelope proteins.

The one or more HBV envelope protein can be one or more of L, M and/or S. The HBV envelope protein can be S.

Exemplary coding regions of (or exemplary nucleic acid sequences encoding) the one or more HBV envelope proteins is shown in SEQ ID NO: 36 (L), 37 (M) or 38 (S). The HBV nucleotides 217 to 222 (TTGTTG) of SEQ ID NO: 38 (S) can be mutated to TAGTAG to prevent the expression of envelope proteins.

The present invention relates to a protein encoded by the nucleic acid molecule as defined and provided herein above.

The protein comprises a tagged hepadnavirus e antigen, preferably a tagged Hepatitis B virus e antigen (HBeAg).

The Hepatitis B virus e antigen (HBeAg) can comprise an amino acid sequence as shown in SEQ ID NO: 18. Preferably, the tagged hepadnavirus e antigen contains only one tag.

The tag can consist of 6 to 22 amino acids. The tag can be hemagglutinin (HA) tag, His-tag, Flag-tag, c-myc-tag, V5-tag or C9-tag. The Flag-tag can be a 1×Flag-tag or a 3×Flag-tag.

The tagged hepadnavirus e antigen can contain two or more tags. Preferably the two or more tags are different tags. The entire length of said two or more tags is from about 14 to about 31 amino acids. The two or more tag can be two or more of a hemagglutinin (HA) tag, His-tag, Flag-tag, c-myc-tag, V5-tag and/or C9-tag. The Flag-tag can be a 1×Flag-tag or a 3×Flag-tag.

Exemplary nucleic acid sequences encoding a tag are a nucleic acid sequence encoding the HA tag as shown in SEQ ID NO: 1, a nucleic acid sequence encoding the His-tag as shown in SEQ ID NO: 2, a nucleic acid sequence encoding the c-myc-tag as shown in SEQ ID NO: 4, a nucleic acid sequence encoding the V5-tag as shown in SEQ ID NO: 5, and/or a nucleic acid sequence encoding the C9-tag as shown in SEQ ID NO: 6.

Exemplary nucleic acid sequences encoding a Flag-tag are a nucleic acid sequence encoding a 1×Flag-tag as shown in SEQ ID NO: 3 or a nucleic acid sequence encoding a 3×Flag-tag as shown in SEQ ID NO: 7.

Exemplary amino acid sequences of a tag are an amino acid sequence of the HA tag as shown in SEQ ID NO: 8, an amino acid sequence of the His-tag as shown in SEQ ID NO: 9, an amino acid sequence of the c-myc-tag as shown in SEQ ID NO: 11, an amino acid sequence of the V5-tag as shown in SEQ ID NO: 12; and/or an amino acid sequence of the C9-tag as shown in SEQ ID NO: 13.

Exemplary amino acid sequences of a Flag-tag are an amino acid sequence of the 1×Flag-tag as shown in SEQ ID NO: 10 or an amino acid sequence of the 3×Flag-tag as shown in SEQ ID NO: 14.

The protein can comprise a hepadnavirus precore protein. An exemplary nucleic acid sequence encoding a hepadnavirus precore protein is shown in SEQ ID NO: 15. An exemplary amino acid sequence of the hepadnavirus precore protein is shown in SEQ ID NO: 17.

The protein can comprise an amino acid sequence of the one or more tag, wherein said sequence is C-terminal of the amino acid sequence of the sequence of the signal peptide and of the linker of the hepadnavirus precore protein. The protein can comprise an amino acid sequence of the one or more tag C-terminal of the amino acid sequence of the N-terminal 29 amino acids of a hepatitis B virus precore protein.

The protein can comprise an amino acid sequence of the one or more tag, wherein said sequence is N-terminal of an amino acid sequence of a hepadnavirus core protein, preferably N-terminal of an amino acid sequence of a HBV core protein. An exemplary nucleic acid encoding a HBV core protein is shown in SEQ ID NO: 23. An exemplary amino acid sequence of a HBV core protein is shown in SEQ ID NO: 24.

The amino acid sequence of the one or more tag can be inserted into an amino acid sequence encoded by the epsilon structure of a hepadnavirus pgRNA, preferably HBV pgRNA, or of an epsilon structure as encoded by a hepadnavirus genome, preferably an HBV genome. An exemplary nucleic acid sequence of the epsilon structure as encoded by an HBV genome is shown in SEQ ID NO: 25. The amino acid sequence of the one or more tag can be inserted into an amino acid sequence encoded by the lower stem of the epsilon structure of a hepadnavirus pgRNA, preferably HBV pgRNA, or of an epsilon structure as encoded by a hepadnavirus genome, preferably an HBV genome, preferably into an amino acid sequence encoded by the lower stem of the epsilon structure of a hepadnavirus pgRNA, preferably HBV pgRNA, or of an epsilon structure as encoded by a hepadnavirus genome, preferably an HBV genome.

The amino acid sequence of the one or more tag can be inserted between amino acid residues corresponding to position G29 and position M30 of a HBV precore protein, such as the one as shown in SEQ ID NO. 17.

The protein can further comprise N-terminal to the amino acid sequence of the one or more tag an amino acid sequence of (up to) 3 amino acids, wherein said amino acid sequence of up to 3 amino acids is encoded by a nucleic acid sequence that is capable of forming base pairs with the lower stem of the epsilon structure of a hepadnavirus pgRNA, preferably HBV pgRNA, or of an epsilon structure as encoded by a hepadnavirus genome, preferably an HBV genome. The nucleic sequence that is capable of forming base pairs with the lower stem of the epsilon structure of a hepadnavirus pgRNA, preferably HBV pgRNA, or of an epsilon structure as encoded by a hepadnavirus genome, preferably an HBV genome, is primarily capable of forming base pairs with nucleotides preferably corresponding to positions T1849 to T1855 or, optionally, corresponding to positions T1849 to T1855 of the HBV genome. An exemplary nucleic acid sequence that is capable of forming base pairs with the lower stem of the epsilon structure of a hepadnavirus pgRNA, preferably HBV pgRNA, or of an epsilon structure as encoded by a hepadnavirus genome, preferably an HBV genome, consists of the sequence shown in SEQ ID No. 26. An exemplary amino acid sequence of (up to) 3 amino acids is shown in SEQ ID NO. 40.

The protein can further comprise C-terminal to the amino acid sequence of the one or more tag a linker. The linker can consist of one or more amino acid residues. Preferably, the linker consists of only one amino acid residue, such as a glycine residue.

The amino acid sequence of a tagged hepadnavirus e antigen can comprise an amino acid sequence encoded by a nucleic acid sequence as shown in SEQ ID NO. 41. The amino acid sequence of a tagged hepadnavirus e antigen can comprise an amino acid sequence as shown in SEQ ID NO. 42.

The one or more tag is preferably fused in frame into the hepadnavirus e antigen, preferably an Hepatitis B virus e antigen (HBeAg).

An exemplary nucleic acid sequence encoding the tagged HBeAg is shown in SEQ ID NO: 20. Preferably, the tagged HBeAg has an amino acid sequence as shown in SEQ ID NO: 22.

An exemplary nucleic acid sequence encoding a tagged HBV precore protein is shown in SEQ ID NO: 19. An exemplary amino acid sequence of a tagged HBV precore protein is shown in SEQ ID NO: 21.

The present invention relates to a host cell comprising the nucleic acid molecule as defined and provided herein and/or to a host cell comprising or the protein as defined and provided herein. The host cell can be a eukaryotic cell. The eukaryotic cell can be of hepatocyte origin. The eukaryotic cell can be a hepatoma cell or can be derived from a hepatoma cell. In a preferred embodiment, the eukaryotic cell is HepG2 (ATCC #HB-8065).

The present invention relates to a process for the production of the protein as defined herein above, said process comprising culturing a host as defined herein above under conditions allowing the expression of the protein and recovering the produced protein from the culture.

The present invention relates to a kit for use in the method of the present invention. Likewise, the present invention relates to the use of a kit for screening candidate molecules suspected to be capable of inhibiting covalently closed circular DNA of hepadnavirus. The explanations provided herein above in relation to the method for assessing the capacity of a candidate molecule to inhibit cccDNA of a hepadnavirus apply mutatis mutandis here.

The kit can comprise an antibody specifically recognizing a hepadnavirus antigen e as defined herein and one or more antibodies specifically recognizing one or more tags as defined herein.

The kit (to be prepared in context) of this invention or the methods and uses of the invention may further comprise or be provided with (an) instruction manual(s). For example, said instruction manual(s) may guide the skilled person (how) to assess the capacity of a candidate molecule to inhibit cccDNA and/or how to assess the level of tagged hepadnavirus e antigen in accordance with the present invention. Particularly, said instruction manual(s) may comprise guidance to use or apply the herein provided methods or uses.

The kit (to be prepared in context) of this invention may further comprise substances/chemicals and/or equipment suitable/required for carrying out the methods and uses of this invention. For example, such substances/chemicals and/or equipment are solvents, diluents and/or buffers for stabilizing and/or storing (a) compound(s) required for specifically determining the (protein (expression)) level of said tagged hepadnavirus e antigen as defined herein.

The present invention relates to the use of the nucleic molecule as defined and provided herein, the protein as defined and provided herein and/or the host cell as defined and provided herein for screening candidate molecules suspected to be capable of inhibiting covalently closed circular DNA of hepadnavirus. The explanations provided herein above in relation to the method for assessing the capacity of a candidate molecule to inhibit cccDNA of a hepadnavirus apply mutatis mutandis here.

As used herein, the terms "comprising" and "including" or grammatical variants thereof are to be taken as specifying the stated features, integers, steps or components but do not preclude the addition of one or more additional features, integers, steps, components or groups thereof. This term encompasses the terms "consisting of" and "consisting essentially of." Thus, the terms "comprising"/"including"/ "having" mean that any further component (or likewise features, integers, steps and the like) can be present.

The term "consisting of" means that no further component (or likewise features, integers, steps and the like) can be present.

The term "consisting essentially of" or grammatical variants thereof when used herein are to be taken as specifying the stated features, integers, steps or components but do not preclude the addition of one or more additional features, integers, steps, components or groups thereof but only if the additional features, integers, steps, components or groups thereof do not materially alter the basic and novel characteristics of the claimed composition, device or method.

Thus, the term "consisting essentially of" means that specific further components (or likewise features, integers, steps and the like) can be present, namely those not materially affecting the essential characteristics of the composition, device or method. In other words, the term "consisting essentially of" (which can be interchangeably used herein with the term "comprising substantially"), allows the presence of other components in the composition, device or method in addition to the mandatory components (or likewise features, integers, steps and the like), provided that the essential characteristics of the device or method are not materially affected by the presence of other components.

The term "method" refers to manners, means, techniques and procedures for accomplishing a given task including, but not limited to, those manners, means, techniques and procedures either known to, or readily developed from known manners, means, techniques and procedures by practitioners of the chemical, biological and biophysical arts.

As used herein, the term "isolated" refers to a composition that has been removed from its in-vivo location. Preferably the isolated compositions or compounds of the present invention are substantially free from other substances (e.g., other proteins or other compounds) that are present in their in-vivo location (i.e. purified or semi-purified compositions or compounds.)

As used herein the term "about" refers to ±10%.

The present invention is further described by reference to the following non-limiting figures and examples.

Unless otherwise indicated, established methods of recombinant gene technology were used as described, for example, in Sambrook, Russell "Molecular Cloning, A Laboratory Manual", Cold Spring Harbor Laboratory, N.Y. (2001) which is incorporated herein by reference in its entirety.

The following example illustrates the invention:

The Figures show:

FIG. 1. Insertion of HA-tag sequence into HBV precore ORF.

The ORF of HBV precore protein (genotype D, subtype ayw, nt 1816-2454) is depicted with the 5' portion (nt 1816-1941) shown in nucleotide sequence. The sequence between nt 1941 and the stop codon of precore ORF is omitted. The start codon of precore ORF, direct repeat sequence 1 (DR1), and in-frame start codon of core ORF are boxed. The start codon of 5' end precore ORF is mutated (ATG to TG) in plasmid pTREHBV-HAe. The authentic pgRNA transcription initiation site (nt 1820) is marked with arrow. The HBV nucleotide position is according to Galibert nomenclature (5). A critical stem-loop structure (epsilon, e), which serves as essential cis-element in HBV pgRNA for subsequent DNA replication, is illustrated with predicted internal structures (lower stem, bulge, upper stem, loop). To place an in-frame fused HA-tag sequence into precore ORF without altering the base paring of epsilon, an HA-tag-containing DNA sequence (gtggacatcTACCCATACGACGTTCCAGATTACGCTggc; SEQ ID NO: 41)

is inserted into an in-frame upstream position adjacent to the start codon of core ORF (see the insert box). The sequence modification results in an in-frame fusion of HA-tag plus linker sequences into precore protein, and the intact ORF of core protein is maintained at the downstream of epsilon.

FIG. 2. Expression and secretion of HA-tagged HBeAg

Figure 2A:
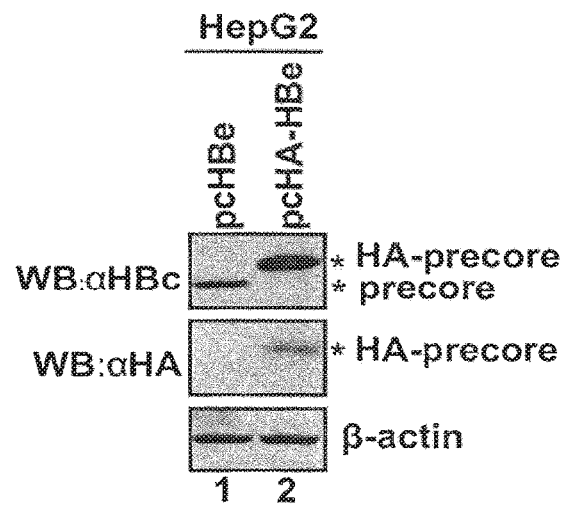

FIG. 2A shows intracellular expression of wildtype and HA-tagged precore. HepG2 cells were transfected with plasmid pcHBe or pcHA-HBe, 5 days later, whole cell lysates were subjected to western blot analysis by using anti-HBc (top panel) and anti-HA (middle panel) antibodies. β-actin served as loading control. Wildtype precore and HA-tagged precore (HA-precore) are labeled.

Figure 2B:
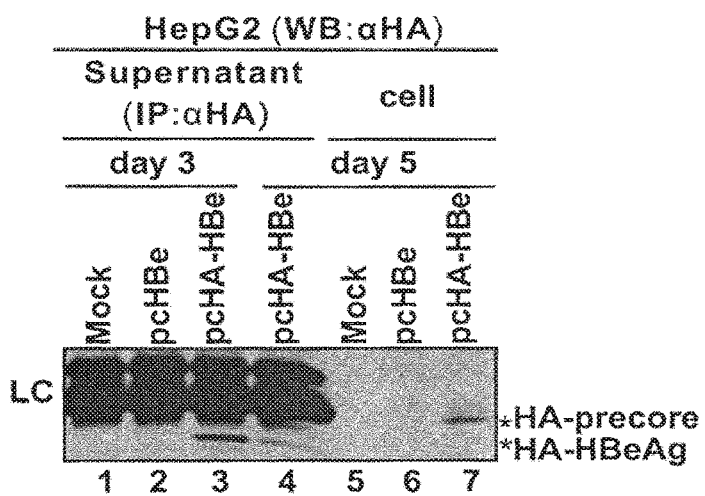

FIG. 2B shows detection of HA-tagged HBeAg in culture fluid. HepG2 cells were mock transfected or transfected with plasmid pcHBe or pcHA-HBe, supernatant samples were collected at indicated time point and cells were harvested at day 5 post transfection. The supernatant samples were subjected to immunoprecipitation (IP) using anti-HA antibody and the HA-tagged HBeAg (HA-HBeAg) were detected by Western blot with antibody against HA. The light chain (LC) of antibody is indicated. The intracellular expression of HA-precore was revealed by HA Western blot.

FIG. 3. Secretion of HA-HBeAg in HepHA-HBe cell lines.

Figure 3A:
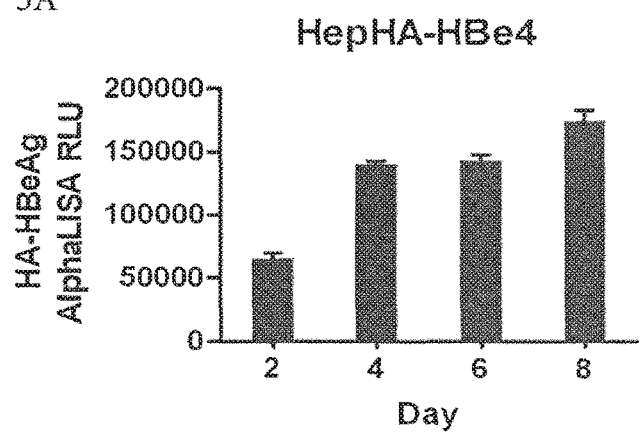
Figure 3B:
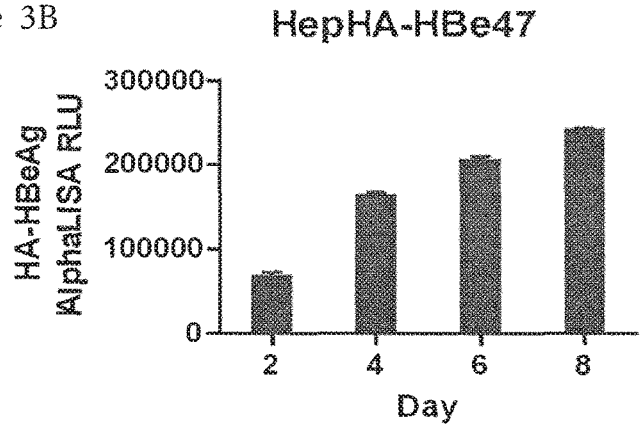

FIGS. 3A and 3B show the results of experiments in which established HA-tagged HBeAg stable expression cell lines, specifically HepHA-HBe4 and HepHA-HBe47 cells, were seeded into collagen-coated 12-well plates at confluent condition. The day when cells were seeded was set as day 0, and media were replenished every other day. The supernatant samples were collected at indicated time point and HA-HBeAg was detected by AlphaLISA analysis as described in Materials and Methods. The AlphaLISA signals (relative light unit) (Y-axis) were plotted in correspondence to the time points (X-axis) in the histogram.

Figure 4:
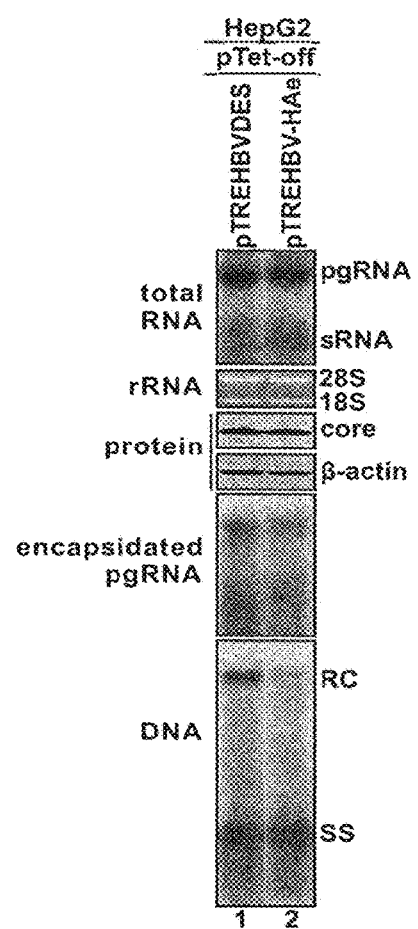

FIG. 4. Replication of HA-recombinant HBV genome in transiently transfected cells.

HepG2 cells were cotransfected with pTREHBVDES or pTREHBV-HAe and plasmid pTet-off. Cells were harvested 5 days post transfection, and plasmid-based production of HBV RNA, core protein, encapsidated pgRNA, and viral DNA replication were analyzed by Northern blot, Western blot, and Southern blot hybridization, respectively. pgRNA: pregenomic RNA; sRNA: surface RNA; RC: relaxed circular DNA; SS: single stranded DNA.

FIG. 5. Schematic illustration of the rational design of HBV cccDNA-dependent HA-tagged HBeAg expression in HepBHAe stable cell line.

Figures 5A, 5B, 5C, 5D, 5E, 5F, 5G:
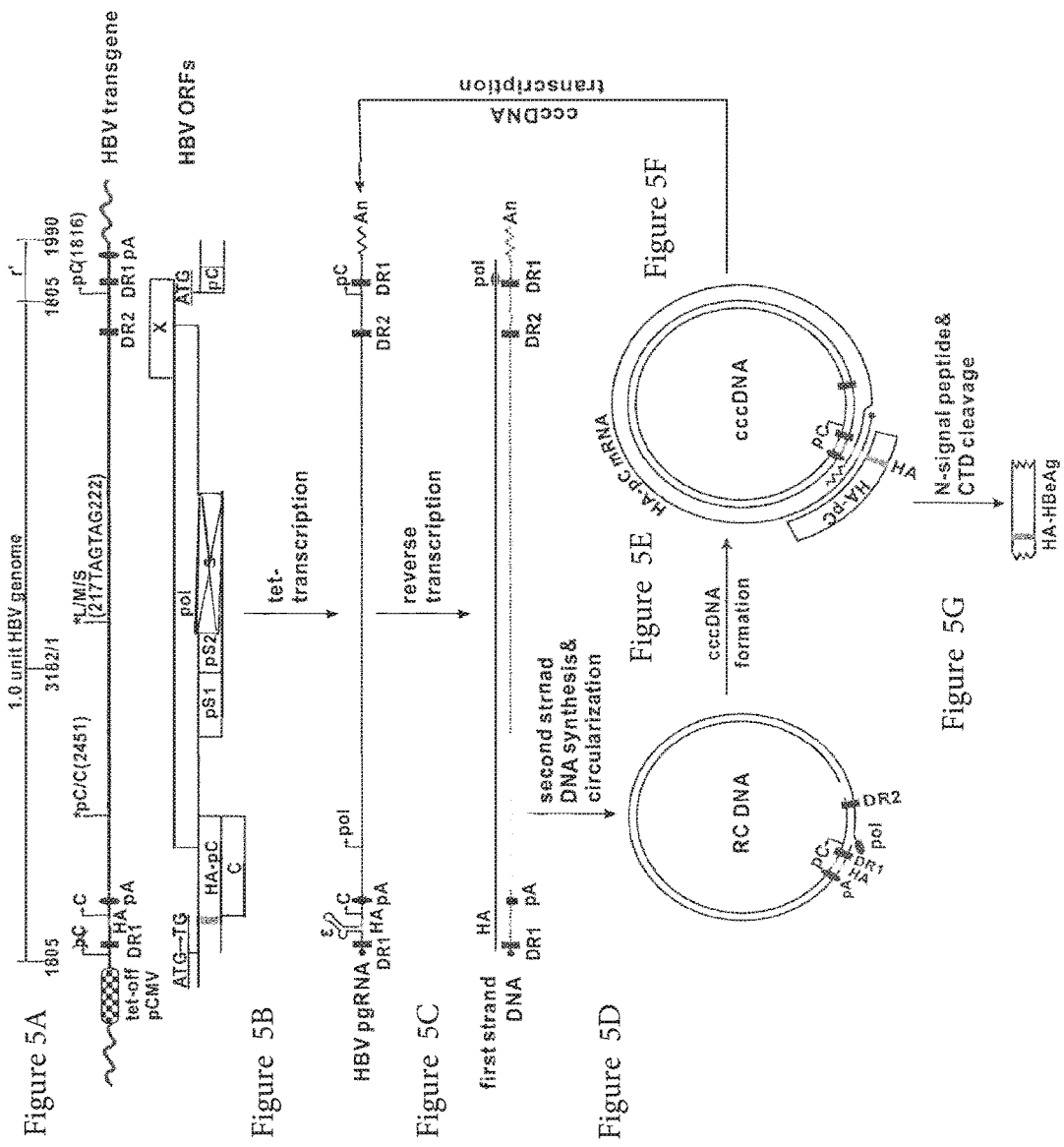

FIG. 5A shows that, in pTREHBV-HAe and pTet-off stably transfected cells, the transgene contains a 1.1 over-length HBV genome under the control of tet-CMV promoter. The start codon (ATG) of precore was mutated at the 5' end of HBV DNA, with the second one unchanged at the 3' redundancy. The HA-tag-containing fragment (shown in gray) was inserted into the precore ORF as described in the Materials and Methods. The transgene also contains two tandem stop codons in the small surface (S) ORF to prevent viral envelope protein expression. FIG. 5B shows that, upon the removal of Tet, pgRNA is transcribed and core and polymerase are produced, resulting in pgRNA packaging and, as shown in FIG. 5C reverse transcription of pgRNA to rcDNA. FIG. 5D shows that DNA Repair mechanisms convert rcDNA to the circular cccDNA template, portrayed in FIG. 5E, in which the HA-precore ORF is restored. This gives rise to HA-precore mRNA, and pgRNA, shown by FIG. 5F, for de novo viral replication. FIG. 5G shows HA-precore translation from HA-precore mRNA and processing into secreted HA-HBeAg, which can be detected by ELISA. preC, C, pol, L, M, S and X represent ORF start codons for precore, core, polymerase, large, middle and small s antigen, and X protein, respectively. DR represents direct repeat sequences. CTD represents C-terminal domain.

Figure 6:
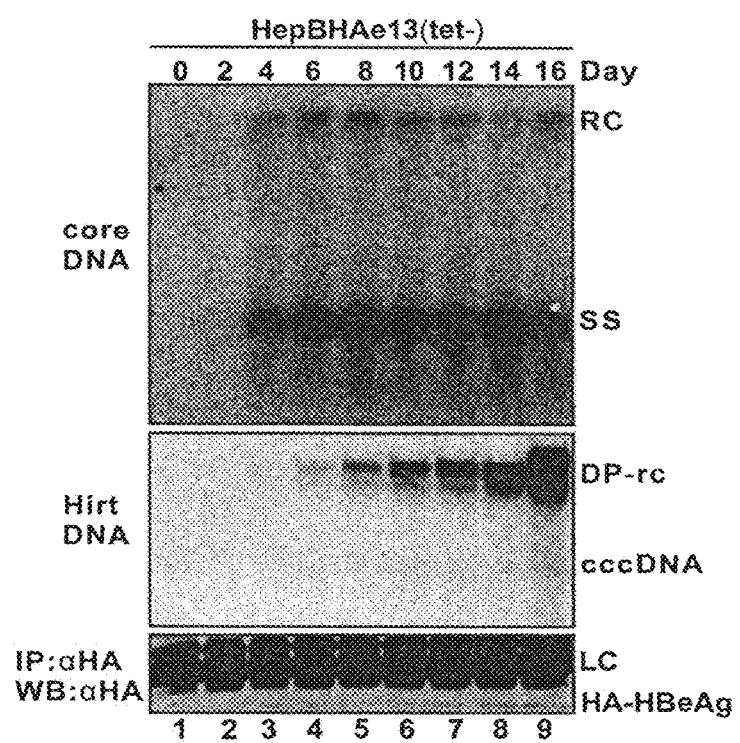

FIG. 6. Kinetics of viral DNA replication, cccDNA accumulation, and HA-tagged HBeAg production in HepBHAe13 cells.

HepBHAe13 cells were seeded in 6-well-plates in the presence of tetracycline. When cell monolayer became confluent, tetracycline was removed from the culture medium and medium was changed every other day. Cells and supernatant samples were harvested at indicated time points. Intracellular core DNA (upper panel) and cccDNA (bottom panel) were extracted and analyzed by Southern blot hybridization. DP-rc represents the deproteinized (protein-free) RC DNA. The secreted HA-tagged HBeAg was detected by HA IP-Western blot as described above.

Figure 7:
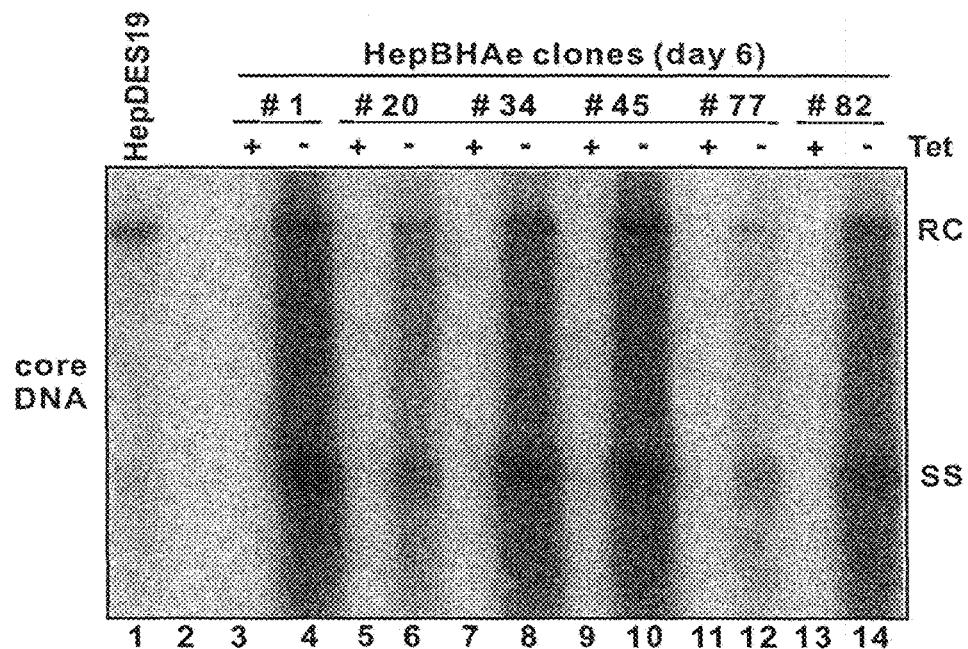

FIG. 7. Additional inducible HepBHAe cell lines that support HA-recombinant HBV DNA replication.

HepDES19 cells and the newly established HepBHAe cells with different clone numbers were seeded in 6-well-plates at the same density in the presence of tetracycline. When cells reached confluent, one set of cells were cultured in the presence of tetracycline, and another set of cells were cultured in the absence of tetracycline. 6 days later, cells were harvested and viral core DNA was analyzed by Southern blot.

Figure 8:
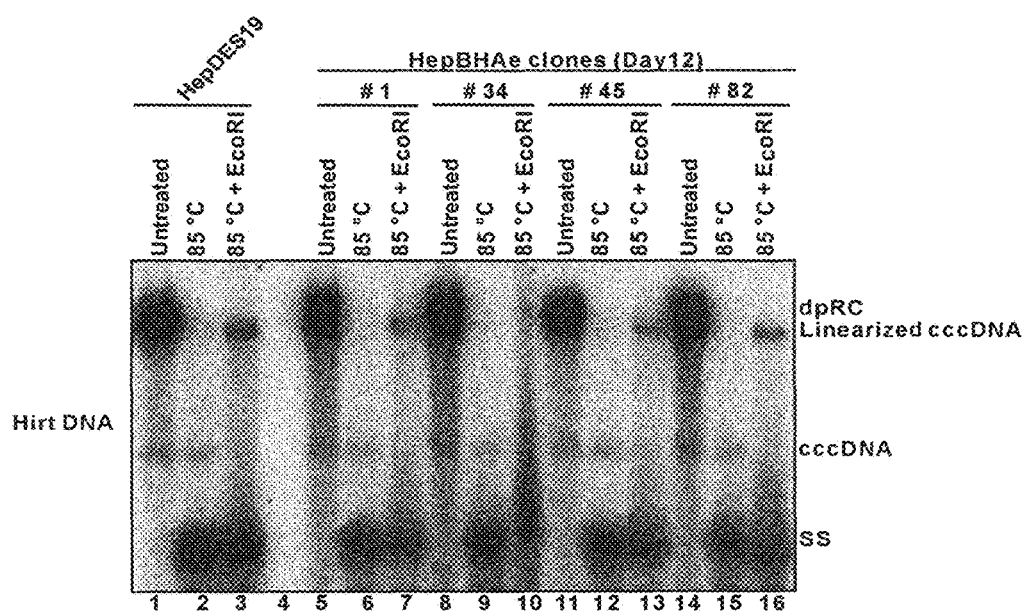

FIG. 8. The authenticity of cccDNA in HepBHAe cell lines.

cccDNA produced in HepDES19 cells and the indicated HepBHAe cells were extracted by Hirt extraction and subjected to gel electrophoresis and Southern blot hybridization (lanes 1, 5, 8, 11, 14). To further validate the authenticity of HBV cccDNA, the Hirt DNA samples were heated to 85° C. for 5 min before gel loading, a condition that denatures DP-rcDNA into SS DNA, while the cccDNA stays undenatured and its electrophoretic mobility remains unchanged (lanes 2, 6, 9, 12, 15). The heat denatured DNA samples were further digested with EcoRI, in which condition the cccDNA is linearized to a genome-length double-stranded DNA (lanes 3, 7, 10, 13, 16).

Figure 9:
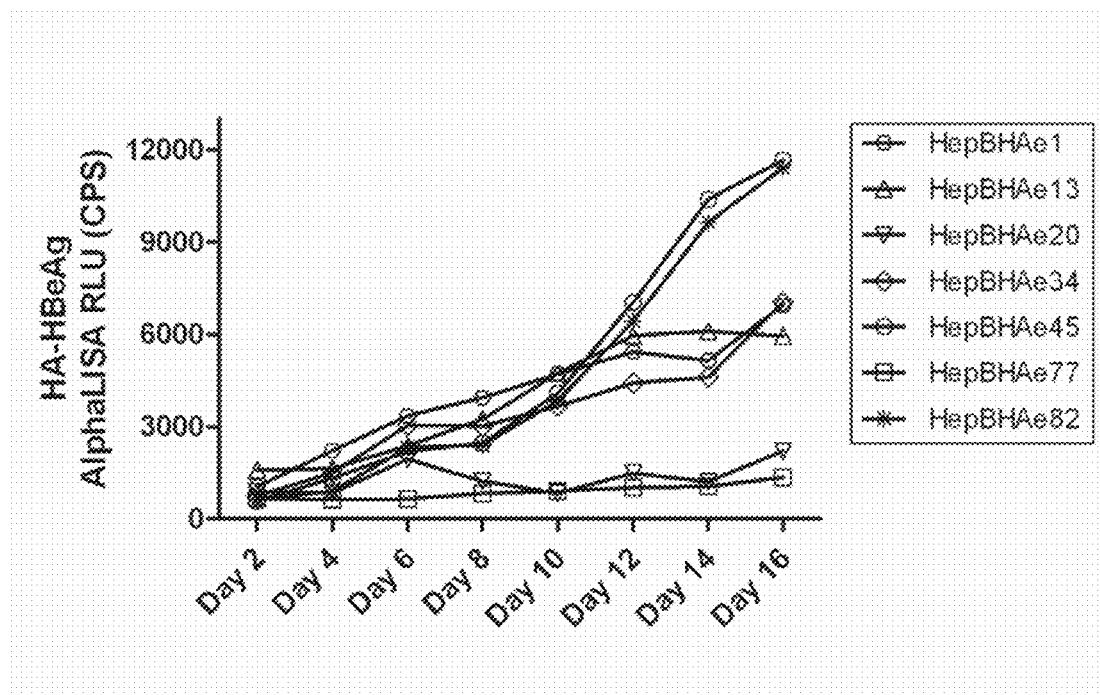

FIG. 9. AlphaLISA detection of HA-HBeAg in HepBHAe cell lines.

HepBHAe cells were seeded in plates in the presence of tetracycline. When cells became confluent, tetracycline was removed from the culture medium and medium was changed every other day. Supernatant samples were harvested at indicated time point and subjected to AlphaLISA for HA-HBeAg detection. The AlphaLISA readouts (relative light unit, RLU) were expressed as counts per second (CPS).

FIG. 10. HBV replication inhibitor (3TC) blocks HA-HBeAg expression in HepBHAe13 cells.

HepBHAe13 cells were cultured in 6-well-plate in the presence of tetracycline until confluent. One set of cells was maintained continually in the presence of tetracycline. The second set of cells was then switched to tetracycline-free medium. The third set of cells was then cultured in tetracycline-free medium containing 10 µM 3TC. The culture medium was replenished every other day, and the harvested supernatant samples at indicated time points were subjected to chemiluminescence immunoassay (CLIA) for HA-tagged HBeAg.

Figure 11:
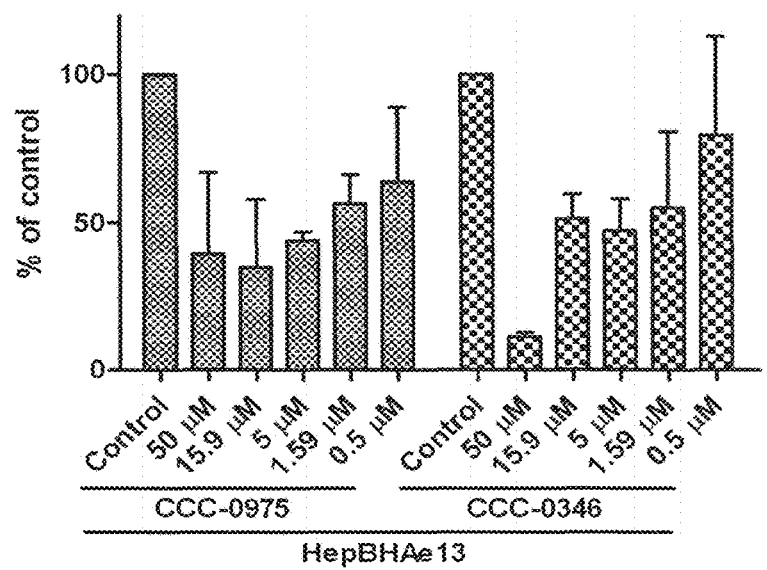

FIG. 11. HBV cccDNA formation inhibitors reduced the HA-HBeAg levels in HepBHAe13 cells. Cells were seeded into 96-well-plate and tetracycline was removed from the medium to induce viral replication when cells became confluent. Simultaneously, cells were left untreated or treated with compounds at indicated concentrations, DMSO concentration was normalized to 0.5% in treated and untreated groups. Treatment was repeated every four days. At day 12 post treatment, culture fluid was subjected to HA-HBeAg CLIA and readout was plotted as percentage (mean±SD) to control.

Figure 12:
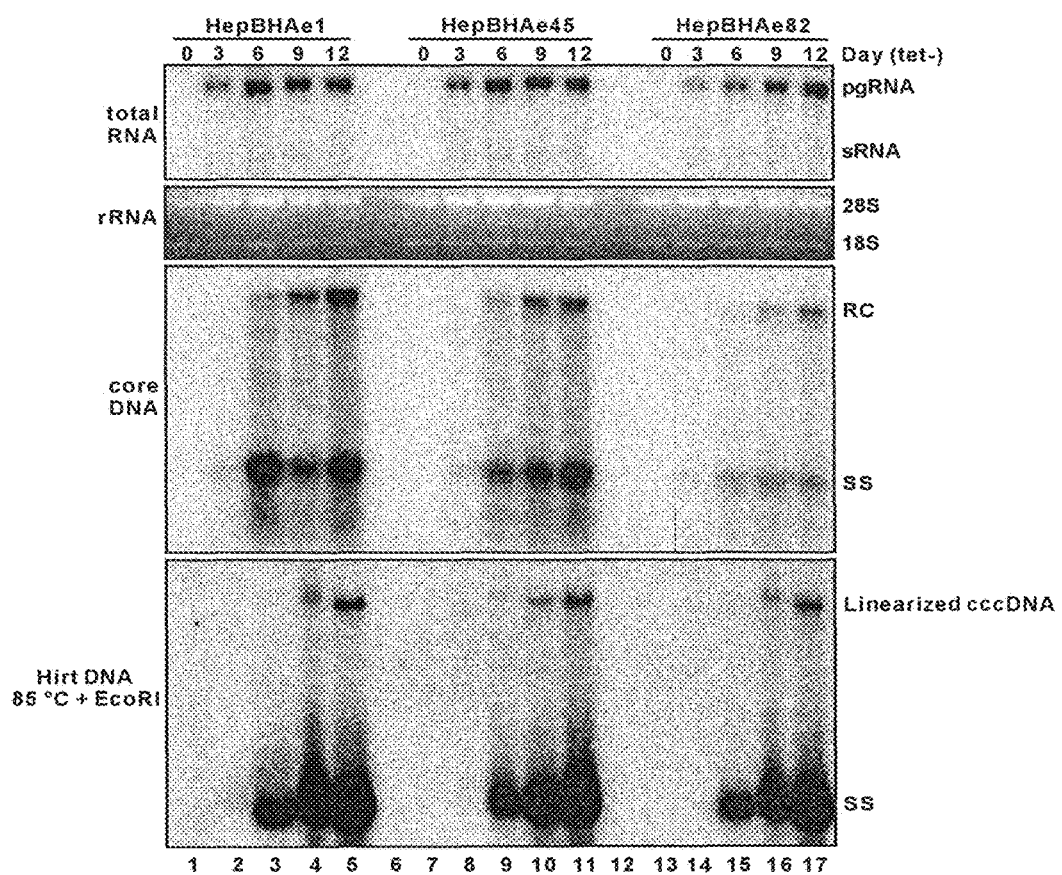

FIG. 12. Kinetics of viral RNA transcription, DNA replication and cccDNA accumulation in additional HepBHAe cell clones.

The indicated HepBHAe cells were seeded in 6-well-plates in the presence of tetracycline. When cell monolayer became confluent, tetracycline was removed from the culture medium and medium was changed every other day. Cells were harvested at indicated time points. Total viral RNA (upper panel), cytoplamic core DNA (middle panel) were extracted and analyzed by Northern and Southern blot hybridization, respectively. The extracted cccDNA was heat denatured at 85° C. for 5 min and then linearized by EcoR I, followed by Southern blot analysis (bottom panel).

Figure 13:
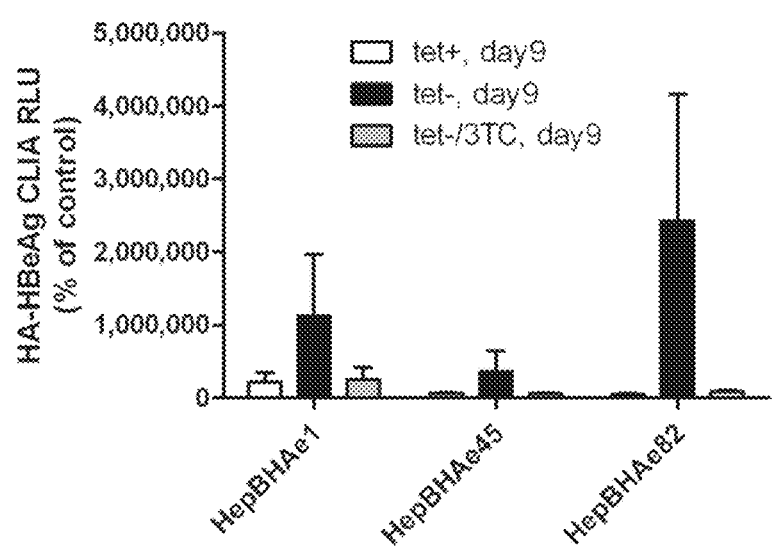

FIG. 13. cccDNA-dependent expression of HA-HBeAg in additional HepBHAe cell clones.

The selected HepBHAe cells were cultured in 96-well-plate in the presence of tetracycline until confluent. One set of cells was maintained continually in the presence of tetracycline. The second set of cells was then switched to tetracycline-free medium. The third set of cells was then cultured in tetracycline-free medium containing 10 µM 3TC. The culture medium was replenished every other day, and the harvested supernatant samples at day 9 post treatment were subjected to chemiluminescence immunoassay (CLIA) for HA-tagged HBeAg detection.

The Example illustrates the invention.

EXAMPLE 1: CULTURED CELL LINE THAT INDUCIBLY EXPRESSES HEPATITIS B VIRUS COVALENTLY CLOSED CIRCULAR DNA-DEPENDENT EPITOPE-TAGGED E ANTIGEN, AND USES THEREOF FOR SCREENING ANTIVIRAL SUBSTANCES

Materials and Methods
Plasmids

In order to construct a tetracycline-inducible HBV replicating vector which contains a Human influenza hemagglutinin (HA) fused precore open reading frame with its start codon knockout, a DNA fragment containing the TATA box motif of CMV-IE promoter and downstream HBV fragment (genotype D, subtype ayw, nt 1805-2335) with a deletion of nt 1816(A) and the insertion of HA-tag sequence in precore ORF was chemically synthesized by Genscript Inc. Within this DNA fragment, a SacI restriction enzyme site is present at the 5' end and an authentic BspEI restriction site exists at the 3' terminus. The vector pTREHBV-HAe was constructed through insertion of the synthesized DNA fragment into the SacI/BspEI restriction sites in plasmid pTREHBVDES. The complete sequence of pTREHBV-HAe is shown in SEQ ID NO. 35.

To generate the HA-fused precore expression vector, a PCR fragment containing HBV nt 1816-2335 with HA sequence insertion was amplified from pTREHBV-HAe by using primers 5'-ATTGGATCCACCATGCAACTTTT-TCACCTCTGC-3' and 5'-ACAGTAGTTTCCGGAAGT-GTTGATAGGATAGGGG-3'. The PCR fragment was restricted with BamHI and BspEI and inserted into the same restriction sites in precore expression vector (pcHBe) to yield plasmid pcHA-HBe. The complete sequence of pcHA-HBe is shown in SEQ ID NO. 39.

Cell Cultures

HepG2 cell (ATCC® HB-8065™), a hepatoblastoma cell line which supports HBV replication, was obtained from ATCC. HepG2-derived HepDES19 cell line that inducibly expressed HBV DNA and cccDNA has been described previously (7). Cell lines were maintained in Dulbecco's modified Eagle's medium (DMEM)-F12 medium (Cellgro) supplemented with 10% fetal bovine serum, 100 U/ml penicillin, and 100 µg/ml streptomycin.

To establish HepBHAe cell line, HepG2 cells were transfected with plasmid pTet-off (Clontech) that expresses the Tet-responsive transcriptional activator and plasmid pTREHBV-HAe, in which the transcription of modified HBV pgRNA is controlled by a CMV-IE promoter with tetracycline-responsive elements. Transfected HepG2 cells were selected with 500 µg/ml G418 in the presence of 1 µg/ml tetracycline. G418-resistant colonies were picked and expanded into cell lines. HBV replication was induced by culturing cells in tetracycline-free medium, and the levels of viral DNA replicative intermediates were determined by Southern blot hybridization. The cell line with high levels of HBV replication were chosen and designated as HepBHAe with different clone numbers.

The HA-tagged HBeAg stable expression cell line HepHA-HBe was generated by transfection of HepG2 cells with pcHA-HBe plasmid, colonies were selected with 500 μg/ml G418 and positive colonies were identified by anti-HA western blot analysis.

HepBHAe and HepHA-HBe stable cell lines were cultured in the same way as HepG2, except for the addition of G418 at 500 μg/ml. For HepBHAe cells, tetracycline was routinely added at 1 μg/ml during maintenance to suppress HBV pgRNA transcription.

Cell Transfection

Cells (~1.0×10⁶) were seeded in a collagen coated 35-mm-diameter dish in antibiotics-free DMEM/F12 medium. After overnight incubation, each well was transfected with a total of 4 μg plasmids with Lipofectamine 2000 (Life Technologies) by following the manufacturer's directions. Transfected cells or supernatant samples were harvested at the indicated time points.

Viral Nucleic Acid Analysis

Total cellular RNA was extracted with TRIzol reagent (Life Technologies) by following the manufacturer's protocols. Encapsidated viral pgRNA was purified as follows, cells from one 12-well plate well were lysed in 250 μl of lysis buffer containing 10 mM Tris-HCl (pH 8.0), 1 mM EDTA, 1% NP-40, and 50 mM NaCl at 37° C. for 10 min and the nuclei were removed by centrifugation. The sample was incubated with 6 U of micrococcal nuclease and 15 μl of 100 mM $CaCl_2$ and incubated for 15 min at 37° C. to digest free nucleic acids. Encapsidated viral pgRNA was extracted by the addition of 750 μl TRIzol LS reagent (Invitrogen) according to the manufacturer's protocols. RNA samples were electrophoresed through 1.5% agarose gel containing 2.2 M formaldehyde and transferred onto Hybond-XL membrane (GE Healthcare) in 20×SSC buffer (1×SSC is 0.15 M NaCl plus 0.015 M sodium citrate).

Cytoplasmic viral core DNA was extracted as follows, cells from one 35-mm diameter dish were lysed with 0.5 ml of lysis buffer containing 10 mM Tris-HCl, pH 8.0, 10 mM EDTA, 1% NP40 and 2% sucrose at 37° C. for 10 min. Cell debris and nuclei were removed by centrifugation, and supernatant was incubated with 3 μl of 1 M $Mg(OAc)_2$ and 5 μl of 10 mg/ml DNase I (Calbiochem) for 30 min at 37° C. The supernatant was then mixed with 15 μl of 0.5 M EDTA and 130 μl of 35% polyethylene glycol (PEG) 8000 containing 1.5 M NaCl for nucleocapsids precipitation. After incubation on ice for 1 h, viral nucleocapsids were pelleted by centrifugation at 10,000 rpm for 5 min at 4° C., followed by digestion at 37° C. for 1 h in 400 μl of digestion buffer containing 0.5 mg/ml pronase (Calbiochem), 0.5% sodium dodecyl sulfate (SDS), 100 mM NaCl, 25 mM Tris-HCl (pH 7.4), and 10 mM EDTA. The digestion mixture was extracted with phenol, and DNA was precipitated with ethanol and dissolved in TE (10 mM Tris-HCl, pH 8.0, 1 mM EDTA) buffer. One-third of the core DNA sample from each plate was resolved by electrophoresis into a 1.2% agarose gel. The gel was then subjected to depurination in a buffer containing 0.2N HCl, denaturation in a solution containing 0.5 M NaOH and 1.5 M NaCl, and neutralization in a buffer containing 1 M Tris-HCl (pH 7.4) and 1.5 M NaCl. DNA was then blotted onto Hybond-XL membrane in 20×SSC buffer.

Extraction of protein-free viral DNA (cccDNA and protein-free rcDNA) was carried out by using a modified Hirt extraction procedure (4, 8). Briefly, cells from one 35-mm diameter dish were lysed in 3 ml of 10 mM Tris-HCl (pH 7.5), 10 mM EDTA, and 0.7% SDS. After 30-min incubation at room temperature, the lysate was transferred into a 15-ml tube, and this step was followed by the addition of 0.8 ml of 5 M NaCl and incubation at 4° C. overnight. The lysate was then clarified by centrifugation at 10,000 rpm for 30 min at 4° C. and extracted twice with phenol and once with phenol:chloroform:isoamyl alcohol (25:24:1). DNA was precipitated in ethanol at room temperature for overnight and dissolved in TE buffer. One-third of the protein-free DNA sample was then resolved in a 1.2% agarose gel and transferred onto Hybond-XL membrane.

For the detection of HBV RNA and DNA, membranes were probed with a [$\alpha$-$^{32}$P]UTP (800 Ci/mmol; Perkin Elmer)-labeled plus- or minus-strand-specific full-length HBV riboprobe. Hybridization was carried out in 5 ml of EKONO hybridization buffer (Genotech) with prehybridization at 65° C. for 1 h and overnight hybridization at 65° C., followed by wash in 0.1×SSC and 0.1% SDS at 65° C. for 1 h. The membrane was exposed to a phosphorimager screen, and hybridization signals were detected by Typhoon FLA-7000 system (GE Healthcare).

Western Blot Analysis

Cells in 35 mm dish were washed once with PBS buffer and lysed in 500 μl of 1× Laemmli buffer. A total of 50 μl of the cell lysate was resolved on an SDS-12% polyacrylamide gel and transferred onto polyvinylidene difluoride membrane (Millipore). The membranes were blocked with Western Breeze blocking buffer (Life Technologies) and probed with antibodies against HBcAg (aa170-183), HA-tag (Sigma-Aldrich, clone M2), β-actin (Sigma-Aldrich). Bound antibodies were revealed by IRDye secondary antibodies. The immunoblot signals were visualized and quantified with the Li-COR Odyssey system.

Immunoprecipitation

Cells from one 35-mm diameter dish were lysed with 0.5 ml of lysis buffer containing 10 mM Tris-HCl, pH 8.0, 10 mM EDTA, 1% NP40, 2% sucrose and 1× protease inhibitor cocktails (G-biosciences). After centrifugation to remove the cell debris, the clarified cell lysates were incubated with 50 μl of Ezview Red Anti-HA (Sigma-Aldrich) at 4° C. for overnight with gentle rotation. 0.5 ml of medium sample from one 35-mm diameter dish (1 ml in total) was subjected to immunoprecipitation directly. The beads were washed with TBS buffer (0.15 M NaCl, 0.05 M Tris-HCl [pH 7.4]) for three times at 4° C. The pelleted beads were subjected to protein sample preparation with Laemmli buffer. Immunoprecipitated HA-tagged proteins were detected by Western blot using antibodies against HA-tag (Sigma-Aldrich).

ELISA for Detection of HA-Tagged HBeAg

For chemiluminescence enzyme immunoassay (CLIA) detection of HA-tagged HBeAg, high sensitivity streptavidin coated plate (Black, cat#: 15525, Thermo Scientific) was washed by PBST (PBS plus 0.05% Tween 20) for 3 times, and then incubated with 50 μl of anti-HA-biotin (cat#: A00203, Genscript; 5 μg/ml in PBS) at RT for 30 min, followed by wash with 200 μl PBST for 3 times. After removal of the wash buffer, 50 μl of culture supernatant samples was added in the ELISA wells and incubated at RT for 30 min, followed by wash with 200 μl PBST for 3 times. Then 50 μl of horseradish peroxidase (HRP)-conjugated anti-HBe antibodies (from HBeAg CLIA kit, cat#: CL0312-2, Autobio Diagnostics) was added in the well and incubated at RT for 30 min. After wash with 200 μl PBST for 5 times, 25 μl of each substrate A and B from the CLIA kit were added and the plate was gently shaken for 10 sec. The plate was read on a luminometer.

For AlphaLISA detection of HA-tagged HBeAg, anti-HA-biotin (cat#: A00203, Genscript) was diluted to 2 μg/ml in 1× assay buffer (25 mM HEPES, 0.1M NaCl, 0.1% BSA, pH7.4) and dispensed 5 µl into each wells of Proxiplate-384 HS (cat#: 6008279, Perkin Elmer). 5 µl of culture fluid samples was then added in wells and mixed gently, followed by incubation at RT for 30 min. Subsequently, 5 µl of 0.2 µg/ml anti-HBe (clone 29, Lot 20110305, Autobio Diagnostics) was added and gently mixed, followed by incubation at RT for 30 min. Then, the assay solution was mixed with 5 µl of diluted Anti-mouse IgG AlphaLISA acceptor beads (cat#: AL105C, Perkin Elmer) (125 pig/ml) and incubated at RT for 30 min, followed by incubation with 5 µl of AlphaScreen Streptavidin donor beads (cat#: 6760002S, Perkin Elmer) (125 µg/ml) at RT for 1 h. After incubation, the plate was read on Envision 2104 Multilabel reader (Perkin Elmer).

Results

Herein provided are two types of novel cell lines for expressing HA-tagged HBeAg (HA-HBeAg) from transgene and HBV cccDNA, respectively, and methods for detecting the recombinant HBeAg by chemiluminescence immunoassay and AlphaLISA assay. The cell lines and assays are suitable for high throughput screen of compounds that reduce HBV cccDNA level and/or silence cccDNA transcription.

The small compact HBV DNA genome size and the overlapped genomic organization restrict the insertion of reporter genes without affecting viral DNA replication and subsequent cccDNA formation in transfected cells.

Precore/HBeAg can be engineered into cccDNA-dependent manner in HepDE19 cells (3). In the art it is known that HBV genome has a highly compact gene organization which exhibits overlapped ORFs and multiple cis elements. Therefore, it was believed that gene insertion/deletion or sequence replacement would very likely affect viral DNA replication. Previous works have replaced HBV sequence, such as envelope coding region in most cases, by GFP to make recombinant HBV genome, but trans-complement of viral proteins was needed to support viral replication and virion assembly (Protzer, et al, PNAS (1999), 96: 10818-23.). Moreover, those reported recombinant HBV genome can only make first round cccDNA synthesis if used to infect permissive cells, intracellular amplification of cccDNA is blocked due to the defective viral DNA replication.

Despite the above prior art knowledge, it was attempted and reasoned herein that an in-frame fused short exogenous epitope tag in precore open reading frame (ORF) could be tolerated by HBV genome and expressed from cccDNA template, thus a pair of tag-specific antibody and HBeAg antibody would significantly improve the specificity of ELISA detection.

In order to construct a tetracycline-inducible HBV replicating vector with a Human influenza hemagglutinin (HA) fused precore open reading frame, an HA-tag-containing DNA sequence (gtggacatcTACCCATACGACGTTCCAGATTACGCTggc;
SEQ ID NO.: 41)

was inserted into an in-frame upstream position adjacent to the start codon of core ORF in HBV expression vector pTREHBVDES, in which the HBV pgRNA expression is governed by a tetracycline (tet) regulated CMV-IE promoter in a Tet-off manner. The flanking sequences (in lower case) of HA-tag (in upper case) were designed to maintain the base pairing of the stem loop structure (epsilon, e) of HBV genome and the Kozak motif of core ORF start codon (FIG. 1). The obtained recombinant plasmid was designated pTREHBV-HAe (SEQ ID NO: 35). Besides the HA-tag insertion, the plasmid pTREHBV-HAe contains a point deletion in the 5' end start codon of precore ORF (ATG to TG), by which prevents the expression of precore from the HBV genome in the plasmid template. In addition, two tandem stop codons were introduced into the coding region of the amino terminus of the small (S) envelope protein (217TTGTTG222 to 217TAGTAG222; mutations are underlined) to block the production of HBV infectious particles.

To test the feasibility of epitope-tagged HBV precore protein expression and HBeAg secretion, the HA-tag-containing DNA sequence was inserted into the same viral DNA position, as described above, in precore expression plasmid pcHBe and the construct was designated pcHA-HBe (SEQ ID NO: 39). Transfection of pcHA-HBe in HepG2 cells led to the intracellular expression of HA-tagged precore protein and extracellular accumulation of HA-tagged HBeAg (FIG. 2), thus confirming that the insertion of HA tag into precore protein does not affect precore expression, post-translational processing, and HBeAg secretion. A chemiluminescence ELISA and an AlphaLISA for detecting HA-tagged HBeAg (HA-HBeAg) has also been established, as described in the Materials and Methods section.

In accordance with the above, a cell line that constitutively expresses HA-tagged HBeAg was established by stably transfecting pcHA-HBe into HepG2 cells. Two clones with the high levels of HA-tagged HBeAg expression were selected through AlphaLISA assay, and were designated HepHA-HBe4 and HepHA-HBe47, respectively (FIG. 3).

The recombinant HBV plasmid pTREHBV-HAe was able to replicate HBV DNA to a comparable level as pTREHB-VDES did in the transient transfection assay (FIG. 4), suggesting the HA-tag insertion was tolerated by HBV genome replication. Then, pTREHBV-HAc was stably co-transfected with pTET-off (Clontech) into HepG2 cells to make tetracycline inducible HBV cell line. Theoretically, in such cell line, upon induction, no precore protein and its derivative HBeAg will be produced from transgene due to the silence of precore ORF start codon. The transcribed pgRNA will express viral core protein and polymerase and initiate reverse transcription to generate rcDNA, resulting in cccDNA formation via the intracellular amplification pathway. The start codon of the incomplete precore ORF at the 3' redundancy of pgRNA will be copied into viral DNA sequence, and the intact ORF of HA-tagged precore will be reconstituted during rcDNA conversion into cccDNA. Thus, the HA-precore mRNA can be transcribed only from cccDNA, making secreted HA-tagged HBeAg a surrogate marker for intranuclear cccDNA (FIG. 5).

We have obtained 5 cell lines (HepBHAe1, HepBHAe13, HepBHAe34, HepBHAe45, HepBHAe82) that support high level of HBV DNA replication in a tetracycline-dependent fashion (FIGS. 6 and 7).

In the representative line HepBHAe13 cells, time-dependent kinetics of the synthesis and accumulation of viral products, including the replicative DNA intermediates and cccDNA, were observed upon tetracycline withdrawal. In the culture fluid of HepBHAe13 cells, the HA-tagged HBeAg was also detected by Western blot at day 6 after the removal of tetracycline and the antigen level gradually increased afterward. The level of HA-tagged HBeAg (HA-HBeAg) was proportional to the intracellular level of viral core DNA and cccDNA (FIG. 6). The authenticity of cccDNA produced from HepBHAe cell lines has been confirmed by heat denature and further restriction enzyme digestion (FIG. 8). Thus, inducible cell lines supporting DNA replication and cccDNA formation of the recombinant HBV with HA-tag insertion in precore have been established.

AlphaLISA assay on the supernatant samples from cultured HepBHAe cells demonstrated the increased levels of HA-tagged HBeAg in a 16-day time course study (FIG. 9). HcpHBAe13 cells were selected for further validation. The cells were cultured under three conditions: 1) in the presence of tetracycline to suppress transgene expression; 2) in the absence of tetracycline to induce viral DNA replication; 3) in the absence of tetracycline but with 3TC treatment to block viral DNA replication and subsequent cccDNA formation. Chemiluminescence immunoassay (CLIA) showed that the HA-tagged HBeAg signal in culture medium appeared at day 6 after tetracycline withdrawn and gradually increased afterward, as a consequence of cccDNA establishment and gene expression. As predicted, no HA-HBeAg was detected in the culture fluid at any time points in the presence of tetracycline or under 3TC treatment (tet-) (FIG. 10). Furthermore, two previously identified cccDNA formation inhibitors, specifically CCC-0975 and CCC-0346 (3), exhibited dose-dependent inhibition of HA-HBeAg production from HepBHAe13 cells (FIG. 11). Therefore, the production of HA-tagged HBeAg is cccDNA-dependent in HepBHAe13 cells.

In addition, time course study of other HepBHAe cell lines, including HepBHAe1, HepBHAe45, and HepBHAe82, demonstrated a time-dependent accumulation of HBV mRNA, cytoplasmic core DNA, and nuclear cccDNA upon withdrawal of tetracycline (FIG. 12). As shown in FIG. 13, a cccDNA-dependent HA-tagged HBeAg production was validated in these three additional HepBHAe cell lines.

Taken together, herein novel inducible cell lines have been established that express HBV cccDNA-dependent HA-tagged HBeAg, which can serve as a surrogate marker for HBV cccDNA in antiviral compound screen with the HA-HBeAg detection methods described herein.

The present invention refers to the following nucleotide and amino acid sequences:

The sequences provided herein are available in the NCBI database and can be retrieved from world wide web at ncbi.nlm.nih.gov/sites/entrez?db=gene; Theses sequences also relate to annotated and modified sequences. The present invention also provides techniques and methods wherein homologous sequences, and variants of the concise sequences provided herein are used. Preferably, such "variants" are genetic variants.

```
SEQ ID No. 1:
Nucleotide sequence encoding a hemagglutinin (HA) tag
TACCCATACGACGTTCCAGATTACGCT SEQ ID No. 2:
Nucleotide sequence encoding a His-tag
CATCATCATCATCATCAC SEQ ID No. 3:
Nucleotide sequence encoding a Flag-tag
GACTACAAGGACGACGACGACAAG SEQ ID No. 4:
Nucleotide sequence encoding c-myc-tag
ATG GCA TCA ATG CAG AAG CTG ATC TCA GAG GAG GAG CTG SEQ ID No. 5:
Nucleotide sequence encoding V5-tag
GGT AAG CCT ATC CCT AAC CCT CTC CTC GGT CTC GAT TCT ACG SEQ ID No. 6:
Nucleotide sequence encoding a C9-tag
ACTGAAACATCTCAAGTAGCTCCAGCT SEQ ID No. 7:
Nucleotide sequence encoding a 3x Flag-tag
GACTACAAAGACCACGACGGTGACTACAAAGACCACGACATCGACTACAAGGAC
GACGACGACAAG SEQ ID No. 8:
Amino acid sequence of a HA tag
YPYDVPDYA SEQ ID No. 9:
Amino acid sequence of a His-tag
HHHHHH SEQ ID No. 10:
Amino acid sequence of a Flag-tag
DYKDDDDK SEQ ID No. 11:
Amino acid sequence of a c-myc-tag
EQKLISEEDL SEQ ID No. 12:
Amino acid sequence of a V5-tag
GKPIPNPLLGLDST
```

-continued

SEQ ID No. 13:
Amino acid sequence of a C9-tag
TETSQVAPA

SEQ ID No. 14:
Amino acid sequence of a 3× Flag-tag
DYKDHDGDYKDHDIDYKDDDDK

SEQ ID No. 15:
Nucleotide sequence encoding a hepatitis B virus precore protein
Precore ORF sequence:
ATGCAACTTTTTCACCTCTGCCTAATCATCTCTTGTTCATGTCCTACTGTTCAAGCC

TCCAAGCTGTGCCTTGGGTGGCTTTGGGGCATGGACATCGACCCTTATAAAGAAT

TTGGAGCTACTGTGGAGTTACTCTCGTTTTTGCCTTCTGACTTCTTTCCTTCAGTAC

GAGATCTTCTAGATACCGCCTCAGCTCTGTATCGGGAAGCCTTAGAGTCTCCTGAG

CATTGTTCACCTCACCATACTGCACTCAGGCAAGCAATTCTTTGCTGGGGGGAACT

AATGACTCTAGCTACCTGGGTGGGTGTTAATTTGGAAGATCCAGCATCTAGAGACC

TAGTAGTCAGTTATGTCAACACTAATATGGGCCTAAAGTTCAGGCAACTCTTGTGG

TTTCACATTTCTTGTCTCACTTTTGGAAGAGAAACCGTTATAGAGTATTTGGTGTCT

TTCGGAGTGTGGATTCGCACTCCTCCAGCTTATAGACCACCAAATGCCCCTATCCT

ATCAACACTTCCGGAAACTACTGTTGTTAGACGACGAGGCAGGTCCCCTAGAAGA

AGAACTCCCTCGCCTCGCAGACGAAGGTCTCAATCGCCGCGTCGCAGAAGATCTC

AATCTCGGGAACCTCAATGTTAG

SEQ ID No. 16:
Nucleotide sequence encoding a hepatitis B virus e antigen (HBeAg)
HBeAg DNA sequence:
TCCAAGCTGTGCCTTGGGTGGCTTTGGGGCATGGACATCGACCCTTATAAAGAAT

TTGGAGCTACTGTGGAGTTACTCTCGTTTTTGCCTTCTGACTTCTTTCCTTCAGTAC

GAGATCTTCTAGATACCGCCTCAGCTCTGTATCGGGAAGCCTTAGAGTCTCCTGAG

CATTGTTCACCTCACCATACTGCACTCAGGCAAGCAATTCTTTGCTGGGGGGAACT

AATGACTCTAGCTACCTGGGTGGGTGTTAATTTGGAAGATCCAGCATCTAGAGACC

TAGTAGTCAGTTATGTCAACACTAATATGGGCCTAAAGTTCAGGCAACTCTTGTGG

TTTCACATTTCTTGTCTCACTTTTGGAAGAGAAACCGTTATAGAGTATTTGGTGTCT

TTCGGAGTGTGGATTCGCACTCCTCCAGCTTATAGACCACCAAATGCCCCTATCCT

ATCAACACTTCCGGAAACTACTGTTGTT

SEQ ID No. 17:
Amino acid sequence of a hepatitis B virus precore protein
precore amino acid sequence:
MQLFHLCLIISCSCPTVQASKLCLGWLWGMDIDPYKEFGATVELLSFLPSDFFPSVRDL

LDTASALYREALESPEHCSPHHTALRQAILCWGELMTLATWVGVNLEDPASRDLVVS

YVNTNMGLKFRQLLWFHISCLTFGRETVIEYLVSFGVWIRTPPAYRPPNAPILSTLPETT

VVRRRGRSPRRRTPSPRRRRSQSPRRRRSQSREPQC

SEQ ID No. 18:
Amino acid sequence of a hepatitis B virus e antigen (HBeAg)
HBeAg amino acid sequence (removes N-terminal signal peptide (19 aa) and C-tetminal
arginine-rich domain (34 aa) from precore):
SKLCLGWLWGMDIDPYKEFGATVELLSFLPSDFFPSVRDLLDTASALYREALESPEHC

SPHHTALRQAILCWGELMTLATWVGVNLEDPASRDLVVSYVNTNMGLKFRQLLWFH

ISCLTFGRETVIEYLVSFGVWIRTPPAYRPPNAPILSTLPETTVV

SEQ ID No. 19:
Nucleotide sequence encoding a HA-tagged hepatitis B virus precore protein.
HA-tagged precore DNA sequence:
ATGCAACTTTTTCACCTCTGCCTAATGATCTCTTGTTCATGTCCTACTGTTCAAGCC TCCAAGCTGTGCGTTGGGTGGCTTTGGGGCGTGGACATC<u>TACCCATACGACGTTCC</u>

<u>AGATTACGCTGGC</u>ATGGACATCGACCCTTATAAAGAATTTGGAGCTACTGTGGAG

TTACTCTCGTTTTTGCCTTCTGACTTCTTTCCTTCAGTACGAGATCTTCTAGATACCG

CCTCAGCTCTGTATCGGGAAGCCTTAGAGTCTCCTGAGCATTGTTCACCTCACCAT

ACTGCACTCAGGCAAGCAATTCTTTGCTGGGGGGAACTAATGACTCTAGCTACCTG

GGTGGGTGTTAATTTGGAAGATCCAGCATCTAGAGACCTAGTAGTCAGTTATGTCA

ACACTAATATGGGCCTAAAGTTCAGGCAACTCTTGTGGTTTCACATTTCTTGTCTCA

CTTTTGGAAGAGAAACCGTTATAGAGTATTTGGTGTCTTTCGGAGTGTGGATTCGC

ACTCCTCCAGCTTATAGACCACCAAATGCCCCTATCCTATCAACACTTCCGGAAAC

TACTGTTGTTAGACGACGAGGCAGGTCCCCTAGAAGAAGAACTCCCTCGCCTCGC

AGACGAAGGTCTCAATCGCCGCGTCGCAGAAGATCTCAATCTCGGGAACCTCAAT

GTTAG

SEQ ID No. 20:
Nucleotide sequence encoding a HA-tagged hepatitis B virus e antigen (HBeAg)
HA-tagged HBeAg DNA sequence:
TCCAAGCTGTGCCTTGGGTGGCTTTGGGGCGTGGACATC<u>TACCCATACGACGTTCC</u>

<u>AGATTACGCTGGC</u>ATGGACATCGACCCTTATAAAGAATTTGGAGCTACTGTGGAG

TTACTCTCGTTTTTGCCTTCTGACTTCTTTCCTTCAGTACGAGATCTTCTAGATACCG

CCTCAGCTCTGTATCGGGAAGCCTTAGAGTCTCCTGAGCATTGTTCACCTCACCAT

ACTGCACTCAGGCAAGCAATTCTTTGCTGGGGGGAACTAATGACTCTAGCTACCTG

GGTGGGTGTTAATTTGGAAGATCCAGCATCTAGAGACCTAGTAGTCAGTTATGTCA

ACACTAATATGGGCCTAAAGTTCAGGCAACTCTTGTGGTTTCACATTTCTTGTCTCA

CTTTTGGAAGAGAAACCGTTATAGAGTATTTGGTGTCTTTCGGAGTGTGGATTCGC

ACTCCTCCAGCTTATAGACCACCAAATGCCCCTATCCTATCAACACTTCCGGAAAC

TACTGTTGTT

SEQ ID No. 21:
Amino acid sequence of a HA-tagged hepatitis B virus precore protein. The HA-tag is
underlined.
HA-tagged precore amino acid sequence:
MQLFHLCLIISCSCPTVQASKLCLGWLWGVDI<u>YPYDVPDYAG</u>MDIDPYKEFGATVELL

SFLPSDFFPSVRDLLDTASALYREALESPEHCSPHHTALRQAILCWGELMTLATWVGV

NLEDPASRDLVVSYVNTNMGLKFRQLLWFHISCLTFGRETVIEYLVSFGVWIRTPPAY

RPPNAPILSTLPETTVVRRRGRSPRRRTPSPRRRRSQSPRRRRSQSREPQC

SEQ ID No. 22:
Amino acid sequence of HA-tagged hepatitis B virus e antigen (HBeAg). The HA-tag is
underlined.
HA-tagged HBeAg amino acid sequence:
SKLCLGWLWGVDI<u>YPYDVPDYAG</u>MDIDPYKEFGATVELLSFLPSDFFPSVRDLLDTAS

ALYREALESPEHCSPHHTALRQAILCWGELMTLATWVGVNLEDPASRDLVVSYVNTN

MGLKFRQLLWFHISCLTFGRETVIEYLVSFGVWIRTPPAYRPPNAPILSTLPETTVV

SEQ ID No. 23:
Nucleotide sequence encoding a HBV core protein
ATGGACATCGACCCTTATAAAGAATTTGGAGCTACTGTGGAGTTACTCTCGTTTTT

GCCTTCTGACTTCTTTCCTTCAGTACGAGATCTTCTAGATACCGCCTCAGCTCTGTA

```
TCGGGAAGCCTTAGAGTCTCCTGAGCATTGTTCACCTCACCATACTGCACTCAGGC

AAGCAATTCTTTGCTGGGGGGAACTAATGACTCTAGCTACCTGGGTGGGTGTTAAT

TTGGAAGATCCAGCATCTAGAGACCTAGTAGTCAGTTATGTCAACACTAATATGGG

CCTAAAGTTCAGGCAACTCTTGTGGTTTCACATTTCTTGTCTCACTTTTGGAAGAGA

AACCGTTATAGAGTATTTGGTGTCTTTCGGAGTGTGGATTCGCACTCCTCCAGCTT

ATAGACCACCAAATGCCCCTATCCTATCAACACTTCCGGAAACTACTGTTGTTAGA

CGACGAGGCAGGTCCCCTAGAAGAAGAACTCCCTCGCCTCGCAGACGAAGGTCTC

AATCGCCGCGTCGCAGAAGATCTCAATCTCGGGAACCTCAATGTTAG

SEQ ID No. 24:
Amino acid sequence of a HBV core protein
MDIDPYKEFGATVELLSFLPSDFFPSVRDLLDTASALYREALESPEHCSPHHTALRQAIL

CWGELMTLATWVGVNLEDPASRDLVVSYVNTNMGLKFRQLLWFHISCLTFGRETVIE

YLVSFGVWIRTPPAYRPPNAPILSTLPETTVVRRRGRSPRRRTPSPRRRRSQSPRRRRSQ

SREPQC

SEQ ID No. 25:
Nucleotide sequence of an epsilon structure as encoded by an HBV genome
TGTTCATGTCCTACTGTTCAAGCCTCCAAGCTGTGCCTTGGGTGGCTTTGGGGCAT

GGACA

SEQ ID No. 26:
Nucleotide sequence capable of forming base pairs with the lower stem
of the epsilon structure of a hepadnavirus genome
GTGGACATC SEQ ID No. 27:
Nucleotide sequence of HBV genome, HBV genotype D, subtype ayw. Genbank accession#
U95551(C1902 and A1903 are in bold. The ORF of precore is underlined.)
AATTCCACAACCTTTCACCAAACTCTGCAAGATCCCAGAGTGAGAGGCCTGTATTT

CCCTGCTGGTGGCTCCAGTTCAGGAGCAGTAAACCCTGTTCCGACTACTGCCTCTC

CCTTATCGTCAATCTTCTCGAGGATTGGGGACCCTGCGCTGAACATGGAGAACATC

ACATCAGGATTCCTAGGACCCCTTCTCGTGTTACAGGCGGGGTTTTTCTTGTTGAC

AAGAATCCTCACAATACCGCAAAGTCTAGACTCGTGGTGGACTTCTCTCAATTTTC

TAGGGGGAACTACCGTGTGTCTTGGCCAAAATTCGCAGTCCCCAACCTCCAATCAC

TCACCAACCTCCTGTCCTCCAACTTGTCCTGGTTATCGCTGGATGTGTCTGCGGCGT

TTTATCATCTTCCTCTTCATCCTGCTGCTATGCCTCATCTTCTTGTTGGTTCTTCTGG

ACTATCAAGGTATGTTGCCCGTTTGTCCTCTAATTCCAGGATCCTCAACCACCAGC

ACGGGACCATGGCGAACCTGCATGACTACTGCTCAAGGAACCTCTATGTATCCCTC

CTGTTGCTGTACCAAACCTTCGGACGGAAATTGCACCTGTATTCCCATCCCATCAT

CCTGGGCTTTCGGAAAATTCCTATGGGAGTGGGCCTCAGCCCGTTTCTCCTGGCTC

AGTTTACTAGTGCCATTTGTTCAGTGGTTCGTAGGGCTTTCCCCCACTGTTTGGCTT

TCAGTTATATGGATGATGTGGTATTGGGGGCCAAGTCTGTACAGCATCTTGAGTCC

CTTTTTACCGCTGTTACCAATTTTCTTTTGTCTTTGGGTATACATTTAAACCCTAAC

AAAACAAAGAGATGGGGTTACTCTCTGAATTTTATGGGTTATGTCATTGGAAGTTA

TGGGTCCTTGCCACAAGAACACATCATACAAAAAATCAAAGAATGTTTTAGAAAA

CTTCCTATTAACAGGCCTATTGATTGGAAAGTATGTCAACGAATTGTGGGTCTTTT

GGGTTTTGCTGCCCCATTTACACAATGTGGTTATCCTGCGTTAATGCCCTTGTATGC

ATGTATTCAATCTAAGCAGGCTTTCACTTTCTCGCCAACTTACAAGGCCTTTCTGTG

TAAACAATACCTGAACCTTTACCCCGTTGCCCGGCAACGGCCAGGTCTGTGCCAAG
```

-continued

```
TGTTTGCTGACGCAACCCCCACTGGCTGGGGCTTGGTCATGGGCCATCAGCGCGTG

CGTGGAACCTTTTCGGCTCCTCTGCCGATCCATACTGCGGAACTCCTAGCCGCTTG

TTTTGCTCGCAGCAGGTCTGGAGCAAACATTATCGGGACTGATAACTCTGTTGTCC

TCTCCCGCAAATATACATCGTATCCATGGCTGCTAGGCTGTGCTGCCAACTGGATC

CTGCGCGGGACGTCCTTTGTTTACGTCCCGTCGGCGCTGAATCCTGCGGACGACCC

TTCTCGGGGTCGCTTGGGACTCTCTCGTCCCCTTCTCCGTCTGCCGTTCCGACCGAC

CACGGGGCGCACCTCTCTTTACGCGGACTCCCCGTCTGTGCCTTCTCATCTGCCGG

ACCGTGTGCACTTCGCTTCACCTCTGCACGTCGCATGGAGACCACCGTGAACGCCC

ACCGAATGTTGCCCAAGGTCTTACATAAGAGGACTCTTGGACTCTCTGCAATGTCA

ACGACCGACCTTGAGGCATACTTCAAAGACTGTTTGTTTAAAGACTGGGAGGAGTT

GGGGGAGGAGATTAGATTAAAGGTCTTTGTACTAGGAGGCTGTAGGCATAAATTG

GTCTGCGCACCAGCACCATGCAACTTTTTCACCTCTCCCTAATCATCTCTTGTTCAT

GTCCTACTGTTCAAGCCTCCAAGCTGTGCCTTGGGTGGCTTTGGGGCATGGACATC

GACCCTTATAAAGAATTTGGAGCTACTGTGGAGTTACTCTCGTTTTTGGCTTCTGAC

TTCTTTCCTTCAGTACGAGATCTTCTAGATACCGCCTCAGCTCTGTATCGGGAAGCC

TTAGAGTCTCCTGAGCATTGTTCACCTCACCATACTGCACTCAGGCAAGCAATTCT

TTGCTGGGGGAACTAATGACTCTAGCTACCTGGGTGGGTGTTAATTTGGAAGATC

CAGCATCTAGAGACCTAGTAGTCAGTTATGTCAACACTAATATGGGCCTAAAGTTC

AGGGAACTCTTGTGGTTTGAGATTTCTTGTCTCACTTTTGGAAGAGAAACCGTTATA

GAGTATTTGGTGTCTTTCGGAGTGTGGATTCGCACTCCTCCAGCTTATAGACCACC

AAATGCCCCTATCCTATCAACACTTCCGGAAACTACTGTTGTTAGACGACGAGGCA

GGTCCCCTAGAAGAAGAACTCCCTCGCCTCGCAGACGAAGGTCTCAATCGCCGCG

TCGCAGAAGATCTCAATCTCGGGAACCTCAATGTTAGTATTCCTTGGACTCATAAG

GTGGGGAACTTTACTGGTCTTTATTCTTCTACTGTACCTGTCTTTAATCCTCATTGG

AAAACACCATCTTTTCCTAATATACATTTACACCAAGACATTATCAAAAAATGTGA

ACAGTTTGTAGGCCCACTTACAGTTAATGAGAAAAGAAGATTGCAATTGATTATGC

CTGCTAGGTTTTATCCAAAGGTTACCAAATATTTACCATTGGATAAGGGTATTAAA

CCTTATTATCCAGAACATCTAGTTAATCATTACTTCCAAACTAGACACTATTTACAC

ACTCTATGGAAGGCGGGTATATTATATAAGAGAGAAACAACACATAGCGCCTCAT

TTTGTGGGTCACCATATTCTTGGGAACAAGATCTACAGCATGGGGGAGAATCTTTC

CACCAGCAATCCTCTGGGATTCTTTCCCGACCACCAGTTGGATCCAGCCTTCAGAG

CAAACACAGCAAATCCAGATTGGGACTTCAATCCCAACAAGGACACCTGGCCAGA

CGCCAACAAGGTAGGAGCTCGAGCATTCGGGCTGGGTTTCACCCCACCGCACGGA

GGCCTTTTGGGGTGGAGCCCTCAGGCTCAGGGCATACTACAAACTTTGCCAGCAA

ATCCGCCTCCTGCCTCCACCAATCGCCAGACAGGAAGGCAGCCTACCCCGCTGTCT

CCACCTTTGAGAAACACTCATCCTCAGGCCATGCAGTGG

SEQ ID No. 28:
Nucleotide sequence of HBV genome, HBV genotype A (Genbank accession# AP007263)
AATTCCACTGCCTTCCACCAAGCTCTGCAGGATCCCAGAGTCAGGGGTCTGTATTT

TCCTGCTGGTGGCTCCAGTTCAGGAACAGTAAACCCTGCTCCGAATATTGCCTCTC

ACATCTCGTCAATCTCCGCGAGGACTGGGGACCCTGTGGCGAACATGGAGAACAT
```

-continued
```
CACATCAGGATTCCTAGGACCCCTGCTCGTGTTACAGGCGGGGTTTTCTTGTTGA

CAAGAATCCTCACAATACCGCAGAGTCTAGACTCGTGGTGGACTTCTCTCAATTTT

CTAGGGGATCACCCGTGTGTCTTGGCCAAAATTCGCAGTCCCCAACCTCCAATCA

CTCACCAACCTCCTGTCCTCCAATTTGTCCTGGTTATCGCTGGATGTGTCTGCGGCG

TTTTATCATATTCCTCTTCATCCTGCTGCTATGCCTCATCTTCTTATTGGTTCTTCTG

GATTATCAAGGTATGTTGCCCGTTTGTCCTCTAATTCCAGGATCAACAACAACCAG

TACGGGACCATGCAAAACCTGCACGACTCCTGCTCAAGGCAACTCTATGTTTCCCT

CATGTTGCTGTACAAAACCTACGGATGGAAATTGCACCTGTATTCCCATCCCATCG

TCCTGGGCTTTCGCAAAATACCTATGGGAGTGGGCCTCAGTCCGTTTCTCTTGGCT

CAGTTTACTAGTGCCATTTGTTCAGTGGTTCGTAGGGCTTTCCCCCACTGTTTGGCT

TTCAGCTATATGGATGATGTGGTATTGGGGGCCAAGTCTGTACAGCATCGTGAGTC

CCTTTATACCGCTGTTACCAATTTTCTTTTGTCTCTGGGTATACATTTAAACCCTAA

CAAAACAAAAGATGGGGTTATTCCCTAAACTTCATGGGTTACATAATTGGAAGTT

GGGGAACTTTGCCACAGGATCATATTGTACAAAAGATCAAACACTGTTTTAGAAA

ACTTCCTGTTAACAGGCCTATTGATTGGAAAGTATGTCAAAGAATTGTGGGTCTTT

TGGGCTTTGCTGCTCCATTTACACAATGTGGATATCCTGCCTTAATGCCTTTGTATG

CATGTATACAAGCTAAACAGGCTTTCACTTTCTCGCCAACTTACAAGGCCTTTCTA

AGTAAACAGTACATGAACCTTTACCCCGTTGCTCGGCAACGGCCTGGTCTGTGCCA

AGTGTTTGCTGACGCAACCCCCACTGGCTGGGGCTTGGCCATAGGCCATCAGCGCA

TGCGTGGAACCTTTGTGGCTCCTCTGCCGATCCATACTGCGGAACTCCTAGCCGCT

TGTTTTGCTCGCAGCGGGTCTGGAGCAAAGCTCATCGGAACTGACAATTCTGTCGT

CCTGTCGCGGAAATATACATCGTTTCCATGGCTGCTAGGCTGTGCTGCCAACTGGA

TCGTTCGCGGAACGTCCTTTGTCTACGTCCCGTCGGCGCTGAATCCCGCGGACGAC

CCCTCTCGGGGCCGCTTGGGACTCTCTCGTCCCCTTCTCCGTCTGCCGTTCCAGCCG

ACCACGGGGCGCACCTCTCTTTACGCGGTCTCCCCGTCTGTGCCTTCTCATCTGCCG

GTCCGTGTGCACTTCGCTTCACCTCTGCACGTTGCATGGAGACCACCGTGAACGCC

CATCAGATCCTGCCCAAGGTCTTACATAAGAGGACTCTTGGACTCCCAGCAATGTC

AACGACCGACCTTGAGGCCTACTTCAAAGACTGTGTGTTTAAGGACTGGGAGGAG

CTGGGGGAGGAGATTAGGTTAAAGGTCTTTGTATTAGGAGGCTGTAGGCATAAAT

TGGTCTGCGCACCAGCACCATGCAACTTTTTCACCTCTGCCTAATCATCTCTTGTAC

ATGTCCCACTGTTCAAGCCTCCAAGCTGTGCCTTGGGTGGCTTTGGGGCATGGACA

TTGACCCTTATAAAGAATTTGGAGCTACTGTGGAGTTACTCTCGTTTTTGCCTTCTG

ACTTCTTTCCTTCCGTCAGAGATCTCCTAGACACCGCCTCAGCTCTGTATCGAGAA

GCCTTAGAGTCTCCTGAGCATTGCTCACCTCACCATACTGCACTCAGGCAAGCCAT

TCTCTGCTGGGGGAATTGATGACTCTAGCTACCTGGGTGGGTAATAATTTGGAAG

ATCCAGCATCCAGGGATCTAGTAGTCAATTATGTTAATACTAACATGGGTTTAAAG

ATCAGGCAACTATTGTGGTTTCATATATCTTGCCTTACTTTTGGAAGAGAGACTGT

ACTTGAATATTTGGTCTCTTTCGGAGTGTGGATTCGCACTCCTCCAGCCTATAGACC

ACCAAATGCCCCTATCTTATCAACAATTCCGGAAACTACTGTTGTTAGACGACGGG

ACCGAGGCAGGTCCCCTAGAAGAAGAACTCCCTCGCCTCGCAGACGCAGATCTCA

ATCGCCGCGTCGCAGAAGATCTCAATCTCGGGAATCTCAATGTTAGTATTCCTTGG
```

ACTCATAAGGTGGGAAACTTTACGGGGCTTTATTCCTCTACAGTACCTATCTTTAA

TCCTGAATGGCAAACTCCTTCCTTTCCTAAGATTCATTTACAAGAGGACATTATTA

ATAGGTGTCAACAATTTGTGGGCCCTCTCACTGTAAATGAAAAGAGAAGATTGAA

ATTAATTATGCCTGCTAGATTCTATCCTACCCACACTAAATATTTGCCCTTAGACAA

AGGAATTAAACCTTATTATCCAGATCAGGTAGTTAATCATTACTTCCAAACCAGAC

ATTATTTACATACTCTTTGGAAGGCTGGTATTCTATATAAGAGGGAAACCACACGT

AGCGCATCATTTTGCGGGTCACCATATTCTTGGGAACAAGAGCTACAGCATGGGA

GGTTGGTCATCAAAACCTCGCAAAGGCATGGGACGAATCTTTCTGTTCCCAACCC

TCTGGGATTCTTTCCCGATCATCAGTTGGACCCTGCATTCGGAGCCAACTCAAACA

ATCCAGATTGGGACTTCAACCCCATCAAGGACCACTGGCCAACAGCCAACCAGGT

AGGAGTGGGAGCATTCGGGCCAGGGCTCACCCCTCCACACGGCGGTATTTTGGGG

GGGAGCCCTCAGGCTCAGGGCATATTGACCACAGTGTCAACAATTCCTCCTCCTGC

CTCCACCAATCGGCAGTCAGGAAGGCAGCCTACTGCCATCTCTCCACCTCTAAGAG

ACAGTCATCCTCAGGCCATGCAGTGG

SEQ ID No. 29:
Nucleotide sequence of HBV genome, HBV genotype B (Genbank accession# AB602818)
AACTCCACCACTTTTCACCAAACTCTTCAAGATCCCAGAGTCCGGGCTCTGTACTT

TCCTGCTGGTGGCTCCAGTTCAGGAACAGTAAGCCCTGCTCAGAATACTGTCTCTG

CCATATCGTCAATCTTATCGAAGACTGGGGACCCTGTGCCGAACATGGAGAACAT

CGCATCAGGACTCCTAGGACCCCTGCTCGTGTTACAGGCGGGGTTTTTCTTGTTGA

CAAAAATCCTCACAATACCACAGAGTCTAGACTCGTGGTGGACTTCTCTCAATTTT

CTAGGGGGAACACCCGTGTGTCTTGGCCAAAATTCGCAGTCCCAAATCTCCAGTCA

CTCACCAACCTGTTGTCCTCCAATTTGTCCTGGTTATCGCTGGATGTGTCTGCGGCG

TTTTATCATCTTCCTCTGCATCCTGCTGCTATGCCTCATCTTCTTGTTGGTTCTTCTG

GACTATCAAGGTATGTTGCCCGTTTGTCCTCTAATTCCAGGATCATCAACCACCAG

CACGGGACCATGCAAGACCTGCACAACTCCTGCTCAAGGAACCTCTATGTTTCCCT

CATGTTGCTGTACAAAACCTACGGATGGAAACTGCACCTGTATTCCCATCCCATCA

TCTTGGGCTTTCGCAAAATACCTATGGGAGTGGGCCTCAGTCCGTTTCTCTTGGCTC

AGTTTACTAGTGCCATTTGTTCAGTGGTTCGTAGGGCTTTCCCCCACTGTCTGGCTT

TCAGTTATATGGATGATGTGGTATTGGGGGCCAAGTCTGTACAACATCTTGAGTCC

CTTTATGCCGCTGTTACCAATTTTCTTTTGTCTTTGGGTATACATTTAAACCCTCAC

AAAACAAAAAGATGGGGATATTCCCTTAACTTCATGGGATATGTAATTGGGAGTT

GGGGCACATTGCCACAGGAACATATTGTACAAAAAATCAAACTATGTTTTAGGAA

ACTTCCTGTAAACAGGCCTATTGATTGGAAAGTATGTCAACGAATTGTGGGTCTTT

TGGGGTTTGCTGCCCCTTTTACGCAATGTGGATATCCTGCTTTAATGCCTTTATATG

CATGTATACAAGCAAAACAGGCTTTTACTTTCTCGCCAACTTACAAGGCCTTTCTA

AGTAAACAGTATCTAGCCCTTTACCCCGTTGCTCGGCAACGGCCTGGTCTGTGCCA

AGTGTTTGCTGACGCAACCCCCACTGGTTGGGGCTTGGCCATAGGCCATCAGCGCA

TGCGTGGAACCTTTGTGTCTCCTCTGCCGATCCATACTGCGGAACTCCTAGCCGCTT

GTTTTGCTCGCAGCAGGTCTGGAGCGAAACTCATCGGGACTGACAATTCTGTCGTG

CTCTCCCGCAAGTATACATCGTTTCCATGGCTGCTAGGCTGTGCTGCCAACTGGAT

```
CCTGCGCGGGACGTCCTTTGTTTACGTCCCGTCGGCGCTGAATCCCGCGGACGACC

CCTCCCGGGCCGCTTGGGGCTCTACCGCCCGCTTCTCCGTCTGCCGTACCGACCG

ACCACGGGGCGCACCTCTCTTTACGCGGACTCCCCGTCTGTGCCTTCTCGTCTGCC

GGACCGTGTGCACTTCGCTTCACCTCTGCACGTCGCATGGAAACCACCGTGAACGC

GCACCGGAACCTGCCCAAGGTCTTGCACAAGAGGACTCTTGGACTTTCAGGAATGT

CAACGACCGACCTTGAGGCATACTTCAAAGACTGTGTGTTTCATGAGTGGGAGGA

GCTGGGGAGGAGATTAGGTTAAAGGTCTTTGTACTAGGAGGCTGTAGGCATAAA

TTGGTCTGTTCACCAGCACCATGCAACTTTTTCACCTCTGCCTAGTCATCTCTTGTT

CATGTCCTACTGTTCAAGCCTCCAAGCTGTGCCTTGGGTGGCTTTGGGACATGGAC

ATTGACCCTTATAAAGAATTTGGAGCTACTGTGGAGTTACTCTCTTTTTTGCCTTCT

GACTTCTTTCCGTCGGTACGAGACCTCCTAGATACCGCTGCTGCTCTGTATCGGGA

AGCCTTAGAATCTCCTGAACATTGCTCACCTCACCACACAGCACTCAGGCAAGCTA

TTCTGTGCTGGGGGGAATTAATGACTCTAGCTACCTGGGTGGGTAATAATTTAGAA

GATCCAGCGTCCAGGGATCTAGTAGTCAATTATGTTAACACTAACATGGGCCTAAA

GATCAGGCAATTATTGTGGTTTCACATTTCCTGTCTTACTTTTGGAAGAGAAACTGT

TGTTGAATATTTGGTGTCTTTTGGAGTGTGGATTCGCACTCCTCCGGCCTACAGACC

ACCAAATGCCCGTATCTTATCAACACTTCCGGAAACTACTGTTGTTAGACGACGAG

GCAGGTCCCTAGAAGAAGAACTCCCTCGCCTCGCAGACGAAGGTCTCAATCACC

GCGTCGCAGAAGATCTCAATCTCGGGAATCCCAATGTTAGTATTCCTTGGACTCAT

AAGGTGGGAAACTTTACGGGGCTCTATTCTTCTACAGTACCTGTCTTTAATCCTGA

ATGGCAAACTCCTTCTTTTCCAGACATTCATTTGCAGGAGGATATTGTTGATAGAT

GTAAGCAATTTGTGGGACCCCTTACAGTAAATGAAAACAGGAGACTAAAATTAAT

AATGCCTGCTAGATTTTATCCTAATGTTACCAAATATTTGCCCTTAGATAAAGGGA

TCAAACCTTATTATCCAGAGCATGTAGTTAATCATTACTTCCAGACAAGACATTAT

TTGCATACTGTTTGGAAGGCGGGTATCTTATATAAGAGAGAGTCAACACATAGCGC

CTCATTTTGCGGGTCACCATATTCTTGGGAACAAGATCTACAGCATGGGAGGTTGG

TCTTCCAAACGTCGAAAAGGCATGGGACAAATCTTTCTGTCCCCAATCCCCTGGG

ATTCTTCCCCGATCATCAGTTGGACCCTGCATTCAAAGCCAACTCAGAAAATCCAG

ATTGGGACCTCAACCCACACAAGGACAACTGGCCGGACGCCCACAAGGTGGGAGT

GGGAGCATTCGGGCCAGGGTTCACCCCTCCCCACGGGGACTGTTGGGGTGGAGC

CCTCAGGCTCAGGGCATACTTACATCTGTGCCAGCAGCTCCTCCTCCTGCCTCCAC

CAATCGGCAGTCAGGAAGGCAGCCTACTCCCTTATCTCCACCTCTAAGGGACACTC

ATCCTCAGGCCATGCAGTGG

SEQ ID No. 30:
Nucleotide sequence of HBV genome, HBV genotype C (Genbank accession# AB540584)
AACTCCACAACTTTCCACCAAGCTCTGCTAGATCCCAGAGTGAGGGGCCTATACTT

TCCTGCTGGTGGCTCCAGTTCCGGAACAGTAAACCCTGTTCCGACTACTGCCTCTC

CCATATCGTCAATCTTCACGAGGACTGGGGACCCTGTACCGAACATGGAGAACAC

AACATGAGGATTCCTAGGACCCCTGCTCGTGTTACAGGCGGGGTTTTCTTGTTGA

CAAGAATCCTCACAATACCGCAGAGTCTAGACTCGTGGTGGACTTCTCTCAATTTT

CTAGGGGGAGCACCCAGGTGTCCTGGCCAAAATTCGCAGTCCCCAACCTCCAATC

ACTCACCAACCTCTTGTCCTCCAATTTTGTCCTGGCTATCGCTGGATGTGTCTGCGGC
```

-continued

```
GTTTTATGATATTCCTCTTCATCCTGCTGCTATGCCTCATCTTCTTGTTGGTTCTTCT

GGACTATCAAGGTATGTTGCCCGTTTGTCCTCTACTTCCAGGAACATCAACTACAA

GGAGGGGACCATGCAAGACCTGCACGATTCCTGCTCAAGGAAMCTCTATGTTTCC

CTCTTGTTGCTGTACAAAACCTTCGGACGGAAACTGCAGTTGTATTCCCATCCCAT

CATCCTGGGCTTTCGCAAGATTGGTATGGGAGTGGGCCTCAGTCCGTTTCTGCTGG

CTCAGTTTACTAGTGCGATTTGTTGAGTGGTTCGTAGGGCTTTCCCCCACTGTTTGG

CTTTCAGCTATATGGATGATGTGGTATTGGGGGCCAAGTCTGTACAACATCTTGAG

TCCCTTTTTACCTCTATTACCAATTTTCTTTTGTCTTTGGGTATACATTTGAACCCTA

ATAAAACCAAGCGTTGGGGCTACTCCCTTAACTTTATGGGATATGTAATTGGAAGT

TGGGGTACTTTACCACAGGAACATATTGTTCTAAAAATCAAACAATGTTTTCGGAA

ACTGCCTGTAAATAGACCTATTGATTGGAAAGTATGTCAACGAATTGTGGGTCTTC

TGGGCTTTGCTGCCCCTTTTACACAATGTGGGTATCCTGCCTTGATGCCTTTGTATG

CATGTATACAAGCTAAGCAGGCTTTCACTTTCTCGCCAACTTATAAGGCCTTTCTGT

GTAAACAATATCTGAACCTTTACCCCGTTGCTCGGCAACGGTCAGGTCTCTGCCAA

GTATTTGCTGACGCAACCCCCACTGGATGGGGCTTGGCAATAGGCCATCAGCGCAT

GCGTGGAACCTTTGTGGCTCCTCTGCCGATCCATACTGCGGAACTCTTAGCAGCCT

GCTTTGCTCGCAGCCGGTCTGGAGCRAATCTTATTGGAACCGACAACTCCGTTGTC

CTCTCTCGGAAATACACCTCCTTTCCATGGCTGCTAGGGTGTGCTGCAAACTGGAT

CCTGCGCGGGACGTCCTTTGTCTACGTCCCGTCGGCGCTGAATCCAGCGGACGACC

CGTCTCGGGGCCGTTTGGGACTCTACCGTCCCCTTCTTCGTCTGCCGTTCCGGCCGA

CCACGGGGCGCACCTCTCTTTACGCGGTCTCCCCGTCTGTGCCTTCTCATCTGCCGG

ACCGTGTGCACTTCGCTTCACCTCTGCACGTCGCATGGAGACCACCGTGAACGCCC

ACCAGGTCTTGCCCAAGGTCTTACATAAGAGGACTCTTGGACTCTCGGCAATGTCA

ACGACCGACCTTGAGGCATACTTCAAAGACTGTGTGTTTAAAGACTGGGAGGAGT

TGGGGGAGGAGATTAGGTTAAAGGTCTTTGTACTAGGAGGCTGTAGGCATAAATT

GGTCTGTTCACCAGCACCATGCAACTTTTTCACCTCTGCCTAATCATCTCATGTTCA

TGTCCTACTGTTCAAGCCTCCAAGCTGTGCCTTGGGTGGCTTTGGGGCATGGACAT

TGACCCGTATAAAGAATTTGGAGCTTCTGTGGAGTTACTCTCTTTTTTGCCTTCTGA

CTTCTTTCCTTCCATTCGAGATCTCCTCGACACCGCCTCTGCTCTGTATCGGGAGGC

CTTAGAGTCTCCGGAACATTGTTCACCTCACCATACAGCACTCAGGCAAGCTATTC

TGTGTTGGGGTGAGTTGATGAATCTGGCCACCTGGGTGGGAAGTAATTTGGAAGA

CCCAGCATCTAGGGAATTAGTAGTCAGTTATGTTAATGTTAATATGGGCCTAAAGA

TCAGACAACTATTGTGGTTTCACATTTCCTGTCTTACTTTTGGAAGAGAAACTGTTC

TTGAGTATTTGGTGTCCTTTGGAGTGTGGATACGCACTCCTCCCGCTTACAGACCA

CCAAATGCCCCTATCTTATCAACACTTCCGGAAACTACTGTTGTTAGACGACGAGG

CAGGTCCCCTAGAAGAAGAACTCCCTCGCCTCGCAGACGAAGGTCTCAATCGCCG

CGTCGGAGAAGATCTCAATCTCGGGAATCTCAATGTTAGTATCCCTTGGACTCATA

AGGTGGGAAATTTTACTGGGCTTTATTCTTCTACTGTACCTGTCTTCAATCCTGAGT

GGCAAACTCCCTCCTTTCCTCACATTCATTTGCAGGAGGACATTATTAATAGATGT

CAACAATATGTGGGCCCTCTTACAGTTAATGAAAAAAGGAGATTAAAATTAATTA
```

-continued
```
TGCCTGCCAGGTTTTATCCTAACCGTACCAAATATTTGCCCCTAGATAAAGGCATT

AAACCTTATTATCCTGAATATACAGTTAATCATTACTTCCAAACCAGGCATTATTT

ACATACTCTGTGGAAGGCTGGCATTCTATATAAGAGAGAAACTACACGCAGCGCC

TCATTTTGTGGGTCACCATATTCTTGGGAACAAGAGCTACAGCATGGGAGGTTGGT

CCTCCAAACCTCGAAAGGGCATGGGACGAATCTTTCTGTTCCCAATCCTCTGGGC

TTCTTTCCCGATCACCAGTTGGACCCTGCATTCGGAGCCAACTCAAACAATCCGGA

TTGGGACTTCAATCCCAACAAGGATCACTGGCCAGCAGCAAACCAGGTAGGAGCG

GGAGCCTTCGGGCCAGGGTTCACCCCACCGCACGGCGGTCTTTTGGGGTGGAGCC

CTCAGGCTCAGGGCGTATTGACAACAGTGCCAGCAGCGCCTCCTCCTGCCTCCACC

AATCGGCAGTCAGGCAGACAGCCTACTCCCATCTCTCCACCTCTAAGAGACAGTCA

TCCTCAGGCCATGCAGTGG

SEQ ID No. 31:
Nucleotide sequence of HBV genome, HBV genotype E (Genbank accession# AP007262)
AATTCCACAACATTCCACCAAGCTCTGCAGGATCCCAGAGTAAGAGGCCTGTATCT

TCGTGCTGGTGGCTCCAGTTCCGGAACAGTGAACCCTGTTCCGACTACTGCCTCAC

TCATCTCGTCAATCTTCTCGAGGATTGGGGACCCTGCACCGAACATGGAAGGCATC

ACATCAGGATTCCTAGGACCCCTGCTCGTGTTACAGGCGGGGTTTTTCTTGTTGAC

AAAAATCCTCACAATACCGCAGAGTCTAGACTCGTGGTGGACTTCTCTCAATTTTC

TAGGGGGAGCTCCCGTGTGTCTTGGCCAAAATTCGCAGTCCCCAATCTTCCAATCAC

TCACCAACCTCTTGTCCTCCAATTTGTCCTGGCTATCGCTGGATGTGTCTGCGGCGT

TTTATCATCTTCCTCTTCATCCTGCTGCTATGCCTCATCTTCTTGTTGGTTCTTCTGG

ACTATCAAGGTATGTTGCCCGTTTGTCCTCTAATTCCAGGATCATGAACCACCAGT

ACGGGACCCTGCCGAACCTGCACGACTCTTGCTCAAGGAACCTCTATGTTTCCCTC

ATGTTGTTGTTTAAAACCTTCGGACGGAAATTGCACTTGTATTCCCATCCCATCATC

ATGGGCTTTCGGAAAATTCCTATGGGAGTGGGCCTCAGCCCGTTTCTCCTGGCTCA

GTTTACTAGTGCCATTTGTTCAGTGGTTCGCCGGGCTTTCCCCCACTGTCTGGCTTT

CAGTTATATGGATGATGTGGTATTGGGGGCCAAGTCTGTACAACATCTTGAGTCCC

TTTATACCTCTGTTACCAATTTTCTTTTGTCTTTGGGTATACATTTAAATCCCAACA

AAACAAAAAGATGGGGATATTCCCTAAATTTCATGGGTTATGTAATTGGTAGTTGG

GGGTCATTACCACAAGAACACATCAGACTGAAAATCAAAGACTGTTTTAGAAAGC

TCCCTGTTAACAGGCCTATTGATTGGAAAGTATGTCAAAGAATTGTGGGTCTTTTG

GGCTTTGCTGCCCCTTTTACACAATGTGGATATCCTGCTTTAATGCCTCTATATGCG

TGTATTCAATCTAAGCAGGCTTTCACTTTCTCGCCAACTTACAAGGCCTTTCTGTGT

AAACAATATATGAACCTTTACCCCGTTGCCCGGCAACGGCCAGGTCTGTGCCAAGT

GTTTGCTGATGCAACCCCCACTGGCTGGGGCTTGGCCATAGGCCATCAGCGCATGC

GTGGAACCTTTGTGGCTCCTCTGCCGATCCATACTGCGGAACTCCTAGCCGCTTGT

TTTGCTCGCAGCAGGTCTGGAGCGAAACTCATAGGGACAGATAATTCTGTCGTTCT

CTCCCGGAAATATACATCATTTCCATGGCTGCTAGGCTGTGCTGCCAACTGGATCC

TGCGAGGGACGTCCTTTGTCTACGTCCCGTCAGCGCTGAATCCTGCGGACGACCCC

TCTCGGGGCCGCTTGGGGGTCTATCGTCCCCTTCTCCGTCTGCCGTTCCGGCCGACC

ACGGGGCGCACCTCTCTTTACGCGGTCTCCCCGTCTGTGCCTTCTCATCTGCCGGAC

CGTGTGCACTTCGCTTCACCTCTGCACGTCGCATGGAGACCACCGTGAACGCCCAC
```

```
CAGATCTTGCCCAAGGTCTTACATAAGAGGACTCTTGGACTCTCTGCAATGTCAAC

GACCGACCTTGAGGCATACTTCAAAGACTGTTTGTTTAAAGACTGGGAGGAGTTG

GGGGAGGAGACTAGATTAATGATCTTTGTACTAGGAGGCTGTAGGCATAAATTGG

TCTGCGCACCAGCACCATGCAACTTTTTCACCTCTGCCTAATCATCTCTTGTTCATG

TCCTACTGTTCAAGCCTCCAAGCTGTGCCTTGGGTGGCTTTGGGACATGGACATTG

ACCCTTATAAAGAATTTGGAGCTACTGTGGAGTTACTCTCGTTTTTGCCTTCTGACT

TCTTTCCTTCAGTAAGAGATCTTCTAGATACCGCCTCTGCTCTGTATCGGGATGCCT

TAGAATCTCCTGAGCATTGTTCACCTCACCATACTGCACTCAGGCAAGCCATTCTT

TGCTGGGGAGAATTAATGACTCTAGCTACCTGGGTGGGTGTAAATTTGGAAGATCC

AGCATCCAGGGACCTAGTAGTCAGTTATGTCAATACTAATATGGGCCTAAAGTTCA

GGCAATTATTGTGGTTTCACATTTCTTGTCTCACTTTTGGAAGAGAAACCGTCATA

GAGTATTTGGTGTCTTTTGGAGTGTGGATTCGCACTCCTCCAGCTTATAGACCACC

AAATGCCCCTATCTTATCAACACTTCCGGAGAATACTGTTGTTAGACGAAGAGGCA

GGTCCCCTAGAAGAAGAACTCCCTCGCCTCGCAGACGAAGATCTCAATCGCCGCG

TCGCAGAAGATCTCAATCTCCAGCTTCCCAATGTTAGTATTCCTTGGACTCACAAG

GTGGGAAATTTTACGGGGCTTTATTCTTCTACTATACCTGTCTTTAATCCTAACTGG

AAAACTCCATCTTTTCCTGATATTCATTTGCACCAGGACATTATTAACAAATGTGA

ACAATTTGTAGGTCCTYTAACAGTAAATGAAAAACGAAGATTAAACTTAGTCATG

CCTGCTAGATTTTTTCCCATCTCCACGAAATATTTGCCCCTAGAGAAAGGTATAAA

ACCTTATTATCCAGATAATGTAGTTAATCATTACTTCCAAACCAGACACTATTTAC

ATACCCTATGGAAGGCGGGCATCTTATATAAAAGAGAAACTACCCGTAGCGCCTC

ATTTTGTGGGTCACCTTATTCTTGGGAACACGAGCTACATCATGGGGCTTTCTTGG

ACGGTCCCTCTCGAATGGGGGAAGAATCATTCCACCACCAATCCTCTGGGATTTTT

TCCCGACCACCAGTTGGATCCAGCATTCAGAGCAAACACCAGAAATCCAGATTGG

GACCACAATCCCAACAAAGACCACTGGACAGAAGCCAACAAGGTAGGAGTGGGA

GCATTTGGGCCGGGGTTCACTCCCCCACACGGAGGCCTTTTGGGGTGGAGCCCTCA

GGCTCAAGGCATGCTAAAAACATTGCCAGCAAATCCGCCTCCTGCCTCCACCAATC

GGCAGTCAGGAAGGCAGCCTACCCCAATCACTCCACCTTTGAGAGACACTCATCCT

CAGGCCATGCAGTGG

SEQ ID No. 32:
Nucleotide sequence of HBV genome, HBV genotype F (Genbank accession# HE974366)
AACTCAACCCAGTTCCATCAGGCTCTGTTGGATCCCAGGGTAAGGGCTCTGTATCT

TCCTGCTGGTGGCTCCAGTTCAGGAACACAAAACCCTGCTCCGACTATTGCCTCTC

TCACATCCTCAATCTTCTCGACGACTGGGGGCCCTGCTATGAACATGGACAACATT

ACATCAGGACTCCTAGGACCCCTGCTCGTGTTACAGGCGGTGTGTTTCTTGTTGAC

AAAAATCCTCACAATACCACAGAGTCTAGACTCGTGGTGGACTTCTCTCAATTTTC

TAGGGGGACTACCCGGGTGTCCTGGCCAAAATTCGCAGTCCCCAACCTCCAATCAC

TTACCAACCTCCTGTCCTCCAACTTGTCCTGGCTATCGTTGGATGTGTCTGCGGCGT

TTTATCATCTTCCTCTTCATCCTGCTGCTATGCCTCATCTTCTTGTTGGTTCTTCTGG

ACTACCAGGGTATGTTGCCCGTTTGTCCTCTACTTCCAGGATCCACGACCACCAGC

ACGGGACCCTGCAAAACCTGCACAACTCTTGCACAAGGAACCTCTATGTTTCCCTC
```

-continued

```
CTGTTGCTGTTCAAAACCCTCGGACGGAAACTGCACTTGTATTCCCATCCCATCAT
CCTGGGCTTTAGGAAAATACCTATGGGAGTGGGCCTCAGCCCGTTTCTCATGGCTC
AGTTTACTAGTGCAATTTGTTCAGTGGTGCGTAGGGCTTTCCCCCACTGTCTGGCTT
TTAGTTATATTGATGATCTGGTATTGGGGGCCAAATCTGTGCAGCACCTTGAGTCC
CTTTATACCGCTGTTACCAATTTTCTGTTATCTGTGGGTATCCATTTAAATACTTCT
AAAACTAAGAGATGGGGTTACACCGTACATTTTATGGGTTATGTCATTGGTAGTTG
GGGATCATTACCTCAAGATCATATTGTACACAAAATCAAAGAATGTTTTCGGAAAC
TGCCTGTAAATCGTCCAATTGATTGGAAAGTCTGTCAACGCATTGTGGGTCTTTTG
GGCTTTGCTGCCCCTTTCACACAATGTGGTTATCCTGCTCTCATGCCTCTGTATGCT
TGTATTACTGCTAAACAGGCTTTTGTTTTTTCGCCAACTTACAAGGCCTTTCTCTGT
AAACAATACATGAACCTTTACCCCGTTGCCAGGCAACGGCCGGGCCTGTGCCAAG
TGTTTGCTGACGCAACCCCCACTGGTTGGGGCTTGGCCATTGGCCATCAGCGCATG
CGTGGAACCTTTGTGGCTCCTCTGCCGATCCATACTGCGGAACTCCTTGCAGCTTG
TTTCGCTCGCAGCAGGTCTGGAGCGACTCTCATCGGCACGGACAACTCTGTTGTCC
TCTCTAGGAAGTACACCTCCTTCCCATGGCTGCTCGGGTGTGCTGCAAACTGGATC
CTGCGCGGGACGTCCTTTGTTTACGTCCCGTCGGCGCTGAATCCCGCGGACGACCC
CTCCCGGGGCCGCTTGGGGCTGTACCGCCCTCTTCTCCGTCTGCCGTTCCAGCCGA
CAACGGGTCGCACCTCTCTTTACGCGGACTCCCCGTCTGTTCCTTCTCATCTGCCGG
ACCGTGTGCACTTCGCTTCACCTCTGCACGTCGCATGGAGACCACCGTGAACGCCC
CTTGGAGTTTGCCAACAGTCTTACATAAGAGGACTCTTGGACTTTCAGGAGGGTCA
ATGACCCGGATTGCAGAATACATCAAAGACTGTGTATTTAAGGACTGGGAGGAGT
TGGGGGAGGAGACTAGGTTAATGATCTTTGTACTAGGAGGCTGTAGGCATAAATT
GGTCTGTTCACCAGCACCATGCAACTTTTTCACCTCTGCCTAATCATCTTTTGTTCA
TGTCCTACTGTTCAAGCCTCCAAGCTGTGCCTTGGGTGGCTTTGGGACATGGACAT
TGACCCTTATAAAGAATTTGGCGCTTCTGTGGAGTTACTCTCTTTTTTGCCTTCTGA
TTTCTTTCCATCGGTTCGGGACCTACTCGACACCGCTTCAGCCCTTTACCGGGATGC
TTTAGAGTGACCTGAACATTGCACTCCCCATCACACTGCCCTCAGGCAAGTTATTT
TGTGCTGGGGTGAGTTAATGACTTTGGCTTCCTGGGTGGGCAATAACTTGGAAGAC
CCTGCTGCCAGGGATTTAGTAGTTAACTATGTTAACACTAACATGGGCCTAAAAAT
TAGACAACTACTGTGGTTTCACATTTCCTGCCTTACTTTTGGAAGAGATATAGTTCT
TGAGTATTTGGTGTCCTTTGGAGTGTGGATTCGCACTCCTCCTGCTTACAGACCAC
AAAATGCCGCTATCCTATCCACACTTCCGGAAACTACTGTTGTTAGACGACGAGGC
AGGTGCCCTAGAAGAAGAACTCCCTCGCCTCGCAGACGAAGATCTCAATCGCCGC
GTCGCCGAAGATCTCAATCTCCAGCTTCCCAATGTTAGTATTCCTTGGACTCATAA
GGTGGGAAATTTTACGGGGCTTTACTCTTCTACTGTGCCTGCTTTTAATCCTGACTG
GTTAACTCCTTCTTTTCCTAATATTCATTTACATCAAGACCTAATTTCTAAATGTGA
ACAATTTGTAGGCCCACTCACTAAAAATGAATTAAGGAGGTTAAAATTGGTTATGC
CAGCTAGATTTTATCCTAAGGTTACCAAATATTTTCCTATGGAGAAAGGAATCAAG
CCTTATTATCCTGAGCATGCAGTTAATCATTACTTTAAAACAAGACATTATTTGCAT
ACTTTATGGAAGGCGGGAATTTTATATAAGAGAGAATCCACACGTAGCGCATCAT
TTTGTGGGTCACCATATTCCTGGGAACAAGAGCTACAGCATGGGAGCACCTCTCTC
```

AACGACAAGAAGAGGCATGGGACAGAATCTTTCTGTGCCCAATCCTCTGGGATTC

TTTCCAGACCATCAGCTGGATCCGCTATTCAAAGCAAATTCCAGCAGTCCCGACTG

GGACTTCAACACAAACAAGGACAGTTGGCCAATGGCAAACAAGGTAGGAGTGGG

AGCATACGGTCCAGGGTTCACACCCCCACACGGTGGCCTGCTGGGGTGGAGCCCT

CAGGCACAAGGTATGTTAACAACCTTGCCAGGAGATCCGCCTCCTGCTTCCACCAA

TCGGCGGTCCGGGAGAAAGCCAACCCCAGTCTCTCCACCTCTAAGAGAGACTCAT

CCACAGGCAATGCAGTGG

SEQ ID No. 33:
Nucleotide sequence of HBV genome, HBV genotype G (Genbank accession# AP007264)
AACTCTACAGCATTCCACCAAGCTCTACAAAATCCCAAAGTCAGGGGCCTGTATTT

TGCTGCTGGTGGCTCCAGTTCAGGGATAGTGAACCCTGTTCCGACTATTGCCTCTC

ACATCTCGTCAATCTTCTCCAGGATTGGGGACCCTGCACCGAACATGGAGAACATC

ACATCAGGATTCCTAGGACCCCTGCTCGTGTTACAGGCGGGGTTTTTCTTGTTGAC

AAGAATCCTCACAATACCGCAGAGTCTAGACTCGTGGTGGACTTCTCTCAATTTTC

TAGGGGGAGTGCCCGTGTGTCCTGGCCTAAATTCGCAGTCCCCAACCTCCAATCAC

TCACCAATCTCCTGTCCTCCAACTTGTCCTGGCTATCGCTGGATGTGTCTGCGGCGT

TTTATCATATTCCTCTTCATCCTGCTGCTATGCCTCATCTTCTTGTTGGTTCTTCTGG

ACTATCAAGGTATGTTGCCCGTTTGTCCTCTGATTCCAGGATCCTCGACCACCAGT

ACGGGACCCTGCAAAACCTGCACGACTCCTGCTCAAGGCAACTCTATGTATCCCTC

ATGTTGCTGTACAAAACCTTCGGACGGAAATTGCACCTGTATTCCGATGCCATCAT

CTTGGGCTTTCGCAAAATACCTATGGGAGTGGGCCTCAGTCGGTTTCTCTTGGCTC

AGTTTACTAGTGCCATTTGTTCAGTGGTTCGTAGGGCTTTCCCCCACTGTCTGGCTT

TCAGCTATATGGATGATGTGGTATTGGGGGCCAAATCTGTACAACATCTTGAGTCC

CTTTATACCGCTGTTACCAATTTTCTTTTGTCTTTGGGTATACATCTAAACCCTAAC

AAAACAAAAAGATGGGGTTATTCCTTAAATTTTATGGGATATGTAATTGGAAGTTG

GGGTACTTTGCCACAAGAACACATCACACAGAAAATTAAGCAATGTTTTCGGAAA

CTCCCTGTTAACAGGCCAATTGATTGGAAACTCTGTGAACGAATAACTGGTCTGTT

GGGTTTCGCTGCTCCTTTTACCCAATGTGGTTACCCTGCCTTAATGCCTTTATATGC

ATGTATACAAGCTAAGCAGGCTTTTACTTTCTCGCCAACTTATAAGGCCTTTCTCTG

TAAACAATACATGAACCTTTACCCCGTTGCTAGGCAACGGCCCGGTCTGTGCCAAG

TGTTTGCTGACGCAACCCCCACTGGTTGGGGCTTGGCCATCGGCCATCAGCGCATG

CGTGGAACCTTTTGTGGCTCCTCTGCCGATCCATACTGCGGAACTCCTAGCTGCTTG

TTTTGCTTCGCAGCCGGTCTGGAGCAAAACTCATTGGGACTGACAATTCTGTCGTCC

TTTCTCGGAAATATACATCCTTTCCATGGCTGCTAGGCTGTGCTGCCAACTGGATC

CTTCGCGGGACGTCCTTTGTTTACGTCCCGTCAGCGCTGAATCCAGCGGACGACCC

CTCCCGGGGCCGTTTGGGGCTCTGTCGCCCCCTTCTCCGTCTGCCGTTCCTGCCGAC

CACGGGGCGCACCTCTCTTTACGCGGTCTCCCCGTCTGTGCCTTCTCATCTGCCGGA

CCGTGTGCACTTCGCTTCACCTCTGCACGTTACATGGAAACCGCCATGAACACCTC

TCATCATCTGCCAAGGCAGTTATATAAGAGGACTCTTGGACTGTTTGTTATGTCAA

CAACCGGGGTGGAGAAATACTTCAAGGACTGTGTTTTGCTGAGTGGGAAGAATT

AGGCAATGAGTCCAGGTTAATGACCTTTGTATTAGGAGGCTGTAGGCATAAATTG

-continued

```
GTCTGCGCACCAGCACCATGTAACTTTTTCACCTCTGCCTAATCATCTCTTGTTCAT

GTCCTACTGTTCAAGCCTCCAAGCTGTGCCTTGGGTGGCTTTAGGGCATGGATAGA

ACAACTTTGCCATATGGCCTTTTTGGCTTAGACATTGACCCTTATAAAGAATTTGG

AGCTACTGTGGAGTTGCTCTCGTTTTTGCCTTCTGACTTTTTCCCGTCTGTTCGTGAT

CTTCTCGACACCGCTTCAGCTTTGTACCGGGAATCCTTAGAGTCCTCTGATCATTGT

TCGCCTCACCATACAGCACTCAGGCAAGCAATCCTGTGCTGGGGTGAGTTGATGAC

TCTAGCTACCTGGGTGGGTAATAATTTGGAAGATCCAGCATCCAGAGATTTGGTGG

TCAATTATGTTAATACTAATATGGGTTTAAAAATCAGGCAACTATTGTGGTTTCAC

ATTTCCTGTCTTACTTTTGGGAGAGAAACCGTTCTTGAGTATTTGGTGTCTTTTGGA

GTGTGGATTCGCACTCCTCCTGCTTATAGACCACCAAATGCCCCTATCCTATCAAC

ACTTCCGGAGACTACTGTTGTTAGACGAAGAGGCAGGTCCCCTCGAAGAAGAACT

CCCTCGCCTCGCAGACGAAGATCTCAATCGCCGCGTCGCAGAAGATCTGCATCTCC

AGCTTCCCAATGTTAGTATTCCTTGGACTCACAAGGTGGGAAACTTTACGGGGCTG

TATTCTTCTACTATACCTGTCTTTAATCCTGATTGGCAAACTCCTTCTTTTCCAAAT

ATCCATTTGCATCAAGACATTATAACTAAATGTGAACAATTTGTGGGCCCTCTCAC

AGTAAATGAGAAACGAAGATTAAAACTAGTTATGCCTGCCAGATTTTTCCCAAACT

CTACTAAATATTTACCATTAGACAAAGGTATCAAACCGTATTATCCAGAAAATGTA

GTTAATCATTACTTCCAGACCAGACATTATTTACATACCCTTTGGAAGGCGGGTAT

TCTATATAAGAGAGAAACGTCCCGTAGCGCTTCATTTTGTGGGTCACCATATACTT

GGGAACAAGATCTACAGCATGGGGCTTTCTTGGACGGTCCCTCTCGAGTGGGGAA

AGAACCTTTCCACCAGCAATCCTCTAGGATTCCTTCCCGATCACCAGTTGGACCCA

GCATTCAGAGCAAATACCAACAATCCAGATTGGGACTTCAATCCCAAAAAGGACC

CTTGGCCAGAGGCCAACAAAGTAGGAGTTGGAGCCTATGGACCCGGGTTCACCCC

TCCACACGGAGGCCTTTTGGGGTGGAGCCCTCAGTCTCAGGGCACACTAACAACTT

TGCCAGCAGATCCGCCTCCTGCCTCCACCAATCGTCAGTCAGGGAGGCAGCCTACT

CCCATCTCTCCACCACTAAGAGACAGTCATCCTCAGGCCATGCAGTGG
```

SEQ ID No. 34:
Nucleotide sequence of HBV genome, HBV genotype H (Genbank accession# AB516393)

```
AACTCAACACAGTTCCACCAAGCACTGTTGGATTCGAGAGTAAGGGGTCTGTATTT

TCCTGCTGGTGGCTCCAGTTCAGAAACACAGAACCCTGCTCCGACTATTGCCTCTC

TCACATCATCAATCTTCTCGAAGACTGGGGACCCTGCTATGAACATGGAGAACATC

ACATCAGGACTCCTAGGACCCCTTTCTCGTGTTACAGGCGGTGTGTTCTTGTTGAC

AAAAATCCTCACAATACCACAGAGTCTAGACTCGTGGTGGACTTCTCTCAATTTTC

TAGGGGTACCACCCGGGTGTCCTGGCCAAAATTCGCAGTCCCCAATCTCCAATCAC

TTACCAACCTCCTGTCCTCCAACTTGTCCTGGCTATCGTTGGATGTGTCTGCGGCGT

TTTATCATCTTCCTCTTCATCCTGCTGCTATGCCTCATCTTCTTGTTGGTTCTTCTGG

ACTATCAAGGTATGTTGCCCGTGTGTCCTCTACTTCCAGGATCTACAACCACCAGC

ACGGGACCCTGCAAAACCTGCACCACTCTTGCTCAAGGAACCTCTATGTTTCCCTC

CTGCTGCTGTACCAAACCTTCGGACGGAAATTGCACCTGTATTCCCATCCCATCAT

CTTGGGCTTTCGGAAAATACCTATGGGAGTGGGCCTCAGCCCGTTTCTCTTGGCTC

AGTTTACTAGTGCAATTTGCTCAGTGGTGCGTAGGGCTTTCCCCCACTGTCTGGCTT

TTAGTTATATGGATGATTTGGTATTGGGGGCCAAATCTGTGCAGCATCTTGAGTCC
```

```
CTTTATACCGCTGTTACCAATTTTTTGTTATCTGTGGGCATCCATTTGAACACAGCT

AAAACAAAATGGTGGGGTTATTCCTTACACTTTATGGGTTATATAATTGGGAGTTG

GGGGACCTTGCCTCAGGAACATATTGTGCATAAAATCAAAGATTGCTTTCGCAAAC

TTCCCGTGAATAGACCCATTGATTGGAAGGTTTGTCAACGCATTGTGGGTCTTTTG

GGCTTTGCAGCCCCTTTTACTCAATGTGGTTATCCTGCTCTCATGCCCTTGTATGCC

TGTATTACCGCTAAGCAGGCTTTTGTTTTCTCGCCAACTTACAAGGCCTTTCTCTGT

CAACAATACATGAACCTTTACCCCGTTGCTCGGCAACGGCGAGGCCTTTGCCAAGT

GTTTGCTGACGCAACCCCCACTGGCTGGGGCTTGGCGATTGGCCATCAGCGCATGC

GCGGAACCTTTGTGGCTCCTCTGCCGATCCATACTGCGGAACTCCTAGCAGCCTGT

TTCGCTCGCAGCAGGTCTGGAGCGGACGTTATCGGCACTGAGAACTCCGTTGTCCT

TTCTCGGAAGTACACCTCCTTCCCATGGCTGCTAGGCTGTGCTGCCAACTGGATCC

TGCGCGGGACGTCCTTTGTCTACGTCCCGTCGGCGCTGAATCCTGCGGACGACCCC

TCTCGTGGTCGCTTGGGGCTCTGCCGCCCTCTTCTCCGCCTACCGTTCCGGCCGACG

ACGGGTCGCACCTCTCTTTACGCGGACTCCCCGCCTGTGCCTTCTCATCTGCCGGCC

CGTGTGCACTTCGCTTCACCTCTGCACGTCGCATGGAGACCACCGTGAACGCCCCT

TGGAACTTGCCAACAACCTTACATAAGAGGACTCTTGGACTTTCGCCCCGGTCAAC

GACCTGGATTGAGGAATACATCAAAGACTGTGTATTTAAGGACTGGGAGGAGTCG

GGGGAGGAGTTGAGGTTAAAGGTCTTTGTATTAGGAGGCTGTAGGCATAAATTGG

TCTGTTCACCAGCACCATGCAACTTTTTCACCTCTGCCTAATCATCTTTTGTTCATG

TCCCACTGTTCAAGCCTCCAAGCTGTGGCTTGGGTGGCTTTGGGGCATGGACATTG

ACCCTTATAAAGAATTTGGAGCTTCTGTGGAGTTACTCTCATTTTTGCCTTCTGACT

TCTTCCCGTCTGTCCGGGACCTACTCGACACCGCTTCAGCCCTCTACCGAGATGCC

TTAGAATCACCCGAACATTGCACCCCCAACCACACTGCTCTCAGGCAAGCTATTTT

GTGCTGGGGTGAGTTGATGACCTTGGCTTCCTGGGTGGGCAATAATTTAGAGGATC

CTGCAGCAAGAGATCTAGTAGTTAATTATGTCAATACTAACATGGGTCTAAAAATT

AGACAATTATTATGGTTTCACATTTCCTGCCTTACATTTGGAAGAGAAACTGTGCT

TGAGTATTTGGTGTCTTTTGGAGTGTGGATCCGCACTCCACCTGCTTACAGACCAC

CAAATGCCCCTATCCTATCAACACTTCCGGAGACTACTGTTGTTAGACAACGAGGC

AGGGCCCCTAGAAGAAGAACTCCCTCGCCTCGCAGACGAAGATCTCAATCACCGC

GTCGCAGAAGATCTCAATCTCCAGCTTCCCAATGTTAGTATTCCTTGGACTCATAA

GGTGGGAAACTTTACCGGTCTTTACTCCTCTACTGTACCTGTTTTCAATCCTGACTG

GTTAACTCCTTCTTTTCCTGACATTCACTTGCATCAAGATCTGATACAAAAATGTGA

ACAATTTGTAGGCCCACTCACTACAAATGAAAGGAGACGATTGAAACTAATTATG

CCAGCTAGGTTTTATCCCAAAGTTACTAAATACTTCCCTTTGGATAAAGGTATTAA

GCCTTACTATCCAGAGAATGTGGTTAATCATTACTTTAAAACTAGACATTATTTAC

ATACTTTGTGGAAGGCAGGAATTCTATATAAGAGAGAATCCACACATAGCGCCTC

ATTTTGTGGGTCACCATATTCCTGGGAACAAGAGCTACAGCATGGGAGCACCTCTC

TCAACGGCGAGAAGGGGCATGGGACAGAATCTTTCTGTGCCCAATCCTCTGGGAT

TCTTTCCAGACCACCAGTTGGATVCACTATTCAGAGCAAATTCCAGCAGTCCCGAT

TGGGACTTCAACACAAACAAGGACAATTGGCCAATGGCAAACAAGGTAGGAGTG
```

```
GGAGGCTTCGGTCCAGGGTTCACACCCCCACACGGTGGCCTTCTGGGGTGGAGCC

CTCAGGCACAGGGCATTCTGACAACCTCGCCACCAGATCCACCTCCTGCTTCCACC

AATCGGAGGTCAGGAAGAAAGCCAACCCCAGTCTCTCCACCTCTAAGGGACACAC

ATCCACAGGCCATGCAGTGG

SEQ ID No. 35:
Nucleotide sequence of Vector: pTREHBV-HAe (5,980 nt)
Vector: pTRE2(Clontech)
nt 356-452: HBV nt 1805-1902 with A1816 deletion
nt 453-491: HA-tag insertion with flanking sequence
nt 462-488: HA-tag sequence
nt 492-3761: HBV nt 1903-3182/1-1990
    1      CTCGAGTTTA CCACTCCCTA TCAGTGATAG AGAAAAGTGA AAGTCGAGTT TACCACTCCC
   61      TATCAGTGAT AGAGAAAAGT GAAAGTCGAG TTTACCACTC CCTATCAGTG ATAGAGAAAA
  121      GTGAAAGTCG AGTTTACCAC TCCCTATCAG TGATAGAGAA AAGTGAAAGT CGAGTTTACC
  181      ACTCCCTATC AGTGATAGAG AAAAGTGAAA GTCGAGTTTA CCACTCCCTA TCAGTGATAG
  241      AGAAAAGTGA AAGTCGAGTT TACCACTCCC TATCAGTGAT AGAGAAAAGT GAAAGTCGAG
  301      CTCGGTACCC GGGTCGAGGT AGGCGTGTAC GGTGGGAGGC CTATATAAGC GTCGAGCACC
  361      AGCACCTGCA ACTTTTTCAC CTCTGCCTAA TCATCTCTTG TTCATGTCCT ACTGTTCAAG
  421      CCTCCAAGCT GTGCCTTGGG TGGCTTTGGG GCGTGGACAT CTACCCATAC GACGTTCCAG
  481      ATTACGCTGG CATGGACATC GACCCTTATA AAGAATTTGG AGCTACTGTG GAGTTACTCT
  541      CGTTTTTGCC TTCTGACTTC TTTCCTTCAG TACGAGATCT TCTAGATACC GCCTCAGCTC
  601      TGTATCGGGA AGCCTTAGAG TCTCCTGAGC ATTGTTCACC TCACCATACT GCACTCAGGC
  661      AAGCAATTCT TTGCTGGGGG GAACTAATGA CTCTAGCTAC CTGGGTGGGT GTTAATTTGG
  721      AAGATCCAGC ATCTAGAGAC CTAGTAGTCA GTTATGTCAA CACTAATATG GGCCTAAAGT
  781      TCAGGCAACT CTTGTGGTTT CACATTTCTT GTCTCACTTT TGGAAGAGAA ACCGTTATAG
  841      AGTATTTGGT GTCTTTCGGA GTGTGGATTC GCACTCCTCC AGCTTATAGA CCACCAAATG
  901      CCCCTATCCT ATCAACACTT CCGGAAACTA CTGTTGTTAG ACGACGAGGC AGGTCCCCTA
  961      GAAGAAGAAC TCCCTCGCCT CGCAGACGAA GGTCTCAATC GCCGCGTCGC AGAAGATCTC
 1021      AATCTCGGGA ACCTCAATGT TAGTATTCCT TGGACTCATA AGGTGGGGAA CTTTACTGGT
 1081      CTTTATTCTT CTACTGTACC TGTCTTTAAT CCTCATTGGA AACACCATC TTTTCCTAAT
 1141      ATACATTTAC ACCAAGACAT TATCAAAAAA TGTGAACAGT TTGTAGGCCC ACTTACAGTT
 1201      AATGAGAAAA GAAGATTGCA ATTGATTATG CCTGCTAGGT TTTATCCAAA GGTTACCAAA
 1261      TATTTACCAT TGGATAAGGG TATTAAACCT TATIATCCAG AACATCTAGT TAATCATTAC
 1321      TTCCAAACTA GACACTATTT ACACACTCTA TGGAAGGCGG GTATATTATA TAAGAGAGAA
 1381      ACAACACATA GCGCCTCATT TTGTGGGTCA CCATATTCTT GGGAACAAGA TCTACAGCAT
 1441      GGGGCAGAAT CTTTCCACCA GCAATCCTCT GGGATTCTTT CCCGACCACC AGTTGGATCC
 1501      AGCCTTCAGA GCAAACACAG CAAATCCAGA TTGGGACTTC AATCCCAACA AGGACACCTG
 1561      GCCAGACGCC AACAAGGTAG GAGCTGGAGC ATTCGGGCTG GGTTTCACCC CACCGCACGG
 1621      AGGCCTTTTG GGGTGGAGCC CTCAGGCTCA GGGCATACTA CAAACTTTGC CAGCAAATCC
 1681      GCCTCCTGCC TCCACCAATC GCCAGACAGG AAGGCAGCCT ACCCCGCTGT CTCCACCTTT
 1741      GAGAAACACT CATCCTCAGG CCATGCAGTG GAATTCCACA ACCTTTCACC AAACTCTGCA
 1801      AGATCCCAGA GTGAGAGGCC TGTATTTCCC TGCTGGTGGC TCCAGTTCAG GAGCAGTAAA
 1861      CCCTGTTCCG ACTACTGCCT CTCCC1TATC GTCAATCITC TCGAGGATTG GGGACCCTGC
 1921      GCTGAACATG GAGAACATCA CATCAGGATT CCTAGGACCC CTTCTCGTGT TACAGGCGGG
```

-continued

```
1981    GTTTTTCTAG TAGACAAGAA TCCTCACAAT ACCGCAAAGT CTAGACTCGT GGTGGACTTC
2041    TCTCAATTTT CTAGGGGGAA CTACCGTGTG TCTTGGCCAA AATTCGCAGT CCCCAACCTC
2101    CAATCACTCA CCAACCTCCT GTCCTCCAAC TTGTCCTGGT TATCGCTGGA TGTGTCTGCG
2161    GCGTTTTATC ATCTTCCTCT TCATCCTGCT GCTATGCCTC ATCTTCTTGT TGGTTCTTCT
2221    CGACTATCAA GGTATGTTGC CCGTTTGTCC TCTAATTCCA GGATCCTCAA CCACCAGCAC
2281    GGGACCATGC CGAACCTGCA TGACTACTGC TCAAGGAACC TCTATGTATC CCTCCTGTTG
2341    CTGTACCAAA CCTTCGGACG GAAATTGCAC CTGTATTCCC ATCCCATCAT CCTGGGCTTT
2401    CGGAAAATTC CTATGGGAGT GGGCCTCAGC CCGTTTCTCC TGGCTCAGTT TACTAGTGCC
2461    ATTTGTTCAG TGGTTCGTAG GCTTTCCCC CACTGTTTGG CTTTCAGTTA TATGGATGAT
2521    GTGGTATTGG GGGCCAAGTC TGTACAGCAT CTTGAGTCCC TTTTTACCGC TGTTACCAAT
2581    TTTCTTTTGT CTTTGGGTAT ACATTTAAAC CCTAACAAAA CAAAGAGATG GGGTTACTCT
2641    CTGAATTTTA TGGGTTATGT CATTGGAAGT TATGGGTCCT TGCCACAAGA ACACATCATA
2701    CAAAAAATCA AAGAATGTTT TAGAAAACTT CCTATTAACA GGCCTATTGA TTCGAAAGTA
2761    TGTCAACGAA TTGTGGGTCT TTTGGGTTTT GCTGCCCCAT TTACACAATG TGGTTATCCT
2821    GCGTTAATGC CCTTGTATGC ATGTATTCAA TCTAAGCAGG CTTTCACTTT CTCGCCAACT
2881    TACAAGGCCT TTCTGTGTAA ACAATACCTG AACCTTTACC CCGTTGCCCG GCAACGGCCA
2941    GGTCTGTGCC AAGTGTTTGC TGACGCAACC CCCACTGGCT GGGGCTTGGT CATGGGCCAT
3001    CAGCGCGTGC GTGGAACCTT TCGGCTCCT CTGCCGATCC ATACTGCGGA ACTCCTAGCC
3061    GCTTGTTTTG CTCGCAGCAG GTCTGGAGCA ACATTATCG GGACTGATAA CTCTGTTGTC
3121    CTCTCCCGCA AATATACATC GTATCCATGG CTGCTAGGCT GTGCTGCCAA CTGGATCCTG
3181    CGCGGGACGT CCTTTGTTTA CGTCCCGTCG GCGCTGAATC CTGCGGACGA CCCTTCTCGG
3241    GGTCGCTTGG GACTCTCTCG TCCCCTTCTC CGTCTGCCGT TCCGACCGAC CACGGGGCGC
3301    ACCTCTCTTT ACGCGGACTC CCCGTCTGTG CCTTCTCATC TGCCGGACCG TGTGCACTTC
3361    GCTTCACCTC TGCACGTCGC ATGGAGACCA CCGTGAACGC CCACCGAATG TTGCCCAAGG
3421    TCTTACATAA GAGGACTCTT GGACTCTCTG CAATGTCAAC GACCGACCTT GAGGCATACT
3481    TCAAAGACTG TTTGTTTAAA GACTGGGAGG AGTTGGGGGA GGAGATTAGA TTAAAGGTCT
3541    TTGTACTAGG AGGCTGTAGG CATAAATTGG TCTGCGCACC AGCACCATGC AACTTTTTCA
3601    CCTCTGCCTA ATCATCTCTT GTTCATGTCC TACTGTTCAA GCCTCCAAGC TGTGCCTTGG
3661    GTGGCTTTGG GGCATGGACA TCGACCCTTA TAAAGAATTT GGAGCTACTG TGGAGTTACT
3721    CTCGTTTTTG CCTTCTGACT TCTTTCCTTC AGTACGAGAT CCACTAGTTC TAGAGCGGCC
3781    CCAAACAATT GCTCAAACCG ATACAATTGT ACTITGTCCC GAGCAAATAT AATCCTGCTG
3841    ACGGCCCATC CAGGCACAAA CCTCCTGATT GGACGGCTTT TCCATACACC CCTCTCTCGA
3901    AAGCAATATA TATTCCACAT AGGCTATGTG GAACTTAAGC TTCCTCGCTC ACTGACTCGC
3961    TGCGCTCGGT CGTTCGGCTG CGGCGAGCGG TATCAGCTCA CTCAAAGGCG GTAATACGGT
4021    TATCCACAGA ATCAGGGGAT AACGCAGGAA AGAACATGTG AGCAAAAGGC CAGCAAAAGG
4081    CCAGGAACCG TAAAAAGGCC GCGTTGCTGG CGTTTTTCCA TAGGCTCCGC CCCCCTGACG
4141    AGCATCACAA AAATCGACGC TCAAGTCAGA GGTGGCGAAA CCCGACAGGA CTATAAAGAT
4201    ACCAGGCGTT TCCCCCTGGA AGCTCCCTCG TGCGCTCTCC TGTTCCGACC CTGCCGCTTA
4261    CCGGATACCT GTCCGCCTTT CTCCCTTCGG GAAGCGTGGC GCTTTCTCAT AGCTCACGCT
4321    GTAGGTATCT CAGTTCGGTG TAGGTCGTTC GCTCCAAGCT GGGCTGTGTG CACGAACCCC
4381    CCGTTCAGCC CGACCGCTGC GCCTTATCCG GTAACTATCG TCTTGAGTCC AACCCGGTAA
```

```
4441    GACACGACTT ATCGCCACTG GCAGCAGCCA CTGGTAACAG GATTAGCAGA GCGAGGTATG
4501    TAGGCGGTGC TACAGAGTTC TTGAAGTGGT GGCCTAACTA CGGCTACACT ATAAGAACAG
4561    TATTTGGTAT CTGCGCTCTG CTGAAGCCAG TTACCTTCGG AAAAAGAGTT GGTAGCTCTT
4621    GATCCGGCAA ACAAACCACC GCTGGTAGCG GTGGTTTTTT TGTTTGCAAG CAGCAGATTA
4681    CGCGCAGAAA AAAGGATCT  CAAGAAGATC CTTTGATCTT TTCTACGGGG TCTGACGCTC
4741    AGTGGAACGA AAACTCACGT TAAGGGATTT TGGTCATGAG ATTATCAAAA AGGATCTTCA
4801    CCTAGATCCT TTTAAATTAA AAATGAAGTT TTAAATCAAT CTAAAGTATA TATGAGTAAA
4861    CTTCGTCTGA CAGTTACCAA TGCTTAATCA GTGAGGCACC TATCTCAGCG ATCTGTCTAT
4921    TTCGTTCATC CATAGTTGCC TGACTCCCCG TCGTGTAGAT AACTACGATA CGGGAGGGCT
4981    TACCATCTGG CCCCAGTGCT GCAATGATAC CGCGAGACCC ACGCTCACCG GCTCCAGATT
5041    TATCAGCAAT AAACCAGCCA GCCGGAAGGG CCGAGCGCAG AAGTGGTCCT GCAACTTTAT
5101    CCGCCTCCAT CCAGTCTATT AATTGTTGCC GGGAAGCTAG AGTAAGTAGT TCGCCAGTTA
5161    ATAGTTTGCG CAACGTTGTT GCCATTGCTA CAGGCATCGT GGTGTCACGC TCGTCGTTTG
5221    GTATGGCTTC ATTCAGCTCC GGTTCCCAAC GATCAAGGCG AGTTACATGA TCCCCCATGT
5281    TGTGCAAAAA AGCGGTTAGC TCCTTCGGTC CTCCGATCGT TGTCAGAAGT AAGTTGGCCG
5341    CAGTGTTATC ACTCATGGTT ATGGCAGCAC TGCATAATTC TCTTACTGTC ATGCCATCCG
5401    TAAGATGCTT TTCTGTGACT GGTGAGTACT CAACCAAGTC ATTCTGAGAA TAGTGTATGC
5461    GGCGACCGAG TTGCTCTTGC CCGGCGTCAA TACGGGATAA TACCGCGCCA CATAGCAGAA
5521    CTTTAAAAGT GCTCATCATT GGAAAACGTT CTTCGGGGCG AAAACTCTCA AGGATCTTAC
5581    CGCTGTTGAG ATCCAGTTCG ATGTAACCCA CTCGTGCACC CAACTGATCT TCAGCATCTT
5641    TTACTTTCAC CAGCGTTTCT GGGTGAGCAA AAACAGGAAG GCAAAATGCC GCAAAAAAGG
5701    GAATAAGGGC GACACGGAAA TGTTGAATAC TCATACTCTT CCTTTTTCAA TATTATTGAA
5761    GCATTTATCA GGGTTATTGT CTCATGAGCG GATACATATT TGAATGTATT TAGAAAAATA
5821    AACAAATAGG GGTTCCGCGC ACATTTCCCC GAAAAGTGCC ACCTGACGTC TAAGAAACCA
5881    TTATTATCAT GACATTAACC TATAAAAATA GGCGTATCAC GAGGCCCTTT CGTCTTCACT
5941    CGAATATCTG CAGGCGTATC ACGAGGCCCT TTCGTCTTCA                        5980
```
SEQ ID No. 36:
Nucleotide sequence encoding HBV envelope protein, Large Surface protein (L)
ATGGGGCAGAATCTTTCCACCAGCAATCCTCTGGGATTCTTTCCCGACCACCAGTT

GGATCCAGCCTTCAGAGCAAACACAGCAAATCCAGATTGGGACTTCAATCCCAAC

AAGGACACCTGGCCAGACGCCAACAAGGTAGGAGCTGGAGCATTCGGGCTGGGTT

TCACCCCACCGCACGGAGGCCTTTTGGGGTGGAGCCCTCAGGCTCAGGGCATACT

ACAAACTTTGCCAGCAAATCCGCCTCCTGCCTCCACCAATCGCCAGACAGGAAGG

CAGCCTACCCCGCTGTCTCCACCTTTGAGAAACACTCATCCTCAGGCCATGCAGTG

GAATTCCACAACCTTTCACCAAACTCTGCAAGATCCCAGAGTGAGAGGCCTGTATT

TCCCTGCTGGTGGCTCCAGTTCAGGAGCAGTAAACCCTGTTCCGACTACTGCCTCT

CCCTTATCGTCAATCTTCTCGAGGATTGGGGACCCTGCGCTGAACATGGAGAACAT

CACATCAGGATTCCTAGGACCCCTTCTCGTGTTACAGGCGGGGTTTTTCTTGTTGAC

AAGAATCCTCACAATACCGCAAAGTCTAGACTCGTGGTGGACTTCTCTCAATTTTC

TAGGGGGAACTACCGTGTGTCTTGGCCAAAATTCGCAGTCCCCAACCTCCAATCAC

TCACCAACCTCCTGTCCTCCAACTTGTCCTGGTTATCGCTGGATGTGTCTGCGGCGT

-continued

TTTATCATCTTCCTCTTCATCCTGCTGCTATGCCTCATCTTCTTGTTGGTTCTTCTGG

ACTATCAAGGTATGTTGCCCGTTTGTCCTCTAATTCCAGGATCCTCAACCACCAGC

ACGGGACCATGCCGAACCTGCATGACTACTGCTCAAGGAACCTCTATGTATCCCTC

CTGTTGCTGTACCAAACCTTCGGACGGAAATTGCACCTGTATTCCCATCCCATCAT

CCTGGGCTTTCGGAAAATTCCTATGGGAGTGGGCCTCAGCCCGTTTCTCCTGGCTC

AGTTTACTAGTGCCATTTGTTCAGTGGTTCGTAGGGCTTTCCCCCACTGTTTGGCTT

TCAGTTATATGGATGATGTGGTATTGGGGGCCAAGTCTGTACAGCATCTTGAGTCC

CTTTTTACCGCTGTTACCAATTTTCTTTTGTCTTTGGGTATACATTTAA

SEQ ID No. 37:
Nucleotide sequence encoding HBV envelope protein, Middle surface protein (M)
ATGCAGTGGAATTCCACAACCTTTCACCAAACTCTGCAAGATCCCAGAGTGAGAG

GCCTGTATTTCCCTGCTGGTGGCTCCAGTTCAGGAGCAGTAAACCCTGTTCCGACT

ACTGCCTCTCCCTTATCGTCAATCTTCTCGAGGATTGGGGACCCTGCGCTGAACAT

GGAGAACATCACATCAGGATTCCTAGGACCCCTTCTCGTGTTACAGGCGGGGTTTT

TCTTGTTGACAAGAATCCTCACAATACCGCAAAGTCTAGACTCGTGGTGGACTTCT

CTCAATTTTCTAGGGGGAACTACCGTGTGTCTTGGCCAAAATTCGCAGTCCCCAAC

CTCCAATCACTCACCAACCTCCTGTCCTCCAACTTGTCCTGGTTATCGCTGGATGTG

TCTGCGGCGTTTTATCATCTTCCTCTTCATCCTGCTGCTATGCCTCATCTTCTTGTTG

GTTCTTCTGGACTATCAAGGTATGTTGCCCGTTTGTCCTCTAATTCCAGGATCCTCA

ACCACCAGCACGGGACCATGCCGAACCTGCATGACTACTGCTCAAGGAACCTCTA

TGTATCCCTCCTGTTGCTGTACCAAACCTTCGGACGGAAATTGCACCTGTATTCCC

ATCCCATCATCCTGGGCTTTCGGAAAATTCCTATGGGAGTGGGCCTCAGCCCGTTT

CTCCTGGCTCAGTTTACTAGTGCCATTTGTTCAGTGGTTCGTAGGGCTTTCCCCCAC

TGTTTGGCTTTCAGTTATATGGATGATGTGGTATTGGGGGCCAAGTCTGTACAGCA

TCTTGAGTCCCTTTTTACCGCTGTTACCAATTTTCTTTTGTCTTTGGGTATACATTTA

A

SEQ ID No. 38:
Nucleotide sequence encoding HBV envelope protein, Small surface protein (S)
ATGGAGAACATCACATCAGGATTCCTAGGACCCCTTCTCGTGTTACAGGCGGGGTT

TTTCTTGTTGACAAGAATCCTCACAATACCGCAAAGTCTAGACTCGTGGTGGACTT

CTCTCAATTTTCTAGGGGGAACTACCGTGTGTCTTGGCCAAAATTCGCAGTCCCCA

ACCTCCAATCACTCACCAACCTCCTGTCCTCCAACTTGTCCTGGTTATCGCTGGATG

TGTCTGCGGCGTTTTATCATCTTCCTCTTCATCCTGCTGCTATGCCTCATCTTCTTGT

TGGTTCTTCTGGACTATCAAGGTATGTTGCCCGTTTGTCCTCTAATTCCAGGATCCT

CAACCACCAGCACGGGACCATGCCGAACCTGCATGACTACTGCTCAAGGAACCTC

TATGTATCCCTCCTGTTGCTGTACCAAACCTTCGGACGGAAATTGCACCTGTATTCC

CATCCCATCATCCTGGGCTTTCGGAAAATTCCTATGGGAGTGGGCCTCAGCCCGTT

TCTCCTGGCTCAGTTTACTAGTGCCATTTGTTCAGTGGTTCGTAGGGCTTTCCCCCA

CTGTTTGGCTTTCAGTTATATGGATGATGTGGTATTGGGGGCCAAGTCTGTACAGC

ATCTTGAGTCCCTTTTTACCGCTGTTACCAATTTTCTTTTGTCTTTGGGTATACATTT

AA

SEQ ID No. 39:
Nucleotide sequence of expression vector pcHA-HBe (6,682 nt)
Vector: pcDNA3.1/V5-His-TOPO (Invitrogen)
nt  929-1015: HBV nt 1816-1902
nt 1016-1054: insertion
nt 1025-1051: HA-tag sequence
nt 1055-2112: HBV 1903-2605/1573-1926

```
   1        GACGGATCGG GAGATCTCCC GATCCCTAT GGTCGACTCT CAGTACAATC TGCTCTGATG

61        CCGCATAGTT AAGCCAGTAT CTGCTCCCTG CTTGTGTGTT GGAGGTCGCT GAGTAGTGCG

121        CGAGCAAAAT TAAGCTACA ACAAGGCAAG GCTTGACCGA CAATTGCATG AAGAATCTGC

181        TTAGGGTTAG GCGTTTTGCG CTGCTTCGCG ATGTACGGGC CAGATATACG CGTTGACATT

241        GATTATTGAC TAGTTATTAA TAGTAATCAA TTACGGGGTC ATTAGTTCAT AGCCCATATA

301        TGGAGTTCCG CGTTACATAA CTTACGGTAA ATGGCCCGCC TGGCTGACCG CCCAACGACC

361        CCCGCCCATT GACGTCAATA ATGACGTATG TTCCCATAGT AACGCCAATA GGGACTTTCC

421        ATTGAGGTCA ATGGGTGGAG TATTTACGGT AAACTGCCCA CTTGGCAGTA CATCAAGTGT

481        ATCATATGCC AAGTACGCCC CCTATTGACG TCAATGACGG TAAATGGCCC GCCTGGCATT

541        ATGCCCAGTA CATGACCTTA TGGGACTTTC CTACTTGGCA GTACATCTAC GTATTAGTCA

601        TCGCTATTAC CATGGTGATG CGGTTTTGGC AGTACATCAA TGGGCGTGGA TAGCGGTTTG

661        ACTCACGGGG ATTTCCAAGT CTCCACCCCA TTGACGTCAA TGGGAGTTTG TTTTGGCACC

721        AAAATCAACG GGACTTTCCA AAATGTCGTA ACAACTCCGC CCCATTGACG CAAATGGGCG

781        GTAGGCGTGT ACGGTGGGAG GTCTATATAA GCAGAGCTCT CTGGCTAACT AGAGAACCCA

841        CTGCTTACTG GCTTATCGAA ATTAATACGA CTCACTATAG GGAGACCCAA GCTGGCTAGT

901        TAAGCTTGGT ACCGAGCTCG GATCCACCAT GCAACTTTTT CACCTCTCCC TAATCATCTC

961        TTGTTCATGT CCTACTGTTC AAGCCTCCAA GCTGTGCCTT GGGTGGCTTT GGGGCGTGGA

1021        CATCTACCCA TACGACGTTC CAGATTACGC TGGCATGGAC ATCGACCCTT ATAAAGAATT

1081        TGGAGCTACT GTGGAGTTAC TCTCGTTTTT GCCTTCTGAC TTCTTTCCTT CAGTACGAGA

1141        TCITCTAGAT ACCGCCTCAG CTCTGTATCG GGAAGCCTTA GAGTCTCCTG AGCATTGTTC

1201        ACCTCACCAT ACTGCACTCA GGCAAGCAAT TCTTTGCTGG GGGGAACTAA TGACTCTAGC

1261        TACCTGGGTG GGTGTTAATT TGGAAGATCC AGCATCTAGA GACCTAGTAG TCAGTTATGT

1321        CAACACTAAT ATGGGCCTAA AGTTCAGGCA ACTCTTGTGG TTTCACATTT CTTGTCTCAC

1383        TTTTGGAAGA GAAACCGTTA TAGAGTATTT GGTGTCTTTC GGAGTGTGGA TTCGCACTCC

1441        TCCAGCTTAT AGACCACCAA ATGCCCCTAT CCTATCAACA CTTCCGGAAA CTACTGTTGT

1501        TAGACGACGA GGCAGGTCCC CTAGAAGAAG AACTCCCTCG CCTCGCAGAC GAAGGTCTCA

1561        ATCGCCGCGT CGCAGAAGAT CTCAATCTCG GAACCTCAA TGTTAGTATT CCTTGGACTC

1621        ATAAGGTGGG GAACTTTACT GGTCTTTATT CTTCTACTGT ACCTGTCTTT AATCCTCATT

1681        GGAAAACACC ATCTTTTCCT AATATACATT TACACCAAGA CATTATCAAA AAATGTGAAC

1741        AGTTTGTAGG CCCACTTACG GACCGTGTGC ACTTCGCTTC ACCTCTGCAC GTCGCATGGA

1801        GACCACCGTG AACGCCCACC GAATGTTGCC CAAGGTCTTA CATAAGAGGA CTCTTGGACT

1861        CTCTGCAATG TCAACGACCG ACCTTGAGGC ATACTTCAAA GACTGTTTGT TTAAAGACTG

1921        GGAGGAGTTG GGGGAGGAGA TTAGATTAAA GGTCTTTGTA CTAGGAGGCT GTAGGCATAA

1981        ATTGGTCTGC GCACCAGCAC CATGCAACTT TTTCACCTCT GCCTAATCAT CTCTTGTTCA

2041        TGTCCTACTG TTCAAGCCTC CAAGCTGTGC CTTGGGTGGC TTTGGGGCAT GGACATCGAC

2101        CCTTATAAAG AAAAGGGCAA TTCTGCAGAT ATCCAGCACA GTGGCGGCCG CTCGAGTCTA

2161        GAGGGCCCGC GGTTCGAAGG TAAGCCTATC CCTAACCCTC TCCTCGGTCT CGATTCTACG
```

-continued

```
2221  CGTACCGGTC ATCATCACCA TCACCATTGA GTTTAAACCC GCTGATCAGC CTCGACTGTG
2281  CCTTCTAGTT GCCAGCCATC TGTTGTTTGC CCCTCCCCCG TGCCTTCCTT GACCCTGGAA
2341  GGTGCCACTC CCACTGTCCT TTCCTAATAA AATGAGGAAA TTGCATCGCA TTGTCTGAGT
2401  AGGTGTCATT CTATTCTGGG GGGTGGGGTG GGGCAGGACA GCAAGGGGGA GGATTGGGAA
2461  GACAATAGCA GGCATGCTGG GGATGCGGTG GGCTCTATGG CTTCTGAGGC GGAAAGAACC
2521  AGCTGGGGCT CTAGGGGGTA TCCCCACGCG CCCTGTAGCG GCGCATTAAG CGCGGCGGGT
2581  GTGGTGGTTA CGCGCAGCGT GACCGCTACA CTTGCCAGCG CCCTAGCGCC CGCTCCTTTC
2641  GCTTTCTTCC CTTCCTTTCT CGCCACGTTC GCCGGCTTTC CCCGTCAAGC TCTAAATCGG
2701  GGCATCCCTT TAGGGTTCCG ATTTAGTGCT TTACGGCACC TCGACCCCAA AAACTTGAT
2761  TAGGGTGATG GTTCACGTAG TGGGCCATCG CCCTGATAGA CGGTTTTTCG CCCTTTGACG
2821  TTGGAGTCCA CGTTCTTTAA TAGTGGACTC TTGTTCCAAA CTGGAACAAC ACTCAACCCT
2881  ATCTCGGTCT ATTCTTTTGA TTTATAAGGG ATTTTGGGGA TTTCGGCCTA TTGGTTAAAA
2941  AATGAGCTGA TTTAACAAAA ATTTAACGCG AATTAATTCT GTGGAATGTG TGTCAGTTAG
3001  GGTGTGGAAA GTCCCCAGGC TCCCCAGGCA GGCAGAAGTA TGCAAAGCAT GCATCTCAAT
3061  TAGTCAGCAA CCAGGTGTGG AAAGTCCCCA GGCTCCCCAG CAGGCAGAAG TATGCAAAGC
3121  ATGCATCTCA ATTAGTCAGC AACCATAGTC CGCCCCTAA CTCCGCCCAT CCCGCCCCTA
3181  ACTCCGCCCA GTTCCGCCCA TTCTCCGCCC CATGGCTGAC TAATTTTTTT TATTTATGCA
3241  GAGGCCGAGG CCGCCTCTGC CTCTGAGCTA TTCCAGAAGT AGTGAGGAGG CTTTTTTGGA
3301  GGCCTAGGCT TTTGCAAAAA GCTCCCGGGA GCTTGTATAT CCATTTTCGG ATCTGATCAA
3361  GAGACAGGAT GAGGATCGTT TCGCATGATT GAACAAGATG GATTGCACGC AGGTTCTCCG
3421  GCCGCTTGGG TGGAGAGGCT ATTCGGCTAT GACTGGGCAC AACAGACAAT CGGCTGCTCT
3481  GATGCCGCCG TGTTCCGGCT GTCAGCGCAG GGGCGCCCGG TTCTTTTTGT CAAGACCGAC
3541  CTGTCCGGTG CCCTGAATGA ACTGCAGGAC GAGGCAGCGC GGCTATCGTG GCTGGCCACG
3601  ACGGGCGTTC CTTGCGCAGC TGTGCTCGAC GTTGTCACTG AAGCGGGAAG GGACTGGCTG
3661  CTATTGGGCG AAGTGCCGGG GCAGGATCTC CTGTCATCTC ACCTTGCTCC TGCCGAGAAA
3721  GTATCCATCA TGGCTGATGC AATGCGGCGG CTGCATACGC TTGATCCGGC TACCTGCCCA
3781  TTCGACCACC AAGCGAAACA TCGCATCGAG CGAGCACGTA CTCGGATGGA AGCCGGTCTT
3841  GTCGATCAGG ATGATCTGGA CGAAGAGCAT CAGGGGCTCG CGCCAGCCGA ACTGTTCGCC
3901  AGGCTCAAGG CGCGCATGCC CGACGGCGAG GATCTCGTCG TGACCCATGG CGATGCCTGC
3961  TTGCCGAATA TCATGGTGGA AAATGGCCGC TTTTCTGGAT TCATCGACTG TGGCCGGCTG
4021  GGTGTGGCGG ACCGCTATCA GGACATAGCG TTGGCTACCC GTGATATTGC TGAAGAGCTT
4081  GGCGGCGAAT GGGCTGACCG CTTCCTCGTG CTTTACGGTA TCGCCGCTCC CGATTCGCAG
4141  CGCATCGCCT TCTATCGCCT TCTTGACGAG TTCTTCTGAG CGGGACTCTG GGGTTCGCGA
4201  AATGACCGAC CAAGCGACGC CCAACCTGCC ATCACGAGAT TTCGATTCCA CCGCCGCCTT
4261  CTATGAAAGG TTGGGCTTCG GAATCGTTTT CCGGGACGCC GGCTGGATGA TCCTCCAGCG
4321  CGGGGATCTC ATGCTGGAGT TCTTCGCCCA CCCCAACTTG TTTATTGCAG CTTATAATGG
4381  TTACAAATAA AGCAATAGCA TCACAAATTT CACAAATAAA GCATTTTTTT CACTGCATTC
4441  TAGTTGTGGT TTGTCCAAAC TCATCAATGT ATCTTATCAT GTCTGTATAC CGTCGACCTC
4501  TAGCTAGAGC TTGGCGTAAT CATGGTCATA GCTGTTTCCT GTGTGAAATT GTTATCCGCT
4561  CACAATTCCA CACAACATAC GAGCCGGAAG CATAAAGTGT AAAGCCTGGG GTGCCTAATG
```

```
4621  AGTGAGCTAA CTCACATTAA TTGCGTTGCG CTCACTGCCC GCTTTCCAGT CGGGAAACCT

4681  GTCGTGCCAG CTGCATTAAT GAATCGGCCA ACGCGCGGGG AGAGGCGGTT TGCGTATTGG

4741  GCGCTCTTCC GCTTCCTCGC TCACTGACTC GCTGCGCTCG GTCGTTCGGC TGCGGCGAGC

4801  GGTATCAGCT CACTCAAAGG CGGTAATACG GTTATCCACA GAATCAGGGG ATAACGCAGG

4861  AAAGAACATG TGAGCAAAAG GCCAGCAAAA GGCCAGGAAC CGTAAAAAGG CCGCGTTGCT

4921  GGCGTTTTTC CATAGGCTCC GCCCCCCTGA CGAGCATCAC AAAAATCGAC GCTCAAGTCA

4981  GAGGTGGCGA AACCCGACAG GACTATAAAG ATACCAGGCG TTTCCCCCTG GAAGCTCCCT

5041  CGTGCGCTCT CCTGTTCCGA CCCTGCCGCT TACCGGATAC CTGTCCCCCT TTCTCCCTTC

5101  GGGAAGCGTG GCGCTTTCTC AATGCTCACG CTGTAGGTAT CTCAGTTCGG TGTAGGTCGT

5161  TCGCTCCAAG CTGGGCTGTG TGCACGAACC CCCCGTTCAG CCCGACCGCT GCGCCTTATC

5221  CGGTAACTAT CGTCTTGAGT CCAACCCGGT AAGACACGAC TTATCGCCAC TGGCAGCAGC

5281  CACTGGTAAC AGGATTAGCA GAGCGAGGTA TGTAGGCGGT GCTACAGAGT TCTTGAAGTG

5341  GTGGCCTAAC TACGGCTACA CTAGAAGGAC AGTATTTGGT ATCTGCGCTC TGCTGAAGCC

5401  AGTTACCTTC GGAAAAAGAG TTGGTAGCTC TTGATCCGGC AAACAAACCA CCGCTGGTAG

5461  CGGTGGTTTT TTTGTTTGCA AGCAGCAGAT TACGCGCAGA AAAAAAGGAT CTCAAGAAGA

5521  TCCTTTGATC TTTTCTACGG GGTCTGACGC TCAGTGGAAC GAAAACTCAC GTTAAGGGAT

5581  TTTGGTCATG AGATTATCAA AAAGGATCTT CACCTAGATC CTTTTAAATT AAAAATGAAG

5641  TTTTAAATCA ATCTAAAGTA TATATGAGTA AACTTGGTCT GACAGTTACC AATGCTTAAT

5701  CAGTGAGGCA CCTATCTCAG CGATCTGTCT ATTTCGTTCA TCCATAGTTG CCTGACTCCC

5761  CGTCGTGTAG ATAACTACGA TACGGGAGGG CTTACCATCT GGCCCCAGTG CTGCAATGAT

5821  ACCGCGAGAC CCACGCTCAC CGGCTCCAGA TTTATCAGCA ATAAACCAGC GAGCCGGAAG

5881  GGCCGAGCGC AGAAGTGGTC CTGCAACTTT ATCCGCCTCC ATCCAGTCTA TTAATTGTTG

5941  CCGGGAAGCT AGAGTAAGTA GTTCGCCAGT TAATAGTTTG CGCAACGTTG TTGCCATTGC

6001  TACAGGCATC GTGGTGTCAC GCTCGTCGTT TGGTATGGCT TCATTCAGCT CCGGTTCCCA

6061  ACGATCAAGG CGAGTTACAT GATCCCCCAT GTTGTGCAAA AAAGCGGTTA GCTCCTTCGG

6121  TCCTCCGATC GTTGTCAGAA GTAAGTTGGC CGCAGTGTTA TCACTCATGG TTATGGCAGC

6181  ACTGCATAAT TCTCTTACTG TCATGCCATC CGTAAGATGC TTTTCTGTGA CTGGTGAGTA

6241  CTCAACCAAG TCATTCTGAG AATAGTGTAT GCGGCGACCG AGTTGCTCTT GCCCGGCGTC

6301  AATACGGGAT AATACCGCGC CACATAGCAG AACTTTAAAA GTGCTCATCA TTGGAAAACG

6361  TTCTTCGGGG CGAAAACTCT CAAGGATCTT ACCGCTGTTG AGATCCAGTT CGATGTAACC

6421  CACTCGTGCA CCCAACTGAT CTTCAGCATC TTTTACTTTC ACCAGCGTTT CTGGGTGAGC

6481  AAAAACAGGA AGGCAAAATG CCGCAAAAAA GGGAATAAGG GCGACACGGA AATGTTGAAT

6541  ACTCATACTC TTCCTTTTTC AATATTATTG AAGCATTTAT CAGGGTTATT GTCTCATGAG

6601  CGGATACATA TTTGAATGTA TTTAGAAAAA TAAACAAATA GGGGTTCCGC GCACATTTCC

6661  CCGAAAAGTG CCACCTGACG TC                                         6682
```

SEQ ID No. 40:
Amino acid sequence N-terminal to a tag
VDI

SEQ ID No. 41:
Nucleotide sequence encoding a HA-tag comprising 5'- and 3'- additional nucleotides. The underlined nucleotides show the sequence encoding the HA-tag.
GTGGACATC<u>TACCCATACGACGTTCCAGATTACGCT</u>GGC.

SEQ ID No. 42:
Amino acid sequence of a HA-tag comprising N-terminal and C-terminal additional amino acids. The underlined amino acid residues show the sequence of the HA-tag.
VDI<u>YPYDVPDYA</u>G

ADDITIONAL REFERENCES AS DISCUSSED HEREIN

1. Arzumanyan, A., H. M. Reis, and M. A. Feltelson. 2013. Pathogenic mechanisms in HBV- and HCV-associated hepatocellular carcinoma. Nature reviews. Cancer 13:123-135.
2. Block, T. M., H. Guo, and J. T. Guo. 2007. Molecular virology of hepatitis B virus for clinicians. Clin Liver Dis 11:685-706, vii.
3. Cal, D, C. Mills, W. Yu, R. Yan, C. E. Aldrich, J. R. Saputelli, W. S. Mason, X. Xu, J. T. Guo, T. M. Block, A. Cuconati, and H. Guo. 2012. Identification of disubstituted sulfonamide compounds as specific inhibitors of hepatitis B virus covalently closed circular DNA formation. Antimicrob Agents Chemother 56:4277-4288.
4. Cai, D., H. Nie, R. Yan, J. T. Guo, T. M. Block, and H. Guo. 2013. A southern blot assay for detection of hepatitis B virus covalently closed circular DNA from cell cultures. Methods Mol Biol 1030:151-161.
5. Galibert, F., E. Mandart, F. Fitoussi, and P. Charnay. 1979. Nucleotide sequence of the hepatitis B virus genome (subtype ayw) cloned in *E. coli*. Nature 281:646-650.
6. Gish, R. G., A. S. Lok, T. T. Chang, R. A. de Man, A. Gadano, J. Sollano, K. H. Han, Y. C. Chao, S. D. Lee, M. Harris, J. Yang, R. Colonno, and H. Brett-Smith. 2007. Entecavir therapy for up to 96 weeks in patients with HBeAg-positive chronic hepatitis B. Gastroenterology 133:1437-1444.
7. Guo, H., D. Jiang, T. Zhou, A. Cuconati, T. M. Block, and J. T. Guo. 2007. Characterization of the intracellular deproteinized relaxed circular DNA of hepatitis B virus: an intermediate of covalently closed circular DNA formation. J Virol 81:12472-12484.
8. Hirt, B. 1967. Selective extraction of polyoma DNA from infected mouse cell cultures. J Mol Biol 26:365-369.
9. Hoofnagle, J. H., E. Doo, T. J. Liang, R. Flelscher, and A. S. Lok. 2007. Management of hepatitis B: summary of a clinical research workshop. Hepatology 45:1056-1075.
10. Ito, K., K. H. Kim, A. S. Lok, and S. Tong. 2009. Characterization of genotype-specific carboxyl-terminal cleavage sites of hepatitis B virus e antigen precursor and identification of furin as the candidate enzyme. J Virol 83:3507-3517.
11. Ladner, S. K., M. J. Otto, C. S. Barker, K. Zaifert, G. H. Wang, J. T. Guo, C. Seeger, and R. W. King. 1997. Inducible expression of human hepatitis B virus (HBV) in stably transfected hepatoblastoma cells: a novel system for screening potential inhibitors of HBV replication. Antimicrob Agents Chemother 41:1715-1720.
12. Llang, T. J. 2009. Hepatitis B: the virus and disease. Hepatology 49:S13-21.
13. Liu, N., L. Ji, M. L. Maguire, and D. D. Loeb. 2004. cis-Acting sequences that contribute to the synthesis of relaxed-circular DNA of human hepatitis B virus. J Virol 78:642-649.
14. McMahon, B. J. 2014. Chronic hepatitis B virus infection. The Medical clinics of North America 98:39-54.
15. Nassal, M. 2008. Hepatitis B viruses: reverse transcription a different way. Virus Res 134:235-249.
16. Pawlotsky, J. M., G. Dusheiko, A. Hatzakis, D. Lau, G. Lau, T. J. Liang, S. Locarnini, P. Martin, D. D. Richman, and F. Zoulim. 2008. Virologic monitoring of hepatitis B virus therapy in clinical trials and practice: recommendations for a standardized approach. Gastroenterology 134:405-415.
17. Protzer, U., M. Nassal, P. W. Chiang, M. Kirschfink, and H. Schaller. 1999. Interferon gene transfer by a hepatitis B virus vector efficiently suppresses wild-type virus infection. Proc Natl Acad Sci USA 96:10818-10823.
18. Quasdorff, M., and U. Protzer. 2010. Control of hepatitis B virus at the level of transcription. J Viral Hepat 17:527-536.
19. Seeger, C., and W. S. Mason. 2000. Hepatitis B virus biology. Microbiol Mol Biol Rev 64:51-68.
20. Sells, M. A., M. Chen, and G. Acs. 1987. Production of hepatitis B virus particles in hepG2 cells transfected with cloned hepatitis B virus DNA. Proc. Natl. Acad. Sci. USA 84:1005-1009.
21. Wang, J., A. S. Lee, and J. H. Ou. 1991. Proteolytic conversion of hepatitis B virus e antigen precursor to end product occurs in a postendoplasmic reticulum compartment. J Virol 65:5080-5083.
22. Wang, Z., L. Wu, X. Cheng, S. Liu, B. Li, H. Li, F. Kang, J. Wang, H. Xla, C. Ping, M. Nassal, and D. Sun. 2013. Replication-competent infectious hepatitis B virus vectors carrying substantially sized transgenes by redesigned viral polymerase translation. PLoS One 8:e60306.
23. Zhou, T., H. Guo, J. T. Guo, A. Cuconati, A. Mehta, and T. M. Block. 2006. Hepatitis B virus e antigen production is dependent upon covalently closed circular (ccc) DNA in HepAD38 cell cultures and may serve as a cccDNA surrogate in antiviral screening assays. Antiviral Res 72:116-124.
24. Zoulim, F., and S. Locarnini. 2009. Hepatitis B virus resistance to nucleos(t)ide analogues. Gastroenterology 137:1593-1608 e1591-1592.

All references cited herein are fully incorporated by reference. Having now fully described the invention, it will be understood by a person skilled in the art that the invention may be practiced within a wide and equivalent range of conditions, parameters and the like, without affecting the spirit or scope of the invention or any embodiment thereof.

In accordance with the above and as also laid down in the appended claims, the present invention relates in particular to the following items:

1. A method for assessing the capacity of a candidate molecule to inhibit covalently closed circular (ccc) DNA of a hepadnavirus comprising the steps of
    (a) contacting a cell comprising a nucleic acid molecule comprising a nucleic acid sequence encoding a tagged hepadnavirus e antigen with said candidate molecule;
    (b) assessing the level of the tagged hepadnavirus e antigen; and
    (c) selecting a candidate molecule when the level of tagged hepadnavirus e antigen is decreased compared to a control.
2. The method of item 1, wherein said hepadnavirus is Hepatitis B virus (HBV) and wherein said hepadnavirus e antigen is Hepatitis B virus e antigen (HBeAg).

3. The method of item 1 or 2, wherein said tagged hepadnavirus e antigen contains only one tag.
4. The method of item 3, wherein said tag consists of 6 to 22 amino acids.
5. The method of item 3 or 4, wherein said tag is selected from the group consisting of a hemagglutinin (HA) tag, His-tag, Flag-tag, c-myc-tag, V5-tag and C9-tag.
6. The method of item 5, wherein said Flag-tag is 1×Flag-tag or 3×Flag-tag.
7. The method of item 1 or 2, wherein said tagged hepadnavirus e antigen contains two or more tags.
8. The method of item 7, wherein said two or more tags are different tags.
9. The method of item 7 or 8, wherein said tag consists of 6 to 22 amino acids.
10. The method of any one of items 7 to 9, wherein said two or more tags are two or more of a hemagglutinin (HA)-tag, His-tag, Flag-tag, c-myc-tag, V5-tag and/or C9-tag.
11. The method of item 10, wherein said Flag-tag is 1×Flag-tag or 3×Flag-tag.
12. The method of item 5 or 10,
    wherein the nucleic acid sequence encoding the HA tag is shown in SEQ ID NO: 1;
    wherein the nucleic acid sequence encoding the His-tag is shown in SEQ ID NO: 2;
    wherein the nucleic acid sequence encoding the c-myc-tag is shown in SEQ ID NO: 4;
    wherein the nucleic acid sequence encoding the V5-tag is shown in SEQ ID NO: 5;
    and/or wherein the nucleic acid sequence encoding the C9-tag is shown in SEQ ID NO: 6.
13. The method of item 6 or 11, wherein the nucleic acid sequence encoding the 1×Flag-tag is shown in SEQ ID NO: 3; or wherein the nucleic acid sequence encoding the 3×Flag-tag is shown in SEQ ID NO: 7.
14. The method of item 5 or 10,
    wherein the amino acid sequence of the HA tag is shown in SEQ ID NO: 8;
    wherein the amino acid sequence of the His-tag is shown in SEQ ID NO: 9; wherein the amino acid sequence of the c-myc-tag is shown in SEQ ID NO: 11;
    wherein the amino acid sequence of the V5-tag is shown in SEQ ID NO: 12; and/or
    wherein the amino acid sequence of the C9-tag is shown in SEQ ID NO: 13.
15. The method of item 6 or 11,
    wherein the amino acid sequence of the 1×Flag-tag is shown in SEQ ID NO: 10; or
    wherein the amino acid sequence of the 3×Flag-tag is shown in SEQ ID NO: 14.
16. The method of any one of items 2 to 15, wherein the nucleic acid sequence encoding the HBeAg is shown in SEQ ID NO: 16.
17. The method of any one of items 2 to 15, wherein the amino acid sequence of the HBeAg is shown in SEQ ID NO: 18.
18. The method of any one of items 1 to 17, wherein the nucleic acid molecule comprises a nucleic acid sequence encoding a hepadnavirus precore protein.
19. The method of item 18, wherein the nucleic acid sequence encoding a hepadnavirus precore protein is shown in SEQ ID NO: 15.
20. The method of item 18, wherein the amino acid sequence of the hepadnavirus precore protein is shown in SEQ ID NO: 17.
21. The method of any one of items 1 to 17, wherein the nucleic acid molecule comprises a nucleic acid sequence encoding the one or more tag, wherein said sequence is 3' downstream of the nucleic acid sequence encoding the N-terminal signal peptide and linker of the hepadnavirus precore protein.
22. The method of item 21, wherein said nucleic acid sequence encoding the one or more tag is 3' downstream of the nucleic acid sequence encoding the N-terminal 29 amino acids of a hepatitis B virus precore protein.
23. The method of any one of items 1 to 22, wherein the nucleic acid molecule comprises a hepadnavirus genome.
24. The method of item 23, wherein said hepadnavirus genome is a Hepatitis B virus (HBV) genome.
25. The method of item 24, wherein said HBV genome is the genome of HBV genotype A, B, C, D, E, F, G or H.
26. The method of item 24, wherein said HBV genome is the genome of HBV genotype D.
27. The method of item 26, wherein said genome of HBV genotype D is a genome of HBV subgenotype ayw.
28. The method of any one of items 1 to 27, wherein the nucleic acid encoding the one or more tag is 5' upstream of a nucleic acid encoding a hepadnavirus core protein.
29. The method of item 28, wherein the hepadnavirus core protein is a HBV core protein.
30. The method of item 29, wherein the nucleic acid encoding the HBV core protein is shown in SEQ ID NO: 23.
31. The method of item 29, wherein the amino acid sequence of the HBV core protein is shown in SEQ ID NO: 24.
32. The method of any one of items 1 to 31, wherein the nucleic acid molecule comprising a sequence encoding the one or more tag is inserted into the epsilon structure as encoded by a hepadnavirus genome.
33. The method of item 32, wherein the hepadnavirus genome is a HBV genome.
34. The method of item 33, wherein the nucleic acid sequence of the epsilon structure as encoded by a HBV genome is shown in SEQ ID NO: 25.
35. The method of any one of items 1 to 34, wherein the nucleic acid molecule comprising a sequence encoding the one or more tag is inserted into the lower stem of the epsilon structure as encoded by a hepadnavirus genome.
36. The method of item 35, wherein the hepadnavirus genome is a HBV genome.
37. The method of any one of items 1 to 36, wherein the nucleic acid molecule comprising a sequence encoding the one or more tag is inserted between nucleotides corresponding to position C1902 and position A1903 of the HBV genome.
38. The method of any one of items 1 to 37, wherein the nucleic acid molecule comprises 5' of the sequence encoding the one or more tag a sequence that is capable of forming base pairs with the lower stem of the epsilon structure as encoded by a hepadnavirus genome.
39. The method of item 38, wherein the sequence that is capable of forming base pairs with the lower stem of the epsilon structure as encoded by a hepadnavirus genome is capable of forming base pairs with nucleotides corresponding to positions T1849 to A1854 of the HBV genome.
40. The method of item 38 or 39, wherein the sequence that is capable of forming base pairs with the lower stem of the epsilon structure as encoded by a hepadnavirus genome consists of up to 9 nucleotides.
41. The method of item 40, wherein the sequence that is capable of forming base pairs with the lower stem of the epsilon structure as encoded by a hepadnavirus genome consists of the sequence shown in SEQ ID No. 26; or wherein the sequence that is capable of forming base pairs with the lower stem of the epsilon structure as encoded by a hepadnavirus genome encodes a polypeptide as shown in SEQ ID NO. 40.
42. The method of any one of items 1 to 41, wherein the nucleic acid molecule comprises 3' of the sequence encoding the one or more tag a sequence encoding a linker.
43. The method of item 42, wherein said linker consists of one or more amino acid residues.
44. The method of item 42, wherein said linker consists of only one amino acid residues.
45. The method of item 44, wherein said amino acid is a glycine residue.
46. The method of any one of items 42 to 44, wherein said sequence encoding a linker consists of the sequence GGC; or wherein said sequence encodes a glycine residue.
47. The method of any one of items 1 to 46, wherein the nucleic acid molecule comprising
a nucleic acid sequence encoding a tagged hepadnavirus e antigen comprises a nucleic acid sequence as shown in SEQ ID NO. 41; or
wherein the nucleic acid molecule comprising a nucleic acid sequence encoding a tagged hepadnavirus e antigen comprises a nucleic acid sequence encoding an amino acid sequence as shown in SEQ ID NO. 42.
48. The method of any one of items 1 to 47, wherein said one or more tag is fused in frame into the hepadnavirus e antigen.
49. The method of item 48, wherein the hepadnavirus e antigen is Hepatitis B virus e antigen (HBeAg).
50. The method of any one of items 2 to 49, wherein the nucleic acid sequence encoding the tagged HBeAg is shown in SEQ ID NO: 20.
51. The method of any one of items 2 to 50, wherein the amino acid sequence of the tagged HBeAg is shown in SEQ ID NO: 22.
52. The method of any one of items 2 to 51, wherein the nucleic acid sequence encoding a tagged HBV precore protein is shown in SEQ ID NO: 19.
53. The method of any one of items 2 to 52, wherein the amino acid sequence of the tagged HBV precore protein is shown in SEQ ID NO: 21.
54. The method of any one of items 24 to 53, wherein the nucleic acid sequence of the HBV genome is shown in any one of SEQ ID NO: 27, 28, 29, 30, 31, 32, 33 or 34.
55. The method of any one of items 23 to 54, wherein the nucleic acid is transcriptable into pregenomic (pg) hepadnavirus RNA, in particular pregenomic (pg) HBV RNA.
56. The method of any one of items 1 to 55, wherein said nucleic acid prevents the translation of the tagged hepadnavirus e antigen.
57. The method of item 56, wherein said nucleic acid does not contain a start codon ATG 5' upstream of the nucleic acid encoding a tagged hepadnavirus e antigen.
58. The method of item 56 or 57, wherein a start codon ATG 5' upstream of the nucleic acid encoding a tagged hepadnavirus e antigen has been replaced by the nucleic acids TG.
59. The method of any one of items 56 to 58, wherein said nucleic has been modified by point mutation in order to prevent the translation of a tagged hepadnavirus e antigen.
60. The method of any one of items 1 to 59, wherein the nucleic acid molecule comprising a nucleic acid sequence encoding the tagged hepadnavirus e antigen is comprised in a vector.
61. The method of item 60, wherein the vector comprises a sequence as shown in SEQ ID NO: 35.
62. The method of any one of items 1 to 61, wherein the nucleic acid molecule comprising a nucleic acid sequence encoding the tagged hepadnavirus e antigen is under control of an inducible promoter.
63. The method of any one of claims 56 to 62, wherein the hepadnavirus e antigen is Hepatitis B virus e antigen (HBeAg).
64. The method of item 62 or 63, wherein the inducible promoter is a tetracycline-inducible promoter, a doxycline-inducible promoter, an antibiotic-inducible promoter, a copper-inducible promoter, an alcohol-inducible promoter, a steroid-inducible promoter, or a herbicide-inducible promoter.
65. The method of any one of items 62 to 64, wherein the inducible promoter is a CMV promoter or a tet-EF-1 alpha promoter.
66. The method of any one of items 23 to 65, wherein one or more stop codons are introduced into the coding region of one or more hepadnavirus envelope proteins.
67. The method of item 66, wherein said one or more hepadnavirus envelope proteins is/are one or more HBV envelope proteins.
68. The method of item 67, wherein the one or more HBV envelope protein is one or more of large surface protein (L), middle surface protein (M) and small surface protein (S).
69. The method of item 67, wherein the HBV envelope protein is small surface protein (S).
70. The method of any one of items 67 to 69, wherein the coding region of the one or more HBV envelope proteins is shown in SEQ ID NO: 36 (L), SEQ ID NO: 37 (M) and/or SEQ ID NO: 38 (S).
71. The method of item 70, wherein the HBV nucleotides 217 to 222 (TTGTTG) of SEQ ID NO: 38 (S) are mutated to TAGTAG to prevent the expression of envelope proteins.
72. The method of any one of items 1 to 71, wherein the cell is a eukaryotic cell.
73. The method of item 72, wherein the eukaryotic cell is of hepatocyte origin.
74. The method of item 72 or 73, wherein the eukaryotic cell is a hepatoma cell or is derived from a hepatoma cell.
75. The method of any one of items 72 to 74, wherein the eukaryotic cell is HepG2 (ATCC #HB-8065).
76. The method of any one of items 1 to 75, wherein the nucleic acid molecule or the vector comprising same is stably integrated in the genome of the cell.
77. The method of any one of items 1 to 76, wherein said step (a) further comprises a step (aa) which comprises culturing a cell comprising a nucleic acid molecule comprising a nucleic acid sequence encoding a tagged hepadnavirus e antigen in conditions allowing
(i) the synthesis of hepadnavirus pregenomic (pg) RNA;
(ii) the reverse transcription of said synthesized pgRNA into a minus strand DNA;
(iii) the synthesis of a second plus strand DNA so that said minus strand DNA and said plus strand DNA form a double stranded relaxed circular DNA;
(iv) formation of cccDNA from said relaxed circular double stranded DNA;
(v) optionally restoration of conditions allowing the translation of the tagged hepadnavirus e antigen;
(vi) transcription of an mRNA encoding a tagged hepadnavirus e antigen;
(vii) translation of a tagged hepadnavirus e antigen.

78. The method of item 77, wherein the restoration of conditions allowing the translation of the tagged hepadnavirus e antigen is the restoration of the start codon.
79. The method of any one of items 1 to 78, wherein said method is for assessing the capacity of a candidate molecule to inhibit the formation of ccc DNA of a hepadnavirus.
80. The method of item 79, wherein the cell is contacted with the candidate molecule before cccDNA has formed.
81. The method of any one of items 1 to 78, wherein said method is for assessing the capacity of a candidate molecule to decrease the amount or number of ccc DNA of a hepadnavirus.
82. The method of any one of items 1 to 78, wherein said method is for assessing the capacity of a candidate molecule to decrease the transcription of ccc DNA of a hepadnavirus.
83. The method of item 81 or 82, wherein the cell is contacted with the candidate molecule after cccDNA has formed.
84. The method of any one of items 1 to 83, wherein assessing the level of the tagged hepadnavirus e antigen according to step (b) is performed by ELSA, CLIA or AlphaLISA.
85. The method of any one of items 1 to 84, wherein assessing the level of the tagged hepadnavirus e antigen according to step (b) comprises the use of an antibody specifically recognizing said hepadnavirus e antigen and one or more antibodies specifically recognizing the one or more tags.
86. The method of any one of items 77 to 85, wherein said hepadnavirus is Hepatitis B virus (HBV) and wherein said hepadnavirus e antigen is Hepatitis B virus e antigen (HBeAg).
87. A nucleic acid molecule comprising a nucleic acid sequence encoding a tagged hepadnavirus e antigen.
88. The nucleic acid molecule of item 87, wherein said hepadnavirus e antigen is Hepatitis B virus e antigen (HBeAg).
89. The nucleic acid molecule of item 87 or 88, wherein said tagged hepadnavirus e antigen contains only one tag.
90. The nucleic acid molecule of item 89, wherein said tag consists of 6 to 22 amino acids.
91. The nucleic acid molecule of item 89 or 90, wherein said tag is selected from the group consisting of a hemagglutinin (HA) tag, His-tag, Flag-tag, c-myc-tag, V5-tag and C9-tag.
92. The nucleic acid molecule of item 91, wherein said Flag-tag is a 1×Flag-tag or a 3×Flag-tag.
93. The nucleic acid molecule of item 87 or 88, wherein said tagged hepadnavirus e antigen contains two or more tags.
94. The nucleic acid molecule of item 93, wherein said two or more tags are different tags.
95. The nucleic acid molecule of item 93 or 94, wherein the entire length of said two or more tags is of from 14 to 31 amino acids.
96. The nucleic acid molecule of any one of items 93 to 95, wherein said two or more tag are two or more of a hemagglutinin (HA) tag, His-tag, Flag-tag, c-myc-tag, V5-tag and/or C9-tag.
97. The nucleic acid molecule of item 96, wherein said Flag-tag is a 1×Flag-tag or a 3×Flag-tag.
98. The nucleic acid molecule of any one of items 91 or 96, wherein the nucleic acid sequence encoding the HA tag is shown in SEQ ID NO: 1;
wherein the nucleic acid sequence encoding the His-tag is shown in SEQ ID NO: 2;
wherein the nucleic acid sequence encoding the c-myc-tag is shown in SEQ ID NO: 4;
wherein the nucleic acid sequence encoding the V5-tag is shown in SEQ ID NO: 5;
and/or wherein the nucleic acid sequence encoding the C9-tag is shown in SEQ ID NO: 6.
99. The nucleic acid molecule of item 92 or 97,
wherein the nucleic acid sequence encoding the 1×Flag-tag is shown in SEQ ID NO: 3; or
wherein the nucleic acid sequence encoding the 3×Flag-tag is shown in SEQ ID NO: 7.
100. The nucleic acid molecule of item 91 or 96,
wherein the amino acid sequence of the HA tag is shown in SEQ ID NO: 8;
wherein the amino acid sequence of the His-tag is shown in SEQ ID NO: 9;
wherein the amino acid sequence of the c-myc-tag is shown in SEQ ID NO: 11;
wherein the amino acid sequence of the V5-tag is shown in SEQ ID NO: 12; and/or
wherein the amino acid sequence of the C9-tag is shown in SEQ ID NO: 13.
101. The nucleic acid molecule of item 92 or 97,
wherein the amino acid sequence of the 1×Flag-tag is shown in SEQ ID NO: 10; or
wherein the amino acid sequence of the 3×Flag-tag is shown in SEQ ID NO: 14.
102. The nucleic acid molecule of any one of items 88 to 101, wherein the nucleic acid sequence encoding the HBeAg is shown in SEQ ID NO: 16.
103. The nucleic acid molecule of any one of items 88 to 101, wherein the amino acid sequence of the HBeAg is shown in SEQ ID NO: 18.
104. The nucleic acid molecule of any one of items 87 to 103, wherein the nucleic acid molecule comprises a nucleic acid sequence encoding a hepadnavirus precore protein.
105. The nucleic acid molecule of item 104, wherein the nucleic acid sequence encoding a hepadnavirus precore protein is shown in SEQ ID NO: 15.
106. The nucleic acid molecule of item 104, wherein the amino acid sequence of the hepadnavirus precore protein is shown in SEQ ID NO: 17.
107. The nucleic acid molecule of any one of items 87 to 106, wherein the nucleic acid molecule comprises a nucleic acid sequence encoding the one or more tag, wherein said sequence is 3' downstream of the nucleic acid sequence encoding the N-terminal signal peptide and linker (the "precore" region) of the hepadnavirus precore protein.
108. The method of item 107, wherein said nucleic acid sequence encoding the one or more tag is 3' downstream of the nucleic acid sequence encoding the N-terminal 29 amino acids of a hepatitis B virus precore protein.
109. The nucleic acid molecule of any one of items 87 to 108, wherein the nucleic acid molecule comprises a hepadnavirus genome.
110. The nucleic acid molecule of item 109, wherein said hepadnavirus genome is a Hepatitis B virus (HBV) genome.
111. The nucleic acid molecule of item 110, wherein said HBV genome is the genome of HBV genotype A, B, C, D, E, F, G or H.
112. The nucleic acid molecule of item 110, wherein said HBV genome is the genome of HBV genotype D.

113. The nucleic acid molecule of item 112, wherein said genome of HBV genotype D is a genome of HBV subgenotype ayw.
114. The nucleic acid molecule of any one of items 87 to 113, wherein the nucleic acid encoding the one or more tag is 5' upstream of the nucleic acid encoding a hepadnavirus core protein.
115. The nucleic acid molecule of item 114, wherein the nucleic acid sequence encodes a HBV core protein.
116. The nucleic acid molecule of item 115, wherein the nucleic acid sequence encoding a HBV core protein is shown in SEQ ID NO: 23.
117. The nucleic acid molecule of item 114, wherein the core protein is a HBV core protein.
118. The nucleic acid molecule of item 116, wherein the amino acid sequence of the HBV core protein is shown in SEQ ID NO: 24.
119. The nucleic acid molecule of any one of items 87 to 118, wherein the nucleic acid molecule comprising a sequence encoding the one or more tag is inserted into the epsilon structure as encoded by a hepadnavirus genome.
120. The nucleic acid molecule of item 119, wherein said hepadnavirus genome is a HBV genome.
121. The nucleic acid molecule of item 120, wherein the nucleic acid sequence of the epsilon structure as encoded by a HBV genome is shown in SEQ ID NO: 25.
122. The nucleic acid molecule of any one of items 87 to 121, wherein the nucleic acid molecule comprising a sequence encoding the one or more tag is inserted into the lower stem of the epsilon structure as encoded by a hepadnavirus genome.
123. The nucleic acid molecule of item 122, wherein said hepadnavirus genome is a HBV genome.
124. The nucleic acid molecule of any one of items 87 to 123, wherein the nucleic acid molecule comprising a sequence encoding the one or more tag is inserted between nucleotides corresponding to position C1902 and A1903 of the HBV genome.
125. The nucleic acid molecule of any one of items 87 to 124, wherein the nucleic acid molecule comprises 5' of the sequence encoding the one or more tag a sequence that is capable of forming base pairs with the lower stem of the epsilon structure as encoded by a hepadnavirus genome.
126. The nucleic acid molecule of item 125, wherein the sequence that is capable of forming base pairs with the lower stem of the epsilon structure as encoded by a hepadnavirus genome is capable of form base pairs with nucleotides corresponding to positions T1849 to A1854 of the HBV genome.
127. The nucleic acid molecule of item 125 or 126, wherein the sequence that is capable of forming base pairs with the lower stem of the epsilon structure as encoded by a hepadnavirus genome consists of up to 9 nucleotides.
128. The nucleic acid molecule of item 127, wherein the sequence that is capable of forming base pairs with the lower stem of the epsilon structure as encoded by a hepadnavirus genome consists of the sequence shown in SEQ ID No. 26; or wherein the sequence that is capable of forming base pairs with the lower stem of the epsilon structure as encoded by a hepadnavirus genome encodes a polypeptide as shown in SEQ ID NO. 40.
129. The nucleic acid molecule of any one of items 87 to 128, wherein the nucleic acid molecule comprises 3' of the sequence encoding the one or more tag a sequence encoding a linker.
130. The nucleic acid molecule of item 129, wherein said linker consists of one or more amino acid residues.
131. The nucleic acid molecule of item 129, wherein said linker consists of only one amino acid residues.
132. The nucleic acid molecule of item 131, wherein said amino acid is a glycine residue.
133. The nucleic acid molecule of any one of items 129 to 131, wherein said sequence encoding a linker consists of the sequence GGC; or wherein said sequence encodes a glycine residue.
134. The nucleic acid molecule of any one of items 87 to 133, wherein the nucleic acid molecule comprising a nucleic acid sequence encoding a tagged hepadnavirus e antigen comprises a nucleic acid sequence as shown in SEQ ID NO. 41; or wherein the nucleic acid molecule comprising a nucleic acid sequence encoding a tagged hepadnavirus e antigen comprises a nucleic acid sequence encoding an amino acid sequence as shown in SEQ ID NO. 42
135. The nucleic acid molecule of any one of items 87 to 134, wherein said one or more tag is fused in frame in the hepadnavirus e antigen.
136. The nucleic acid molecule of item 135, wherein said hepadnavirus e antigen is Hepatitis B virus e antigen (HBeAg).
137. The nucleic acid molecule of any one of items 88 to 136, wherein the nucleic acid sequence encoding the tagged HBeAg is shown in SEQ ID NO: 20.
138. The nucleic acid molecule of any one of items 88 to 137, wherein the amino acid sequence of the tagged HBeAg is shown in SEQ ID NO: 22.
139. The nucleic acid molecule of any one of items 88 to 138, wherein the nucleic acid sequence encoding the tagged HBV precore protein is shown in SEQ ID NO: 19.
140. The nucleic acid molecule of any one of items 88 to 139, wherein the amino acid sequence of the tagged HBV precore protein is shown in SEQ ID NO: 21.
141. The nucleic acid molecule of any one of items 110 to 140, wherein the nucleic acid sequence of the HBV genome is shown in any one of SEQ ID NO: 27, 28, 29, 30, 31, 32, 33 or 34.
142. The nucleic acid molecule of any one of items 109 to 141, wherein the nucleic acid is transcriptable into pregenomic (pg) hepadnavirus RNA.
143. The nucleic acid molecule of item 142, wherein said hepadnavirus RNA is HBV RNA.
144. The nucleic acid molecule of any one of items 87 to 143, wherein the nucleic acid molecule comprising a nucleic acid sequence encoding the tagged hepadnavirus e antigen is comprised in a vector.
145. The nucleic acid molecule of item 144, wherein said hepadnavirus e antigen is Hepatitis B virus e antigen (HBeAg)
146. The nucleic acid molecule of any one of items 87 to 145, wherein said nucleic acid allows the translation of the tagged hepadnavirus e antigen.
147. The nucleic acid molecule of item 146, wherein said hepadnavirus e antigen is Hepatitis B virus e antigen (HBeAg).
148. The nucleic acid molecule of item 147, wherein the nucleic acid is comprised in a vector that comprises a sequence as shown in SEQ ID NO: 39.
149. The nucleic acid molecule of any one of items 87 to 148, wherein said nucleic acid prevents the translation of the tagged hepadnavirus e antigen.
150. The nucleic acid molecule of item 149, wherein said nucleic acid does not contain a start codon ATG 5' upstream of the nucleic acid encoding a tagged hepadnavirus e antigen.

151. The nucleic acid molecule of item 147 or 150, wherein a start codon ATG 5' upstream of the nucleic acid encoding a tagged hepadnavirus e antigen has been replaced by the nucleic acids TG.

152. The nucleic acid molecule of any one of items 147 to 151, wherein said nucleic has been modified by point mutation in order to prevent the translation of a tagged hepadnavirus e antigen.

153. The nucleic acid molecule of any one of items 144, 145 and 149 to 152, wherein the vector comprises a sequence as shown in SEQ ID NO: 35.

154. The nucleic acid molecule of any one of items 87 to 153, wherein the nucleic acid molecule comprising a nucleic acid sequence encoding the tagged hepadnavirus e antigen is under control of an inducible promoter.
155. The nucleic acid molecule of any one of items 149 to 154, wherein the hepadnavirus e antigen is Hepatitis B virus e antigen (HBeAg).
156. The nucleic acid molecule of item 154 or 155, wherein the inducible promoter is a tetracycline-inducible promoter, a doxycline-inducible promoter, an antibiotic-inducible promoter, a copper-inducible promoter, an alcohol-inducible promoter, a steroid-inducible promoter, or a herbicide-inducible promoter.
157. The nucleic acid molecule of any one of items 154 to 156, wherein the inducible promoter is a CMV promoter or a tet-EF-1 alpha promoter.
158. The nucleic acid molecule of any one of items 110 to 157, wherein one or more stop codons are introduced into the coding region of one or more hepadnavirus envelope proteins.
159. The nucleic acid molecule of item 158, wherein said one or more hepadnavirus envelope proteins is/are one or more HBV envelope proteins.
160. The nucleic acid molecule of item 159, wherein the one or more HBV envelope protein is one or more of L, M and/or S.
161. The nucleic acid molecule of item 159, wherein the HBV envelope protein is S.
162. The nucleic acid molecule of any one of items 159 to 161, wherein the coding region of the one or more HBV envelope proteins is shown in SEQ ID NO: 36 (L), 37 (M) or 38 (S).
163. The nucleic acid molecule of item 162, wherein the HBV nucleotides 217 to 222 (TTGTTG) of SEQ ID NO: 38 (S) are mutated to TAGTAG to prevent the expression of envelope proteins.
164. A protein encoded by the nucleic acid molecule as defined in any one of items 87 to 163.
165. A protein comprising a tagged hepadnavirus e antigen.
166. The protein of item 165, wherein said hepadnavirus e antigen is Hepatitis B virus e antigen (HBeAg).
167. The protein of item 166, wherein the Hepatitis B virus e antigen (HBeAg) comprises an amino acid sequence as shown in SEQ ID NO: 18.
168. The protein of any one of items 165 to 167, wherein said tagged hepadnavirus e antigen contains only one tag.
169. The protein of item 168, wherein said tag consists of 6 to 22 amino acids.
170. The protein of any one of items 165 to 169, wherein said tag is selected from the group consisting of a hemagglutinin (HA) tag, His-tag, Flag-tag, c-myc-tag, V5-tag and C9-tag.
171. The protein of item 170, wherein said Flag-tag is a 1×Flag-tag or a 3×Flag-tag.
172. The protein of any one of items 165 to 167, wherein said tagged hepadnavirus e antigen contains two or more tags.
173. The protein of item 172, wherein said two or more tags are different tags.
174. The protein of item 172 or 173, wherein the entire length of said two or more tags is of from 14 to 31 amino acids.
175. The protein of any one of items 172 to 174, wherein said two or more tag are two or more of a hemagglutinin (HA) tag, His-tag, Flag-tag, c-myc-tag, V5-tag and/or C9-tag.
176. The protein of item 175, wherein said Flag-tag is a 1×Flag-tag or a 3×Flag-tag.
177. The protein of item 170 or 175,
wherein the nucleic acid sequence encoding the HA tag is shown in SEQ ID NO: 1;
wherein the nucleic acid sequence encoding the His-tag is shown in SEQ ID NO: 2;
wherein the nucleic acid sequence encoding the c-myc-tag is shown in SEQ ID NO: 4;
wherein the nucleic acid sequence encoding the V5-tag is shown in SEQ ID NO: 5;
and/or wherein the nucleic acid sequence encoding the C9-tag is shown in SEQ ID NO: 6.
178. The protein of item 171 or 176,
wherein the nucleic acid sequence encoding the 1×Flag-tag is shown in SEQ ID NO: 3; or
wherein the nucleic acid sequence encoding the 3×Flag-tag is shown in SEQ ID NO: 7.
179. The protein of item 170 or 175,
wherein the amino acid sequence of the HA tag is shown in SEQ ID NO: 8;
wherein the amino acid sequence of the His-tag is shown in SEQ ID NO: 9;
wherein the amino acid sequence of the c-myc-tag is shown in SEQ ID NO: 11;
wherein the amino acid sequence of the V5-tag is shown in SEQ ID NO: 12; and/or
wherein the amino acid sequence of the C9-tag is shown in SEQ ID NO: 13.
180. The protein of item 171 or 176,
wherein the amino acid sequence of the 1×Flag-tag is shown in SEQ ID NO: 10; or
wherein the amino acid sequence of the 3×Flag-tag is shown in SEQ ID NO: 14.
181. The protein of any one of items 165 to 180, comprising a hepadnavirus precore protein.
182. The protein of item 181, wherein the nucleic acid sequence encoding a hepadnavirus precore protein is shown in SEQ ID NO: 15.
183. The protein of item 181, wherein the amino acid sequence of the hepadnavirus precore protein is shown in SEQ ID NO: 17.
184. The protein of any one of items 165 to 183, wherein the protein comprises an amino acid sequence of the one or more tag, wherein said sequence is C-terminal of the amino acid sequence of the sequence of the signal peptide and of the linker of the hepadnavirus precore protein.
185. The protein of item 184, wherein said protein comprising an amino acid sequence of the one or more tag is C-terminal of the amino acid sequence of the N-terminal 29 amino acids of a hepatitis B virus precore protein.
186. The protein of any one of items 165 to 183, wherein protein comprises an amino acid sequence of the one or more tag, wherein said sequence is N-terminal of an amino acid sequence of a hepadnavirus core protein.

187. The protein of item 186, wherein the hepadnavirus core protein is a HBV core protein.
188. The protein of item 187, wherein the nucleic acid encoding the HBV core protein is shown in SEQ ID NO: 23.
189. The protein of item 187, wherein the amino acid sequence of the HBV core protein is shown in SEQ ID NO: 24.
190. The protein of any one of items 165 to 189, wherein the amino acid sequence of the one or more tag is inserted into an amino acid sequence encoded by the epsilon structure as encoded by a hepadnavirus genome.
191. The protein of item 190, wherein the hepadnavirus genome is a HBV genome.
192. The protein of item 191, wherein the nucleic acid sequence of the epsilon structure as encoded by a HBV genome is shown in SEQ ID NO: 25.
193. The protein of any one of items 165 to 192, wherein the amino acid sequence of the one or more tag is inserted into an amino acid sequence encoded by the lower stem of the epsilon structure as encoded by a hepadnavirus genome.
194. The protein of item 193, wherein the hepadnavirus genome is a HBV genome.
195. The protein of any one of items 165 to 194, wherein the amino acid sequence of the one or more tag is inserted between amino acid residues corresponding to position G29 and position M30 of a HBV precore protein (such as the one as shown in SEQ ID NO. 17).
196. The protein of any one of items 165 to 195, further comprising N-terminal to the amino acid sequence of the one or more tag an amino acid sequence of up to 3 amino acids, wherein said amino acid sequence of up to 3 amino acids is encoded by a nucleic acid sequence that is capable of forming base pairs with the lower stem of the epsilon structure as encoded by a hepadnavirus genome.
197. The protein of item 196, wherein the nucleic sequence that is capable of forming base pairs with the lower stem of the epsilon structure as encoded by a hepadnavirus genome is capable of form base pairs with nucleotides corresponding to positions T1849 to A1854 of the HBV genome.
198. The protein of item 196, wherein the nucleic acid sequence that is capable of forming base pairs with the lower stem of the epsilon structure as encode by a hepadnavirus genome consists of the sequence shown in SEQ ID No. 26.
199. The protein of any one of items 196 to 198, wherein said amino acid sequence of up to 3 amino acids is shown in SEQ ID NO. 40.
200. The protein of any one of items 165 to 199, further comprising C-terminal to the amino acid sequence of the one or more tag a linker.
201. The protein of item 200, wherein said linker consists of one or more amino acid residues.
202. The protein of item 201, wherein said linker consists of only one amino acid residue.
203. The protein of item 202, wherein said amino acid is a glycine residue.
204. The protein of any one of items 1 to 46, wherein the amino acid sequence of a tagged hepadnavirus e antigen comprises an amino acid sequence encoded by a nucleic acid sequence as shown in SEQ ID NO. 41; or
wherein the amino acid sequence of a tagged hepadnavirus e antigen comprises an amino acid sequence as shown in SEQ ID NO. 42
205. The protein of any one of items 165 to 204, wherein said one or more tag is fused in frame into the hepadnavirus e antigen.
206. The protein of item 205, wherein the hepadnavirus e antigen is Hepatitis B virus e antigen (HBeAg).
207. The protein of any one of items 166 to 206, wherein the nucleic acid sequence encoding the tagged HBeAg is shown in SEQ ID NO: 20.
208. The protein of any one of items 166 to 207, wherein the amino acid sequence of the tagged HBeAg is shown in SEQ ID NO: 22.
209. The protein of any one of items 166 to 208, wherein the nucleic acid sequence encoding a tagged HBV precore protein is shown in SEQ ID NO: 19.
210. The protein of any one of items 166 to 209, wherein the amino acid sequence of a tagged HBV precore protein is shown in SEQ ID NO: 21.
211. A host cell comprising the nucleic acid molecule of any one of items 87 to 163 or the protein of any one of items 164 to 210.
212. The host cell of item 211, wherein the cell is a eukaryotic cell.
213. The host cell of item 212, wherein the eukaryotic cell is of hepatocyte origin.
214. The host cell of item 212 or 213, wherein the eukaryotic cell is a hepatoma cell or is derived from a hepatoma cell.
215. The host cell of any one of items 212 to 214, wherein the eukaryotic cell is HepG2 (ATCC #HB-8065).
216. A process for the production of the protein as defined in any one of items 164 to 210, said process comprising culturing a host of any one of items 210 to 215 under conditions allowing the expression of the protein and recovering the produced protein from the culture.
217. Kit for use in the method of any one of items 1 to 86.
218. Kit comprising an antibody specifically recognizing a hepadnavirus antigen e as defined in any one of items 165 to 167 and one or more antibodies specifically recognizing one or more tags as defined in any one of items 168 to 180.
219. Use of the nucleic molecule of any one of items 87 to 163, the protein of any one of items 164 to 210 and/or the host cell of any one of items 211 to 215 for screening candidate molecules suspected to be capable of inhibiting covalently closed circular DNA of hepadnavirus.

The invention claimed is:

1. A nucleic acid molecule comprising a nucleic acid sequence encoding a tagged hepadnavirus e antigen, wherein the nucleic acid molecule comprises a sequence encoding one or more tags, wherein the sequence is inserted into an epsilon structure as encoded by a hepadnavirus genome, wherein said nucleic acid molecule comprising a sequence encoding the one or more tag is inserted between nucleotides corresponding to position C1902 and position A1903 of the HBV genome, wherein said nucleic acid molecule comprises 5' of the sequence encoding the one or more tag a sequence that is capable of forming base pairs with the lower stem of the epsilon structure as encoded by a hepadnavirus genome and wherein the sequence that is capable of forming base pairs with said lower stem of the epsilon structure as encoded by a hepadnavirus genome is capable of forming base pairs with nucleotides corresponding to positions T1849 to A1854 of the HBV genome.

2. The nucleic acid molecule of claim 1, wherein said hepadnavirus is Hepatitis B virus (HBV) and wherein said hepadnavirus e antigen is Hepatitis B virus e antigen (HBeAg).

3. The nucleic acid molecule of claim 1, wherein said tagged hepadnavirus e antigen contains only one tag; or wherein said tagged hepadnavirus e antigen contains two or more tags.

4. The nucleic acid molecule of claim 3, wherein said tag is selected from the group consisting of a hemagglutinin (HA) tag, His-tag, Flag-tag (like 1×Flag-tag or a 3×Flag-tag), c-myc-tag, V5-tag, and C9-tag.

5. The nucleic acid molecule of claim 4, wherein the nucleic acid sequence encoding the HA tag is shown in SEQ ID NO: 1;

wherein the nucleic acid sequence encoding the His-tag is shown in SEQ ID NO: 2;

wherein the nucleic acid sequence encoding the 1×Flag-tag is shown in SEQ ID NO: 3;

wherein the nucleic acid sequence encoding the 3×Flag-tag is shown in SEQ ID NO: 7;

wherein the nucleic acid sequence encoding the c-myc-tag is shown in SEQ ID NO: 4;

wherein the nucleic acid sequence encoding the V5-tag is shown in SEQ ID NO: 5; and/or wherein the nucleic acid sequence encoding the C9-tag is shown in SEQ ID NO: 6; or wherein the amino acid sequence of the HA tag is shown in SEQ ID NO: 8;

wherein the amino acid sequence of the His-tag is shown in SEQ ID NO: 9;

wherein the amino acid sequence of the 1×Flag-tag is shown in SEQ ID NO: 10;

wherein the amino acid sequence of the 3×Flag-tag is shown in SEQ ID NO: 14;

wherein the amino acid sequence of the c-myc-tag is shown in SEQ ID NO: 11;

wherein the amino acid sequence of the V5-tag is shown in SEQ ID NO: 12; and/or wherein the amino acid sequence of the C9-tag is shown in SEQ ID NO: 13.

6. The nucleic acid molecule of claim 1, wherein the nucleic acid molecule comprises a nucleic acid sequence encoding a hepadnavirus precore protein.

7. The nucleic acid molecule of claim 6, wherein the nucleic acid sequence encoding a hepadnavirus precore protein is shown in SEQ ID NO: 15; or wherein the amino acid sequence of the hepadnavirus precore protein is shown in SEQ ID NO: 17.

8. The nucleic acid molecule of claim 6, wherein said nucleic acid sequence encoding the one or more tag is 3' downstream of the nucleic acid sequence encoding the N-terminal 29 amino acids of a hepatitis B virus precore protein.

9. The nucleic acid molecule of claim 1, wherein the nucleic acid molecule comprises a hepadnavirus genome, such as a Hepatitis B virus (HBV) genome as shown in any one of SEQ ID NO: 27, 28, 29, 30, 31, 32, 33 or 34.

10. The nucleic acid molecule of claim 9, wherein said HBV genome is a genome of HBV subgenotype ayw.

11. The nucleic acid molecule of claim 1, wherein the nucleic acid sequence of the epsilon structure as encoded by a HBV genome is shown in SEQ ID NO: 25.

12. The nucleic acid molecule of claim 1, wherein the sequence that is capable of forming base pairs with the lower stem of the epsilon structure as encoded by a hepadnavirus genome consists of the sequence shown in SEQ ID NO: 26; or wherein the sequence that is capable of forming base pairs with the lower stem of the epsilon structure as encoded by a hepadnavirus genome encodes a polypeptide as shown in SEQ ID NO: 40.

13. The nucleic acid molecule of claim 1, wherein the nucleic acid molecule comprising a nucleic acid sequence encoding a tagged hepadnavirus e antigen comprises a nucleic acid sequence as shown in SEQ ID NO: 41; or wherein the nucleic acid molecule comprising a nucleic acid sequence encoding a tagged hepadnavirus e antigen comprises a nucleic acid sequence encoding an amino acid sequence as shown in SEQ ID NO: 42.

14. The nucleic acid molecule of claim 2, wherein the nucleic acid sequence encoding the tagged HBeAg is shown in SEQ ID NO: 20; or wherein the amino acid sequence of the tagged HBeAg is shown in SEQ ID NO: 22.

15. The nucleic acid molecule of claim 2, wherein said tagged hepadnavirus e antigen contains only one tag; or wherein said tagged hepadnavirus e antigen contains two or more tags.

16. The nucleic acid molecule of claim 7, wherein said nucleic acid sequence encoding the one or more tag is 3' downstream of the nucleic acid sequence encoding the N-terminal 29 amino acids of a hepatitis B virus precore protein.

17. The nucleic acid molecule of claim 6, wherein the nucleic acid sequence encoding the tagged HBV precore protein is shown in SEQ ID NO: 19; or wherein the amino acid sequence of the tagged HBV precore protein is shown in SEQ ID NO: 21.

18. The nucleic acid molecule of claim 2, wherein the nucleic acid sequence encoding the HBeAg is shown in SEQ ID NO: 16; or wherein the amino acid sequence of the HBeAg is shown in SEQ ID NO: 18.

19. The nucleic acid molecule of claim 1, wherein the nucleic acid molecule comprises 3' of the sequence encoding the one or more tag a sequence encoding a linker.

20. The nucleic acid molecule of claim 19, wherein said sequence encoding a linker consists of the sequence GGC; or wherein said sequence encodes a glycine residue.

* * * * *